United States Patent
Ban et al.

(10) Patent No.: US 11,414,394 B2
(45) Date of Patent: *Aug. 16, 2022

(54) PROCESS FOR PRODUCING A HYDRATE OF A HYDROCHLORIDE SALT OF 2,2'-((((((2-ACETYLNAPHTHO[2,3-B]FURAN-4,9-DIYL)BIS(OXY))BIS(CARBONYL)) BIS(AZANEDIYL))BIS(ETHANE-2,1-DIYL)) BIS(AZANEDIYL))DIACETIC ACID

(71) Applicants: SUMITOMO PHARMA ONCOLOGY, INC., Cambridge, MA (US); SUMITOMO PHARMA CO., LTD., Osaka (JP)

(72) Inventors: Hitoshi Ban, Osaka (JP); Seiji Kamioka, Osaka (JP); Yusuke Sawayama, Osaka (JP); Chiang Jia Li, Cambridge, MA (US)

(73) Assignees: SUMITOMO PHARMA ONCOLOGY, INC., Cambridge, MA (US); SUMITOMO PHARMA CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/005,597

(22) Filed: Aug. 28, 2020

(65) Prior Publication Data
US 2020/0392098 A1 Dec. 17, 2020

Related U.S. Application Data

(63) Continuation of application No. 16/194,525, filed on Nov. 19, 2018, now Pat. No. 10,800,752, which is a continuation of application No. 15/561,828, filed as application No. PCT/IB2016/051706 on Mar. 25, 2016, now Pat. No. 10,183,925.

(60) Provisional application No. 62/139,077, filed on Mar. 27, 2015.

(51) Int. Cl.
    C07D 307/92   (2006.01)
    C07D 405/14   (2006.01)
    C07D 405/12   (2006.01)
    A61P 35/02    (2006.01)
    A61P 35/00    (2006.01)

(52) U.S. Cl.
    CPC .......... *C07D 307/92* (2013.01); *A61P 35/00* (2018.01); *A61P 35/02* (2018.01); *C07D 405/12* (2013.01); *C07D 405/14* (2013.01)

(58) Field of Classification Search
    CPC ................................................ C07D 549/458
    USPC ............................................................ 549/458
    See application file for complete search history.

(56) References Cited

FOREIGN PATENT DOCUMENTS

| | | | |
|---|---|---|---|
| CN | 103402993 A | 11/2013 |
| CN | 104080449 A | 10/2014 |
| JP | 2014-511384 A | 5/2014 |
| WO | 2009/036059 A2 | 3/2009 |
| WO | 2012/119265 A1 | 9/2012 |
| WO | 2013/120229 A1 | 8/2013 |
| WO | 2013/166618 A1 | 11/2013 |
| WO | 2016/157052 A1 | 10/2016 |

OTHER PUBLICATIONS

Vippagunta, et al. Advanced Drug Delivery Reviews, 48, 2001, 18.*
Communication dated Feb. 26, 2021 in Chinese Application No. 201680030052.0.
Ponti, et al., "Isolation and In vitro Propagation of Tumorigenic Breast Cancer Cells with Stem/Progenitor Cell Properties", Cancer Research, Jul. 1, 2005, vol. 65, No. 13, pp. 5506-5511 (total 7 pages).
Hackam, et al., "Translation of Research Evidence From Animals to Humans", JAMA, 2006, vol. 296, vol. 14, pp. 1731-1732.
Written Opinion for PCT/IB2016/051706 dated May 11, 2016.
Communication dated Nov. 5, 2019, from the Intellectual Property Office of Taiwan in Application No. 105109636.
Communication dated Jan. 28, 2020 from the European Patent Office in application No. 16714015.1.

(Continued)

*Primary Examiner* — Douglas M Willis
(74) *Attorney, Agent, or Firm* — Sughrue Mion, PLLC

(57) ABSTRACT

A process for producing a hydrate of a hydrochloride salt of 2,2'-((((((2-acetylnaphtho[2,3-b]furan-4,9-diyl)bis(oxy))bis (carbonyl))bis(azanediyl))bis(ethane-2,1-diyl))bis (azanediyl))diacetic acid of the formula:

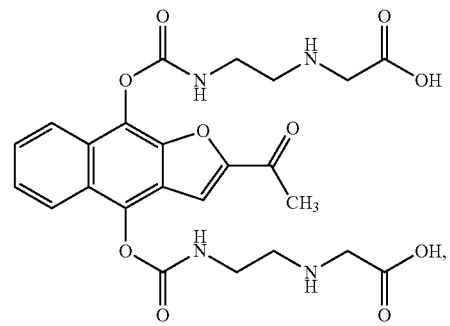

wherein the process comprises the following step:
  recrystallizing the hydrochloride salt of 2,2'-((((((2-acetylnaphtho[2,3-b]furan-4,9-diyl)bis(oxy))bis(carbonyl))bis(azanediyl))bis(ethane-2,1-diyl))bis (azanediyl))diacetic acid, in the presence of hydrochloric acid and a recrystallization solvent;
wherein the recrystallization solvent is methanol, ethanol, 2-propanol, diethyl ether, ethyl acetate, benzene, toluene, acetone, dichloromethane, chloroform, hexane, dimethylformamide, acetonitrile, or water; or mixed solvent thereof.

8 Claims, No Drawings

(56) References Cited

OTHER PUBLICATIONS

Rao, et al., "Plant Anticancer Agents. XII. Isolation and Structure Elucidation of New Cytotoxic Quinones From Tabebuia Cassinoides", Journal of Natural Products, 1982, vol. 45, No. 5, pp. 600-604.
Jordan, V.C., "Tamoxifen: A Most Unlikely Pioneering Medicine", Nature Reviews: Drug Discovery, vol. 2, 2003, pp. 205-213.
International Search Report for PCT/IB2016/051706 dated May 11, 2016.
Communication dated Oct. 18, 2019, from the Japanese Patent Office in Application No. 2017-549601.
Lobo, et al., "The Biology of Cancer Stem Cells", The Annual Review of Cell and Development Biology, 2007, vol. 23, pp. 675-699 (total 27 pages).
Office Action dated Aug. 24, 2020 in Chinese Application No. 201680030052.0.
Yashveer Singh, et al., "Recent Trends in Targeted Anticancer Prodrug and Conjugate Design", Current Medicinal Chemistry, 2008, vol. 15, No. 18, pp. 1802-1826.
Decision dated Apr. 14, 2020, from the Taiwanese Intellectual Property Office in Application No. 105109636.
Rautio, et al., "Prodrugs: design and clinical applications", Nature Reviews, Drug Discovery, Mar. 2008, vol. 7, pp. 255-270.
Balvinder S. Vig., et al., "Amino acids as promoieties in prodrug design and development", Advanced Drug Delivery Reviews, 2013, vol. 65, No. 10, pp. 1370-1385.
Communication dated Nov. 9, 2018, from European Patent Office in counterpart application No. 16714015.1.
Communication dated Jun. 27, 2019 in corresponding European Patent Application No. 16714015.1.
Communication dated Oct. 8, 2020, issued by the European Patent Office in application No. 16 714 015.1.
Communication dated Aug. 27, 2021 from the European Patent Office in Application No. 16714015.1.
Communication dated Jul. 19, 2021 from the China National Intellectual Property Administration in Application No. 201680030052.0.
Office Action dated Jun. 9, 2022 in Canadian Application No. 2,980,845.

\* cited by examiner

PROCESS FOR PRODUCING A HYDRATE OF A HYDROCHLORIDE SALT OF 2,2'-(((((2-ACETYLNAPHTHO[2,3-B]FURAN-4,9-DIYL)BIS(OXY))BIS(CARBONYL)) BIS(AZANEDIYL))BIS(ETHANE-2,1-DIYL)) BIS(AZANEDIYL))DIACETIC ACID

CROSS-REFERENCE TO RELATED APPLICATIONS

This application is a continuation of U.S. application Ser. No. 16/194,525 filed Nov. 19, 2018, which is a continuation of U.S. application Ser. No. 15/561,828 filed Sep. 26, 2017, now U.S. Pat. No. 10,183,925, which is a 371 of PCT/IB2016/051706, filed Mar. 25, 2016, which claims priority to U.S. Provisional Patent Application No. 62/139,077 filed Mar. 27, 2015, the contents of all of which are incorporated herein by reference in their entirety.

TECHNICAL FIELD

The present invention relates to novel water-soluble prodrugs of 2-acetylnaphtho[2,3-b]furan-4,9-dione, pharmaceutically acceptable salts thereof, or hydrates or solvates thereof useful as a medicament. The invention also relates to pharmaceutical compositions comprising a novel water-soluble prodrug of 2-acetylnaphtho[2,3-b]furan-4,9-dione, a pharmaceutically acceptable salt thereof, or a hydrate or solvate thereof. Further, the invention relates to therapeutic agents or prophylactic agents, wherein the therapeutic agents or prophylactic agents comprise a novel water-soluble prodrug of 2-acetylnaphtho[2,3-b]furan-4,9-dione, a pharmaceutically acceptable salt thereof, or a hydrate or solvate thereof, or treating methods for treating cancer using the same.

BACKGROUND ART

Cancer develops when abnormality in gene occurs by an action of radiation, ultra violet rays, carcinogen, virus, and the like. The number of deaths by cancer increases year by year, and cancer is currently the top cause of death in Japan. As means for such cancer therapy, antitumor agents, surgical operation, radiotherapy, immunotherapy, and the like are performed. However, among these, the therapeutic use of an antitumor agent is the most important as an internally therapeutic means. Major antitumor agents act on any of metabolism of a nucleic acid precursor, DNA synthesis, RNA synthesis, or protein synthesis. However, such metabolic processes occur in not only cancer cells, but also normal cells. Therefore, many antitumor agents act on not only on cancer cells, but also on normal cells, and consequently a variety of side effects develop.

In recent years, a new type of antitumor agent, called molecular targeting agent, has been introduced. This molecular targeting agent is a pharmaceutical agent designed to target a molecule specifically expressed in each cancer. Therefore, it is believed that a molecular targeting agent has higher specificity to cancer cells than conventional antitumor agents, and has fewer side effects. However, with regard to molecular targeting agents, although previous side effects are reduced, there are problems that new side effects are exhibited and alternatives of pharmaceutical agents are limited. Although the aforementioned antitumor agents were clinically used for the purpose of cancer therapy and prolonging the life of a cancer patient, there are still a number of unsolved problems including problems of side effects and the like as described above. Accordingly, it is recognized that the development of a novel antitumor agent is an important object in the future.

In recent studies, the existence of cancer stem cells (CSC) having self-replication competence has been revealed, the CSC is closely related to the malignant transformation of cancer. In nearly all of major types of cancer in human, such as breast cancer, colon cancer, lung cancer, hematological malignancy, and the like, CSCs are identified. A CSC and a conventional cancer cell differentiated from the CSC are significantly different in biological characteristics. A CSC is shown to be important in continuous proliferation of malignant tumor, metastasis and recurrence of cancer, and its resistance to an antitumor agent. Although Conventional therapy that targets conventional cancer cells accounting for most part of tumor lumps can reduce the size of a tumor, as long as a CSC is also targeted at the same time, a meaningful survival effect cannot be expected. Therefore, targeting a CSC is very promising as a new method to treat a cancer (Non Patent Literature 1). One of the characteristics of CSCs is to have replication competence. Reliable methods established as a method of measuring replication competence of a cell include measurement of cancer cell sphere-forming ability in non-adhesion state in the absence of serum (Non Patent Literature 2). A compound that inhibits not only the proliferation of a non-CSC cancer cell, but also cancer cell sphere-forming ability is possibly very useful as a novel antitumor agent.

(1) Non Patent Literature 3 discloses that the following quinone derivatives isolated from the extract of a plant of the *Tabebuia* genus in the Bignoniaceae family have antitumor activity:

[Chem. 1]

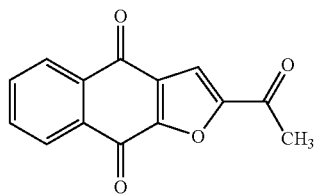

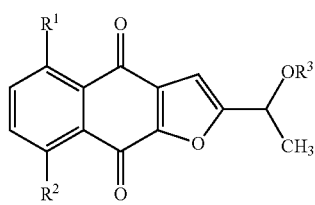

[wherein $R^1$, $R^2$, and $R^3$ are hydrogen atoms; $R^1$ and $R^3$ are hydrogen atoms, and $R^2$ is a hydroxyl group; $R^1$ is a hydroxyl group, and $R^2$ and $R^3$ are hydrogen atoms; $R^1$ and $R^2$ are hydrogen atoms, and $R^3$ is $COCH_3$; or $R^1$ and $R^2$ are hydrogen atoms, and $R^3$ is COC $(CF_3)(OCH_3)C_6H_5$].

(2) Patent Literature 1 describes the following compound having antitumor activity and suppressing cancer cell sphere-forming ability:

[Chem. 2]

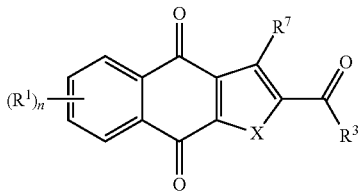

[wherein X is O or S, $R^1$ is a hydrogen atom, a halogen atom, a cyano group, a nitro group, a trifluoromethyl group, a trifluoromethoxy group, an optionally substituted alkyl group, or the like, $R^3$ is a hydrogen atom, a cyano group, an optionally substituted alkyl group, or the like, $R^7$ is a hydrogen atom, a halogen atom, a cyano group, a nitro group, an optionally substituted alkyl group, or the like, n is 1 to 4, with the proviso that when $R^3$ is not an amino group, $R^7$ is not a hydrogen atom and at least one of $R^1$ and $R^7$ is a halogen atom, an aryl group, or an optionally substituted aryl group].

(3) Patent Literature 2 describes the following compound as a hydrophobic prodrug for oral administration that is administered as a non-crystalline compound:

[Chem. 3]

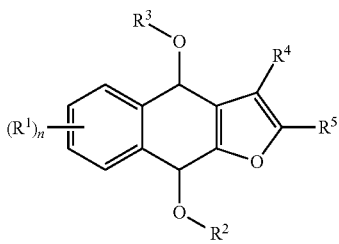

[wherein n is 0 to 4, each $R^1$ is independently halogen, —$NO_2$, —CN, —OR, —SR, —$N^+(R)_3$, —$N(R)_2$, —C(O)R, $CO_2R$, or the like, each of $R^2$ and $R^3$ is independently a hydrogen atom, —$S(=O)_2OR^a$, —$P(=O)OR^aOR^b$, or —$C(=O)R^c$, each of $R^a$ and $R^b$ is independently a hydrogen atom, sodium, potassium, an amine cation, a $C_{1-12}$aliphatic, or the like, $R^c$ is a hydrogen atom, —$N(R)_2$, —OR, —SR, a $C_{1-12}$aliphatic, or the like, $R^4$ is independently a hydrogen atom, halogen, —$NO_2$, —OR, —SR, —$N^+(R)_3$, —$N(R)_2$, —C(O)R, $CO_2R$, or the like, $R^5$ is independently halogen, —$NO_2$, —CN, —OR, —SR, —$N^+(R)_3$, —$N(R)_2$, —C(O)R, $CO_2R$, or the like, and each R is independently a hydrogen atom, or an optionally substituted group selected from a $C_{1-12}$aliphatic, a 3- to 14-membered carbocycle, or a 3- to 14-membered heterocycle, a 6- to 14-membered aryl ring, or a 5- to 14-membered heteroaryl ring, with the proviso that (a) when each of $R^2$ and $R^3$ is acetyl, $R^1$ is not acetoxy, (b) when each of $R^2$ and $R^3$ is acetyl and $R^4$ is ethoxycarbonyl, $R^5$ is not 2-oxo-propyl, (c) when each of $R^2$, $R^3$, and $R^5$ is acetyl, either of $R^1$ or $R^4$ is not hydrogen].

(4) Patent Literature 3 describes the following compound exhibiting antitumor activity against various drug-resistant cancer cells:

[Chem. 4]

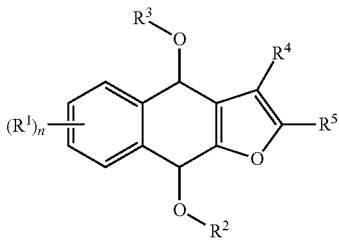

[wherein n is 0 to 4, each R is independently halogen, —$NO_2$, —CN, —OR, —SR, —$N^+(R)_3$, —$N(R)_2$, —C(O)R, $CO_2R$, or the like, each of $R^2$ and $R^3$ is independently a hydrogen atom, —$S(=O)_2OR^a$, —$P(=O)OR^aOR^b$, —$C(=O)R^c$, each of $R^a$ and $R^b$ is independently a hydrogen atom, sodium, potassium, an amine cation, a $C_{1-12}$aliphatic, or the like, $R^c$ is a hydrogen atom, —$N(R)_2$, —OR, —SR, a $C_{1-12}$aliphatic, or the like, $R^4$ is independently a hydrogen atom, halogen, —$NO_2$, —OR, —SR, —$N^+(R)_3$, —$N(R)_2$, —C(O)R, $CO_2R$, or the like, $R^5$ is independently halogen, —$NO_2$, —CN, —OR, —SR, —$N^+(R)_3$, —$N(R)_2$, —C(O)R, $CO_2R$, or the like, and each R is independently a hydrogen atom, or an optionally substituted group selected from a $C_{1-12}$aliphatic, a 3- to 14-membered carbocycle, or a 3- to 14-membered heterocycle, a 6- to 14-membered aryl ring, or a 5- to 14-membered heteroaryl ring].

(5) Patent Literature 4 describes the following compound as a hydrophobic prodrug for parenteral administration that is administered as aqueous nanoparticle suspension:

[Chem. 5]

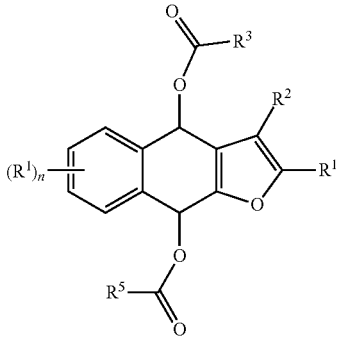

[wherein n is 0 to 4, each $R^1$ is independently halogen, —$NO_2$, —CN, —OR, —SR, —$N^+(R)_3$, —$N(R)_2$, —C(O)R, $CO_2R$, or the like, $R^2$ is independently a hydrogen atom, halogen, —$NO_2$, —OR, —SR, —$N^+(R)_3$, —$N(R)_2$, —C(O)R, $CO_2R$, or the like, each of $R^3$ and $R^5$ is independently optionally substituted a $C_{1-12}$ aliphatic, $R^4$ is independently halogen, —$NO_2$, —CN, —OR, —SR, —$N^+(R)_3$, —$N(R)_2$, —C(O)R, $CO_2R$, or the like, and each R is independently a hydrogen atom, or an optionally substituted group selected from a $C_{1-12}$aliphatic, a 3- to 14-membered carbocycle, or a 3- to 14-membered heterocycle, a 6- to 14-membered aryl ring, or a 5- to 14-membered heteroaryl ring].

Generally, for most hydrophobic prodrugs to be enzymatically converted to an activated form, since interspecies difference and individual difference in conversion to an activated form are observed, a problem of drug concentration estimation in clinical practice occurs (Non Patent Literature 4). A prodrug for oral administration described in Patent Literature 2, after administration, is affected by a first-pass effect in a small intestine and a liver, which causes interspecies difference. Even in the case of an intravenously-administrable prodrug for parenteral administration described in Patent Literature 4, although it is not affected by a first-pass effect in a small intestine and a liver, it is converted to an activated form by an in vivo enzyme, esterase, and accordingly interspecies difference and individual difference may be observed in conversion to an activated form.

CITATION LIST

Patent Literature

[PTL 1]
International Publication No. 2009/036059 pamphlet
[PTL 2]
International Publication No. 2012/119265 pamphlet
[PTL 3]
International Publication No. 2013/166618 pamphlet
[PTL 4]
International Publication No. 2013/120229 pamphlet Non Patent Literature

[NPL 1]
Ponti et al. Cancer Res 65(13): 5506-11. (2005)
[NPL 2]
Lodo et al. Annu Rev Cell Dev Biol 23: 675-99. (2007)
[NPL 3]
Rao et al. J Nat Prod 45(5): 600-4. (1982)
[NPL 4]
Kumpulainen et al. Nature Reviews Drug Discovery 7(3): 255-270. (2008)

SUMMARY OF INVENTION

Solution to Problem

Since 2-acetylnaphtho[2,3-b]furan-4,9-dione targets a cancer stem cell in addition to a conventional cancer cell, it is expected as a novel anticancer agent. The present invention solves problems associated with its absorption in oral administration due to its high crystallizability as well as its use in parenteral administration has been limited.

The present invention provides improvements for known hydrophobic prodrugs for oral administration that is administered as a non-crystalline compound, and hydrophobic prodrugs for parenteral administration that is administered as aqueous nanoparticle suspension.

Specifically, known prodrugs for oral administration are affected by a first-pass effect in an intestine and a liver after administration, which causes interspecies difference. In addition, since known prodrugs for parenteral administration are intravenously administrable, they are not affected by a first-pass effect in an intestine and a liver. However, since they are metabolized by an esterase in vivo and converted to an activated form, problems of interspecies difference and individual difference are concerned. Therefore, the present invention provides improvements for developing a prodrug compound that is hard to be affected by enzymatic conversion and exhibit slight interspecies difference and individual difference.

The present invention provides an orally and intravenously administrable, water-soluble prodrug of 2-acetylnaphtho[2,3-b]furan-4,9-dione that is converted to an activated form in vivo via a route other than an enzymatic conversion, and provides a compound very useful as a novel anticancer agent.

The present invention relates to a prodrug that has high water-solubility and is converted to an activated form without the need of an enzyme. When a prodrug of the present invention is orally administrated, since the prodrug is dissolved in the stomach and subsequently converted to an activated form depending on pH in the following digestive tract, it is not affected by an in vivo enzyme, which causes interspecies difference and individual difference. On the other hand, when it is intravenously administered, it is not affected by a first-pass effect in an small intestine and a liver, which causes interspecies difference and individual difference, and that is converted to an activated form depending from pH in the plasma and without depending on an enzyme.

Therefore, none of Non Patent Literatures 1, 2, and 3 and Patent Literatures 1-4 discloses or suggests any compound represented by the following formula (1).

[Chem. 6]

(1)

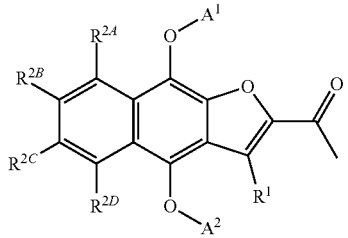

The present inventors intensively studied to provides improvements, and consequently found that a compound having a soluble side chain of a certain structure exhibits high water-solubility suitable for oral administration and intravenous administration, and additionally is converted to an active form by chemical conversion. The present inventors finally reached the completion of the present invention.

The present invention is as described below.
[Item 1] A compound represented by formula (1A) or a pharmaceutically acceptable salt thereof:

[Chem. 7]

(1A)

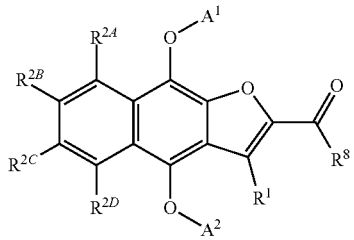

wherein
$A^1$ and $A^2$ are identical or different, and each independently —C(=O)B, —C(=O)CR$^{3A}$R$^{3B}$B, —CO$_2$B, —C(=S)OB, —CONR$^{3C}$B, —C(=S)NR$^{3C}$B, —SO$_2$B, —SO$_2$CR$^{3A}$R$^{3B}$B, —SO$_2$(OB), —SO$_2$NR$^{3C}$B, —P(=O)(B)$_2$, —P(=O)(CR$^{3A}$R$^{3B}$B)$_2$, —P(=O)(OB)$_2$, —P(=O)(NR$^{3C}$B)$_2$, or a hydrogen atom, wherein $A^1$ and $A^2$ are not both hydrogen atoms, wherein
B is an optionally substituted 3- to 12-membered monocyclic or polycyclic heterocyclic group, an optionally substituted 3- to 12-membered cyclic amino group, or a group represented by the following formula (B):

[Chem. 8]

(B)

wherein
* denotes a bonding position,
X is a single bond, an optionally substituted $C_{1-10}$alkylene, an optionally substituted $C_{3-10}$cycloalkylene, an optionally substituted 3- to 12-membered monocyclic or polycyclic heterocycle, an optionally substituted 3- to 12-membered cyclic aminyl linker group, an optionally substituted $C_{2-10}$alkenylene, an optionally substituted $C_{2-10}$alkynylene, an optionally substituted $C_{6-10}$arylene, or an optionally substituted $C_{5-10}$heteroarylene,
Y is a single bond, an oxygen atom, —OCO—, —OCO$_2$—, —OCONR$^{4A}$—, —OSO$_2$—, —OSO$_2$NR$^{4A}$—, —CO—, —CO$_2$—, —CONR$^{4A}$—, —NR$^{4A}$—, —NR$^{4A}$CO—, —NR$^{4A}$CO$_2$—, —NR$^{4A}$CONR$^{4B}$—, —NR$^{4A}$SO$_2$—, —NR$^{4A}$SO$_2$O—, —NR$^{4A}$SO$_2$NR$^{4B}$—, a sulfur atom, —SO—, —SO$_2$—, —SO$_2$O—, —SO$_2$NR$^{4A}$—, or an optionally substituted 3- to 12-membered cyclic aminyl linker group,
$R^{4A}$ and $R^{4B}$ are identical or different, and each independently a hydrogen atom, an optionally substituted $C_{1-10}$alkyl group, an optionally substituted $C_{3-10}$cycloalkyl group, an optionally substituted 3- to 12-membered monocyclic or polycyclic heterocyclic group, an optionally substituted $C_{2-10}$alkenyl group, an optionally substituted $C_{2-10}$alkynyl group, an optionally substituted $C_{6-10}$aryl group, or an optionally substituted $C_{5-10}$heteroaryl group,
Z is a single bond, an optionally substituted $C_{1-10}$alkylene, an optionally substituted $C_{3-10}$cycloalkylene, an optionally substituted 3- to 12-membered monocyclic or polycyclic heterocycle, an optionally substituted 3- to 12-membered cyclic aminyl linker group, an optionally substituted $C_{2-10}$alkenylene, an optionally substituted $C_{2-10}$alkynylene, an optionally substituted $C_{6-10}$arylene, or an optionally substituted $C_{5-10}$heteroarylene,
n is 0, 1, or 2,
V is —NHR$^5$, an optionally substituted 3- to 12-membered monocyclic or polycyclic heterocyclic group, or an optionally substituted 3- to 12-membered cyclic amino group, wherein the 3- to 12-membered monocyclic or polycyclic heterocyclic group and the 3- to 12-membered cyclic amino group have at least one or more secondary nitrogen atoms in the ring, and
$R^5$ is a hydrogen atom, an optionally substituted $C_{1-10}$alkyl group, an optionally substituted $C_{3-10}$cycloalkyl group, an optionally substituted 3- to 12-membered monocyclic or polycyclic heterocyclic group, an optionally substituted $C_{2-10}$alkenyl group, an optionally substituted $C_{2-10}$alkynyl group, an optionally substituted $C_{6-10}$aryl group, or an optionally substituted $C_{5-10}$heteroaryl group, and wherein
the 3- to 12-membered monocyclic or polycyclic heterocyclic group and the 3- to 12-membered cyclic amino group have at least one or more secondary nitrogen atoms in the ring, and
$R^{3A}$, $R^{3B}$, and $R^{3C}$ are identical or different, and each independently a hydrogen atom, an optionally substituted $C_{1-10}$alkyl group, an optionally substituted $C_{3-10}$cycloalkyl group, an optionally substituted 3- to 12-membered monocyclic or polycyclic heterocyclic group, an optionally substituted $C_{2-10}$alkenyl group, an optionally substituted $C_{2-10}$alkynyl group, an optionally substituted $C_{6-10}$aryl group, or an optionally substituted $C_{5-10}$heteroaryl group;
$R^1$ is a hydrogen atom, a halogen atom, a cyano group, a hydroxyl group, an optionally substituted amino group, an optionally substituted 3- to 12-membered cyclic amino group, an optionally substituted $C_{1-6}$alkyl group, an optionally substituted $C_{3-10}$cycloalkyl group, an optionally substituted $C_{2-6}$alkenyl group, an optionally substituted $C_{2-6}$alkynyl group, an optionally substituted $C_{1-6}$alkoxy group, an optionally substituted $C_{6-10}$aryl group, an optionally substituted 3- to 12-membered monocyclic or polycyclic heterocyclic group, an optionally substituted $C_{1-6}$alkylcarbonyl group, an optionally substituted $C_{3-10}$cycloalkylcarbonyl group, an optionally substituted $C_{6-10}$arylcarbonyl group, an optionally substituted 3- to 12-membered monocyclic or polycyclic heterocyclylcarbonyl group, a carboxyl group, an optionally substituted $C_{1-6}$alkoxycarbonyl group, an optionally substituted $C_{3-10}$cycloalkoxycarbonyl group, an optionally substituted $C_{6-10}$aryloxycarbonyl group, an optionally substituted 3- to 12-membered monocyclic or polycyclic heterocyclyloxycarbonyl group, an optionally substituted aminocarbonyl group, an optionally substituted 3- to 12-membered cyclic aminocarbonyl group, an optionally substituted $C_{1-6}$alkylthio group, an optionally substituted $C_{3-10}$cycloalkylthio group, an optionally substituted $C_{6-10}$arylthio group, an optionally substituted 3- to 12-membered monocyclic or polycyclic heterocyclylthio group, a sulfinate group, an optionally substituted $C_{1-6}$alkylsulfinyl group, an optionally substituted $C_{3-10}$cycloalkylsulfinyl group, an optionally substituted $C_{6-10}$arylsulfinyl group, an optionally substituted 3- to 12-membered monocyclic or polycyclic heterocyclylsulfinyl group, an optionally substituted aminosulfinyl group, an optionally substituted 3- to 12-membered cyclic aminosulfinyl group, a sulfonate group, an optionally substituted $C_{1-6}$alkylsulfonyl group, an optionally substituted $C_{3-10}$cycloalkylsulfonyl group, an optionally substituted $C_{6-10}$arylsulfonyl group, an optionally substituted 3- to 12-membered monocyclic or polycyclic heterocyclylsulfonyl group, an optionally substituted aminosulfonyl group, or an optionally substituted 3- to 12-membered cyclic aminosulfonyl group;
$R^{2A}$, $R^{2B}$, $R^{2C}$, and $R^{2D}$ are identical or different, and each independently a hydrogen atom, a halogen atom, a cyano group, a hydroxyl group, an optionally substituted amino group, an optionally substituted 3- to 12-membered cyclic amino group, an optionally substituted $C_{1-6}$alkyl group, an optionally substituted $C_{3-10}$cycloalkyl group, an optionally substituted $C_{6-10}$aryl group, an optionally substituted 3- to 12-membered monocyclic or polycyclic heterocyclic group, an optionally substituted $C_{1-6}$alkoxy group, an optionally substituted $C_{3-10}$cycloalkoxy group, an optionally substituted $C_{6-10}$aryloxy group, an optionally substituted 3- to 12-membered monocyclic or polycyclic heterocyclyloxy group, a carboxyl group, an optionally substituted $C_{1-6}$alkylcarbonyl group, an optionally substituted $C_{3-10}$cycloalkylcarbonyl group, an optionally substituted $C_{6-10}$arylcarbonyl group, an optionally substituted 3- to 12-membered monocyclic or polycyclic heterocyclylcarbonyl group, an optionally substituted $C_{1-6}$alkoxycarbonyl group, an optionally substituted $C_{3-10}$cycloalkoxycarbonyl group, an optionally substituted $C_{6-10}$aryloxycarbonyl group, an optionally substituted 3- to 12-membered monocyclic or polycyclic heterocyclyloxycarbonyl group, an optionally substituted aminocarbonyl group, an optionally substituted 3- to 12-membered cyclic aminocarbonyl group, an optionally substituted $C_{1-6}$alkylthio group, an optionally substituted $C_{3-10}$cycloalkylthio group, an optionally substituted $C_{6-10}$arylthio group, an optionally substituted 3- to 12-membered monocyclic or polycyclic heterocyclylthio group, a sulfinate group, an optionally substituted $C_{1-6}$alkylsulfinyl group, an optionally substituted $C_{3-10}$cycloalkylsulfinyl group, an optionally substituted $C_{6-10}$arylsulfinyl group, an optionally substituted 3- to 12-membered monocyclic or polycyclic heterocyclylsulfinyl group, an optionally substituted aminosulfinyl group, an optionally substituted 3- to 12-membered cyclic aminosulfinyl group, a sulfonate group, an optionally substituted $C_{1-6}$alkylsulfonyl group, an optionally substituted $C_{3-10}$cycloalkylsulfonyl group, an optionally substituted $C_{6-10}$arylsulfonyl group, an optionally substituted 3- to 12-membered monocyclic or polycyclic heterocyclylsulfonyl group, an optionally substituted aminosulfonyl group, or an optionally substituted 3- to 12-membered cyclic aminosulfonyl group; and $R^8$ is an optionally substituted $C_{1-10}$alkyl group.

[Item 2] A compound represented by formula (1) or a pharmaceutically acceptable salt thereof:

[Chem. 9]

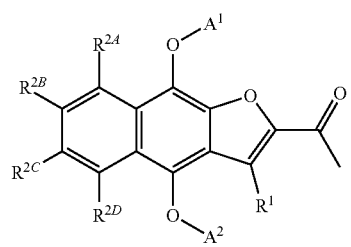

(1)

wherein $A^1$ and $A^2$ are identical or different, and each independently —C(=O)B, —C(=O)CR$^{3A}$R$^{3B}$B, —CO$_2$B, —C(=S)OB, —CONR$^{3C}$B, —C(=S)NR$^{3C}$B, —SO$_2$B, —SO$_2$CR$^{3A}$R$^{3B}$B, —SO$_2$(OB), —SO$_2$NR$^{3C}$B, —P(=O)(B)$_2$, —P(=O)(CR$^{3A}$R$^{3B}$B)$_2$, —P(=O)(OB)$_2$, —P(=O)(NR$^{3C}$B)$_2$, or a hydrogen atom, wherein $A^1$ and $A^2$ are not both hydrogen atoms, wherein B is an optionally substituted 3- to 12-membered monocyclic or polycyclic heterocyclic group, an optionally substituted 3- to 12-membered cyclic amino group, or a group represented by the following formula (B):

[Chem. 10]

(B)

wherein
* denotes a bonding position,
X is a single bond, an optionally substituted $C_{1-10}$alkylene, an optionally substituted $C_{3-10}$cycloalkylene, an optionally substituted 3- to 12-membered monocyclic or polycyclic heterocycle, an optionally substituted 3- to 12-membered cyclic aminyl linker group, an optionally substituted $C_{2-10}$alkenylene, an optionally substituted $C_{2-10}$alkynylene, an optionally substituted $C_{6-10}$arylene, or an optionally substituted $C_{5-10}$heteroarylene,
Y is a single bond, an oxygen atom, —OCO—, —OCO$_2$—, —OCONR$^{4A}$—, —OSO$_2$—, —OSO$_2$NR$^{4A}$—, —CO—, —CO$_2$—, —CONR$^{4A}$—, —NR$^{4A}$—, —NR$^{4A}$CO—, —NR$^{4A}$CO$_2$—, —NR$^{4A}$CONR$^{4B}$—, —NR$^{4A}$SO$_2$—, —NR$^{4A}$SO$_2$O—, —NR$^{4A}$SO$_2$NR$^{4B}$—, a sulfur atom, —SO—, —SO$_2$—, —SO$_2$O—, —SO$_2$NR$^{4A}$—, or an optionally substituted 3- to 12-membered cyclic aminyl linker group,
$R^{4A}$ and $R^{4B}$ are identical or different, and each independently a hydrogen atom, an optionally substituted $C_{1-10}$alkyl group, an optionally substituted $C_{3-10}$cycloalkyl group, an optionally substituted 3- to 12-membered monocyclic or polycyclic heterocyclic group, an optionally substituted $C_{2-10}$alkenyl group, an optionally substituted $C_{2-10}$alkynyl group, an optionally substituted $C_{6-10}$aryl group, or an optionally substituted $C_{5-10}$heteroaryl group,
Z is a single bond, an optionally substituted $C_{1-10}$alkylene, an optionally substituted $C_{3-10}$cycloalkylene, an optionally substituted 3- to 12-membered monocyclic or polycyclic heterocycle, an optionally substituted 3- to 12-membered cyclic aminyl linker group, an optionally substituted $C_{2-10}$alkenylene, an optionally substituted $C_{2-10}$alkynylene, an optionally substituted $C_{6-10}$arylene, or an optionally substituted $C_{5-10}$heteroarylene,
n is 0, 1, or 2,
V is —NHR$^5$, an optionally substituted 3- to 12-membered monocyclic or polycyclic heterocyclic group, or an optionally substituted 3- to 12-membered cyclic amino group, wherein the 3- to 12-membered monocyclic or polycyclic heterocyclic group and the 3- to 12-membered cyclic amino group have at least one or more secondary nitrogen atoms in the ring, and
$R^5$ is a hydrogen atom, an optionally substituted $C_{1-10}$alkyl group, an optionally substituted $C_{3-10}$cycloalkyl group, an optionally substituted 3- to 12-membered monocyclic or polycyclic heterocyclic group, an optionally substituted $C_{2-10}$alkenyl group, an optionally substituted $C_{2-10}$alkynyl group, an optionally substituted $C_{6-10}$aryl group, or an optionally substituted $C_{5-10}$heteroaryl group, and wherein the 3- to 12-membered monocyclic or polycyclic heterocyclic group and the 3- to 12-membered cyclic amino group have at least one or more secondary nitrogen atoms in the ring, and
$R^{3A}$, $R^{3B}$, and $R^{3C}$ are identical or different, and each independently a hydrogen atom, an optionally substituted $C_{1-10}$alkyl group, an optionally substituted $C_{3-10}$cycloalkyl group, an optionally substituted 3- to 12-membered monocyclic or polycyclic heterocyclic group, an optionally substituted $C_{2-10}$alkenyl group, an optionally substituted $C_{2-10}$alkynyl group, an optionally substituted $C_{6-10}$aryl group, or an optionally substituted $C_{5-10}$heteroaryl group;

$R^1$ is a hydrogen atom, a halogen atom, a cyano group, a hydroxyl group, an optionally substituted amino group, an optionally substituted 3- to 12-membered cyclic amino group, an optionally substituted $C_{1-6}$alkyl group, an optionally substituted $C_{3-10}$cycloalkyl group, an optionally substituted $C_{2-6}$alkenyl group, an optionally substituted $C_{2-6}$alkynyl group, an optionally substituted $C_{1-6}$alkoxy group, an optionally substituted $C_{6-10}$aryl group, an optionally substituted 3- to 12-membered monocyclic or polycyclic heterocyclic group, an optionally substituted $C_{1-6}$alkylcarbonyl group, an optionally substituted $C_{3-10}$cycloalkylcarbonyl group, an optionally substituted $C_{6-10}$arylcarbonyl group, an optionally substituted 3- to 12-membered monocyclic or polycyclic heterocyclylcarbonyl group, a carboxyl group, an optionally substituted $C_{1-6}$alkoxycarbonyl group, an optionally substituted $C_{3-10}$cycloalkoxycarbonyl group, an optionally substituted $C_{6-10}$aryloxycarbonyl group, an optionally substituted 3- to 12-membered monocyclic or polycyclic heterocyclyloxycarbonyl group, an optionally substituted aminocarbonyl group, an optionally substituted 3- to 12-membered cyclic aminocarbonyl group, an optionally substituted $C_{1-6}$alkylthio group, an optionally substituted $C_{3-10}$cycloalkylthio group, an optionally substituted $C_{6-10}$arylthio group, an optionally substituted 3- to 12-membered monocyclic or polycyclic heterocyclylthio group, a sulfinate group, an optionally substituted $C_{1-6}$alkylsulfinyl group, an optionally substituted $C_{3-10}$cycloalkylsulfinyl group, an optionally substituted $C_{6-10}$arylsulfinyl group, an optionally substituted 3- to 12-membered monocyclic or polycyclic heterocyclylsulfinyl group, an optionally substituted aminosulfinyl group, an optionally substituted 3- to 12-membered cyclic aminosulfinyl group, a sulfonate group, an optionally substituted $C_{1-6}$alkylsulfonyl group, an optionally substituted $C_{3-10}$cycloalkylsulfonyl group, an optionally substituted $C_{6-10}$arylsulfonyl group, an optionally substituted 3- to 12-membered monocyclic or polycyclic heterocyclylsulfonyl group, an optionally substituted aminosulfonyl group, or an optionally substituted 3- to 12-membered cyclic aminosulfonyl group; and $R^{2A}$, $R^{2B}$, $R^{2C}$, and $R^{2D}$ are identical or different, and each independently a hydrogen atom, a halogen atom, a cyano group, a hydroxyl group, an optionally substituted amino group, an optionally substituted 3- to 12-membered cyclic amino group, an optionally substituted $C_{1-6}$alkyl group, an optionally substituted $C_{3-10}$cycloalkyl group, an optionally substituted $C_{6-10}$aryl group, an optionally substituted 3- to 12-membered monocyclic or polycyclic heterocyclic group, an optionally substituted $C_{1-6}$alkoxy group, an optionally substituted $C_{3-10}$cycloalkoxy group, an optionally substituted $C_{6-10}$aryloxy group, an optionally substituted 3- to 12-membered monocyclic or polycyclic heterocyclyloxy group, a carboxyl group, an optionally substituted $C_{1-6}$alkylcarbonyl group, an optionally substituted $C_{3-10}$cycloalkylcarbonyl group, an optionally substituted $C_{6-10}$arylcarbonyl group, an optionally substituted 3- to 12-membered monocyclic or polycyclic heterocyclylcarbonyl group, an optionally substituted $C_{1-6}$alkoxycarbonyl group, an optionally substituted $C_{3-10}$cycloalkoxycarbonyl group, an optionally substituted $C_{6-10}$aryloxycarbonyl group, an optionally substituted 3- to 12-membered monocyclic or polycyclic heterocyclyloxycarbonyl group, an optionally substituted aminocarbonyl group, an optionally substituted 3- to 12-membered cyclic aminocarbonyl group, an optionally substituted $C_{1-6}$alkylthio group, an optionally substituted $C_{3-10}$cycloalkylthio group, an optionally substituted $C_{6-10}$arylthio group, an optionally substituted 3- to 12-membered monocyclic or polycyclic heterocyclylthio group, a sulfinate group, an optionally substituted $C_{1-6}$alkylsulfinyl group, an optionally substituted $C_{3-10}$cycloalkylsulfinyl group, an optionally substituted $C_{6-10}$arylsulfinyl group, an optionally substituted 3- to 12-membered monocyclic or polycyclic heterocyclylsulfinyl group, an optionally substituted aminosulfinyl group, an optionally substituted 3- to 12-membered cyclic aminosulfinyl group, a sulfonate group, an optionally substituted $C_{1-6}$alkylsulfonyl group, an optionally substituted $C_{3-10}$cycloalkylsulfonyl group, an optionally substituted $C_{6-10}$arylsulfonyl group, an optionally substituted 3- to 12-membered monocyclic or polycyclic heterocyclylsulfonyl group, an optionally substituted aminosulfonyl group, or an optionally substituted 3- to 12-membered cyclic aminosulfonyl group.

[Item 3] The compound according to item 1 or 2, or a pharmaceutically acceptable salt thereof,
wherein
a substituent of the optionally substituted 3- to 12-membered monocyclic or polycyclic heterocyclic group, the optionally substituted 3- to 12-membered cyclic amino group, the optionally substituted amino group, the optionally substituted $C_{1-10}$alkyl group, the optionally substituted $C_{1-6}$alkyl group, the optionally substituted $C_{3-10}$cycloalkyl group, the optionally substituted $C_{2-10}$alkenyl group, the optionally substituted $C_{2-6}$alkenyl group, the optionally substituted $C_{2-10}$alkynyl group, the optionally substituted $C_{2-6}$alkynyl group, the optionally substituted $C_{1-6}$alkoxy group, the optionally substituted $C_{3-10}$cycloalkoxy group, the optionally substituted $C_{6-10}$aryloxy group, the optionally substituted 3- to 12-membered monocyclic or polycyclic heterocyclyloxy group, the optionally substituted $C_{6-10}$aryl group, the optionally substituted $C_{1-6}$alkylcarbonyl group, the optionally substituted $C_{3-10}$cycloalkylcarbonyl group, the optionally substituted $C_{6-10}$arylcarbonyl group, the optionally substituted 3- to 12-membered monocyclic or polycyclic heterocyclylcarbonyl group, the optionally substituted $C_{1-6}$alkoxycarbonyl group, the optionally substituted $C_{3-10}$cycloalkoxycarbonyl group, the optionally substituted $C_{6-10}$aryloxycarbonyl group, the optionally substituted 3- to 12-membered monocyclic or polycyclic heterocyclyloxycarbonyl group, the optionally substituted aminocarbonyl group, the optionally substituted 3- to 12-membered cyclic aminocarbonyl group, the optionally substituted $C_{1-6}$alkylthio group, the optionally substituted $C_{3-10}$cycloalkylthio group, the optionally substituted $C_{6-10}$arylthio group, the optionally substituted 3- to 12-membered monocyclic or polycyclic heterocyclylthio group, the optionally substituted $C_{1-6}$alkylsulfinyl group, the optionally substituted $C_{3-10}$cycloalkylsulfinyl group, the optionally substituted $C_{6-10}$arylsulfinyl group, the optionally substituted 3- to 12-membered monocyclic or polycyclic heterocyclylsulfinyl group, the optionally substituted aminosulfinyl group, the optionally substituted 3- to 12-membered cyclic aminosulfinyl group, the optionally substituted $C_{1-6}$alkylsulfonyl group, the optionally substituted $C_{3-10}$cycloalkylsulfonyl group, the optionally substituted $C_{6-10}$arylsulfonyl group, the optionally substituted 3- to 12-membered monocyclic or polycyclic heterocyclylsulfonyl group, the optionally substituted aminosulfonyl group, the optionally substituted 3- to 12-membered cyclic aminosulfonyl group, the optionally substituted $C_{5-10}$heteroaryl group, the optionally substituted $C_{1-10}$alkylene, the optionally substituted $C_{3-10}$cycloalkylene, the optionally substituted 3- to 12-membered monocyclic or polycyclic heterocycle, the optionally substituted 3- to 12-membered cyclic aminyl linker group, the optionally substituted $C_{2-10}$alkenylene, the optionally substituted $C_{2-10}$alkynylene, the optionally substituted $C_{6-10}$arylene, and optionally substituted $C_{5-10}$heteroarylene in B, $R^1$, $R^{2A}$, $R^{2B}$, $R^{2C}$, $R^{2D}$, $R^{3A}$, $R^{3B}$, $R^{3C}$, $R^{4A}$, $R^{4B}R^5$, $R^8$, X, Y, Z, and V is a group optionally substituted with one to five identical or different substituents each independently selected from the group consisting of (1) a halogen atom,
(2) a hydroxyl group,
(3) a carboxyl group,
(4) a sulfinate group,
(5) a sulfonate group,
(6) a phosphate group,
(7) an optionally substituted $C_{1-6}$alkyl group,
(8) an optionally substituted $C_{3-10}$cycloalkyl group,
(9) an optionally substituted $C_{6-10}$aryl group,
(10) an optionally substituted $C_{5-10}$heteroaryl group,
(11) an optionally substituted $C_{1-6}$alkoxy group,
(12) an optionally substituted $C_{3-10}$cycloalkoxy group,
(13) an optionally substituted $C_{1-6}$alkoxycarbonyl group,
(14) an optionally substituted $C_{1-6}$alkylcarbonyl group,
(15) an optionally substituted 3- to 12-membered monocyclic or polycyclic heterocyclic group,
(16) an optionally substituted 3- to 12-membered cyclic amino group,
(17) —$NR^6R^7$,
(18) —$CO_2R^6$,
(19) a guanidine group,
(20) —$CONR^6R^7$,
(21) —$SO_2R^6$,
(22) —$SO_2NR^6R^7$,
(23) a cyano group,
(24) —$OCO_2R^6$,
(25) —$OCONR^6R^7$, and
(26) —$NR^6CO_2R^7$
wherein a substituent in the (7), (8), (9), (10), (11), (12), (13), (14), (15), and (16) is a group optionally substituted with one to five identical or different substituents each independently selected from the group consisting of
(a) a halogen atom,
(b) a hydroxyl group,
(c) a $C_{1-6}$alkyl group,
(d) a $C_{1-6}$alkoxy group,
(e) a cyano group,
(f) a carboxyl group,
(g) a sulfinate group,
(h) a sulfonate group,
(i) a phosphate group,
(j) a $C_{1-6}$alkoxycarbonyl group,
(k) a $C_{1-6}$alkylcarbonyl group,
(l) —$NR^6R^7$,
(m) —$CO_2R^6$,
(n) a guanidine group,
(o) —$CONR^6R^7$,
(p) —$SO_2R^6$,
(q) —$SO_2NR^6R^7$,
(r) a $C_{6-10}$aryl group,
(s) a $C_{5-10}$heteroaryl group,
(t) a 3- to 12-membered cyclic amino group optionally substituted with one to three $C_{1-6}$alkyl groups, and
(u) a 3- to 12-membered monocyclic or polycyclic heterocyclic group optionally substituted with one to three $C_{1-6}$alkyl groups; and $R^6$ and $R^7$ are identical or different, and each independently a hydrogen atom, or a $C_{1-10}$alkyl group optionally substituted with one to two groups selected from the group consisting of a halogen atom and a carboxyl group, wherein $R^6$ and $R^7$, when both are optionally substituted $C_{1-10}$alkyl groups, may be taken together with the nitrogen atom to which they are attached to form a 3- to 12-membered cyclic amino group.

[Item 4] The compound according to any one of items 1 to 3, or a pharmaceutically acceptable salt thereof, wherein
a substituent of the optionally substituted 3- to 12-membered monocyclic or polycyclic heterocyclic group, the optionally substituted 3- to 12-membered cyclic amino group, the optionally substituted amino group, the optionally substituted $C_{1-10}$alkyl group, the optionally substituted $C_{1-6}$alkyl group, the optionally substituted $C_{3-10}$cycloalkyl group, the optionally substituted $C_{2-10}$alkenyl group, the optionally substituted $C_{2-6}$alkenyl group, the optionally substituted $C_{2-10}$alkynyl group, the optionally substituted $C_{2-6}$alkynyl group, the optionally substituted $C_{1-6}$alkoxy group, the optionally substituted $C_{3-10}$cycloalkoxy group, the optionally substituted $C_{6-10}$aryloxy group, the optionally substituted 3- to 12-membered monocyclic or polycyclic heterocyclyloxy group, the optionally substituted $C_{6-10}$aryl group, the optionally substituted $C_{1-6}$alkylcarbonyl group, the optionally substituted $C_{3-10}$cycloalkylcarbonyl group, the optionally substituted $C_{6-10}$arylcarbonyl group, the optionally substituted 3- to 12-membered monocyclic or polycyclic heterocyclylcarbonyl group, the optionally substituted $C_{1-6}$alkoxycarbonyl group, the optionally substituted $C_{3-10}$cycloalkoxycarbonyl group, the optionally substituted $C_{6-10}$aryloxycarbonyl group, the optionally substituted 3- to 12-membered monocyclic or polycyclic heterocyclyloxycarbonyl group, the optionally substituted aminocarbonyl group, the optionally substituted 3- to 12-membered cyclic aminocarbonyl group, the optionally substituted $C_{1-6}$alkylthio group, the optionally substituted $C_{3-10}$cycloalkylthio group, the optionally substituted $C_{6-10}$arylthio group, the optionally substituted 3- to 12-membered monocyclic or polycyclic heterocyclylthio group, the optionally substituted $C_{1-6}$alkylsulfinyl group, the optionally substituted $C_{3-10}$cycloalkylsulfinyl group, the optionally substituted $C_{6-10}$arylsulfinyl group, the optionally substituted 3- to 12-membered monocyclic or polycyclic heterocyclylsulfinyl group, the optionally substituted aminosulfinyl group, the optionally substituted 3- to 12-membered cyclic aminosulfinyl group, the optionally substituted $C_{1-6}$alkylsulfonyl group, the optionally substituted $C_{3-10}$cycloalkylsulfonyl group, the optionally substituted $C_{6-10}$arylsulfonyl group, the optionally substituted 3- to 12-membered monocyclic or polycyclic heterocyclylsulfonyl group, the optionally substituted aminosulfonyl group, the optionally substituted 3- to 12-membered cyclic aminosulfonyl group, the optionally substituted $C_{5-10}$heteroaryl group, the optionally substituted $C_{1-10}$alkylene, the optionally substituted $C_{3-10}$cycloalkylene, the optionally substituted 3- to 12-membered monocyclic or polycyclic heterocycle, the optionally substituted 3- to 12-membered cyclic aminyl linker group, the optionally substituted $C_{2-10}$alkenylene, the optionally substituted $C_{2-10}$alkynylene, the optionally substituted $C_{6-10}$arylene, and optionally substituted $C_{5-10}$heteroarylene in B, $R^1$, $R^{2A}$, $R^{2B}$, $R^{2C}$, $R^{2D}$, $R^{3A}$, $R^{3B}$, $R^{3C}$, $R^{4A}$, $R^{4B}R^5$, X, Y, Z, and V is a group optionally substituted with one to five identical or different substituents each independently selected from the group consisting of
  (1) a halogen atom,
  (2) a hydroxyl group,
  (3) a carboxyl group,
  (4) a sulfinate group,
  (5) a sulfonate group,
  (6) a phosphate group,
  (7) an optionally substituted $C_{1-6}$alkyl group,
  (8) an optionally substituted $C_{3-10}$cycloalkyl group,
  (9) an optionally substituted $C_{1-10}$aryl group,
  (10) an optionally substituted $C_{5-10}$heteroaryl group,
  (11) an optionally substituted $C_{1-6}$alkoxy group,
  (12) an optionally substituted $C_{3-10}$cycloalkoxy group,
  (13) an optionally substituted $C_{1-6}$alkoxycarbonyl group,
  (14) an optionally substituted $C_{1-6}$alkylcarbonyl group,
  (15) an optionally substituted 3- to 12-membered monocyclic or polycyclic heterocyclic group,
  (16) an optionally substituted 3- to 12-membered cyclic amino group,
  (17) —$NR^6R^7$,
  (18) —$CO_2R^6$,
  (19) a guanidine group,
  (20) —$CONR^6R^7$,
  (21) —$SO_2R^6$,
  (22) —$SO_2NR^6R^7$, and
  (23) a cyano group,
  wherein a substituent in the (7), (8), (9), (10), (11), (12), (13), (14), (15), and (16) is a group optionally substituted with one to five identical or different substituents each independently selected from the group consisting of
  (a) a halogen atom,
  (b) a hydroxyl group,
  (c) a $C_{1-6}$alkyl group,
  (d) a $C_{1-6}$alkoxy group,
  (e) a cyano group,
  (f) a carboxyl group,
  (g) a sulfinate group,
  (h) a sulfonate group,
  (i) a phosphate group,
  (j) a $C_{1-6}$alkoxycarbonyl group,
  (k) a $C_{1-6}$alkylcarbonyl group,
  (l) —$NR^6R^7$,
  (m) —$CO_2R^6$,
  (n) a guanidine group,
  (o) —$CONR^6R^7$,
  (p) —$SO_2R^6$,
  (q) —$SO_2NR^6R^7$,
  (r) a $C_{6-10}$aryl group,
  (s) a $C_{5-10}$heteroaryl group,
  (t) a 3- to 12-membered cyclic amino group optionally substituted with one to three $C_{1-6}$alkyl groups, and
  (u) a 3- to 12-membered monocyclic or polycyclic heterocyclic group optionally substituted with one to three $C_{1-6}$alkyl groups; and
$R^6$ and $R^7$ are identical or different, and each independently a hydrogen atom, or a $C_{1-10}$alkyl group optionally substituted with one to two groups selected from the group consisting of a halogen atom and a carboxyl group, wherein $R^6$ and $R^7$, when both are optionally substituted $C_{1-10}$alkyl groups, may be taken together with the nitrogen atom to which they are attached to form a 3- to 12-membered cyclic amino group.

[Item 5] The compound according to any one of items 1 to 4, or a pharmaceutically acceptable salt thereof,
  wherein
    a substituent of the optionally substituted $C_{1-10}$alkyl group, the optionally substituted $C_{1-6}$alkyl group, the optionally substituted $C_{3-10}$cycloalkyl group, the optionally substituted 3- to 10-membered monocyclic or polycyclic heterocyclic group, the optionally substituted $C_{2-10}$alkenyl group, the optionally substituted $C_{2-6}$alkenyl group, the optionally substituted $C_{2-10}$alkynyl group, the optionally substituted $C_{2-6}$alkynyl group, the optionally substituted $C_{6-10}$aryl group, the optionally substituted $C_{5-10}$heteroaryl group, the optionally substituted 3- to 10-membered cyclic amino group, the optionally substituted $C_{1-10}$alkylene, the optionally substituted $C_{3-10}$cycloalkylene, the optionally substituted 3- to 12-membered monocyclic or polycyclic heterocycle, the optionally substituted 3- to 12-membered cyclic aminyl linker group, the optionally substituted $C_{2-10}$alkenylene, the optionally substituted $C_{2-10}$alkynylene, the optionally substituted $C_{6-10}$arylene, and the optionally substituted $C_{5-10}$heteroarylene in B, $R^{3A}$, $R^{3B}$, $R^{3C}$, $R^{4A}$, $R^{4B}$, $R^5$, X, Y, Z, and V is a group optionally substituted with one to five identical or different substituents each independently selected from the group consisting of
  (1) a halogen atom,
  (2) a hydroxyl group,
  (3) a carboxyl group,
  (4) a sulfinate group,
  (5) a sulfonate group,
  (6) a phosphate group,
  (7) a $C_{1-6}$alkyl group,
  (8) a $C_{3-10}$cycloalkyl group,
  (9) an optionally substituted $C_{6-10}$aryl group,
  (10) an optionally substituted $C_{5-10}$heteroaryl group,
  (11) a $C_{1-6}$alkoxy group,
  (12) a $C_{3-8}$cycloalkoxy group,
  (13) a $C_{1-6}$alkoxycarbonyl group,
  (14) a $C_{1-6}$alkylcarbonyl group,
  (15) a 3- to 12-membered monocyclic or polycyclic heterocyclic group,
  (16) a 3- to 12-membered cyclic amino group
  (17) —$NR^6R^7$,
  (18) —$CO_2R^6$,
  (19) a guanidine group,
  (20) —$CONR^6R^7$,
  (21) —$SO_2R^6$, and
  (22) —$SO_2NR^6R^7$,
  wherein
    a substituent in the (9) and (10) is a group optionally substituted with one to five identical or different substituents each independently selected from the group consisting of
  (a) a halogen atom,
  (b) a hydroxyl group,
  (c) a $C_{1-6}$alkyl group,
  (d) a $C_{1-6}$alkoxy group,
  (e) a cyano group,
  (f) a carboxyl group,
  (g) a sulfinate group,
  (h) a sulfonate group,
  (i) a phosphate group,
  (j) a $C_{1-6}$alkoxycarbonyl group,
  (k) a $C_{1-6}$alkylcarbonyl group,
  (l) —$NR^6R^7$,
  (m) —$CO_2R^6$,
  (n) a guanidine group,
  (o) —$CONR^6R^7$, (p) —SO$_2$R$^6$, and
(q) —SO$_2$NR$^6$R$^7$; and
R$^6$ and R$^7$ are identical or different, and each independently a hydrogen atom, or a C$_{1-10}$alkyl group optionally substituted with one to two groups selected from the group consisting of a halogen atom and a carboxyl group, wherein R$^6$ and R$^7$, when both are optionally substituted C$_{1-10}$alkyl groups, may be taken together with the nitrogen atom to which they are attached to form a 3- to 12-membered cyclic amino group.

[Item 6] The compound according to any one of items 1 to 5, or a pharmaceutically acceptable salt thereof,
wherein
a substituent of the optionally substituted C$_{1-10}$alkyl group, the optionally substituted C$_{1-6}$alkyl group, the optionally substituted C$_{3-10}$cycloalkyl group, the optionally substituted 3- to 10-membered monocyclic or polycyclic heterocyclic group, the optionally substituted C$_{2-10}$alkenyl group, the optionally substituted C$_{2-6}$alkenyl group, the optionally substituted C$_{2-10}$alkynyl group, the optionally substituted C$_{2-6}$alkynyl group, the optionally substituted C$_{6-10}$aryl group, the optionally substituted C$_{5-10}$heteroaryl group, the optionally substituted 3- to 12-membered cyclic amino group, the optionally substituted C$_{1-10}$alkylene, the optionally substituted C$_{3-10}$cycloalkylene, the optionally substituted 3- to 12-membered monocyclic or polycyclic heterocycle, the optionally substituted 3- to 12-membered cyclic aminyl linker group, the optionally substituted C$_{2-10}$alkenylene, the optionally substituted C$_{2-10}$alkynylene, the optionally substituted C$_{6-10}$arylene, and the optionally substituted C$_{5-10}$heteroarylene in B, R$^{3A}$, R$^{3B}$, R$^{3C}$, R$^{4A}$, R$^{4B}$, R$^5$, X, Y, Z, and V is a group optionally substituted with one to five identical or different substituents each independently selected from the group consisting of
(1) a halogen atom,
(2) a hydroxyl group,
(3) a carboxyl group,
(4) a sulfinate group,
(5) a sulfonate group,
(6) a phosphate group,
(7) a C$_{1-6}$alkoxy group,
(8) —NR$^6$R$^7$,
(9) —CO$_2$R$^6$,
(10) a guanidine group,
(11) —CONR$^6$R$^7$, and
(12) —SO$_2$NR$^6$R$^7$; and
R$^6$ and R$^7$ are identical or different, and each independently a hydrogen atom, or a C$_{1-10}$alkyl group optionally substituted with one to two groups selected from the group consisting of a halogen atom and a carboxyl group, wherein R$^6$ and R$^7$, when both are optionally substituted C$_{1-10}$alkyl groups, may be taken together with the nitrogen atom to which they are attached to form a 3- to 12-membered cyclic amino group.

[Item 7] The compound according to any one of items 1 to 6, or a pharmaceutically acceptable salt thereof,
wherein
a substituent of the optionally substituted C$_{1-10}$alkyl group, the optionally substituted C$_{1-6}$alkyl group, the optionally substituted C$_{3-10}$cycloalkyl group, the optionally substituted 3- to 10-membered monocyclic or polycyclic heterocyclic group, the optionally substituted C$_{2-10}$alkenyl group, the optionally substituted C$_{2-6}$alkenyl group, the optionally substituted C$_{2-10}$alkynyl group, the optionally substituted C$_{2-6}$alkynyl group, the optionally substituted C$_{6-10}$aryl group, the optionally substituted C$_{5-10}$heteroaryl group, the optionally substituted 3- to 12-membered cyclic amino group, the optionally substituted C$_{1-10}$alkylene, the optionally substituted C$_{3-10}$cycloalkylene, the optionally substituted 3- to 12-membered monocyclic or polycyclic heterocycle, the optionally substituted 3- to 12-membered cyclic aminyl linker group, the optionally substituted C$_{2-10}$alkenylene, the optionally substituted C$_{2-10}$alkynylene, the optionally substituted C$_{6-10}$arylene, and the optionally substituted C$_{5-10}$heteroarylene in B, R$^{3A}$, R$^{3B}$, R$^{3C}$, R$^{4A}$, R$^{4B}$, R$^5$, R$^8$, X, Y, Z, and V is a group optionally substituted with one to five identical or different substituents each independently selected from the group consisting of
(1) a halogen atom,
(2) a carboxyl group,
(3) a C$_{6-10}$aryl group,
(4) —NR$^6$R$^7$,
(5) —CO$_2$R$^6$,
(6) —CONR$^6$R$^7$,
(7) —SO$_2$R$^6$,
(8) —SO$_2$NR$^6$R$^7$,
(9) —OCO$_2$R$^6$,
(10) —OCONR$^6$R$^7$, and
(11) —NR$^6$CO$_2$R$^7$; and
R$^6$ and R$^7$ are identical or different, and each independently a hydrogen atom, or a C$_{1-6}$alkyl group optionally substituted with one to two groups selected from the group consisting of a halogen atom and a carboxyl group, wherein R$^6$ and R$^7$, when both are optionally substituted C$_{1-6}$alkyl groups, may be taken together with the nitrogen atom to which they are attached to form a 3- to 6-membered cyclic amino group.

[Item 8] The compound according to any one of items 1 to 7, or a pharmaceutically acceptable salt thereof, wherein A$^1$ and A$^2$ are identical or different, and each independently —C(=O)B, —C(=O)CR$^{3A}$R$^{3B}$B, —CO$_2$B, —CONR$^{3C}$B, —SO$_2$B, —SO$_2$CR$^{3A}$R$^{3B}$B, —SO$_2$(OB), —SO$_2$NR$^{3C}$B, —P(=O)(B)$_2$, —P(=O)(CR$^{3A}$R$^{3B}$B)$_2$, —P(=O)(OB)$_2$, —P(=O)(NR$^{3C}$B)$_2$, or a hydrogen atom.

[Item 9] The compound according to any one of items 1 to 7, or a pharmaceutically acceptable salt thereof, wherein A$^1$ and A$^2$ are identical or different, and each independently —C(=O)B, —C(=O)CR$^{3A}$R$^{3B}$B. —CO$_2$B, —CONR$^{3C}$B, or a hydrogen atom.

[Item 10] The compound according to any one of items 1 to 7, or a pharmaceutically acceptable salt thereof, wherein A$^1$ and A$^2$ are identical or different, and each independently —C(=O)B, —CO$_2$B, —CONR$^{3C}$B, or a hydrogen atom.

[Item 11] The compound according to any one of items 1 to 7, or a pharmaceutically acceptable salt thereof, wherein A$^1$ and A$^2$ are identical or different, and each independently —SO$_2$B, —SO$_2$CR$^{3A}$R$^{3B}$B, —SO$_2$(OB), —SO$_2$NR$^{3C}$B, or a hydrogen atom.

[Item 12] The compound according to any one of items 1 to 7, or a pharmaceutically acceptable salt thereof, wherein A$^1$ and A$^2$ are identical or different, and each independently —P(=O)(B)$_2$, —P(=O)(CR$^{3A}$R$^{3B}$B)$_2$, —P(=O)(OB)$_2$, —P(=O)(NR$^{3C}$B)$_2$, or a hydrogen atom.

[Item 13] The compound according to any one of items 1 to 12, or a pharmaceutically acceptable salt thereof, wherein n is 0 or 1.

[Item 14] The compound according to any one of items 1 to 13, or a pharmaceutically acceptable salt thereof, wherein R$^1$ is a hydrogen atom, a halogen atom, a cyano group, a hydroxyl group, an optionally substituted amino group, an optionally substituted 3- to 12-membered cyclic amino group, an optionally substituted C$_{1-6}$alkyl group, an optionally substituted C$_{3-10}$cycloalkyl group, an optionally substituted C$_{2-6}$alkenyl group, an optionally substituted C$_{2-6}$alkynyl group, an optionally substituted $C_{1-6}$alkoxy group, an optionally substituted 3- to 12-membered monocyclic or polycyclic heterocyclic group, an optionally substituted $C_{1-6}$alkylcarbonyl group, an optionally substituted $C_{3-10}$cycloalkylcarbonyl group, an optionally substituted 3- to 12-membered monocyclic or polycyclic heterocyclylcarbonyl group, a carboxyl group, an optionally substituted $C_{1-6}$alkoxycarbonyl group, an optionally substituted $C_{3-10}$cycloalkoxycarbonyl group, an optionally substituted aminocarbonyl group, or an optionally substituted 3- to 12-membered cyclic aminocarbonyl group.

[Item 15] The compound according to any one of items 1 to 13, or a pharmaceutically acceptable salt thereof, wherein $R^1$ is (1) a hydrogen atom;

(2) a halogen atom;

(3) a cyano group;

(4) a hydroxyl group;

(5) a 3- to 12-membered cyclic amino group (the cyclic amino group is optionally substituted with one to three groups selected from the group consisting of a halogen atom, a hydroxyl group, a $C_{1-6}$alkyl group, and a $C_{1-6}$alkoxy group);

(6) a $C_{1-6}$alkyl group (the alkyl group is optionally substituted with one to three groups selected from the group consisting of a halogen atom, a hydroxyl group, a $C_{1-6}$alkoxy group, a $C_{3-10}$cycloalkyl group, and a 3- to 12-membered cyclic amino group);

(7) a $C_{1-6}$alkoxy group (the alkoxy group is optionally substituted with one to three groups selected from the group consisting of a halogen atom, a hydroxyl group, a $C_{1-6}$alkoxy group, and a $C_{3-10}$cycloalkyl group);

(8) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group);

(9) a $C_{1-6}$alkylcarbonyl group (the alkyl is optionally substituted with one to three groups selected from the group consisting of a halogen atom, a hydroxyl group, a $C_{1-6}$alkoxy group, a $C_{3-10}$cycloalkyl group, and a 3- to 12-membered cyclic amino group);

(10) a carboxyl group;

(11) an aminocarbonyl group (the amino is optionally substituted with one or two groups selected from the group consisting of (a) a $C_{1-6}$alkyl group (the alkyl group is optionally substituted with one to three groups selected from the group consisting of a halogen atom, a hydroxyl group, a $C_{1-6}$alkyl group, and a $C_{1-6}$alkoxy group), (b) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and (c) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group)); or

(12) a 3- to 12-membered cyclic aminocarbonyl group (the cyclic amino is optionally substituted with one to three $C_{1-6}$alkyl groups).

[Item 16] The compound according to any one of items 1 to 13, or a pharmaceutically acceptable salt thereof, wherein $R^1$ is (1) a hydrogen atom, (2) a hydroxyl group, (3) a $C_{1-6}$alkyl group (the alkyl group is optionally substituted with one to three groups selected from the group consisting of a halogen atom, a hydroxyl group, a $C_{1-6}$alkoxy group, and a $C_{3-10}$cycloalkyl group), (4) a $C_{1-6}$alkoxy group (the alkoxy group is optionally substituted with one to three groups selected from the group consisting of a halogen atom, a hydroxyl group, a $C_{1-6}$alkoxy group, and a $C_{3-10}$cycloalkyl group), (5) a $C_{1-6}$alkylcarbonyl group (the alkyl is optionally substituted with one to three groups selected from the group consisting of a halogen atom, a hydroxyl group, a $C_{1-6}$alkoxy group, a $C_{3-10}$cycloalkyl group, and a 3- to 12-membered cyclic amino group), or (6) a carboxyl group.

[Item 17] The compound according to any one of items 1 to 13, or a pharmaceutically acceptable salt thereof, wherein $R^1$ is a hydrogen atom, a hydroxyl group, a $C_{1-6}$alkoxy group, a $C_{1-6}$alkylcarbonyl group, or a carboxyl group.

[Item 18] The compound according to any one of items 1 to 13, or a pharmaceutically acceptable salt thereof, wherein $R^1$ is a hydrogen atom.

[Item 19] The compound according to any one of items 1 to 18, or a pharmaceutically acceptable salt thereof, wherein $R^{2A}$, $R^{2B}$, $R^{2C}$, and $R^{2D}$ are identical or different, and each independently (1) a hydrogen atom;

(2) a halogen atom;

(3) a cyano group;

(4) a hydroxyl group;

(5) an amino group (the amino group is optionally substituted with one or two groups selected from the group consisting of (a) a $C_{1-6}$alkyl group (the alkyl group is optionally substituted with one to three groups selected from the group consisting of a halogen atom, a hydroxyl group, a $C_{1-6}$alkoxy group, a $C_{1-10}$aryl group, and a 3- to 12-membered monocyclic or polycyclic heterocyclic group, which is optionally substituted with one to three $C_{1-6}$alkyl groups), (b) a $C_{1-6}$alkylcarbonyl group (the alkyl is optionally substituted with one to three groups selected from the group consisting of a halogen atom, a hydroxyl group, a $C_{1-6}$alkoxy group, and a 3- to 12-membered monocyclic or polycyclic heterocyclic group, which is optionally substituted with one to three $C_{1-6}$alkyl groups), (c) a $C_{1-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and (d) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group));

(6) a 3- to 12-membered cyclic amino group (the cyclic amino group is optionally substituted with one to three $C_{1-6}$alkyl groups);

(7) a $C_{1-6}$alkyl group (the alkyl group is optionally substituted with one to three groups selected from the group consisting of a halogen atom, a hydroxyl group, —NR$^6$R$^7$, a C$_{1-6}$alkoxy group, a C$_{3-10}$cycloalkyl group, a C$_{6-10}$aryl group, and a 3- to 12-membered monocyclic or polycyclic heterocyclic group);

(8) a C$_{3-10}$cycloalkyl group (the cycloalkyl group is optionally substituted with one to three groups selected from the group consisting of a halogen atom, a hydroxyl group, a C$_{1-6}$alkyl group, and a C$_{1-6}$alkoxy group);

(9) a C$_{6-10}$aryl group (the aryl group is optionally substituted with one to three groups selected from the group consisting of a halogen atom, a hydroxyl group, a C$_{1-6}$alkyl group, and a C$_{1-6}$alkoxy group);

(10) a 3- to 12-membered monocyclic or polycyclic heterocyclic group (the heterocyclic group is optionally substituted with one to three groups selected from the group consisting of a halogen atom, a hydroxyl group, a C$_{1-6}$alkyl group, and a C$_{1-6}$alkoxy group);

(11) a C$_{1-6}$alkoxy group (the alkoxy group is optionally substituted with one to three groups selected from the group consisting of a halogen atom, a hydroxyl group, —NR$^6$R$^7$, a C$_{1-6}$alkoxy group, a C$_{3-10}$cycloalkyl group, and a 3- to 12-membered monocyclic or polycyclic heterocyclic group);

(12) a C$_{3-10}$cycloalkoxy group (the cycloalkoxy group is optionally substituted with one to three groups selected from the group consisting of a halogen atom, a hydroxyl group, a C$_{1-6}$alkyl group, and a C$_{1-6}$alkoxy group);

(13) a C$_{6-10}$aryloxy group (the aryl is optionally substituted with one to three groups selected from the group consisting of a halogen atom, a hydroxyl group, a C$_{1-6}$alkyl group, and a C$_{1-6}$alkoxy group);

(14) a 3- to 12-membered monocyclic or polycyclic heterocyclyloxy group (the heterocycle is optionally substituted with one to three groups selected from the group consisting of a halogen atom, a hydroxyl group, a C$_{1-6}$alkyl group, and a C$_{1-6}$alkoxy group);

(15) a carboxyl group;

(16) a C$_{1-6}$alkylcarbonyl group (the alkyl is optionally substituted with one to three groups selected from the group consisting of a halogen atom, a hydroxyl group, —NR$^6$R$^7$, a C$_{1-6}$alkoxy group, a C$_{3-10}$cycloalkyl group, and a 3- to 12-membered monocyclic or polycyclic heterocyclic group);

(17) a C$_{3-10}$cycloalkylcarbonyl group (the cycloalkyl is optionally substituted with one to three groups selected from the group consisting of a halogen atom, a hydroxyl group, a C$_{1-6}$alkyl group, and a C$_{1-6}$alkoxy group);

(18) a C$_{6-10}$arylcarbonyl group (the aryl is optionally substituted with one to three groups selected from the group consisting of a halogen atom, a hydroxyl group, a C$_{1-6}$alkyl group, and a C$_{1-6}$alkoxy group);

(19) a 3- to 12-membered monocyclic or polycyclic heterocyclylcarbonyl group (the heterocycle is optionally substituted with one to three groups selected from the group consisting of a halogen atom, a hydroxyl group, a C$_{1-6}$alkyl group, and a C$_{1-6}$alkoxy group);

(20) a C$_{1-6}$alkoxycarbonyl group (the alkoxy is optionally substituted with one to three groups selected from the group consisting of a halogen atom, a hydroxyl group, —NR$^6$R$^7$, a C$_{1-6}$alkoxy group, a C$_{3-10}$cycloalkyl group, and a 3- to 12-membered monocyclic or polycyclic heterocyclic group);

(21) a C$_{3-10}$cycloalkoxycarbonyl group (the cycloalkoxy is optionally substituted with one to three groups selected from the group consisting of a halogen atom, a hydroxyl group, a C$_{1-6}$alkyl group, and a C$_{1-6}$alkoxy group);

(22) a C$_{6-10}$aryloxycarbonyl group (the aryl is optionally substituted with one to three groups selected from the group consisting of a halogen atom, a hydroxyl group, a C$_{1-6}$alkyl group, and a C$_{1-6}$alkoxy group);

(23) a 3- to 12-membered monocyclic or polycyclic heterocyclyloxycarbonyl group (the heterocycle is optionally substituted with one to three groups selected from the group consisting of a halogen atom, a hydroxyl group, a C$_{1-6}$alkyl group, and a C$_{1-6}$alkoxy group);

(24) an aminocarbonyl group (the amino is optionally substituted with one or two groups selected from the group consisting of (a) a C$_{1-6}$alkyl group (the alkyl group is optionally substituted with one to three groups selected from the group consisting of a halogen atom, a hydroxyl group, a C$_{1-6}$alkoxy group, and 3- to 12-membered monocyclic or polycyclic heterocyclic group, which is optionally substituted with one to three C$_{1-6}$alkyl groups), (b) a C$_{3-10}$cycloalkyl group (the cycloalkyl group is optionally substituted with one to three groups selected from the group consisting of a halogen atom, a hydroxyl group, a C$_{1-6}$alkyl group, and a C$_{1-6}$alkoxy group), and (c) a 3- to 12-membered monocyclic or polycyclic heterocyclic group (the heterocyclic group is optionally substituted with one to three groups selected from the group consisting of a halogen atom, a hydroxyl group, a C$_{1-6}$alkyl group, and a C$_{1-6}$alkoxy group));

(25) a 3- to 12-membered cyclic aminocarbonyl group (the cyclic amino is optionally substituted with one to three C$_{1-6}$alkyl groups);

(26) a C$_{1-6}$alkylthio group (the alkyl is optionally substituted with one to three groups selected from the group consisting of a halogen atom, a hydroxyl group, —NR$^6$R$^7$, a C$_{1-6}$alkoxy group, a C$_{3-10}$cycloalkyl group, and a 3- to 12-membered monocyclic or polycyclic heterocyclic group);

(27) a C$_{3-10}$cycloalkylthio group (the cycloalkyl is optionally substituted with one to three groups selected from the group consisting of a halogen atom, a hydroxyl group, a C$_{1-6}$alkyl group, and a C$_{1-6}$alkoxy group);

(28) a C$_{6-10}$arylthio group (the aryl is optionally substituted with one to three groups selected from the group consisting of a halogen atom, a hydroxyl group, a C$_{1-6}$alkyl group, and a C$_{1-6}$alkoxy group);

(29) a 3- to 12-membered monocyclic or polycyclic heterocyclylthio group (the heterocycle is optionally substituted with one to three groups selected from the group consisting of a halogen atom, a hydroxyl group, a C$_{1-6}$alkyl group, and a C$_{1-6}$alkoxy group);

(30) a sulfinate group;

(31) a C$_{1-6}$alkylsulfinyl group (the alkyl is optionally substituted with one to three groups selected from the group consisting of a halogen atom, a hydroxyl group, —NR$^6$R$^7$, a C$_{1-6}$alkoxy group, a C$_{3-10}$cycloalkyl group, and a 3- to 12-membered monocyclic or polycyclic heterocyclic group);

(32) a C$_{3-10}$cycloalkylsulfinyl group (the cycloalkyl is optionally substituted with one to three groups selected from the group consisting of a halogen atom, a hydroxyl group, a C$_{1-6}$alkyl group, and a C$_{1-6}$alkoxy group);

(33) a C$_{6-10}$arylsulfinyl group (the aryl is optionally substituted with one to three groups selected from the group consisting of a halogen atom, a hydroxyl group, a C$_{1-6}$alkyl group, and a C$_{1-6}$alkoxy group);

(34) a 3- to 12-membered monocyclic or polycyclic heterocyclylsulfinyl group (the heterocycle is optionally substituted with one to three groups selected from the group consisting of a halogen atom, a hydroxyl group, a $C_{1-6}$alkyl group, and a $C_{1-6}$alkoxy group);

(35) an aminosulfinyl group (the amino is optionally substituted with one or two groups selected from the group consisting of
- (a) a $C_{1-6}$alkyl group (the alkyl group is optionally substituted with one to three groups selected from the group consisting of a halogen atom, a hydroxyl group, a $C_{1-6}$alkoxy group, and a 3- to 12-membered monocyclic or polycyclic heterocyclic group, which is optionally substituted with one to three $C_{1-6}$alkyl groups),
- (b) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
- (c) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group));

(36) a 3- to 12-membered cyclic aminosulfinyl group (the cyclic amino is optionally substituted with one to three $C_{1-6}$alkyl groups);

(37) a sulfonate group;

(38) a $C_{1-6}$alkylsulfonyl group (the alkyl is optionally substituted with one to three groups selected from the group consisting of a halogen atom, a hydroxyl group, —NR$^6$R$^7$, a $C_{1-6}$alkoxy group, a $C_{3-10}$cycloalkyl group, and a 3- to 12-membered monocyclic or polycyclic heterocyclic group);

(39) a $C_{3-10}$cycloalkylsulfonyl group (the cycloalkyl is optionally substituted with one to three groups selected from the group consisting of a halogen atom, a hydroxyl group, a $C_{1-6}$alkyl group, and a $C_{1-6}$alkoxy group);

(40) a $C_{6-10}$arylsulfonyl group (the aryl is optionally substituted with one to three groups selected from the group consisting of a halogen atom, a hydroxyl group, a $C_{1-6}$alkyl group, and a $C_{1-6}$alkoxy group);

(41) a 3- to 12-membered monocyclic or polycyclic heterocyclylsulfonyl group (the heterocycle is optionally substituted with one to three groups selected from the group consisting of a halogen atom, a hydroxyl group, a $C_{1-6}$alkyl group, and a $C_{1-6}$alkoxy group);

(42) an aminosulfonyl group (the amino is optionally substituted with one or two groups selected from the group consisting of
- (a) a $C_{1-6}$alkyl group (the alkyl group is optionally substituted with one to three groups selected from the group consisting of a halogen atom, a hydroxyl group, a $C_{1-6}$alkoxy group, and a 3- to 12-membered monocyclic or polycyclic heterocyclic group, which is optionally substituted with one to three $C_{1-6}$alkyl groups),
- (b) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
- (c) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group)); or

(43) a 3- to 12-membered cyclic aminosulfonyl group (the cyclic amino is optionally substituted with one to three $C_{1-6}$alkyl groups).

[Item 20] The compound according to any one of items 1 to 18, or a pharmaceutically acceptable salt thereof, wherein $R^{2A}$, $R^{2B}$, $R^{2C}$, and $R^{2D}$ are identical or different, and each independently (1) a hydrogen atom;

(2) a halogen atom;

(3) a cyano group;

(4) a hydroxyl group;

(5) an amino group (the amino group is optionally substituted with one or two groups selected from the group consisting of
- (a) a $C_{1-6}$alkyl group (the alkyl group is optionally substituted with one to three groups selected from the group consisting of a halogen atom, a hydroxyl group, and a $C_{1-6}$alkoxy group),
- (b) a $C_{1-6}$alkylcarbonyl group (the alkyl is optionally substituted with one to three groups selected from the group consisting of a halogen atom, a hydroxyl group, and $C_{1-6}$alkoxy group),
- (c) a $C_{1-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
- (d) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group));

(6) a 3- to 12-membered cyclic amino group (the cyclic amino group is optionally substituted with one to three $C_{1-6}$alkyl groups);

(7) a $C_{1-6}$alkyl group (the alkyl group is optionally substituted with one to three groups selected from the group consisting of a halogen atom, a hydroxyl group, —NR$^6$R$^7$, a $C_{1-6}$alkoxy group, a $C_{3-10}$cycloalkyl group, and a 3- to 12-membered monocyclic or polycyclic heterocyclic group);

(8) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group);

(9) a $C_{1-6}$alkoxy group (the alkoxy group is optionally substituted with one to three groups selected from the group consisting of a halogen atom, a hydroxyl group, —NR$^6$R$^7$, a $C_{1-6}$alkoxy group, a $C_{3-10}$cycloalkyl group, and a 3- to 12-membered monocyclic or polycyclic heterocyclic group);

(10) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group);

(11) a $C_{1-6}$alkylcarbonyl group (the alkyl is optionally substituted with one to three groups selected from the group consisting of a halogen atom, a hydroxyl group, —NR$^6$R$^7$, a $C_{1-6}$alkoxy group, a $C_{3-10}$cycloalkyl group, a $C_{6-10}$aryl group, and a 3- to 12-membered monocyclic or polycyclic heterocyclic group);

(12) a $C_{3-10}$cycloalkylcarbonyl group (the cycloalkyl is optionally substituted with one to three groups selected from the group consisting of a halogen atom, a hydroxyl group, a $C_{1-6}$alkyl group, and a $C_{1-6}$alkoxy group);

(13) a carboxyl group;

(14) an aminocarbonyl group (the amino is optionally substituted with one or two groups selected from the group consisting of
  (a) a $C_{1-6}$alkyl group (the alkyl group is optionally substituted with one to three groups selected from the group consisting of a halogen atom, a hydroxyl group, a $C_{1-6}$alkoxy group, and a 3- to 12-membered monocyclic or polycyclic heterocyclic group, which is optionally substituted with one to three $C_{1-6}$alkyl groups),
  (b) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
  (c) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group)); or

(15) a sulfonate group.

[Item 21] The compound according to any one of items 1 to 18, or a pharmaceutically acceptable salt thereof, wherein $R^{2A}$, $R^{2B}$, $R^{2C}$, and $R^{2D}$ are identical or different, and each independently
(1) a hydrogen atom,
(2) a halogen atom,
(3) a hydroxyl group,
(4) an amino group (the amino group is optionally substituted with one or two groups selected from the group consisting of a $C_{1-6}$alkyl group and a $C_{1-6}$alkylcarbonyl group),
(5) a $C_{1-6}$alkyl group (the alkyl group is optionally substituted with one to three groups selected from the group consisting of a halogen atom, a hydroxyl group, and a $C_{1-6}$alkoxy group),
(6) a $C_{3-10}$cycloalkyl group,
(7) a $C_{1-6}$alkoxy group (the alkoxy group is optionally substituted with one to three groups selected from the group consisting of a halogen atom, a hydroxyl group, and a $C_{1-6}$alkoxy group),
(8) a carboxyl group, or
(9) an aminocarbonyl group (the amino is optionally substituted with a $C_{1-6}$alkyl group).

[Item 22] The compound according to any one of items 1 to 18, or a pharmaceutically acceptable salt thereof, wherein $R^{2A}$, $R^{2B}$, $R^{2C}$, and $R^{2D}$ are identical or different, and each independently a hydrogen atom, a halogen atom, a $C_{1-6}$alkyl group, a $C_{3-10}$cycloalkyl group, a $C_{1-6}$alkoxy group, or a carboxyl group.

[Item 23] The compound according to any one of items 1 to 18, or a pharmaceutically acceptable salt thereof, wherein $R^{2A}$, $R^{2B}$, $R^{2C}$, and $R^{2D}$ are all hydrogen atoms.

[Item 24] The compound according to any one of items 1 to 23, or a pharmaceutically acceptable salt thereof, wherein $R^{3A}$, $R^{3B}$, and $R^{3C}$ are identical or different, and each independently a hydrogen atom, or a $C_{1-10}$alkyl group optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$C_2R^6$, —$CONR^6R^7$, —$SO_2R^6$, and —$SO_2NR^6R^7$.

[Item 25] The compound according to any one of items 1 to 23, or a pharmaceutically acceptable salt thereof, wherein $R^{3A}$, $R^{3B}$, and $R^{3C}$ are identical or different, and each independently a hydrogen atom, or a $C_{1-10}$alkyl group optionally substituted with one to three substituents selected from the group consisting of a halogen atom, a carboxyl group, —$NR^6R^7$, and —$CO_2R^6$.

[Item 26] The compound according to any one of items 1 to 23, or a pharmaceutically acceptable salt thereof, wherein $R^{3A}$, $R^{3B}$, and $R^{3C}$ are all hydrogen atoms.

[Item 27] The compound according to any one of items 1 to 26, or a pharmaceutically acceptable salt thereof, wherein $R^8$ is a $C_{1-10}$alkyl group optionally substituted with one to three groups selected from the group consisting of a halogen atom, a hydroxyl group, —$NR^6R^7$, a $C_{1-6}$alkoxy group, a $C_{3-10}$cycloalkyl group, a $C_{6-10}$aryl group, and a 3- to 12-membered monocyclic or polycyclic heterocyclic group.

[Item 28] The compound according to any one of items 1 to 26, or a pharmaceutically acceptable salt thereof, wherein $R^8$ is a $C_{1-10}$alkyl group optionally substituted with one to three groups selected from the group consisting of a halogen atom, —$NR^6R^7$, a $C_{1-6}$alkoxy group, and a $C_{3-10}$cycloalkyl group.

[Item 29] The compound according to any one of items 1 to 26, or a pharmaceutically acceptable salt thereof, wherein $R^8$ is a $C_{1-6}$alkyl group optionally substituted with one to three halogen atoms.

[Item 30] The compound according to any one of items 1 to 26, or a pharmaceutically acceptable salt thereof, wherein $R^8$ is a methyl group.

[Item 31] The compound according to any one of items 1 to 30, or a pharmaceutically acceptable salt thereof, wherein
B is
(1) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(2) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or
(3) a group represented by the formula (B), wherein the 3- to 12-membered monocyclic or polycyclic heterocyclic group and the 3- to 12-membered cyclic amino group have at least one or more secondary nitrogen atoms in the ring.

[Item 32] The compound according to any one of items 1 to 30, or a pharmaceutically acceptable salt thereof, wherein B is a 3- to 6-membered monocyclic heterocyclic group optionally substituted with one to two substituents selected from the group consisting of a fluorine atom, a carboxyl group, and —$CO_2R^6$, or a group represented by the formula (B), wherein the 3- to 6-membered monocyclic heterocyclic group has at least one or more secondary nitrogen atoms in the ring.

[Item 33] The compound according to any one of items 1 to 30, or a pharmaceutically acceptable salt thereof, wherein B is a 3- to 6-membered monocyclic heterocyclic group optionally substituted with one to two substituents selected from the group consisting of a carboxyl group and —$CO_2R^6$, or a group represented by the formula (B), wherein the 3- to 6-membered monocyclic heterocyclic group has at least one or more secondary nitrogen atoms in the ring.

[Item 34] The compound according to any one of items 1 to 30, or a pharmaceutically acceptable salt thereof, wherein B is a 3- to 6-membered monocyclic heterocyclic group, a 3- to 6-membered cyclic amino group, or a group represented by the formula (B), wherein the 3- to 6-membered monocyclic heterocyclic group and the 3- to 6-membered cyclic amino group have at least one or more secondary nitrogen atoms in the ring.

[Item 35] The compound according to any one of items 1 to 34, or a pharmaceutically acceptable salt thereof, wherein X is
(1) a single bond,
(2) $C_{1-6}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or
(5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$).

[Item 36] The compound according to any one of items 1 to 34, or a pharmaceutically acceptable salt thereof, wherein X is
(1) a single bond,
(2) $C_{1-6}$alkylene (the alkylene is optionally substituted with one to three substituents selected from the group consisting of a halogen atom, a carboxyl group, a sulfinate group, a sulfonate group, a phosphate group, —$NR^6R^7$, and —$CO_2R^6$),
(3) $C_{3-10}$cycloalkylene (the cycloalkylene is optionally substituted with one to three substituents selected from the group consisting of a halogen atom, a carboxyl group, a sulfinate group, a sulfonate group, a phosphate group, —$NR^6R^7$, and —$CO_2R^6$),
(4) a 3- to 12-membered monocyclic or polycyclic heterocycle (the heterocycle is optionally substituted with one to three substituents selected from the group consisting of a halogen atom, a carboxyl group, a sulfinate group, a sulfonate group, a phosphate group, —$NR^6R^7$, and —$CO_2R^6$), or
(5) a 3- to 12-membered cyclic aminyl linker group (the cyclic aminyl linker group is optionally substituted with one to three substituents selected from the group consisting of a halogen atom, a carboxyl group, a sulfinate group, a sulfonate group, a phosphate group, —$NR^6R^7$, and —$CO_2R^6$).

[Item 37] The compound according to any one of items 1 to 34, or a pharmaceutically acceptable salt thereof, wherein X is
(1) a single bond;
(2) $C_{1-6}$alkylene (the alkylene is optionally substituted with one to three substituents selected from the group consisting of a halogen atom, a carboxyl group, a sulfinate group, a sulfonate group, a phosphate group, —$NR^6R^7$, and —$CO_2R^6$); or
(3) $C_{3-10}$cycloalkylene (the cycloalkylene is optionally substituted with one to three substituents selected from the group consisting of a halogen atom, a carboxyl group, a sulfinate group, a sulfonate group, a phosphate group, —$NR^6R^7$, and —$CO_2R^6$).

[Item 38] The compound according to any one of items 1 to 34, or a pharmaceutically acceptable salt thereof, wherein X is a single bond, or $C_{1-6}$alkylene optionally substituted with one to two substituents selected from the group consisting of a fluorine atom, a carboxyl group, and —$CO_2R^6$.

[Item 39] The compound according to any one of items 1 to 38, or a pharmaceutically acceptable salt thereof, wherein Y is a single bond, an oxygen atom, —$OCO_2$—, —$OCONR^{4A}$—, —$CONR^{4A}$—, —$NR^{4A}$—, —$NR^{4A}CO$—, —$NR^{4A}CO_2$—, —$NR^{4A}CONR^{4B}$—, —$NR^{4A}SO_2$—, —$NR^{4A}SO_2NR^{4B}$—, a sulfur atom, —$SO_2$—, —$SO_2NR^{4A}$—, or an optionally substituted 3- to 12-membered cyclic aminyl linker group.

[Item 40] The compound according to any one of items 1 to 38, or a pharmaceutically acceptable salt thereof, wherein Y is a single bond, an oxygen atom, —$CONR^{4A}$—, —$NR^{4A}CO$—, or a sulfur atom.

[Item 41] The compound according to any one of items 1 to 38, or a pharmaceutically acceptable salt thereof, wherein Y is a single bond, an oxygen atom, or —$NR^{4A}$—.

[Item 42] The compound according to any one of items 1 to 41, or a pharmaceutically acceptable salt thereof, wherein $R^{4A}$ and $R^{4B}$ are identical or different, and each independently a hydrogen atom, or a $C_{1-10}$alkyl group optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$.

[Item 43] The compound according to any one of items 1 to 41, or a pharmaceutically acceptable salt thereof, wherein $R^{4A}$ and $R^{4B}$ are hydrogen atoms.

[Item 44] The compound according to any one of items 1 to 43, or a pharmaceutically acceptable salt thereof, wherein Z is
(1) a single bond,
(2) $C_{1-10}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (6) $C_{6-10}$arylene (the arylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (7) $C_{5-10}$heteroarylene (the heteroarylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$).

[Item 45] The compound according to any one of items 1 to 43, or a pharmaceutically acceptable salt thereof, wherein
Z is
(1) a single bond,
(2) $C_{1-6}$alkylene (the alkylene is optionally substituted with one to three substituents selected from the group consisting of a halogen atom, a carboxyl group, a sulfinate group, a sulfonate group, a phosphate group, —$NR^6R^7$, and —$CO_2R^6$),
(3) $C_{3-10}$cycloalkylene (the cycloalkylene is optionally substituted with one to three substituents selected from the group consisting of a halogen atom, a carboxyl group, a sulfinate group, a sulfonate group, a phosphate group, —$NR^6R^7$, and —$CO_2R^6$),
(4) a 3- to 12-membered monocyclic or polycyclic heterocycle (the heterocycle is optionally substituted with one to three substituents selected from the group consisting of a halogen atom, a carboxyl group, a sulfinate group, a sulfonate group, a phosphate group, —$NR^6R^7$, and —$CO_2R^6$), or
(5) a 3- to 12-membered cyclic aminyl linker group (the cyclic aminyl linker group is optionally substituted with one to three substituents selected from the group consisting of a halogen atom, a carboxyl group, a sulfinate group, a sulfonate group, a phosphate group, —$NR^6R^7$, and —$CO_2R^6$).

[Item 46] The compound according to any one of items 1 to 43, or a pharmaceutically acceptable salt thereof, wherein Z is a single bond, or $C_{1-6}$alkylene optionally substituted with one to two substituents selected from the group consisting of a fluorine atom, a carboxyl group, and —$CO_2R^6$.

[Item 47] The compound according to any one of items 1 to 43, or a pharmaceutically acceptable salt thereof, wherein Z is a single bond, or $C_{1-6}$alkylene optionally substituted with one to two substituents selected from the group consisting of a carboxyl group and —$CO_2R^6$.

[Item 48] The compound according to any one of items 1 to 47, or a pharmaceutically acceptable salt thereof, wherein
V is
(1) —$NHR^5$,
(2) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or
(3) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$); and
wherein the 3- to 12-membered monocyclic or polycyclic heterocyclic group and the 3- to 12-membered cyclic amino group have at least one or more secondary nitrogen atoms in the ring.

[Item 49] The compound according to any one of items 1 to 47, or a pharmaceutically acceptable salt thereof, wherein V is —$NHR^5$, a 3- to 6-membered monocyclic heterocyclic group, or a 3- to 6-membered cyclic amino group, wherein the 3- to 6-membered monocyclic heterocyclic group and the 3- to 6-membered cyclic amino group have at least one or more secondary nitrogen atoms in the ring.

[Item 50] The compound according to any one of items 1 to 3 and 7 to 49, or a pharmaceutically acceptable salt thereof, wherein
$R^5$ is
(1) a hydrogen atom;
(2) a $C_{1-10}$alkyl group (the alkyl group is optionally substituted with one to three substituents selected from the group consisting of a halogen atom, a hydroxyl group, a carboxyl group, a sulfinate group, a sulfonate group, a phosphate group, a $C_{6-10}$aryl group, a $C_{1-6}$alkoxy group, a $C_{3-8}$cycloalkoxy group, —$NR^6R^7$, —$CO_2R^6$, —$CONR^6R^7$, —$SO_2R^6$, —$SO_2NR^6R^7$, —$OCO_2R^6$, —$OCONR^6R^7$, and —$NR^6CO_2R^7$);
(3) a $C_{3-10}$cycloalkyl group (the cycloalkyl group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$);
(4) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$);
(5) a $C_{6-10}$aryl group (the aryl group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$); or
(6) a $C_{5-10}$heteroaryl group (the heteroaryl group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —NR$^6$R$^7$, —CO$_2$R$^6$, —CONR$^6$R$^7$, —SO$_2$R$^6$, and —SO$_2$NR$^6$R$^7$).

[Item 51] The compound according to any one of items 1 to 49, or a pharmaceutically acceptable salt thereof,
wherein
R$^5$ is
(1) a hydrogen atom,
(2) a C$_{1-10}$alkyl group (the alkyl group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$),
(3) a C$_{3-10}$cycloalkyl group (the cycloalkyl group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$),
(4) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$),
(5) a C$_{6-10}$aryl group (the aryl group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$), or
(6) a C$_{5-10}$heteroaryl group (the heteroaryl group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$).

[Item 52] The compound according to any one of items 1 to 49, or a pharmaceutically acceptable salt thereof,
wherein
R$^5$ is
(1) a hydrogen atom,
(2) C$_{1-10}$alkyl group (the alkyl group is optionally substituted with one to three substituents selected from the group consisting of a halogen atom, a carboxyl group, a sulfinate group, a sulfonate group, a phosphate group, —NR$^6$R$^7$, and —CO$_2$R$^6$),
(3) a C$_{3-10}$cycloalkyl group (the cycloalkyl group is optionally substituted with one to three substituents selected from the group consisting of a halogen atom, a carboxyl group, a sulfinate group, a sulfonate group, a phosphate group, —NR$^6$R$^7$, and —CO$_2$R$^6$), or
(4) a 3- to 12-membered monocyclic or polycyclic heterocyclic group (the heterocyclic group is optionally substituted with one to three substituents selected from the group consisting of a halogen atom, a carboxyl group, a sulfinate group, a sulfonate group, a phosphate group, —NR$^6$R$^7$, and —CO$_2$R$^6$).

[Item 53] The compound according to any one of items 1 to 3 and 7 to 49, or a pharmaceutically acceptable salt thereof,
wherein
R$^5$ is
(1) a hydrogen atom; or
(2) a C$_{1-10}$alkyl group (the alkyl group is optionally substituted with one to three substituents selected from the group consisting of a halogen atom, a hydroxyl group, a carboxyl group, a sulfinate group, a sulfonate group, a phosphate group, a C$_{6-10}$aryl group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, —SO$_2$NR$^6$R$^7$, —OCO$_2$R$^6$, —OCONR$^6$R$^7$, and —NR$^6$CO$_2$R$^7$).

[Item 54] The compound according to any one of items 1 to 53, or a pharmaceutically acceptable salt thereof, wherein R$^6$ and R$^7$ are identical or different, and each independently a hydrogen atom, or a C$_{1-6}$alkyl group optionally substituted with one to two groups selected from the group consisting of a halogen atom and a carboxyl group, wherein R$^6$ and R$^7$, when both are optionally substituted C$_{1-6}$alkyl groups, may be taken together with the nitrogen atom to which they are attached to form a 3- to 12-membered cyclic amino group.

[Item 55] The compound according to item 1 or 2, or a pharmaceutically acceptable salt thereof,
wherein
A$^1$ and A$^2$ are identical or different, and each independently —C(=O)B, —C(=O)CR$^{3A}$R$^{3B}$B, —CO$_2$B, —CONR$^{3C}$B, or a hydrogen atom, wherein A$^1$ and A$^2$ are not both hydrogen atoms,
wherein
B is
(1) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$),
(2) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$), or
(3) a group represented by the formula (B),
wherein
X is
(1) a single bond,
(2) C$_{1-6}$alkylene (the alkylene is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$),
(3) C$_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, and —SO$_2$NR$^6$R$^7$),
(4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), Y is a single bond, an oxygen atom, —$CONR^{4A}$—, —$NR^{4A}CO$—, or a sulfur atom, $R^{4A}$ is a hydrogen atom, or a $C_{1-6}$alkyl group optionally substituted with one to three substituents selected from the group consisting of a halogen atom, a hydroxyl group, a carboxyl group, a $C_{1-6}$alkoxy group, a $C_{3-8}$cycloalkoxy group, —$NR^6R^7$, —$CO_2R^6$, and —$CONR^6R^7$, Z is (1) a single bond, (2) $C_{1-6}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a C-cycloalkoxy group, —$NR^6R^7$, —$CO_2R^6$, —$CONR^6R^7$, —$SO_2R^6$, and —$SO_2NR^6R^7$), (3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), n is 0 or 1, V is (1) —$NHR^5$, (2) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (3) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), wherein the 3- to 12-membered monocyclic or polycyclic heterocyclic group and the 3- to 12-membered cyclic amino group have at least one or more secondary nitrogen atoms in the ring, $R^5$ is (1) a hydrogen atom, (2) a $C_{1-10}$alkyl group (the alkyl group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (3) a $C_{3-10}$cycloalkyl group (the cycloalkyl group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (4) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), and $R^6$ and $R^7$ are identical or different, and each independently a hydrogen atom, or a $C_{1-6}$alkyl group optionally substituted with one to two groups selected from the group consisting of a halogen atom and a carboxyl group, wherein $R^6$ and $R^7$, when both are optionally substituted $C_{1-6}$alkyl groups, may be taken together with the nitrogen atom to which they are attached to form a 3- to 12-membered cyclic amino group, and wherein the 3- to 12-membered monocyclic or polycyclic heterocyclic group and the 3- to 12-membered cyclic amino group have at least one or more secondary nitrogen atoms in the ring, and $R^{3A}$, $R^{3B}$, and $R^{3C}$ are identical or different, and each independently a hydrogen atom, or a $C_{1-6}$alkyl group optionally substituted with one to three substituents selected from the group consisting of a halogen atom, a carboxyl group, —$NR^6R^7$, and —$C_2R^6$;

$R^1$ is a hydrogen atom; and $R^{2A}$, $R^{2B}$, $R^{2C}$, and $R^{2D}$ are all hydrogen atoms.

[Item 56] The compound according to item 1 or 2, or a pharmaceutically acceptable salt thereof,
wherein
$A^1$ and $A^2$ are identical or different, and each independently —$CO_2B$, —$CONR^{3C}B$, or a hydrogen atom, wherein $A^1$ and $A^2$ are not both hydrogen atoms,
wherein
B is
(1) a 3- to 12-membered monocyclic or polycyclic heterocyclic group (the heterocyclic group is optionally substituted with one to three substituents selected from the group consisting of a halogen atom, a carboxyl group, —$NR^6R^7$, and —$CO_2R^6$), or
(2) a group represented by the formula (B),
wherein
X is
(1) a single bond,
(2) $C_{1-6}$alkylene (the alkylene is optionally substituted with one to three substituents selected from the group consisting of a halogen atom, a carboxyl group, —$NR^6R^7$, and —$C_2R^6$),
(3) $C_{3-10}$cycloalkylene (the cycloalkylene is optionally substituted with one to three substituents selected from the group consisting of a halogen atom, a carboxyl group, —$NR^6R^7$, and —$CO_2R^6$),
(4) a 3- to 12-membered monocyclic or polycyclic heterocycle (the heterocycle is optionally substituted with one to three substituents selected from the group consisting of a halogen atom, a carboxyl group, —$NR^6R^7$, and —$CO_2R^6$), or
(5) a 3- to 12-membered cyclic aminyl linker group (the cyclic aminyl linker group is optionally substituted with one to three substituents selected from the group consisting of a halogen atom, a carboxyl group, —$NR^6R^7$, and —$CO_2R^6$),
Y is a single bond or an oxygen atom,
Z is
(1) a single bond,
(2) $C_{1-6}$alkylene (the alkylene is optionally substituted with one to three substituents selected from the group consisting of a halogen atom, a carboxyl group, —$NR^6R^7$, and —$C_2R^6$),
(3) $C_{3-10}$cycloalkylene (the cycloalkylene is optionally substituted with one to three substituents selected from the group consisting of a halogen atom, a carboxyl group, —$NR^6R^7$, and —$C_2R^6$),
(4) a 3- to 12-membered monocyclic or polycyclic heterocycle (the heterocycle is optionally substituted with one to three substituents selected from the group consisting of a halogen atom, a carboxyl group, —$NR^6R^7$, and —$CO_2R^6$), or
(5) a 3- to 12-membered cyclic aminyl linker group (the cyclic aminyl linker group is optionally substituted with one to three substituents selected from the group consisting of a halogen atom, a carboxyl group, —$NR^6R^7$, and —$CO_2R^6$),
n is 0 or 1,
V is
(1) —$NHR^5$,
(2) a 3- to 12-membered monocyclic or polycyclic heterocyclic group (the heterocyclic group is optionally substituted with one to three substituents selected from the group consisting of a halogen atom, a carboxyl group, —$NR^6R^7$, and —$CO_2R^6$), or
(3) a 3- to 12-membered cyclic amino group (the cyclic amino group is optionally substituted with one to three substituents selected from the group consisting of a halogen atom, a carboxyl group, —$NR^6R^7$, and —$CO_2R^6$),
wherein the 3- to 12-membered monocyclic or polycyclic heterocyclic group and the 3- to 12-membered cyclic amino group have at least one or more secondary nitrogen atoms in the ring,
$R^5$ is
(1) a hydrogen atom,
(2) a $C_{1-6}$alkyl group (the alkyl group is optionally substituted with one to three substituents selected from the group consisting of a halogen atom, a carboxyl group, —$NR^6R^7$, and —$C_2R^6$),
(3) a $C_{3-10}$cycloalkyl group (the cycloalkyl group is optionally substituted with one to three substituents selected from the group consisting of a halogen atom, a carboxyl group, —$NR^6R^7$, and —$CO_2R^6$), or
(4) a 3- to 12-membered monocyclic or polycyclic heterocyclic group (the heterocyclic group is optionally substituted with one to three substituents selected from the group consisting of a halogen atom, a carboxyl group, —$NR^6R^7$, and —$CO_2R^6$), and
$R^6$ and $R^7$ are identical or different, and each independently a hydrogen atom, or a $C_{1-6}$alkyl group optionally substituted with one to two groups selected from the group consisting of a carboxyl group, wherein $R^6$ and $R^7$, when both are optionally substituted $C_{1-6}$alkyl groups, may be taken together with the nitrogen atom to which they are attached to form a 3- to 6-membered cyclic amino group, and
wherein
the 3- to 12-membered monocyclic or polycyclic heterocyclic group and the 3- to 12-membered cyclic amino group have at least one or more secondary nitrogen atoms in the ring, and
$R^{3C}$ is a hydrogen atom, or a $C_{1-6}$alkyl group optionally substituted with one to two groups selected from the group consisting of a carboxyl group and —$CO_2R^6$;
$R^1$ is a hydrogen atom; and
$R^{2A}$, $R^{2B}$, $R^{2C}$, and $R^{2D}$ are all hydrogen atoms.
[Item 57] The compound according to item 1, or a pharmaceutically acceptable salt thereof,
wherein
$A^1$ and $A^2$ are identical or different, and each independently —$C(=O)B$, —$CO_2B$, —$CONR^{3C}B$, or a hydrogen atom, wherein $A^1$ and $A^2$ are not both hydrogen atoms,
wherein
B is
(1) a 3- to 6-membered monocyclic or polycyclic heterocyclic group,
(2) a 3- to 6-membered cyclic amino group, or
(3) a group represented by the formula (B),
wherein
X is
(1) a single bond,
(2) $C_{1-6}$alkylene (the alkylene is optionally substituted with one to three substituents selected from the group consisting of a carboxyl group and —$CO_2R^6$), or
(3) $C_{3-10}$cycloalkylene;
Y is a single bond, an oxygen atom, or —$NR^{4A}$—;
$R^{4A}$ is a hydrogen atom;
Z is
(1) a single bond, or
(2) $C_{1-6}$alkylene;
n is 0 or 1;

V is
(1) —NHR$^5$,
(2) a 3- to 6-membered monocyclic or polycyclic heterocyclic group, or
(3) a 3- to 6-membered cyclic amino group, wherein the 3- to 6-membered monocyclic or polycyclic heterocyclic group and the 3- to 6-membered cyclic amino group have at least one or more secondary nitrogen atoms in the ring;

R$^5$ is
(1) a hydrogen atom, or
(2) a C$_{1-6}$alkyl group (the alkyl group is optionally substituted with one to three substituents selected from the group consisting of a halogen atom, a hydroxyl group, a carboxyl group, a sulfinate group, a sulfonate group, a phosphate group, a C$_{6-10}$aryl group, a C$_{1-6}$alkoxy group, a C$_{3-8}$cycloalkoxy group, —NR$^6$R$^7$, —CO$_2$R$^6$, —CONR$^6$R$^7$, —SO$_2$R$^6$, —SO$_2$NR$^6$R$^7$, —OCO$_2$R$^6$, —OCONR$^6$R$^7$, and —NR$^6$CO$_2$R$^7$), and R$^6$ and R$^7$ are identical or different, and each independently a hydrogen atom, or a C$_{1-6}$alkyl group optionally substituted with one to two carboxyl groups, wherein R$^6$ and R$^7$, when both are optionally substituted C$_{1-6}$alkyl groups, may be taken together with the nitrogen atom to which they are attached to form a 3- to 12-membered cyclic amino group, and
wherein
the 3- to 6-membered monocyclic heterocyclic group and the 3- to 6-membered cyclic amino group have at least one or more secondary nitrogen atoms in the ring, and R$^{3C}$ is a hydrogen atom;
R$^1$ is a hydrogen atom;
R$^{2A}$, R$^{2B}$, R$^{2C}$, and R$^{2D}$ are all hydrogen atoms; and
R$^8$ is a methyl group.

[Item 58] The compound according to any one of items 1 to 57, or a pharmaceutically acceptable salt thereof, wherein X is a single bond, or C$_{1-6}$alkylene optionally substituted with one to two substituents selected from the group consisting of a carboxyl group and —CO$_2$R$^6$.

[Item 59] The compound according to any one of items 1 to 58, or a pharmaceutically acceptable salt thereof, wherein B is a 3- to 6-membered monocyclic heterocyclic group, or a group represented by the formula (B), wherein the 3- to 6-membered monocyclic heterocyclic group has at least one or more secondary nitrogen atoms in the ring.

[Item 60] The compound according to any one of items 1 to 59, or a pharmaceutically acceptable salt thereof, wherein V is —NHR$^5$.

[Item 61] The compound according to any one of items 1 to 60, or a pharmaceutically acceptable salt thereof, wherein R$^5$ is a hydrogen atom, or a C$_{1-6}$alkyl group optionally substituted with one to two groups selected from the group consisting of a fluorine atom, a carboxyl group, and —CO$_2$R$^6$.

[Item 62] The compound according to any one of items 1 to 60, or a pharmaceutically acceptable salt thereof, wherein R$^5$ is a hydrogen atom, or C$_{1-6}$alkyl optionally substituted with one to two substituents selected is from the group consisting of a carboxyl group and —CO$_2$R$^6$.

[Item 63] The compound according to any one of items 1 to 62, or a pharmaceutically acceptable salt thereof, wherein R$^6$ and R$^7$ are C$_{1-6}$alkyl groups optionally substituted with one to two carboxyl groups.

[Item 64] The compound according to any one of items 1 to 62, or a pharmaceutically acceptable salt thereof, wherein R$^6$ and R$^7$ are C$_{1-6}$alkyl groups.

[Item 65] The compound according to any one of items 1 to 64, or a pharmaceutically acceptable salt thereof, wherein n is 1.

[Item 66] The compound according to any one of items 1 to 64, or a pharmaceutically acceptable salt thereof, wherein n is 0.

[Item 67] The compound according to any one of items 1 to 66, or a pharmaceutically acceptable salt thereof, wherein A$^1$ and A$^2$ are identical or different, and each independently —CO$_2$B or a hydrogen atom.

[Item 68] The compound according to any one of items 1 to 66, or a pharmaceutically acceptable salt thereof, wherein A$^1$ and A$^2$ are identical or different, and each independently —CONR$^{3C}$B or a hydrogen atom.

[Item 69] The compound according to any one of items 1 to 66, or a pharmaceutically acceptable salt thereof, wherein A$^1$ and A$^2$ are identical or different, and each independently —CONHB or a hydrogen atom.

[Item 70] The compound according to item 1 or 2, or a pharmaceutically acceptable salt thereof,
wherein
A$^1$ and A$^2$ are —CONHB,
wherein
B is a 3- to 6-membered monocyclic heterocyclic group, or a group represented by the formula (B),
wherein
X is C$_{1-6}$alkylene optionally substituted with one to two substituents selected from the group consisting of a carboxyl group and —CO$_2$R$^6$,
n is 0,
V is —NHR$^5$ or a 3- to 6-membered monocyclic heterocyclic group, wherein the 3- to 6-membered monocyclic heterocyclic group has at least one or more secondary nitrogen atoms in the ring,
R$^5$ is a hydrogen atom, or a C$_{1-6}$alkyl group optionally substituted with one to two carboxyl groups, and
R$^6$ is a C$_{1-6}$alkyl group, and
wherein
the 3- to 6-membered monocyclic heterocyclic group has at least one or more secondary nitrogen atoms in the ring;
R$^1$ is a hydrogen atom;
R$^{2A}$, R$^{2B}$, R$^{2C}$, and R$^{2D}$ are all hydrogen atoms.

[Item 71] The compound according to item 1 or 2, or a pharmaceutically acceptable salt thereof, wherein the compound is selected from the following compounds:

2-acetylnaphtho[2,3-b]furan-4,9-diylbis((3-aminopropyl) carbamate),
2-acetylnaphtho[2,3-b]furan-4,9-diylbis((2-aminoethyl)carbamate),
(2S,2'S)-4,4'-((((2-acetylnaphtho[2,3-b]furan-4,9-diyl)bis (oxy))bis(carbonyl))bis(azanediyl))bis(2-(methylamino) butanoic acid),
2,2'-(((((2-acetylnaphtho[2,3-b]furan-4,9-diyl)bis(oxy))bis (carbonyl))bis(azanediyl))bis(ethane-2,1-diyl))bis (azanediyl))diacetic acid,
3,3'-(((((2-acetylnaphtho[2,3-b]furan-4,9-diyl)bis(oxy))bis (carbonyl))bis(azanediyl))bis(ethane-2,1-diyl))bis (azanediyl))dipropionic acid,
(2S,2'S)-3,3'-((((2-acetylnaphtho[2,3-b]furan-4,9-diyl)bis (oxy))bis(carbonyl))bis(azanediyl))bis(2-aminopropionic acid), dimethyl 4,4'-(((((2-acetylnaphtho[2,3-b]furan-4,9-diyl)bis(oxy))bis(carbonyl))bis(azanediyl))(2S,2'S)-bis(2-aminobutanoate),
dimethyl 3,3'-(((((2-acetylnaphtho[2,3-b]furan-4,9-diyl)bis(oxy))bis(carbonyl))bis(azanediyl))(2S,2'S)-bis(2-aminopropanoate),
2,2'-((((((2-acetylnaphtho[2,3-b]furan-4,9-diyl)bis(oxy))bis(carbonyl))bis(azanediyl))bis(propane-3,1-diyl))bis(azanediyl))diacetic acid,
2,2'-((2,2'-((((((2-acetylnaphtho[2,3-b]furan-4,9-diyl)bis(oxy))bis(carbonyl))bis(azanediyl))bis(ethane-2,1-diyl))bis(azanediyl))bis(acetyl))bis(azanediyl))diacetic, acid,
2-acetylnaphtho[2,3-b]furan-4,9-diyl bis((2-((2-(piperidin-1-ylsulfonyl)ethyl)amino)ethyl)carbamate),
2-acetylnaphtho[2,3-b]furan-4,9-diyl bis((2-((2-(N,N-dimethylsulfamoyl)ethyl)amino)ethyl)carbamate),
2-acetylnaphtho[2,3-b]furan-4,9-diyl bis((2-((2-(isopropylsulfonyl)ethyl)amino)ethyl)carbamate),
2-acetylnaphtho[2,3-b]furan-4,9-diyl bis((3-((2-(N,N-dimethylsulfamoyl)ethyl)amino)propyl)carbamate),
2-acetylnaphtho[2,3-b]furan-4,9-diyl bis((3-((2-(methylsulfonyl)ethyl)amino)propyl)carbamate),
2-acetylnaphtho[2,3-b]furan-4,9-diyl bis((2-((2-(methylsulfonyl)ethyl)amino)ethyl)carbamate),
2-acetylnaphtho[2,3-b]furan-4,9-diyl bis((2-((2-(azetidin-1-yl)-2-oxoethyl)amino)ethyl)carbamate),
2-acetylnaphtho[2,3-b]furan-4,9-diyl bis((3-((2-(azetidin-1-yl)-2-oxoethyl)amino)propyl)carbamate),
2,2'-((2,2'-((((((2-acetylnaphtho[2,3-b]furan-4,9-diyl)bis(oxy))bis(carbonyl))bis(azanediyl))bis(propane-3,1-diyl))bis(azanediyl))bis(acetyl))bis(azane diyl))diacetic acid,
2-acetylnaphtho[2,3-b]furan-4,9-diyl bis((2-((2-(carbamoyloxy)ethyl)amino)ethyl)carbamate),
2-acetylnaphtho[2,3-b]furan-4,9-diyl bis((3-((2-(carbamoyloxy)ethyl)amino)propyl)carbamate),
2-acetylnaphtho[2,3-b]furan-4,9-diyl bis((2-((2-((methoxycarbonyl)amino)ethyl)amino)ethyl)carbamate),
2-acetylnaphtho[2,3-b]furan-4,9-diyl bis((3-((2-((methoxycarbonyl)amino)ethyl)amino)propyl)carbamate),
2-acetylnaphtho[2,3-b]furan-4,9-diyl bis((2-((2-((methoxycarbonyl)oxy)ethyl)amino)ethyl)carbamate),
2-acetylnaphtho[2,3-b]furan-4,9-diyl bis((3-((2-((methoxycarbonyl)oxy)ethyl)amino)propyl)carbamate),
2-acetyl-4-hydroxynaphtho[2,3-b]furan-9-yl (3-((2-(N,N-dimethylsulfamoyl)ethyl)amino)propyl)carbamate,
2-acetyl-4-hydroxynaphtho[2,3-b]furan-9-yl (3-((2-(methylsulfonyl)ethyl)amino)propyl)carbamate,
(3-(((((2-acetyl-4-hydroxynaphtho[2,3-b]furan-9-yl)oxy)carbonyl)amino)propyl)glycylglycine,
2-acetyl-4-hydroxynaphtho[2,3-b]furan-9-yl (3-((2-(azetidin-1-yl)-2-oxoethyl)amino)propyl)carbamate,
2-acetyl-4-hydroxynaphtho[2,3-b]furan-9-yl (3-((2-(carbamoyloxy)ethyl)amino)propyl)carbamate,
2-acetyl-4-hydroxynaphtho[2,3-b]furan-9-yl (3-((2-((methoxycarbonyl)amino)ethyl)amino)propyl)carbamate, and
2-acetyl-4-hydroxynaphtho[2,3-b]furan-9-yl (3-((2-((methoxycarbonyl)oxy)ethyl)amino)propyl)carbamate.
[Item 72] The compound according to item 1 or 2, or a pharmaceutically acceptable salt thereof, wherein the compound is selected from the following compounds:
2,2'-((((((2-acetylnaphtho[2,3-b]furan-4,9-diyl)bis(oxy))bis(carbonyl))bis(azanediyl))bis(ethane-2,1-diyl))bis(azanediyl))diacetic acid,
3,3'-((((((2-acetylnaphtho[2,3-b]furan-4,9-diyl)bis(oxy))bis(carbonyl))bis(azanediyl))bis(ethane-2,1-diyl))bis(azanediyl))dipropionic acid,
dimethyl 4,4'-(((((2-acetylnaphtho[2,3-b]furan-4,9-diyl)bis(oxy))bis(carbonyl))bis(azanediyl))(2S,2'S)-bis(2-aminobutanoate),
2,2'-((((((2-acetylnaphtho[2,3-b]furan-4,9-diyl)bis(oxy))bis(carbonyl))bis(azanediyl))bis(propane-3,1-diyl))bis(azanediyl))diacetic acid,
2-acetylnaphtho[2,3-b]furan-4,9-diyl bis((2-((2-(N,N-dimethylsulfamoyl)ethyl)amino)ethyl)carbamate),
2-acetylnaphtho[2,3-b]furan-4,9-diyl bis((2-((2-(isopropylsulfonyl)ethyl)amino)ethyl)carbamate),
2-acetylnaphtho[2,3-b]furan-4,9-diyl bis((2-((2-(methylsulfonyl)ethyl)amino)ethyl)carbamate),
2-acetylnaphtho[2,3-b]furan-4,9-diyl bis((2-((2-(azetidin-1-yl)-2-oxoethyl)amino)ethyl)carbamate)),
2-acetylnaphtho[2,3-b]furan-4,9-diyl bis((2-((2-(carbamoyloxy)ethyl)amino)ethyl)carbamate),
2-acetylnaphtho[2,3-b]furan-4,9-diyl bis((2-((2-((methoxycarbonyl)amino)ethyl)amino)ethyl)carbamate), and
2-acetylnaphtho[2,3-b]furan-4,9-diyl bis((2-((2-((methoxycarbonyl)oxy)ethyl)amino)ethyl)carbamate).
[Item 73] The compound according to item 1 or 2, or a pharmaceutically acceptable salt thereof, wherein the compound is selected from the following compounds:
2,2'-((((((2-acetylnaphtho[2,3-b]furan-4,9-diyl)bis(oxy))bis(carbonyl))-bis (azanediyl))bis(ethane-2,1-diyl))bis(azanediyl))diacetic acid,
3,3'-((((((2-acetylnaphtho[2,3-b]furan-4,9-diyl)bis(oxy))bis(carbonyl))-bis (azanediyl))bis(ethane-2,1-diyl))bis(azanediyl))dipropionic acid, and
dimethyl 4,4'-(((((2-acetylnaphtho[2,3-b]furan-4,9-diyl)bis(oxy))bis-(carbonyl))bis (azanediyl))(2S,2'S)-bis(2-aminobutanoate).
[Item 74] The compound according to item 1 or 2, or a pharmaceutically acceptable salt thereof, wherein the compound is 2,2'-((((((2-acetylnaphtho[2,3-b]furan-4,9-diyl)bis(oxy))bis(carbonyl))bis (azanediyl))bis(ethane-2,1-diyl))bis(azanediyl))diacetic acid.
[Item 75] The compound according to item 1 or 2, or a pharmaceutically acceptable salt thereof, wherein the compound is 3,3'-((((((2-acetylnaphtho[2,3-b]furan-4,9-diyl)bis(oxy))bis(carbonyl))bis(azanediyl)) bis(ethane-2,1-diyl))bis(azanediyl))dipropionic acid.
[Item 76] The compound according to item 1 or 2, or a pharmaceutically acceptable salt thereof, wherein the compound is dimethyl 4,4'-(((((2-acetylnaphtho[2,3-b]furan-4,9-diyl)bis(oxy))bis(carbonyl))bis(azanediyl)) (2S,2'S)-bis(2-aminobutanoate).
[Item 77] The compound according to item 1 or 2, which is dimethyl 4,4'-(((((2-acetylnaphtho[2,3-b]furan-4,9-diyl)bis(oxy))bis(carbonyl)bis-(azanediyl))(2S,2'S)-bis(2-aminobutanoate) dihydrochloride.
[Item 78] The compound according to item 1 or 2, which is 2,2'-((((((2-acetylnaphtho[2,3-b]furan-4,9-diyl)bis(oxy))bis(carbonyl)-bis(azanediyl))bis(ethane-2,1-diyl))bis(azanediyl))diacetic acid dihydrochloride.
[Item 79] The compound according to item 1 or 2, which is 3,3'-((((((2-acetylnaphtho[2,3-b]furan-4,9-diyl)bis(oxy))bis(carbonyl))bis-(azanediyl))bis(ethane-2,1-diyl))bis(azanediyl))dipropionic acid dihydrochloride.
[Item 80] The compound according to item 1 or 2, which is 2,2'-((((((2-acetylnaphtho[2,3-b]furan-4,9-diyl)bis(oxy))bis(carbonyl)-bis(azanediyl))bis(ethane-2,1-diyl))bis(azanediyl))diacetic acid monohydrochloride dihydrate.

[Item 81] The compound according to item 1 or 2, which is 2,2'-[(2-acetylnaphtho[2,3-b]furan-4,9-diyl)bis(oxycarbonyliminoethane-2,1-diylimino)]diacetic acid dimethanesulfonate salt monohydrate.

[Item 82] The compound according to item 1 or 2, which is dimethyl 4,4'-(((((2-acetylnaphtho[2,3-b]furan-4,9-diyl)bis(oxy))bis(carbonyl))bis-(azanediyl))(2S,2'S)-bis(2-aminobutanoate)dimethanesulfonate salt.

[Item 83] The compound according to item 1 or 2, which is dimethyl 4,4'-(((((2-acetylnaphtho[2,3-b]furan-4,9-diyl)bis(oxy))bis(carbonyl))bis-(azanediyl))(2S,2'S)-bis(2-aminobutanoate)ditoluenesulfonate salt monohydrate.

[Item 84] The compound according to item 1 or 2, which is dimethyl 4,4'-(((((2-acetylnaphtho[2,3-b]furan-4,9-diyl)bis(oxy))bis(carbonyl))bis-(azanediyl))(2S,2'S)-bis(2-aminobutanoate) dibenzenesulfonate salt.

[Item 85] The compound according to item 1 or 2, which is 3,3'-(((((((2-acetylnaphtho[2,3-b]furan-4,9-diyl)bis(oxy))bis(carbonyl))-bis(azanediyl))bis(ethane-2,1-diyl))bis(azanediyl))dipropionic acid dimethanesulfonate salt monohydrate.

[Item 86] The compound according to item 1 or 2, which is 3,3'-(((((((2-acetylnaphtho[2,3-b]furan-4,9-diyl)bis(oxy))bis(carbonyl))-bis(azanediyl))bis(ethane-2,1-diyl))bis(azanediyl))dipropionic acid ditoluenesulfonate salt monohydrate.

[Item 87] The compound according to item 1 or 2, which is 3,3'-(((((((2-acetylnaphtho[2,3-b]furan-4,9-diyl)bis(oxy))bis(carbonyl))-bis(azanediyl))bis(ethane-2,1-diyl))bis(azanediyl))dipropionic acid dibenzenesulfonate salt.

[Item 88] A pharmaceutical composition comprising a compound according to any one of items 1 to 87, or a pharmaceutically acceptable salt thereof.

[Item 89] A therapeutic agent and/or prophylactic agent for cancer, wherein the agent comprises a compound according to any one of items 1 to 87, or a pharmaceutically acceptable salt thereof as an active ingredient, or the agent comprises a pharmaceutical composition according to item 88.

[Item 90] The therapeutic agent and/or prophylactic agent according to item 89, wherein the cancer is at least one type of cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

[Item 91] A method for treating and/or preventing a cancer, characterized by administering to a patient in need thereof a therapeutically and/or prophylactically effective amount of a compound according to any one of items 1 to 87, or a pharmaceutically acceptable salt thereof, a pharmaceutical composition according to item 88 or a therapeutic agent and/or prophylactic agent according to item 89 or 90.

[Item 92] The method for treating and/or preventing according to item 91, wherein the cancer is at least one type of cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

[Item 93] The use of a compound according to any one of items 1 to 87, or a pharmaceutically acceptable salt thereof, or a pharmaceutical composition according to item 88, for the manufacture of a therapeutic agent and/or prophylactic agent for cancer.

[Item 94] The use of a compound according to item 93, or a pharmaceutically acceptable salt thereof, wherein the cancer is at least one type of cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

[Item 95] The compound according to any one of items 1 to 87, or a pharmaceutically acceptable salt thereof, or a pharmaceutical composition according to item 88, for use in treating and/or preventing cancer.

[Item 96] The compound, or a pharmaceutically acceptable salt thereof, or the pharmaceutical composition according to item 95, wherein the cancer is at least one type of cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

[Item 97] A pharmaceutical composition for treating and/or preventing a cancer, wherein the pharmaceutical composition comprises:

(a) a composition comprising a first active substance consisting of a compound according to any one of items 1 to 87 or a pharmaceutically acceptable salt thereof; and (b) a composition comprising a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 98] A pharmaceutical composition for treating and/or preventing a cancer, comprising (a) a first active substance consisting of a compound according to any one of items 1 to 87 or a pharmaceutically acceptable salt thereof, wherein the pharmaceutical composition is characterized in that the first active substance is administered in combination with (b) a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 99] A pharmaceutical composition for treating and/or preventing a cancer, comprising (a) a second active substance selected from the group consisting of a chemotherapeutic agent, a hormonal therapeutic agent, an immunotherapeutic agent, a biological agent, a cell growth factor inhibitor, and a cell growth factor receptor inhibitor, wherein the pharmaceutical composition is characterized in that the second active substance is administered in combination with (b) a first active substance consisting of a compound according to any one of items 1 to 87 or a pharmaceutically acceptable salt thereof.

[Item 100] The pharmaceutical composition according to any one of items 97 to 99, which is a kit.

[Item 101] The pharmaceutical composition according to any one of items 97 to 100, characterized by administering the first active substance and the second active substance in combination simultaneously, separately, or sequentially or over time.

[Item 102] The pharmaceutical composition according to any one of items 97 to 100, wherein the chemotherapeutic agent is an alkylating agent, an antimetabolite, a topoisomerase inhibiting drug, a DNA intercalator, an antimitotic agent, an anticancer antibiotic, a plant-derived anticancer agent, an epigenome drug, an immunomodulator, a molecule-targeting therapeutic drug, an angiogenesis inhibitor, or an other chemotherapeutic agent.

[Item 103] The pharmaceutical composition according to any one of items 97 to 102, wherein the alkylating agent is selected from the consisting of Nitrogen mustard, Nitrogen mustard N-oxide hydrochloride, Chlorambucil, Cyclophosphamide, Ifosfamide, Thiotepa, Carboquone, Improsulfan tosylate, Busulfan, Nimustine hydrochloride, Mitobronitol, Melphalan, Dacarbazine, Ranimustine, Estramustine phosphate sodium, Triethylenemelamine, Carmustine, Lomustine, Streptozocin, Pipobroman, Etoglucide, Carboplatin, Cisplatin, Miboplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, Adozelesin, Cystemustine, Bizelesin, Mechlorethamine, Uracil mustard, Streptozocin, Satraplatin, Trabectedin, Becatecarin, Chlormethine, Bendamustine, Uramustine, Semustine, Triplatin tetranitrate, Mannosulfan, Triaziquon, Procarbazine, Canfosfamide, and nitrosourea.

[Item 104] The pharmaceutical composition according to any one of items 97 to 103, wherein the antimetabolite is a folic acid antagonist, a pyrimidine metabolism-inhibiting drug, a purine metabolism-inhibiting drug, a ribonucleotide reductase inhibiting drug, or a nucleotide analog.

[Item 105] The pharmaceutical composition according to any one of items 97 to 103, wherein the antimetabolite is selected from the group consisting of Mercaptopurine, 6-Mercaptopurine riboside, Thioinosine, Methotrexate, Pemetrexed, Enocitabine, Cytarabine, Cytarabin ocfosfate, Ancitabine hydrochloride, Fluorouracil, Tegafur, UFT, Doxifluridine, Carmofur, Galocitabine, Emitefur, Capecitabine, Aminopterin, Nelzarabine, Leucovorin calcium, tabloid, Butocin, calcium folinate, calcium levofolinate, Cladribine, Emitefur, Fludarabine, Gemcitabine, hydroxycarbamide, Pentostatin, Piritrexim, Idoxuridine, Mitoguazone, Tiazofurin, Ambamustine, Bendamustine, Floxuridine, Nelarabine, Leucovorin, Hydroxyurea, Thioguanine, Asparaginase, Bortezomib, Raltitrexed, Clofarabine, Enocitabine, Sapacitabine, Azacytidine, Sulfadiazine, Sulfamethoxazole, and Trimethoprim.

[Item 106] The pharmaceutical composition according to any one of items 97 to 105, wherein the topoisomerase inhibiting drug is selected from the group consisting of Doxorubicin, Daunorubicin, Epirubicin, Idarubicin, Anthracenedione, Mitoxantrone, Mitomycin C, Bleomycin, Dactinomycin, Plicamycin, Irinotecan, Camptothecin, Rubitecan, Belotecan, Etoposide, Teniposide, Topotecan, and Amsacrine.

[Item 107] The pharmaceutical composition according to any one of items 97 to 106, wherein the DNA intercalator is selected from the group consisting of Proflavine, Doxorubicin (Adriamycin), Daunorubicin, Dactinomycin, and Thalidomide.

[Item 108] The pharmaceutical composition according to any one of items 97 to 107, wherein the antimitotic agent is selected from the group consisting of Paclitaxel, DHA Paclitaxel, Paclitaxel Polyglutamate, Nab-paclitaxel, Paclitaxel Micelle, 7α-Glucosyloxyacetylpaclitaxel, BMS-275183, Docetaxel, Vinorelbine, Vincristine, Vinblastine, Vindesine, Vinzolidine, Etoposide, Teniposide, Ixabepilone, Larotaxel, Ortataxel, Tesetaxel, Ispinesib, Colchicine, and Vinflunine.

[Item 109] The pharmaceutical composition according to any one of items 97 to 108, wherein the anticancer antibiotic is selected from the group consisting of Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Idarubicin hydrochloride, and mithramycin.

[Item 110] The pharmaceutical composition according to any one of items 97 to 109, wherein the plant-derived anticancer agent is selected from the group consisting of Etoposide, Etoposide phosphate, Vinblastine sulfate, Vincristine sulfate, Vindesine sulfate, Teniposide, Paclitaxel, Docetaxel, DJ-927, Vinorelbine, Irinotecan, and Topotecan.

[Item 111] The pharmaceutical composition according to any one of items 97 to 110, wherein the epigenome drug is selected from the group consisting of Vorinostat, Belinostat, Entinostat, Romidepsin, Azacytidine, and Decitabine.

[Item 112] The pharmaceutical composition according to any one of items 97 to 111, wherein the immunomodulator is selected from the group consisting of Thalidomide, Lenalidomide, and Pomalidomide.

[Item 113] The pharmaceutical composition according to any one of items 97 to 112, wherein the molecule-targeting therapeutic drug is selected from the group consisting of a kinase inhibitor, a proteasome inhibitor, a monoclonal antibody, a mTOR inhibitor, a TNF inhibiting drug, and a T-cell inhibiting drug.

[Item 114] The pharmaceutical composition according to any one of items 97 to 113, wherein the kinase inhibitor is a tyrosine kinase inhibitor, a serine/threonine kinase inhibitor, a Raf kinase inhibitor, a CDK inhibitor, or a MEK inhibitor.

[Item 115] The pharmaceutical composition according to any one of items 97 to 113, wherein the kinase inhibitor is selected from the group consisting of Imatinib, Gefitinib, Erlotinib, Afatinib, Dasatinib, Bosutinib, Vandetanib, Sunitinib, Axitinib, Pazopanib, Lenvatinib, Lapatinib, Nintedanib, Nilotinib, Crizotinib, Ceritinib, Alectinib, Ruxolitinib, Tofacitinib, Ibrutinib, Sorafenib, Vemurafenib, Dabrafenib, Palbociclib, Trametinib, Regorafenib, Cediranib, Lestaurtinib, Vandetinib, Vatalanib, Seliciclib, Tivantinib, Canertinib, Pelitinib, Tesevatinib, Motesanib, Midostaurin, Foretinib, Cabozantinib, Selumetinib, Neratinib, Volasertib, Saracatinib, Enzastaurin, Tandutinib, Semaxanib, Alvocidib, ICR-62, AEE788, PD0325901, PD153035, TK787, and BBI503.

[Item 116] The pharmaceutical composition according to any one of items 97 to 115, wherein the proteasome inhibitor is selected from the group consisting of Bortezomib and Carfilzomib.

[Item 117] The pharmaceutical composition according to any one of items 97 to 116, wherein the monoclonal antibody is selected from the group consisting of an anti-CD22 antibody, an anti-CD20 antibody, an anti-CD25 antibody, an anti-CD30 antibody, an anti-CD33 antibody, an anti-CD5 antibody, an anti-CD52 antibody, an anti-epidermal growth factor receptor antibody, an anti-endothelial cell growth factor antibody, an anti-TNF-α antibody, an anti-IL-1 receptor antibody, an anti-IL-2 receptor antibody, an anti-IL-5 receptor antibody, an anti-IL-6 receptor antibody, an anti-HER2 antibody, an anti-IgE antibody, an anti-IgG antibody, an anti-RS virus antibody, an anti-CCR4 antibody, an anti-CTLA-4 antibody, an anti-PD-1 antibody, an anti-RANKL antibody, or an anti-c-Met antibody.

[Item 118] The pharmaceutical composition according to any one of items 97 to 117, wherein the monoclonal antibody is selected from the group consisting of Ibritumomab tiuxetan, Rituximab, Cetuximab, Infliximab, Basiliximab, Brentuximab vedotin, Tocilizumab, Trastuzumab, Bevacizumab, Omalizumab, Mepolizumab, Gemtuzumab ozogamicin, Palivizumab, Ranibizumab, Certolizumab, Ocrelizumab, Mogamulizumab, Eculizumab, Pertuzumab, Alemtuzumab, Inotuzumab, Panitumumab, Ofatumumab, Golimumab, Adalimumab, Ramucirumab, Nivolumab, Infliximab, Anakinra, Denosumab, Ipilimumab, Pembrolizumab, and matuzumab.

[Item 119] The pharmaceutical composition according to any one of items 97 to 118, wherein the mTOR inhibitor is selected from the group consisting of Everolimus, Rapamycin, and Temsirolimus.

[Item 120] The pharmaceutical composition according to any one of items 97 to 119, wherein the TNF inhibiting drug is Etanercept.

[Item 121] The pharmaceutical composition according to any one of items 97 to 120, wherein the T-cell inhibiting drug is Abatacept.

[Item 122] The pharmaceutical composition according to any one of items 97 to 121, wherein the angiogenesis inhibitor is selected from the group consisting of CM101, IFN-α, IL-12, platelet factor-4, Suramin, Semaxanib, Thrombospondin, a VEGFR antagonist, an angiogenesis inhibiting steroid plus heparin, cartilage-derived angiogenesis inhibitory factor, a matrix metalloproteinase inhibitor, Batimastat, Marimastat, Angiostatin, Endostatin, 2-methoxyestradiol, Tecogalan, Thrombospondin, an αVβ3 inhibitor, Linomide, and ADH-1.

[Item 123] The pharmaceutical composition according to any one of items 97 to 122, wherein the other chemotherapeutic agent is selected from the group consisting of Sobuzoxane, Obatoclax, Efaproxiral, Tipifarnib, and Lonafarnib.

[Item 124] The pharmaceutical composition according to any one of items 97 to 123, wherein the "hormonal therapeutic agent" is selected from the group consisting of Fosfestrol, Diethylstilbestrol, Fluoxymesterone, Chlorotrianisene, Medroxyprogesterone acetate, Megestrol acetate, Chlormadinone acetate, Cyproterone acetate, Danazol, Dienogest, Asoprisnil, Allylestrenol, Gestrinone, Nomegestrol, Tadenan, Mepartricin, Raloxifene, Ormeloxifene, Levormeloxifene, Tamoxifen citrate, Toremifene citrate, Idoxifene, a pill formulation, Mepitiostane, Testololactone, Aminoglutethimide, Goserelin acetate, Buserelin, Leuprorelin, Leuprolide, Droloxifene, Epitiostanol, Ethynylestradiol sulfonate, Fadrozole hydrochloride, Anastrozole, Tetrazole, Ketoconazole, Letrozole, Exemestane, Vorozole, Formestane, Exemestane, Flutamide, Bicalutamide, Nilutamide, Enzalutamide, Mifepristone, Finasteride, Dexamethasone, Prednisolone, Betamethasone, Triamcinolone, Abiraterone, Liarozole, Bexarotene, and DN101.

[Item 125] The pharmaceutical composition according to any one of items 97 to 124, wherein the immunotherapeutic agent is selected from the group consisting of Picibanil, Krestin, Schizophyllan, Lentinan, Ubenimex, an interferon, an interleukin, macrophage colony stimulating factor, granulocyte colony stimulating factor, erythropoietin, lymphotoxin, BCG vaccine, *Corynebacterium parvum*, Levamisole, Polysaccharide K, Procodazole, an anti-CTLA4 antibody, a PD-1 antibody, and Toll-like Receptors agonist.

[Item 126] The pharmaceutical composition according to any one of items 97 to 125, wherein the biological agent is selected from the group consisting of Interleukin-2, Interferon-α, Interferon-β, Interferon-γ, Erythropoietin, Filgrastim, granulocytes, Sargramostim, IL13-PE38QQR, *Bacillus* Calmette-Guerin, Levamisole, Octreotide, CPG7909, Provenge, GVAX, Myvax, Favld, Lenalidomide, Trastuzumab, Rituximab, Gemtuzumab ozogamicin, Alemtuzumab, Endostatin, Ibritumomab tiuxetan, Tositumomab, Cetuximab, Zanolimumab, Ofatumumab, HGS-ETR1, Pertuzumab, M200, SGN-30, Matuzumab, Adecatumumab, Denosumab, Zalutumumab, MDX-060, Nimotuzumab, MORAb-003, Vitaxin, MDX-101, MDX-010, a DPC4 antibody, a NF-1 antibody, a NF-2 antibody, a Rb antibody, a p53 antibody, a WT1 antibody, a BRCA1 antibody, a BRCA2 antibody, Ganglioside, a prostate-specific antigen, α-Fetoprotein, a carcinoembryonic antigen, a melanoma-associated antigen, and Papilloma virus E6 and E7 fragments.

[Item 127] The pharmaceutical composition according to any one of items 97 to 126, wherein the cell growth factor inhibitor is selected from the group consisting of a epidermal growth factor inhibitor, an insulin-like growth factor inhibitor, a nerve growth factor inhibitor, a brain-derived neurotrophic factor inhibitor, an endothelial cell growth factor inhibitor, a colony stimulating factor inhibitor, a platelet-derived growth factor inhibitor, an Erythropoietin inhibitor, a fibroblast growth factor inhibitor, a hepatocyte growth factor inhibitor, a heregulin inhibitor, and an Angiopoietin inhibitor.

[Item 128] The pharmaceutical composition according to any one of items 97 to 127, wherein the cell growth factor receptor inhibitor is selected from the group consisting of an epidermal growth factor receptor inhibitor, an insulin-like growth factor receptor inhibitor, a nerve growth factor receptor inhibitor, a brain-derived neurotrophic factor receptor inhibitor, an endothelial cell growth factor inhibitor, a colony stimulating factor inhibitor, a platelet-derived growth factor receptor inhibitor, an Erythropoietin receptor inhibitor, a fibroblast growth factor receptor inhibitor, a hepatocyte growth factor receptor inhibitor, a heregulin receptor inhibitor, and an Angiopoietin receptor inhibitor.

[Item 129] The pharmaceutical composition according to any one of items 97 to 128, wherein the second active substance is a chemotherapeutic agent or a hormonal therapeutic agent.

[Item 130] The pharmaceutical composition according to any one of items 97 to 101, wherein the second active substance is selected from the group consisting of Cisplatin, Oxaliplatin, Temozolomide, Pemetrexed, Fluorouracil, Capecitabine, Gemcitabine, Leucovorin, Bortezomib, Irinotecan, Paclitaxel, Imatinib, Ibrutinib, Sorafenib, Regorafenib, Bortezomib, Cetuximab, Bevacizumab, Panitumumab, Nivolumab, Ipilimumab, Pembrolizumab, and Dexamethasone.

[Item 131] The pharmaceutical composition according to any one of items 97 to 130, wherein the cancer is at least one type of cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

[Item 132] The pharmaceutical composition according to any one of items 97 to 131, wherein the first active substance is administered prior to the second active substance or the second active substance is administered prior to the first active substance.

[Item 133] The pharmaceutical composition according to any one of items 97 to 131, characterized in that the second active substance or the first active substance is administered between administrations of the first active substance or the second active substance, respectively.

[Item 134] A method for treating and/or preventing a cancer in a subject in need thereof, comprising:
(a) a step of administering to the subject a first active substance consisting of a compound according to any one of items 1 to 87, or a pharmaceutically acceptable salt thereof; and
(b) a step of administering to the subject a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 135] A method for treating and/or preventing a cancer in a subject in need thereof, comprising a step of administering to the subject (a) a first active substance consisting of a compound according to any one of items 1 to 87 or a pharmaceutically acceptable salt thereof in combination with (b) a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 136] The method according to item 134 or 135, characterized by administering to the subject the first active substance and the second active substance in combination simultaneously, separately, sequentially or over time.

[Item 137] The method according to any one of items 134 to 136, wherein the first active substance is administered prior to the second active substance or the second active substance is administered prior to the first active substance.

[Item 138] The method according to any one of items 134 to 136, wherein the administration of the first active substance and the administration of the second active substance are carried out simultaneously.

[Item 139] The method according to any one of items 134 to 138, wherein the first active substance and the second active substance are administered in therapeutically and/or prophylactically effective amounts.

[Item 140] The method according to any one of items 134 to 139, wherein the amount of the first active substance administered and/or the amount of the second active substance administered are less than a therapeutically and/or prophylactically effective amount when administered alone, however, both are administered in therapeutically and/or prophylactically effective amounts when they are combined.

[Item 141] The method according to any one of items 134 to 140, further having the characteristic(s) in any one or more of items 102 to 133.

[Item 142] The compound according to any one of items 1 to 87 or a pharmaceutically acceptable salt thereof, for use as a medicament.

[Item 143] The compound according to any one of items 1 to 87 or a pharmaceutically acceptable salt thereof, for the treatment and/or prevention or prophylaxis of a cancer.

[Item 144] The compound according to item 143 or a pharmaceutically acceptable salt thereof, wherein the cancer is at least one type of cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

[Item 145] A combination for treating and/or preventing a cancer, comprising:
(a) a first active substance consisting of a compound according to any one of items 1 to 87 or a pharmaceutically acceptable salt thereof; and
(b) a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 146] (a) A first active substance consisting of a compound according to any one of items 1 to 87 or a pharmaceutically acceptable salt thereof, for treating and/or preventing a cancer, characterized in that the first active substance is administered in combination with (b) a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 147] (a) A second active substance selected from the group consisting of a hormonal therapeutic agent, an immunotherapeutic agent, a biological agent, a cell growth factor inhibitor, and a cell growth factor receptor inhibitor, for treating and/or preventing a cancer, characterized in that the second active substance is administered in combination with (b) a first active substance consisting of a compound according to any one of items 1 to 87 or a pharmaceutically acceptable salt thereof.

[Item 148] The combination according to item 145, the first active substance according to item 146, or the second active substance according to item 147, further having the characteristic(s) according to any one or more of items 100 to 133.

[Item 149] Use of a combination comprising (a) a first active substance consisting of a compound according to any one of items 1 to 87 or a pharmaceutically acceptable salt thereof, and (b) a second active substance selected from the group consisting of a chemotherapeutic agent, a hormonal therapeutic agent, an immunotherapeutic agent, a biological agent, a cell growth factor inhibitor, and a cell growth factor receptor inhibitor, in the manufacture of a medicament for treating and/or preventing a cancer.

[Item 150] Use of (a) a first active substance consisting of a compound according to any one of items 1 to 87 or a pharmaceutically acceptable salt thereof, in the manufacture of a medicament for treating and/or preventing a cancer, characterized in that the first active substance is administered in combination with (b) a second active substance selected from the group consisting of a chemotherapeutic agent, a hormonal therapeutic agent, an immunotherapeutic agent, a biological agent, a cell growth factor inhibitor, and a cell growth factor receptor inhibitor.

[Item 151] The use of (a) a second active substance selected from the group consisting of a hormonal therapeutic agent, an immunotherapeutic agent, a biological agent, a cell growth factor inhibitor, and a cell growth factor receptor inhibitor, in the manufacture of a medicament for treating and/or preventing a cancer, characterized in that the second active substance is administered in combination with (b) a first active substance consisting of a compound according to any one of items 1 to 87 or a pharmaceutically acceptable salt thereof.

[Item 152] The use according to any one of items 149 to 151, further having the characteristic(s) according to any one or more of items 100 to 133.

Other than the above, the present invention also provides treatment methods, prevention or prophylaxis methods, uses, and the like using a compound of the present invention, or a pharmaceutically acceptable salt thereof, a pharmaceutical composition thereof, a therapeutic agent, or a prophylactic agent, and further details and embodiments of these methods and uses can be understood by those skilled in the art from the description of the present specification.

It is understood that one or a plurality of the above-mentioned characteristics can be further combined and used. These still further embodiments and advantages of the present invention will be recognized by those skilled in the art if the following detailed descriptions are read and understood as necessary.

Advantageous Effects of Invention

Since 2-acetylnaphtho[2,3-b]furan-4,9-dione targets a cancer stem cell in addition to a conventional cancer cell, it is expected as a novel anticancer agent. However, since 2-acetylnaphtho[2,3-b]furan-4,9-dione has high crystallizability, its absorption in oral administration is an object as well as its use in parenteral administration has been limited. The compound represented by formula (1A) or (1) or a pharmaceutically acceptable salt thereof (optionally, also referred to as the present compound) is a water-soluble prodrug of 2-acetylnaphtho[2,3-b]furan-4,9-dione. Due to its high water-solubility, it is useful as a medicament to be successful in prevention or prophylaxis and/or treatment of cancer as an oral agent and an agent for intravenous administration.

DESCRIPTION OF EMBODIMENTS

Since the compound of the present invention may be present in the form of a hydrate and/or a solvate, hydrates and/or solvates of the compound represented by formula (1A) or (1) or a pharmaceutically acceptable salt thereof are also encompassed by the present compound.

Since the compound represented by formula (1A) or (1) may have one, or optionally one or more, asymmetric carbon atom(s), and may result in geometrical isomerism or axial chirality, it may be present as several types of stereoisomers. In the present invention, these stereoisomers, and mixtures and racemates thereof are also encompassed by the present compound.

Further, a deuterated form in which any one or two or more $^1$H of a compound represented by formula (1A) or (1) has been converted to $^2$H (D) is encompassed by the compound represented by formula (1A) or (1).

Compounds represented by formula (1A) or (1) or pharmaceutically acceptable salts thereof obtained as crystal may be present as crystalline polymorphism, and those in any crystalline forms are encompassed by the present compound.

Next, the terms in the present specification are described below.

In the present specification, the number of substituents of a group defined by "optionally substituted" or "substituted" is not particularly limited if it is substitutable, and is one or plural. In addition, unless otherwise indicated, the description for each group is also applied when the group is one part of or a substituent on other groups.

Examples of the substituents in the present invention include a hydroxyl group, a carboxyl group, a sulfinate group, a sulfonate group, a phosphate group, a guanidine group, a cyano group, a nitro group, a halogen atom, an alkyl group, an alkylthio group, an alkenyl group, an alkynyl group, a cycloalkyl group, a cycloalkylcarbonyl group, a cycloalkylsulfinyl group, an alkoxy group, a cycloalkoxy group, an alkoxycarbonyl group, an alkylcarbonyl group, an aryl group, an arylcarbonyl group, a heteroaryl group, a heterocyclic group, an amino group, an aminocarbonyl group, an aminosulfinyl group, an aminosulfonyl group, a heterocyclyloxy group, a heterocyclylthio group, a heterocyclyloxycarbonyl group, a heterocyclylsulfinyl group, a heterocyclylsulfonyl group, a heterocyclylcarbonyl group, an alkylsulfonyl group, an arylsulfonyl group, an alkoxycarbonyloxy group, an aminocarbonyloxy group, and alkoxycarbonylamino group. The substituents may be further substituted with a substituent(s) described above.

In the present specification, examples of a "halogen atom" include a fluorine atom, a chlorine atom, a bromine atom, and an iodine atom. Preferred is a fluorine atom or a chlorine atom. Further preferred is a fluorine atom.

An "alkyl group" means a linear or branched, saturated hydrocarbon group, and for example, a "$C_{1-4}$ alkyl group" or a "C alkyl group" means an alkyl group having one to four or six carbon atoms. The same applies to cases of other numbers.

A "$C_{1-10}$alkyl group" includes, preferably a "$C_{1-6}$alkyl group", and further preferably a "$C_{1-4}$ alkyl group". Specific examples of the "$C_{1-10}$alkyl group" include, for example, a methyl group, an ethyl group, a propyl group, a 1-methylethyl group, a butyl group, a 2-methylpropyl group, a 1-methylpropyl group, a 1,1-dimethylethyl group, a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a hexyl group, a heptyl group, an octyl group, a nonyl group, a decyl group, and the like. Specific examples of the "$C_{1-6}$alkyl group" include examples of those having one to six carbon atoms in the specific examples of the "C$_{1-10}$alkyl group". Specific examples of the "C$_{1-4}$ alkyl group" include examples of those having one to four carbon atoms in the specific examples of the "C$_{1-10}$alkyl group".

The "C$_{1-6}$alkyl" moiety of the "C$_{1-6}$alkylthio group", the "C$_{1-6}$alkylsulfinyl group", and the "C$_{1-6}$alkylsulfonyl group" is defined the same as the above-described "C$_{1-6}$alkyl group". Specific examples of the "C$_{1-6}$alkylthio group" include, for example, a methylthio group and the like. Specific examples of the "C$_{1-6}$alkylsulfinyl group" include, for example, a methylsulfinyl group and the like. Specific examples of the "C$_{1-6}$alkylsulfonyl group" include, for example, a methylsulfonyl group and the like.

A "C$_{2-10}$alkenyl group" means a linear or branched, unsaturated hydrocarbon group having two to ten carbon atoms and containing one to five double bonds. Examples of the "C$_{2-10}$alkenyl group" include, preferably, a "C$_{2-6}$ alkenyl group". Specific examples of the "C$_{2-10}$alkenyl group" include, for example, a vinyl group, a propenyl group, a methylpropenyl group, a butenyl group, a methylbutenyl a group, a pentenyl group, a hexenyl group, a heptenyl group, a octenyl group, a nonenyl group, a decenyl group, and the like.

A "C$_{2-10}$alkynyl group" means a linear or branched, unsaturated hydrocarbon group having two to ten carbon atoms and containing one triple bond. The "C$_{2-10}$alkynyl group" includes, preferably, a "C$_{2-6}$ alkynyl group". Specific examples of the "C$_{2-10}$alkynyl group" include, for example, propynyl, methylpropynyl, butynyl, methylbutynyl, a pentynyl group, a hexynyl group, a heptynyl group, an octynyl group, a nonynyl group, a decynyl group, and the like.

A "C$_{1-10}$alkylene" means a linear or branched, saturated hydrocarbon having one to ten carbon atoms. The "C$_{1-10}$alkylene" includes, preferably, "C$_{1-6}$alkylene". Specific examples of the "C$_{1-10}$alkylene" include, for example, methylene, ethylene, propylene, 1-methylethylene, butylene, 2-methylpropylene, 1-methylpropylene, 1,1-dimethylethylene, pentylene, 3-methylbutylene, 2-methylbutylene, 2,2-dimethylpropylene, 1-ethylpropylene, 1,1-dimethylpropylene, hexylene, 4-methylpentylene, 3-methylpentylene, 2-methylpentylene, 1-methylpentylene, heptylene, octylene, nonylene, decylene, and the like.

A "C$_{2-10}$alkenylene" means a linear or branched, unsaturated hydrocarbon having two to ten carbon atoms and containing one to five double bonds. The "C$_{2-10}$alkenylene" includes, preferably, "C$_{2-6}$ alkenylene". Specific examples of the "C$_{2-10}$alkenylene" include, for example, vinylene, propenylene, methylpropenylene, butenylene, methylbutenylene, pentenylene, hexenylene, heptenylene, octenylene, nonenylene, decenylene, and the like.

A "C$_{2-10}$alkynylene" means a linear or branched, unsaturated hydrocarbon having two to ten carbon atoms and containing one triple bond. The "C$_{2-10}$alkynylene" includes, preferably, "C$_{2-6}$ alkynylene". Specific examples of the "C$_{2-10}$alkynylene" include, for example, propynylene, methylpropynylene, butynylene, methylbutynylene, pentynylene, hexynylene, heptynylene, octynylene, nonynylene, decynylene, and the like.

A "C$_{3-10}$cycloalkyl group" means a cyclic alkyl having three to ten carbon atoms, and includes those cyclic alkyl having a partially bridged structure. The "C$_{3-10}$cycloalkyl group" includes, preferably a "C$_{3-7}$ cycloalkyl group", and more preferably a "C$_{4-6}$ cycloalkyl group". Specific examples of the "C$_{3-10}$cycloalkyl group" include, for example, a cyclopropyl group, a cyclobutyl group, a cyclopentyl group, a cyclohexyl group, a cycloheptyl group, a cyclooctyl group, an adamantyl group, and the like. Specific examples of the "C$_{3-7}$ cycloalkyl group" include, for example, a cyclopropyl group, a cyclobutyl group, a cyclopentyl group, a cyclohexyl group, a cycloheptyl group, and the like.

The above-described "C$_{3-10}$cycloalkyl group" encompasses those compounds in which it is fused to an aromatic ring. Specific examples thereof include, for example, groups represented by the following and the like.

[Chem. 11]

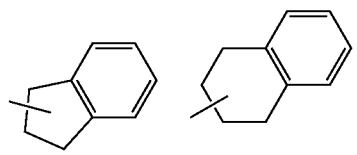

The above-described "C$_{3-10}$cycloalkyl group" also encompasses a saturated bicyclo ring. Specific examples thereof include, for example, groups represented by the following group and the like.

[Chem. 12]

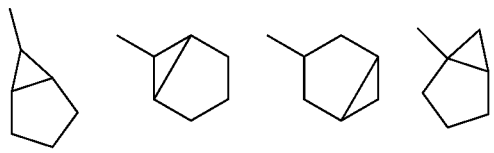

The "C$_{3-10}$cycloalkyl" moiety of the "C$_{3-10}$cycloalkylcarbonyl group", the "C$_{3-10}$cycloalkylthio group", the "C$_{3-10}$cycloalkylsulfinyl group", and the "C$_{3-10}$cycloalkylsulfonyl group" is defined the same as the above-described "C$_{3-10}$cycloalkyl group". The "C$_{3-10}$cycloalkylcarbonyl group", the "C$_{3-10}$cycloalkylthio group", the "C$_{3-10}$cycloalkylsulfinyl group", and the "C$_{3-10}$cycloalkylsulfonyl group" include, preferably, those groups in which the "C$_{3-10}$cycloalkyl" moiety is the "C$_{3-7}$ cycloalkyl group". Specific examples of the "C$_{3-10}$cycloalkylcarbonyl group" include, for example, a cyclopropylcarbonyl group and the like. Specific examples of the "C$_{3-10}$cycloalkylthio group" include, for example, a cyclopropylthio group and the like. Specific examples of the "C$_{3-10}$cycloalkylsulfinyl group" include, for example, a cyclopropylsulfinyl group and the like. Specific examples of the "C$_{3-10}$cycloalkylsulfonyl group" include, for example, a cyclopropylsulfonyl group and the like.

A "C$_{3-10}$cycloalkylene" means a cyclic alkylene having three to ten carbon atoms, and encompasses those cycloalkylene having a partially bridged structure. The "C$_{3-10}$cycloalkylene" includes, preferably, "C$_{4-7}$ cycloalkylene". Specific examples of the "C$_{3-10}$cycloalkylene" include, for example, cyclopropylene, cyclobutylene, cyclopentylene, cyclohexylene, cycloheptylene, cyclooctylene, adamantylene, and the like. Specific examples of the "C$_{4-7}$ cycloalkylene" include, for example, cyclobutylene, cyclopentylene, cyclohexylene, cycloheptylene, and the like.

The above-described "C$_{3-10}$cycloalkylene" and "C$_{4-7}$ cycloalkylene" encompass those compounds in which it is fused to an aromatic ring. Specific examples thereof include, for example, groups represented by the following and the like.

[Chem. 13]

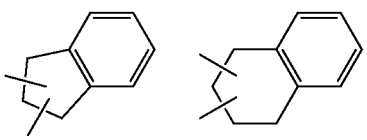

The above-described "$C_{3-10}$cycloalkylene" and "$C_{4-7}$ cycloalkylene" encompass a saturated bicyclo ring. Specific examples thereof include, for example, groups represented by the following group and the like.

[Chem. 14]

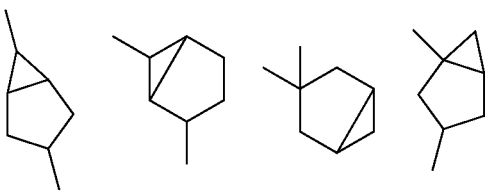

A "$C_{1-6}$alkoxy group" refers to a "$C_{1-6}$alkyloxy group", and the "$C_{1-6}$alkyl" moiety is defined the same as the above-described "$C_{1-6}$alkyl group". The "$C_{1-6}$alkoxy group" includes, preferably, a "$C_{1-4}$ alkoxy group" and the like. Specific examples of the "$C_{1-6}$alkoxy group" include, for example, a methoxy group, an ethoxy group, a propoxy group, a 1-methylethoxy group, a butoxy group, a 2-methylpropoxy group, a 1-methylpropoxy group, a 1,1-dimethylethoxy group, a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, and the like.

A "$C_{3-10}$cycloalkoxy group" refers to a "$C_{3-10}$cycloalkyloxy group", and the "$C_{3-10}$cycloalkyl" moiety is defined the same as the above-described "$C_{3-10}$cycloalkyl group". The "$C_{3-10}$cycloalkoxy group" includes, preferably, a "$C_{3-7}$ cycloalkoxy group". Specific examples of the "$C_{3-10}$cycloalkyloxy group" include, for example, a cyclopropoxy group, a cyclobutoxy group, a cyclopentyloxy group, a cyclohexyloxy group, a cycloheptyloxy group, a cyclooctyloxy group, an adamantyloxy group, and the like. Specific examples of the "$C_{3-7}$ cycloalkoxy group" include, for example, a cyclopropoxy group, a cyclobutoxy group, a cyclopentyloxy group, a cyclohexyloxy group, a cycloheptyloxy group, and the like.

The "$C_{3-10}$cycloalkoxy" moiety of the "$C_{3-10}$cycloalkoxycarbonyl group" are defined the same as the above-described "$C_{3-10}$cycloalkoxy group". The "$C_{3-10}$cycloalkoxycarbonyl group" includes, preferably, a "$C_{3-7}$ cycloalkoxycarbonyl group". Specific examples of the "$C_{3-10}$cycloalkoxycarbonyl group" include a cyclopropoxycarbonyl group and the like.

The "$C_{1-6}$alkoxy" moiety of the "$C_{1-6}$alkoxycarbonyl group" is defined the same as the above-described "$C_{1-6}$alkoxy group". The "$C_{1-6}$alkoxycarbonyl group" includes, preferably, a "$C_{1-4}$ alkoxycarbonyl group". Specific examples of the "$C_{1-6}$alkoxycarbonyl group" include, for example, a methoxycarbonyl group, an ethoxycarbonyl group, and the like.

The "$C_{1-6}$alkyl" moiety of the "$C_{1-6}$alkylcarbonyl group" is defined the same as the above-described "$C_{1-6}$alkyl group". The "$C_{1-6}$alkylcarbonyl group" includes, preferably, a "$C_{1-4}$ alkylcarbonyl group". Specific examples of the "$C_{1-6}$alkylcarbonyl group" include, for example, a methylcarbonyl group, an ethylcarbonyl group, a propylcarbonyl group, a 1-methylethylcarbonyl group, a butylcarbonyl group, a 2-methylpropylcarbonyl group, a 1-methylpropylcarbonyl group, a 1,1-dimethylethylcarbonyl group, and the like.

A "$C_{6-10}$aryl group" means an aromatic hydrocarbon having six to ten carbon atoms. Specific examples of the "$C_{6-10}$aryl group" include, for example, a phenyl group, a 1-naphthyl group, a 2-naphthyl group, and the like. Particularly preferably, it includes a phenyl group.

The "$C_{6-10}$aryl" also encompasses a 8- to 14-membered polycyclic group in which an aromatic ring is fused to a $C_{4-6}$ cycloalkyl, or a 9- to 14-membered polycyclic group in which an aromatic ring is fused to, for example, a 5- to 6-membered heterocyclic group having one to three homogeneous or heterogeneous atoms selected from a nitrogen atom, an oxygen atom, or a sulfur atom. Specific examples thereof include, for example, groups represented by the following and the like.

[Chem. 15]

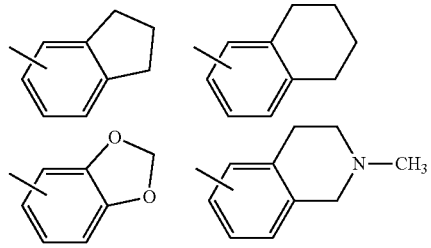

The "$C_{6-10}$aryl" moiety of the "$C_{6-10}$arylcarbonyl group", the "$C_{6-10}$aryloxycarbonyl group", the "$C_{6-10}$arylthio group", the "$C_{6-10}$arylsulfinyl group", the "$C_{6-10}$arylsulfonyl group", and the "$C_{6-10}$aryloxy group" is defined the same as the above-described "$C_{6-10}$aryl group". For the "$C_{6-10}$aryl" moiety, a phenyl group is preferable. Specific examples of the "$C_{6-10}$arylcarbonyl group" include a phenylcarbonyl group and the like. Specific examples of the "$C_{6-10}$aryloxycarbonyl group" include a phenyloxycarbonyl group and the like. Specific examples of the "$C_{6-10}$arylthio group" include a phenylthio group and the like. Specific examples of the "$C_{6-10}$arylsulfinyl group" include a phenylsulfinyl group and the like. Specific examples of the "$C_{6-10}$arylsulfonyl group" include a phenylsulfonyl group and the like. Specific examples of the "$C_{6-10}$aryloxy group" include a phenyloxy group and the like.

An "arylene" means an aromatic hydrocarbon. The "arylene" includes, preferably, "$C_{6-10}$arylene". For the "$C_{6-10}$arylene", phenylene is preferable. Specific examples of the "$C_{6-10}$arylene" include, for example, phenylene, 1-naphthylene, 2-naphthylene, and the like.

The "$C_{6-10}$arylene" also encompasses a 8- to 14-membered polycyclic group in which an aromatic ring is fused to a $C_{4-6}$ cycloalkyl, or a 9- to 14-membered polycyclic group in which an aromatic ring is fused to, for example, a 5- to 6-membered heterocyclic group having one to three homogeneous or heterogeneous atoms selected from a nitrogen atom, an oxygen atom, or a sulfur atom. Specific examples thereof include, for example, groups represented by the following and the like.

[Chem. 16]

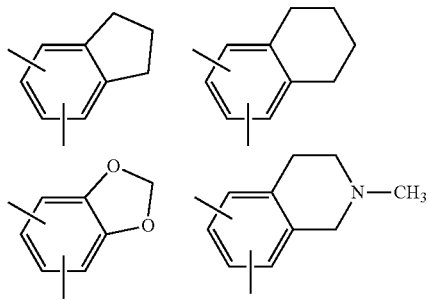

A "$C_{5-10}$heteroaryl group" includes a 5- to 7-membered monocyclic aromatic heterocyclic group ("$C_{5-7}$ heteroaryl group") and an 8- to 10-membered bicyclic aromatic heterocyclic group ("$C_{8-10}$ heteroaryl group"), which contain one to four atoms independently selected from the group consisting of a nitrogen atom, an oxygen atom, and a sulfur atom. The "$C_{5-10}$heteroaryl group" includes, preferably, a 5- to 7-membered monocyclic aromatic heterocyclic group ("$C_{5-7}$ heteroaryl group"), and further preferably, a 5- or 6-membered monocyclic aromatic heterocyclic group ("$C_{5-6}$ heteroaryl group").

Specific example of the "$C_{5-10}$heteroaryl" include a pyridyl group, a pyridazinyl group, an isothiazolyl group, a pyrrolyl group, a furyl group, a thienyl group, a thiazolyl group, an imidazolyl group, a pyrimidinyl group, a thiadiazolyl group, a pyrazolyl group, an oxazolyl group, an isoxazolyl group, a pyrazinyl group, a triazinyl group, a triazolyl group, an imidazolidinyl group, an oxadiazolyl group, a triazolyl group, a tetrazolyl group, an indolyl group, an indazolyl group, a quinolyl group, an isoquinolyl group, a benzofuranyl group, a benzothienyl group, a benzoxazolyl group, a benzothiazolyl group, a benzisoxazolyl group, a benzisothiazolyl group, a benzotriazolyl group, a benzimidazolyl group, a 6,11-dihydrodibenzo[b,e]thiepinyl group, and the like. It is preferably a pyridyl group, a pyrimidinyl group, a quinolyl group, an isoquinolyl group, and further preferably a pyridyl group.

A "$C_{5-10}$heteroarylene" includes a 5- to 7-membered monocyclic aromatic heterocycle and an 8- to 10-membered bicyclic aromatic heterocycle, which contain one to four atoms independently selected from the group consisting of a nitrogen atom, an oxygen atom, and a sulfur atom. The "$C_{5-10}$heteroarylene" includes, preferably, "$C_{5-7}$ heteroarylene". Specific examples thereof include pyridylene, pyridazinylene, isothiazolylene, pyrrolylene, furylene, thienylene, thiazolylene, imidazolylene, pyrimidinylene, thiadiazolylene, pyrazolylene, oxazolylene, isoxazolylene, pyrazinylene, triazinylene, triazolylene, imidazolidinylene, oxadiazolylene, triazolylene, tetrazolylene, indolylene, indazolylene, quinolylene, isoquinolylene, benzofuranylene, benzothienylene, benzoxazolylene, benzothiazolylene, benzisoxazolylene, benzisothiazolylene, benzotriazolylene, benzimidazolylene, 6,11-dihydrodibenzo[b,e]thiepinylene, and the like. It is preferably pyridylene, pyrimidinylene, quinolylene, and isoquinolylene, and further preferably pyridylene.

A "3- to 12-membered monocyclic or polycyclic heterocyclic group" includes a monocyclic or polycyclic heterocyclic group and the like, which contain one to four atoms independently selected from the group consisting of a nitrogen atom, an oxygen atom, and a sulfur atom. It is preferably a 3- to 10-membered group, more preferably a 3- to 8-membered group, and further preferably a 3- to 6-membered group. All of the nitrogen atom, oxygen atom, and sulfur atom are atoms constituting the ring. The heterocyclic group may be either saturated or partially unsaturated, and a saturated heterocyclic group is more preferable. Specific examples of the "heterocyclic group" include, an epoxy group, an aziridine group, an azetidine group, a pyranyl group, a tetrahydrofuryl group, a pyrrolidinyl group, an imidazolidinyl group, a piperidinyl group, a morpholinyl group, a thiomorpholinyl group, a dioxothiomorpholinyl group, a hexamethyleneiminyl group, an oxazolidinyl group, a thiazolidinyl group, an imidazolidinyl group, an oxoimidazolidinyl group, a dioxoimidazolidinyl group, an oxooxazolidinyl group, a dioxooxazolidinyl group, a dioxothiazolidinyl group, a tetrahydrofuranyl group, a tetrahydropyridinyl group, an oxetanyl group, a tetrahydropyranyl group, and the like. It should be noted that the group also encompasses a heterocyclic group having a bridged structure. Regarding the group, a nitrogen atom constituting the ring cannot be at a position to be attached in "the group". That is, the group does not encompass ideas of, for example, a 1-pyrrolidino group and the like.

The "3- to 12-membered monocyclic or polycyclic heterocyclic group" may form a fused ring with a 6-membered aromatic hydrocarbon or a 6-membered heteroaryl. Examples thereof include a bicyclic "heterocycle" having nine or ten ring-constituting atoms in which the above-described 5- or 6-membered "heterocyclic group" is fused to a 6-membered aromatic hydrocarbon or a 6-membered heteroaryl. The 6-membered aromatic hydrocarbon includes benzene and the like. The 6-membered unsaturated heterocycle includes a pyridine group, a pyrimidine group, a pyridazine group, and the like. Specific examples of the fused ring include a dihydroindolyl group, a dihydroisoindolyl group, a dihydropurinyl group, a dihydrothiazolopyrimidinyl group, a dihydrobenzodioxanyl group, an isoindolyl group, an indazolyl group, a tetrahydroquinolinyl group, a tetrahydroisoquinolinyl group, a tetrahydronaphthyridinyl group, a tetrahydropyridoazepinyl group, and the like.

Examples of an "optionally substituted amino group" include amino, and mono- or di-substituted amino.

Examples of a substituent of the "mono- or di-substituted amino" include "$C_{1-6}$ alkyl", "$C_{3-10}$cycloalkyl", "$C_{3-10}$cycloalkyl $C_{1-4}$ alkyl", "$C_{3-7}$ cycloalkyl $C_{1-4}$ alkoxycarbonyl", "$C_{1-4}$ alkylcarbonyl", "$C_{1-4}$ alkyloxycarbonyl", a "3- to 8-membered saturated heterocycle", "3- to 8-membered saturated heterocyclyl $C_{1-4}$ alkyl", "3- to 8-membered saturated heterocyclylcarbonyl", "3- to 8-membered saturated heterocyclyloxycarbonyl", "3- to 8-membered saturated heterocyclyl $C_{1-4}$ alkylcarbonyl", "$C_{6-10}$aryl", "$C_{7-14}$ aralkyl", "$C_{6-10}$arylcarbonyl", "$C_{6-10}$aryloxycarbonyl", "$C_{5-6}$ heteroaryl", "$C_{5-6}$ heteroaryl $C_{1-4}$ alkyl", and the like.

As used herein, the "3- to 8-membered saturated heterocyclyl $C_{1-4}$ alkyl" means a group in which the "$C_{1-4}$ alkyl group" is substituted with a "3- to 8-membered saturated heterocycle". The "3- to 8-membered saturated heterocyclyl$C_{1-4}$ alkylcarbonyl" means a group in which the "$C_{1-4}$ alkyl group" is substituted with a "3- to 8-membered saturated heterocycle". The "$C_{7-14}$ aralkyl" means a group in which the "$C_{1-4}$ alkyl group" is substituted with a "$C_{6-10}$aryl group". The "$C_{5-6}$ heteroaryl $C_{1-4}$ alkyl" means a group in which the "$C_{1-4}$ alkyl group" is substituted with a "$C_{5-6}$ heteroaryl".

Specific examples of the "mono-substituted amino" include, for example,
"$C_{1-6}$alkylamino" (e.g., methylamino, ethylamino, propylamino, 1-methylethylamino, butylamino, 2-methylpropylamino, 1-methylpropylamino, 1,1-dimethylethylamino, and the like),
"$C_{3-8}$cycloalkylamino" (e.g., cyclopropylamino, cyclobutylamino, cyclopentylamino, cyclohexylamino, cycloheptylamino, and the like),
"($C_{3-8}$cycloalkyl$C_{1-4}$ alkyl)amino" (e.g., cyclopropylmethylamino, cyclobutylmethylamino, cyclopentylmethylamino, cyclohexylmethylamino, cycloheptylmethylamino, and the like),
"($C_{3-8}$cycloalkyl$C_{1-4}$ alkoxycarbonyl)amino" (e.g., cyclopropoxycarbonylamino, cyclobutoxycarbonylamino, cyclopentoxycarbonylamino, cyclohexyloxycarbonylamino, cycloheptyloxycarbonylamino, and the like),
"($C_{1-4}$ alkylcarbonyl)amino" (e.g., methylcarbonylamino, ethylcarbonylamino, propylcarbonylamino, 1-methylpropylcarbonylamino, 2-methylpropylcarbonylamino, butylcarbonylamino, 2,2-dimethylethylcarbonylamino, and the like),
"($C_{1-4}$ alkyloxycarbonyl)amino" (e.g., methoxycarbonylamino, ethoxycarbonylamino, propoxycarbonylamino, 1-methylpropoxycarbonylamino, 2-methylpropoxycarbonylamino, butoxycarbonylamino, 2,2-dimethylethoxycarbonylamino, and the like),
"$C_{5-10}$arylamino" (e.g., phenylamino, 1-naphthylamino, 2-naphthylamino, and the like),
"$C_{7-14}$ aralkylamino" (e.g., benzylamino, 1-naphthylmethylamino, 2-naphthylmethylamino, and the like),
"$C_{6-10}$arylcarbonylamino" (e.g., phenylcarbonylamino, 1-naphthylcarbonylamino, 2-naphthylcarbonylamino, and the like),
"$C_{6-10}$aryloxycarbonylamino" (e.g., phenoxycarbonylamino, 1-naphthoxycarbonylamino, 2-naphthoxycarbonylamino, and the like),
"3- to 8-membered saturated heterocyclylamino" (e.g., tetrahydropyranylamino, tetrahydropyridinylamino, pyrrolidinylamino, oxopyrrolidinylamino, tetrahydrofuranylamino, piperidinylamino, and the like),
"(3- to 8-membered saturated heterocyclyl$C_{1-4}$ alkyl)amino" (e.g., tetrahydropyranylmethylamino, tetrahydropyridinylmethylamino, pyrrolidinylmethylamino, oxopyrrolidinylmethylamino, tetrahydrofuranylmethylamino, piperidinylmethylamino, piperazinylmethylamino, morpholinylmethylamino, and the like),
"3- to 8-membered saturated heterocyclylcarbonylamino" (e.g., tetrahydropyranylcarbonylamino, tetrahydropyridinylcarbonylamino, pyrrolidinylcarbonylamino, oxopyrrolidinylcarbonylamino, tetrahydrofuranylcarbonylamino, piperidinylcarbonylamino, and the like),
"3- to 8-membered saturated heterocyclyloxycarbonylamino" (e.g., tetrahydropyranyloxycarbonylamino, tetrahydropyridinyloxycarbonylamino, pyrrolidinyloxycarbonylamino, oxopyrrolidinyloxycarbonylamino, tetrahydrofuranyloxycarbonylamino, piperidinyloxycarbonylamino, and the like),
"($C_{5-6}$ heteroaryl)amino" (e.g., pyrrolylamino, thienylamino, furylamino, oxazolylamino, thiazolylamino, isoxazolylamino, isothiazolylamino, imidazolylamino, pyrazolylamino, triazolylamino, oxadiazolylamino, thiadiazolylamino, tetrazolylamino, pyridylamino, pyrazylamino, pyrimidylamino, pyridazylamino, triazylamino, and the like),
"($C_{5-6}$ heteroaryl$C_{1-4}$ alkyl)amino" (e.g., pyrrolylmethylamino, thienylmethylamino, furylmethylamino, oxazolylmethylamino, thiazolylmethylamino, isoxazolylmethylamino, isothiazolylmethylamino, imidazolylmethylamino, pyrazolylmethylamino, triazolylmethylamino, oxadiazolylmethylamino, thiadiazolylmethylamino, tetrazolylmethylamino, pyridylmethylamino, pyrazylmethylamino, pyrimidylmethylamino, pyridazylmethylamino, triazylmethylamino, and the like), and the like.

Specific examples of the "di-substituted amino" include, for example, "di-$C_{1-6}$alkylamino" (e.g., dimethylamino, diethylamino, dipropylamino, di-1-methylethylamino, dibutylamino, di-2-methylpropylamino, di-1-methylpropylamino, di-1,1-dimethylethylamino, and the like), "N—($C_{1-6}$alkyl)-N—($C_{3-10}$cycloalkyl)amino" (e.g., methylcyclopropylamino, methylcyclobutylamino, methylcyclopentylamino, methylcyclohexylamino, methylcycloheptylamino, and the like), "N—($C_{1-6}$alkyl)-N-(3- to 8-membered saturated heterocyclyl)amino" (e.g., methyltetrahydropyranylamino, methyltetrahydropyridinylamino, methylpyrrolidinylamino, methyloxopyrrolidinylamino, methyltetrahydrofuranylamino, methylpiperidinylamino, and the like), and the like.

An "aminocarbonyl group" means a group in which the above-described "amino group" is bonded to a carbonyl group. As used herein, the "amino" means unsubstituted amino, mono-substituted amino, di-substituted amino, or 3- to 12-membered cyclic amino. Specific examples thereof include, for example, a methylaminocarbonyl group, a cyclopropylaminocarbonyl group, a dimethylaminocarbonyl group, a dicyclopropyl aminocarbonyl group, and the like.

An "aminosulfinyl group" means a group in which the above-described "amino group" is bonded to a sulfinyl group. As used herein, the "amino" means unsubstituted amino, mono-substituted amino, di-substituted amino, or 3- to 12-membered cyclic amino. Specific examples thereof include, for example, a methylaminosulfinyl group, a cyclopropylaminosulfinyl group, a dimethylaminosulfinyl group, a dicyclopropylaminosulfinyl group, and the like.

An "aminosulfonyl group" means a group in which the above-described "amino group" is bonded to a sulfonyl group. As used herein, the "amino" is unsubstituted amino, mono-substituted amino, di-substituted amino, or 3- to 12-membered cyclic amino. Specific examples thereof include, for example, a methylaminosulfonyl group, a cyclopropylaminosulfonyl group, a dimethylaminosulfonyl group, a dicyclopropylaminosulfonyl group, and the like.

The "3- to 12-membered monocyclic or polycyclic heterocycle" moiety of the "3- to 12-membered monocyclic or polycyclic heterocyclyloxy group", the "3- to 12-membered monocyclic or polycyclic heterocyclylthio group", the "3- to 12-membered monocyclic or polycyclic heterocyclyloxycarbonyl group", the "3- to 12-membered monocyclic or polycyclic heterocyclylsulfinyl group", the "3- to 12-membered monocyclic or polycyclic heterocyclylsulfonyl group", and the "3- to 12-membered monocyclic or polycyclic heterocyclylcarbonyl group" is defined the same as the above-described "3- to 12-membered monocyclic or polycyclic heterocyclic group". It is preferably a 3- to 10-membered group, more preferably a 3- to 8-membered group, and further preferably a 3- to 6-membered group. Specific examples of the "3- to 12-membered monocyclic or polycyclic heterocyclyloxy group" include, for example, a pyridyloxy group and the like. Specific examples of the "3- to 12-membered monocyclic or polycyclic heterocyclylthio group" include, for example, a pyridylthio group and the like. Specific examples of the "3- to 12-membered monocyclic or polycyclic heterocyclyloxycarbonyl group" include, for example, a pyridyloxycarbonyl group and the like. Specific examples of the "3- to 12-membered monocyclic or polycyclic heterocyclylsulfinyl group" include, for example, a pyridylsulfinyl group and the like. Specific examples of the "3- to 12-membered monocyclic or polycyclic heterocyclylsulfonyl group" include, for example, a pyridylsulfonyl group and the like. Specific examples of the "3- to 12-membered monocyclic or polycyclic heterocyclylcarbonyl group" include, for example, a pyridylcarbonyl group and the like.

A "3- to 12-membered cyclic amino group" means a 3- to 12-membered cyclic amino group in which the nitrogen atom in the ring is at a position to be directly attached in "the group", and also encompasses those amino groups having a partially bridged structure. It is preferably 3- to 8-membered, and further preferably 3- to 7-membered. It is most preferably 3- to 6-membered. Specific examples thereof include, for example, groups represented by the following, and the like. It should be noted that the group encompasses also a cyclic amino group containing a partially unsaturated ring.

[Chem. 17]

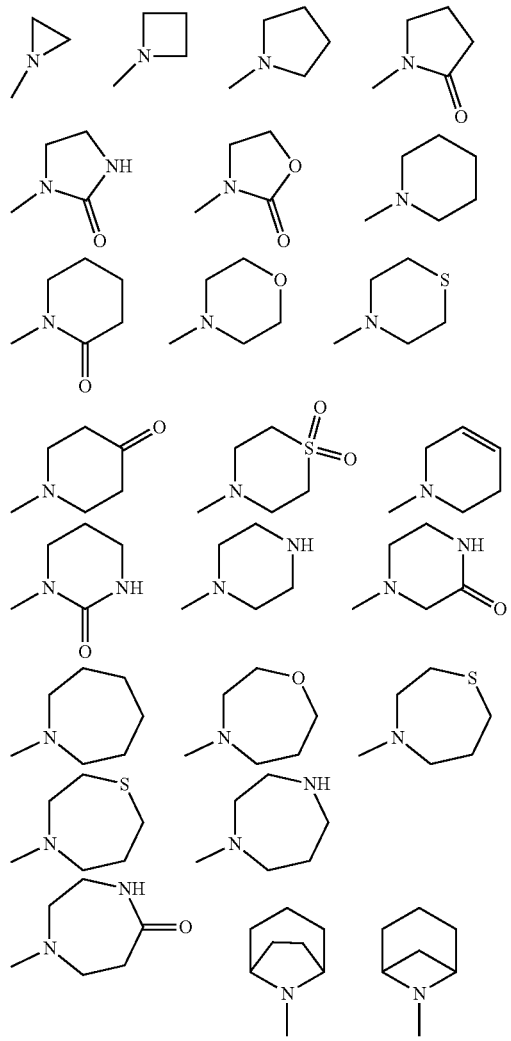

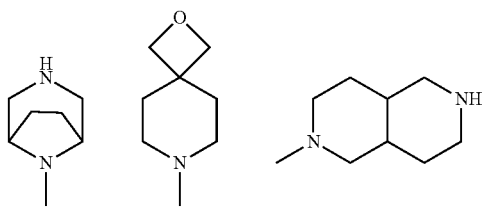

The "3- to 12-membered cyclic amino group" may form a fused ring with a 6-membered aromatic hydrocarbon or a 5- or 6-membered heteroaryl. Specific examples thereof include, "the groups" represented by the following, and the like.

[Chem. 18]

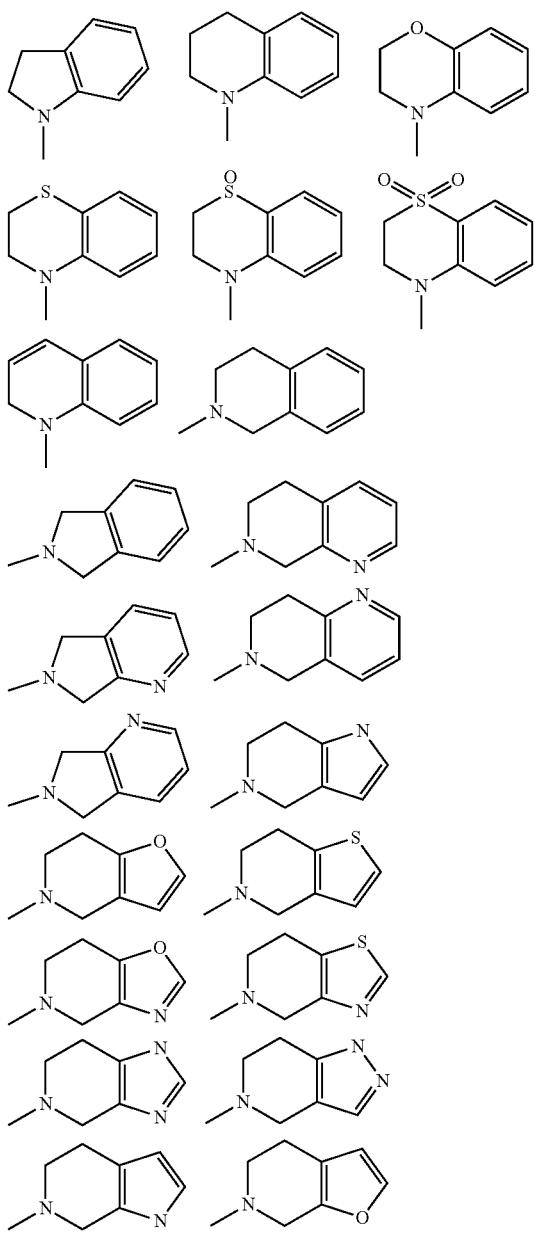

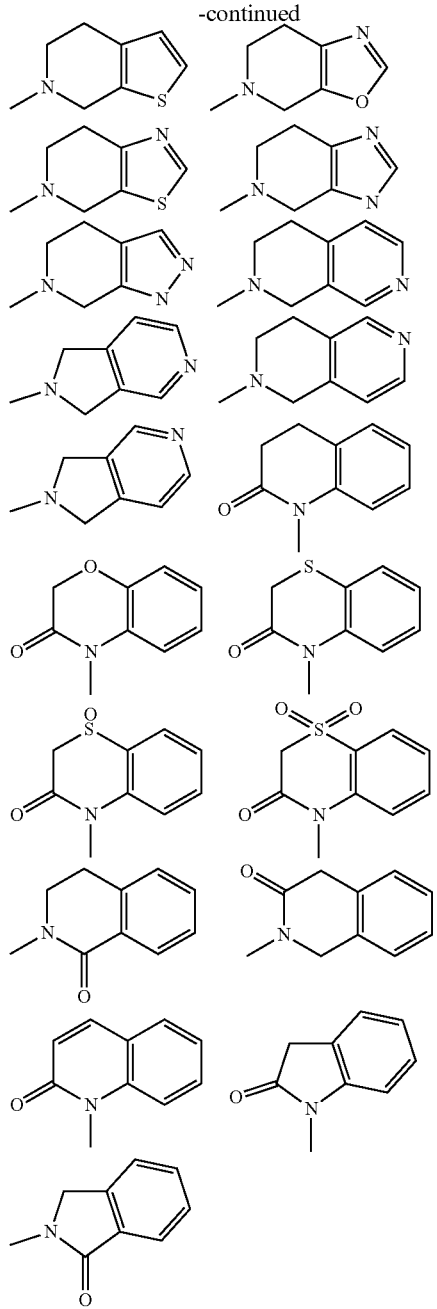

A "3- to 12-membered cyclic aminyl linker group" means a 3- to 12-membered cyclic amino in which the nitrogen atom in the ring is at a position to be directly attached in "the ring", and also encompasses those cyclic aminyl linker group having a partially bridged structure. It is preferably 3- to 8-membered, and further preferably 3- to 7-membered. It is most preferably 3- to 6-membered. Specific examples thereof include, for example, groups represented by the following, and the like. It should be noted that the group also encompasses a cyclic amino group containing a partially unsaturated ring.

[Chem. 19]

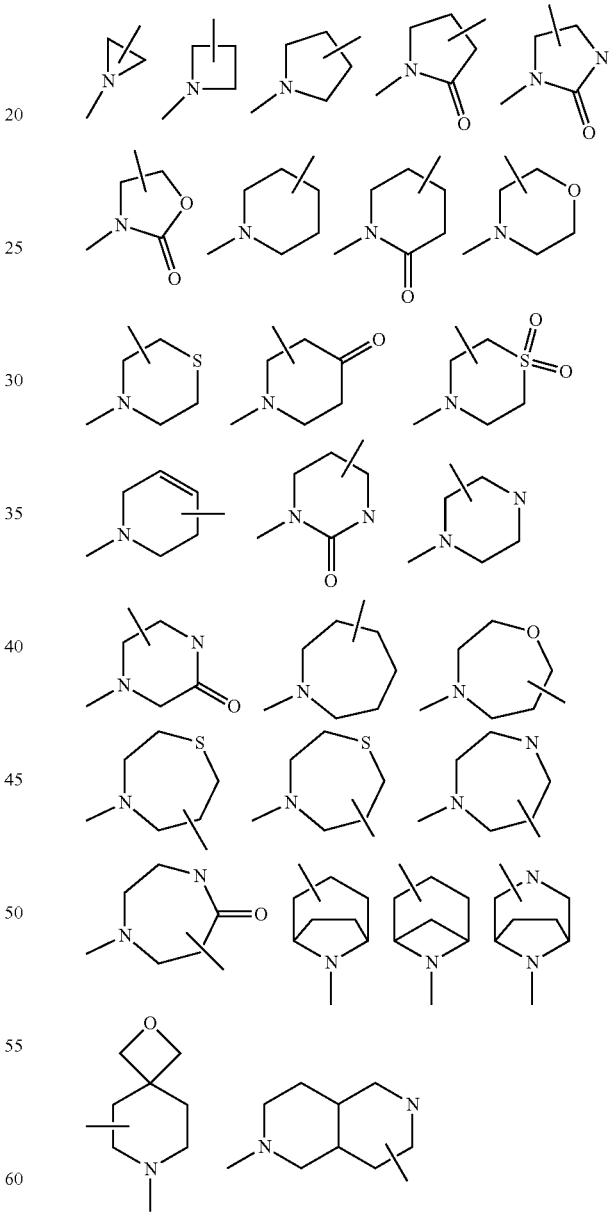

The "3- to 12-membered cyclic amino" moiety of the "3- to 12-membered cyclic aminocarbonyl group", the "3- to 12-membered cyclic aminosulfinyl group", and the "3- to 12-membered cyclic aminosulfonyl group" is defined the same as the above-described "3- to 12-membered cyclic amino group". It is preferably 3- to 8-membered, and further preferably 3- to 7-membered. It is most preferably 3- to 6-membered. Specific examples of the "3- to 12-membered cyclic aminocarbonyl group" include, for example, a 1-piperidinylcarbonyl group and the like. Specific examples of the "3- to 12-membered cyclic aminosulfinyl group" include, for example, a 1-piperidinylsulfinyl group and the like. Specific examples of the "3- to 12-membered cyclic aminosulfonyl group" include, for example, a 1-piperidinylsulfonyl group and the like.

Specific examples of the 3- to 12-membered monocyclic or polycyclic heterocyclic group having at least one or more secondary nitrogen atoms in the ring include, for example, groups represented by the following, and the like.

[Chem. 20]

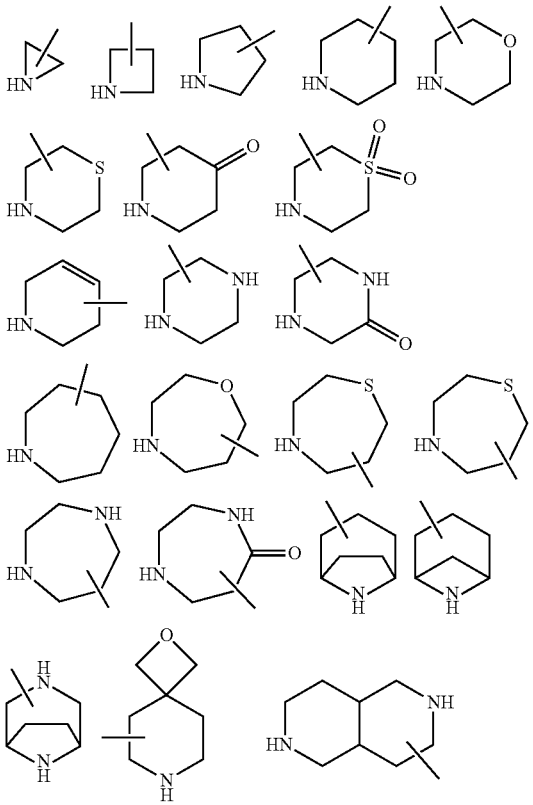

Specific examples of the 3- to 12-membered cyclic amino group having at least one or more secondary nitrogen atoms in the ring include, for example, groups represented by the following, and the like.

[Chem. 21]

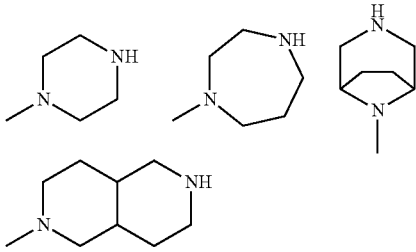

In the compound of the present invention represented by formula (1A) or (1), the following is preferable for $A^1$, $A^2$, B, $R^1$, $R^{2A}$, $R^{2B}$, $R^{2C}$, $R^{2D}$, $R^{3A}$, $R^{3B}$, $R^{3C}$, $R^{4A}$, $R^{4B}$, $R^5$, $R^6$, $R^7$, $R^8$, X, Y, Z, V, and n. However, the technical scope of the present invention is not limited to the scope of compounds set forth below.

Preferably, $A^1$ and $A^2$ are identical or different and each independently include —C(=O)B, —C(=O)$CR^{3A}R^{3B}$B, —$CO_2$B, —$CONR^{3C}$B, and a hydrogen atom.

More preferably, $A^1$ and $A^2$ are identical or different, and each independently include —$CO_2$B, —$CONR^{3C}$B, and a hydrogen atom.

Further preferably, $A^1$ and $A^2$ are identical or different, and each independently —$CONR^{3C}$B, or a hydrogen atom.

Most preferably, $A^1$ and $A^2$ include —$CONR^{3C}$B.

B includes, preferably, (1) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (2) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), and (3) a group represented by the formula (B).

As used herein, the 3- to 12-membered monocyclic or polycyclic heterocyclic group and the 3- to 12-membered cyclic amino group have at least one or more secondary nitrogen atoms in the ring.

B is, more preferably, (1) a 3- to 12-membered monocyclic or polycyclic heterocyclic group (the heterocyclic group is optionally substituted with one to three substituents selected from the group consisting of a halogen atom, a carboxyl group, —$NR^6R^7$, and —$CO_2R^6$), or (2) a group represented by the formula (B), wherein the 3- to 12-membered monocyclic or polycyclic heterocyclic group has at least one or more secondary nitrogen atoms in the ring.

B is, further preferably, a 3- to 6-membered monocyclic heterocyclic group optionally substituted with one to two substituents selected from the group consisting of a fluorine atom, a carboxyl group, and —$CO_2R^6$, or a group represented by the formula (B), wherein the 3- to 6-membered monocyclic heterocyclic group has at least one or more secondary nitrogen atoms in the ring.

B includes, most preferably, a 3- to 6-membered monocyclic heterocyclic group, or a group represented by the formula (B). As used herein, the 3- to 6-membered monocyclic heterocyclic group has at least one or more secondary nitrogen atoms in the ring.

$R^1$ includes, preferably, (1) a hydrogen atom,
(2) a halogen atom
(3) a cyano group,
(4) a hydroxyl group,
(5) a 3- to 12-membered cyclic amino group (the cyclic amino group is optionally substituted with one to three groups selected from the group consisting of a halogen atom, a hydroxyl group, a $C_{1-6}$alkyl group, and a $C_{1-6}$alkoxy group),
(6) a $C_{1-6}$alkyl group (the alkyl group is optionally substituted with one to three groups selected from the group consisting of a halogen atom, a hydroxyl group, a $C_{1-6}$alkoxy group, a $C_{3-10}$cycloalkyl group, and a 3- to 12-membered cyclic amino group),
(7) a $C_{1-6}$alkoxy group (the alkoxy group is optionally substituted with one to three groups selected from the group consisting of a halogen atom, a hydroxyl group, a $C_{1-6}$alkoxy group, and a $C_{3-10}$cycloalkyl group),
(8) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group), (9) a $C_{1-6}$alkylcarbonyl group (the alkyl is optionally substituted with one to three groups selected from the group consisting of a halogen atom, a hydroxyl group, a $C_{1-6}$alkoxy group, a $C_{3-10}$cycloalkyl group, and a 3- to 12-membered cyclic amino group),
(10) a carboxyl group,
(11) an aminocarbonyl group (the amino is optionally substituted with one or two groups selected from the group consisting of
 (a) a $C_{1-6}$alkyl group (the alkyl group is optionally substituted with one to three groups selected from the group consisting of a halogen atom, a hydroxyl group, a $C_{1-6}$alkyl group, and a $C_{1-6}$alkoxy group),
 (b) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
 (c) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group)), and
(12) a 3- to 12-membered cyclic aminocarbonyl group (the cyclic amino is optionally substituted with one to three $C_{1-6}$alkyl groups).

$R^1$ includes, more preferably,
(1) a hydrogen atom,
(2) a hydroxyl group,
(3) a $C_{1-6}$alkyl group (the alkyl group is optionally substituted with one to three groups selected from the group consisting of a halogen atom, a hydroxyl group, a $C_{1-6}$alkoxy group, and a $C_{3-10}$cycloalkyl group),
(4) a $C_{1-6}$alkoxy group (the alkoxy group is optionally substituted with one to three groups selected from the group consisting of a halogen atom, a hydroxyl group, a $C_{1-6}$alkoxy group, and a $C_{3-10}$cycloalkyl group),
(5) a $C_{1-6}$alkylcarbonyl group (the alkyl is optionally substituted with one to three groups selected from the group consisting of a halogen atom, a hydroxyl group, a $C_{1-6}$alkoxy group, a $C_{3-10}$cycloalkyl group, and a 3- to 12-membered cyclic amino group), and
(6) a carboxyl group.

$R^1$ includes, further preferably, a hydrogen atom, a hydroxyl group, a $C_{1-6}$alkoxy group, a $C_{1-6}$alkylcarbonyl group, and a carboxyl group.

$R^1$ includes, most preferably, a hydrogen atom.

Preferably, $R^{2A}$, $R^{2B}$, $R^{2C}$, and $R^{2D}$ are identical or different, and each independently include
(1) a hydrogen atom,
(2) a halogen atom,
(3) a cyano group,
(4) a hydroxyl group,
(5) an amino group (the amino group is optionally substituted with one or two groups selected from the group consisting of
 (a) a $C_{1-6}$alkyl group (the alkyl group is optionally substituted with one to three groups selected from the group consisting of a halogen atom, a hydroxyl group, and a $C_{1-6}$alkoxy group),
 (b) a $C_{1-6}$alkylcarbonyl group (the alkyl is optionally substituted with one to three groups selected from the group consisting of a halogen atom, a hydroxyl group, and $C_{1-6}$alkoxy group),
 (c) a $C_{1-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
 (d) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group)),
(6) a 3- to 12-membered cyclic amino group (the cyclic amino group is optionally substituted with one to three $C_{1-6}$alkyl groups),
(7) a $C_{1-6}$alkyl group (the alkyl group is optionally substituted with one to three groups selected from the group consisting of a halogen atom, a hydroxyl group, —$NR^6R^7$, a $C_{1-6}$alkoxy group, a $C_{3-10}$cycloalkyl group, and a 3- to 12-membered monocyclic or polycyclic heterocyclic group),
(8) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group),
(9) a $C_{1-6}$alkoxy group (the alkoxy group is optionally substituted with one to three groups selected from the group consisting of a halogen atom, a hydroxyl group, —$NR^6R^7$, a $C_{1-6}$alkoxy group, a $C_{3-10}$cycloalkyl group, and a 3- to 12-membered monocyclic or polycyclic heterocyclic group),
(10) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group),
(11) a $C_{1-6}$alkylcarbonyl group (the alkyl is optionally substituted with one to three groups selected from the group consisting of a halogen atom, a hydroxyl group, —$NR^6R^7$, a $C_{1-6}$alkoxy group, a $C_{3-10}$cycloalkyl group, a $C_{6-10}$aryl group, and a 3- to 12-membered monocyclic or polycyclic heterocyclic group),
(12) a $C_{3-10}$cycloalkylcarbonyl group (the cycloalkyl is optionally substituted with one to three groups selected from the group consisting of a halogen atom, a hydroxyl group, a $C_{1-6}$alkyl group, and a $C_{1-6}$alkoxy group),
(13) a carboxyl group
(14) an aminocarbonyl group (the amino is optionally substituted with one or two groups selected from the group consisting of
 (a) a $C_{1-6}$alkyl group (the alkyl group is optionally substituted with one to three groups selected from the group consisting of a halogen atom, a hydroxyl group, a $C_{1-6}$alkoxy group, and a 3- to 12-membered monocyclic or polycyclic heterocyclic group, which is optionally substituted with one to three $C_{1-6}$alkyl groups),
 (b) a $C_{3-10}$cycloalkyl group (the cycloalkyl group is optionally substituted with one to three groups selected from the group consisting of a halogen atom, a hydroxyl group, a $C_{1-6}$alkyl group, and a $C_{1-6}$alkoxy group), and
 (c) a 3- to 12-membered monocyclic or polycyclic heterocyclic group (the heterocyclic group is optionally substituted with one to three groups selected from the group consisting of a halogen atom, a hydroxyl group, a $C_{1-6}$alkyl group, and a $C_{1-6}$alkoxy group)), and
(15) a sulfonate group.

More preferably, $R^{2A}$, $R^{2B}$, $R^{2C}$, and $R^{2D}$ are identical or different, and each independently include
(1) a hydrogen atom,
(2) a halogen atom,
(3) a hydroxyl group, (4) an amino group (the amino group is optionally substituted with one or two groups selected from the group consisting of a $C_{1-6}$alkyl group and a $C_{1-6}$alkylcarbonyl group),
(5) a $C_{1-6}$alkyl group (the alkyl group is optionally substituted with one to three groups selected from the group consisting of a halogen atom, a hydroxyl group, and a $C_{1-6}$alkoxy group),
(6) a $C_{3-10}$cycloalkyl group,
(7) a $C_{1-6}$alkoxy group (the alkoxy group is optionally substituted with one to three groups selected from the group consisting of a halogen atom, a hydroxyl group, and a $C_{1-6}$alkoxy group),
(8) a carboxyl group, and
(9) an aminocarbonyl group (the amino is optionally substituted with a $C_{1-6}$alkyl group).

Further preferably, $R^{2A}$, $R^{2B}$, $R^{2C}$, and $R^{2D}$ are identical or different, and each independently include a hydrogen atom, a halogen atom, a $C_{1-6}$alkyl group, a $C_{3-10}$cycloalkyl group, a $C_{1-6}$alkoxy group, and a carboxyl group.

Most preferably, $R^{2A}$, $R^{2B}$, $R^{2C}$, and $R^{2D}$ include the case where they all are hydrogen atoms.

Preferably, $R^{3A}$, $R^{3B}$, and $R^{3C}$ are identical or different, and each independently include a hydrogen atom, and a $C_{1-10}$alkyl group optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$.

More preferably, $R^{3A}$, $R^{3B}$, and $R^{3C}$ are identical or different, and each independently include a hydrogen atom, and a $C_{1-10}$alkyl group optionally substituted with one to three substituents selected from the group consisting of a halogen atom, a carboxyl group, —$NR^6R^7$, and —$CO_2R^6$.

Further preferably, $R^{3A}$, $R^{3B}$, and $R^{3C}$ are identical or different, and each independently include a hydrogen atom, and a $C_{1-6}$alkyl group optionally substituted with one to two substituents selected from the group consisting of a carboxyl group and —$CO_2R^6$.

Most preferably, $R^{3A}$, $R^{3B}$, and $R^{3C}$ include the case where they all are hydrogen atoms.

Preferably, $R^{4A}$ and $R^{4B}$ are identical or different, and each independently include a hydrogen atom, and a $C_{1-10}$alkyl group optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$.

More preferably, $R^{4A}$ and $R^{4B}$ are identical or different, and each independently include a hydrogen atom, and a $C_{1-10}$alkyl group optionally substituted with one to three substituents selected from the group consisting of a halogen atom, a hydroxyl group, a carboxyl group, a $C_{1-6}$alkoxy group, a $C_{3-8}$cycloalkoxy group, —$NR^6R^7$, —$CO_2R^6$, and —$CONR^6R^7$.

Further preferably, $R^{4A}$ and $R^{4B}$ are identical or different, and each independently include a hydrogen atom, and a $C_{1-6}$alkyl group optionally substituted with one to two substituents selected from the group consisting of a carboxyl group and —$CO_2R^6$.

Most preferably, $R^{4A}$ and $R^{4B}$ are identical or different, and each independently include a hydrogen atom, and a $C_{1-6}$alkyl group.

$R^5$ includes, preferably,
(1) a hydrogen atom,
(2) a $C_{1-10}$alkyl group (the alkyl group is optionally substituted with one to three substituents selected from the group consisting of a halogen atom, a hydroxyl group, a carboxyl group, a sulfinate group, a sulfonate group, a phosphate group, a $C_{6-10}$aryl group, a $C_{1-6}$alkoxy group, a $C_{3-8}$cycloalkoxy group, —$NR^6R^7$, —$CO_2R^6$, —$CONR^6R^7$, —$SO_2R^6$, —$SO_2NR^6R^7$, —$OCO_2R^6$, —$OCONR^6R^7$, and —$NR^6CO_2R^7$),
(3) a $C_{3-10}$cycloalkyl group (the cycloalkyl group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), and
(4) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$).

$R^5$ includes, more preferably,
(1) a hydrogen atom and
(2) a $C_{1-6}$alkyl group (the alkyl group is optionally substituted with one to three substituents selected from the group consisting of a halogen atom, a hydroxyl group, a carboxyl group, a sulfinate group, a sulfonate group, a phosphate group, a $C_{6-10}$aryl group, a $C_{1-6}$alkoxy group, a $C_{3-8}$cycloalkoxy group, —$NR^6R^7$, —$CO_2R^6$, —$CONR^6R^7$, —$SO_2R^6$, —$SO_2NR^6R^7$, —$OCO_2R^6$, —$OCONR^6R^7$, and —$NR^6CO_2R^7$).

$R^5$ includes, further preferably, a hydrogen atom, and a $C_{1-6}$alkyl group optionally substituted with one to two substituents selected from the group consisting of a fluorine atom, a carboxyl group, a $C_{6-10}$aryl group, —$NR^6R^7$, —$CO_2R^6$, —$CONR^6R^7$, —$SO_2R^6$, —$SO_2NR^6R^7$, —$OC_2R^6$, —$OCONR^6R^7$, and —$NR^6CO_2R^7$.

$R^5$ includes, most preferably, a hydrogen atom, and a $C_{1-6}$alkyl group optionally substituted with one to two carboxyl groups.

Preferably, $R^6$ and $R^7$ are identical or different, and each independently include a hydrogen atom, and a $C_{1-10}$alkyl group optionally substituted with one to two groups selected from the group consisting of a halogen atom and a carboxyl group. As used herein, $R^6$ and $R^7$, when both are optionally substituted $C_{1-10}$alkyl groups, may be taken together with the nitrogen atom to which they are attached to form a 3- to 12-membered cyclic amino group.

More preferably, $R^6$ and $R^7$ are identical or different, and each independently include a hydrogen atom, and a $C_{1-6}$alkyl group optionally substituted with one to two groups selected from the group consisting of a halogen atom and a carboxyl group. As used herein, $R^6$ and $R^7$, when both are optionally substituted $C_{1-6}$alkyl groups, may be taken together with the nitrogen atom to which they are attached to form a 3- to 12-membered cyclic amino group.

Further preferably, $R^6$ and $R^7$ are identical or different, and each independently include a hydrogen atom, and a $C_{1-6}$alkyl group optionally substituted with one to two groups selected from the group consisting of a carboxyl group. As used herein, $R^6$ and $R^7$, when both are optionally substituted $C_{1-6}$alkyl groups, may be taken together with the nitrogen atom to which they are attached to form a 3- to 6-membered cyclic amino group.

Most preferably, $R^6$ and $R^7$ include a $C_{1-6}$alkyl group optionally substituted with one to two carboxyl groups.

$R^8$ includes, preferably, a $C_{1-10}$alkyl group optionally substituted with one to three groups selected from the group consisting of a halogen atom, a hydroxyl group, $-NR^6R^7$, a $C_{1-6}$alkoxy group, a $C_{3-10}$cycloalkyl group, a $C_{6-10}$aryl group, and a 3- to 12-membered monocyclic or polycyclic heterocyclic group.

$R^8$ includes, more preferably, a $C_{1-10}$alkyl group optionally substituted with one to three groups selected from the group consisting of a halogen atom, $-NR^6R^7$, a $C_{1-6}$alkoxy group, and a $C_{3-10}$cycloalkyl group.

$R^8$ includes, further preferably, a $C_{1-6}$alkyl group optionally substituted with one to three halogen atoms.

$R^8$ includes, further preferably, a methyl group.

X includes, preferably,
(1) a single bond,
(2) $C_{1-6}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$),
(3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$),
(4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$), and
(5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$).

X includes, more preferably,
(1) a single bond,
(2) $C_{1-6}$alkylene (the alkylene is optionally substituted with one to three substituents selected from the group consisting of a halogen atom, a carboxyl group, $-NR^6R^7$, and $-CO_2R^6$),
(3) $C_{3-10}$cycloalkylene (the cycloalkylene is optionally substituted with one to three substituents selected from the group consisting of a halogen atom, a carboxyl group, $-NR^6R^7$, and $-CO_2R^6$),
(4) a 3- to 12-membered monocyclic or polycyclic heterocycle (the heterocycle is optionally substituted with one to three substituents selected from the group consisting of a halogen atom, a carboxyl group, $-NR^6R^7$, and $-CO_2R^6$), and
(5) a 3- to 12-membered cyclic aminyl linker group (the cyclic aminyl linker group is optionally substituted with one to three substituents selected from the group consisting of a halogen atom, a carboxyl group, $-NR^6R^7$, and $-CO_2R^6$).

X includes, further preferably, a single bond, and $C_{1-6}$alkylene optionally substituted with one to two substituents selected from the group consisting of a fluorine atom, a carboxyl group, and $-CO_2R^6$.

X includes, most preferably, a single bond, and $C_{1-6}$alkylene optionally substituted with one to two substituents selected from the group consisting of a carboxyl group, and $-CO_2R^6$.

Y includes, preferably, a single bond, an oxygen atom, $-OCO_2-$, $-OCONR^{4A}-$, $-CONR^{4A}-$, $-NR^{4A}-$, $-NR^{4A}CO-$, $-NR^{4A}CO_2-$, $-NR^{4A}CONR^{4B}-$, $-NR^{4A}SO_2-$, $-NR^{4A}SO_2NR^{4B}-$, a sulfur atom, $-SO_2-$, $-SO_2NR^{4A}-$, and an optionally substituted 3- to 12-membered cyclic aminyl linker group.

Y includes, more preferably, a single bond, an oxygen atom, $-CONR^{4A}-$, $-NR^{4A}CO-$, and a sulfur atom.

Y includes, most preferably, a single bond and an oxygen atom.

Z include, preferably,
(1) a single bond,
(2) $C_{1-6}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$),
(3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$),
(4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$), and
(5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, $-NR^6R^7$, $-CO_2R^6$, $-CONR^6R^7$, $-SO_2R^6$, and $-SO_2NR^6R^7$).

Z includes, more preferably,
(1) a single bond,
(2) $C_{1-6}$alkylene (the alkylene is optionally substituted with one to three substituents selected from the group consisting of a halogen atom, a carboxyl group, $-NR^6R^7$, and $-CO_2R^6$),
(3) $C_{3-10}$cycloalkylene (the cycloalkylene is optionally substituted with one to three substituents selected from the group consisting of a halogen atom, a carboxyl group, $-NR^6R^7$, and $-CO_2R^6$),
(4) a 3- to 12-membered monocyclic or polycyclic heterocycle (the heterocycle is optionally substituted with one to three substituents selected from the group consisting of a halogen atom, a carboxyl group, $-NR^6R^7$, and $-CO_2R^6$), and
(5) a 3- to 12-membered cyclic aminyl linker group (the cyclic aminyl linker group is optionally substituted with one to three substituents selected from the group consisting of a halogen atom, a carboxyl group, $-NR^6R^7$, and $-CO_2R^6$).

Z includes, further preferably, a single bond, or $C_{1-6}$alkylene optionally substituted with one to two substituents selected from the group consisting of a fluorine atom, a carboxyl group, and $-CO_2R^6$.

Z includes, most preferably, a single bond, and $C_{1-6}$alkylene optionally substituted with one to two substituents selected from the group consisting of a carboxyl group and —$CO_2R^6$.

V includes, preferably,
(1) —$NHR^5$,
(2) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), and
(3) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$). As used herein, the 3- to 12-membered monocyclic or polycyclic heterocyclic group and the 3- to 12-membered cyclic amino group have at least one or more secondary nitrogen atoms in the ring.

V includes, more preferably,
(1) —$NHR^5$,
(2) a 3- to 12-membered monocyclic or polycyclic heterocyclic group (the heterocyclic group is optionally substituted with one to three substituents selected from the group consisting of a halogen atom, a carboxyl group, —$NR^6R^7$, and —$CO_2R^6$), and
(3) a 3- to 12-membered cyclic amino group (the cyclic amino group is optionally substituted with one to three substituents selected from the group consisting of a halogen atom, a carboxyl group, —$NR^6R^7$, and —$CO_2R^6$). As used herein, the 3- to 12-membered monocyclic or polycyclic heterocyclic group and the 3- to 12-membered cyclic amino group have at least one or more secondary nitrogen atoms in the ring.

V includes, further preferably, —$NHR^5$, a 3- to 6-membered monocyclic heterocyclic group, and a 3- to 6-membered cyclic amino group. As used herein, the 3- to 6-membered monocyclic heterocyclic group and the 3- to 6-membered cyclic amino group have at least one or more secondary nitrogen atoms in the ring.

V includes, most preferably, —$NHR_5$ and a 3- to 6-membered monocyclic heterocyclic group. As used herein, the 3- to 6-membered monocyclic heterocyclic group has at least one or more secondary nitrogen atoms in the ring.

Preferably, n includes 0, 1, and 2. More preferably, n includes 0 and 1. Most preferably, n includes 0.

In the compound represented by formula (1A), preferable compounds include compounds as described below, and pharmaceutically acceptable salts.

In the compound represented by formula (1A), preferable embodiments include the following (A).

(A)
A compound or a pharmaceutically acceptable salt thereof, wherein
$A^1$ and $A^2$ are identical or different, and each independently —$C(=O)B$, —$C(=O)CR^{3A}R^{3B}B$, —$CO_2B$, —$CONR^{3C}B$, or a hydrogen atom, wherein $A^1$ and $A^2$ are not both hydrogen atoms,
wherein
B is
(1) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(2) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or
(3) a group represented by the formula (B),
wherein
X is
(1) a single bond,
(2) $C_{1-6}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
(4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or
(5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$),
Y is a single bond, an oxygen atom, —$OCO_2$—, —$OCONR^{4A}$—, —$CONR^{4A}$—, —$NR^{4A}$—, —$NR^{4A}CO$—, —$NR^{4A}CO_2$—, —$NR^{4A}CONR^{4B}$—, —$NR^{4A}SO_2$—, —$NR^{4A}SO_2NR^{4B}$—, a sulfur atom, —$SO_2$—, —$SO_2NR^{4A}$—, or an optionally substituted 3- to 12-membered cyclic aminyl linker group,
$R^{4A}$ and $R^{4B}$ are identical or different, and each independently a hydrogen atom, or $C_{1-6}$alkyl optionally substituted with one to two substituents selected from the group consisting of a carboxyl group and —$CO_2R^6$,
Z is
(1) a single bond,
(2) $C_{1-6}$alkylene (the alkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (3) $C_{3-10}$cycloalkylene (the cycloalkylene is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), (4) a 3- to 12-membered monocyclic or polycyclic heterocycle (the heterocycle is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (5) a 3- to 12-membered cyclic aminyl linker group (the cyclic aminyl linker group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), n is 0, 1, or 2, V is (1) —$NHR^5$, (2) a 3- to 12-membered monocyclic or polycyclic heterocyclic group (the heterocyclic group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), or (3) a 3- to 12-membered cyclic amino group (the cyclic amino group is optionally substituted with one to three substituents selected from the group consisting of a halogen atom, a hydroxyl group, a carboxyl group, a sulfinate group, a sulfonate group, a phosphate group, a $C_{1-6}$alkoxy group, a $C_{3-8}$cycloalkoxy group, —$NR^6R^7$, —$CO_2R^6$, —$CONR^6R^7$, —$SO_2R^6$, and —$SO_2NR^6R^7$), wherein the 3- to 12-membered monocyclic or polycyclic heterocyclic group and the 3- to 12-membered cyclic amino group have at least one or more secondary nitrogen atoms in the ring, $R^5$ is (1) a hydrogen atom, or (2) a $C_{1-10}$alkyl group (the alkyl group is optionally substituted with one to three substituents selected from the group consisting of a halogen atom, a hydroxyl group, a carboxyl group, a sulfinate group, a sulfonate group, a phosphate group, a $C_{6-10}$aryl group, a $C_{1-6}$alkoxy group, a $C_{3-8}$cycloalkoxy group, —$NR^6R^7$, —$CO_2R^6$, —$CONR^6R^7$, —$SO_2R^6$, —$SO_2NR^6R^7$, —$OCO_2R^6$, —$OCONR^6R^7$, and —$NR^6CO_2R^7$), and $R^6$ and $R^7$ are identical or different, and each independently a hydrogen atom, or a $C_{1-6}$alkyl group optionally substituted with one to two groups selected from the group consisting of a halogen atom and a carboxyl group, wherein $R^6$ and $R^7$, when both are optionally substituted $C_{1-6}$alkyl groups, may be taken together with the nitrogen atom to which they are attached to form a 3- to 12-membered cyclic amino group, and wherein the 3- to 12-membered monocyclic or polycyclic heterocyclic group and the 3- to 12-membered cyclic amino group have at least one or more secondary nitrogen atoms in the ring, and $R^{3A}$, $R^{3B}$, and $R^{3C}$ are identical or different, and each independently a hydrogen atom, or a $C_{1-6}$alkyl group optionally substituted with one to three substituents selected from the group consisting of a halogen atom, a carboxyl group, —$NR^6R^7$, and —$CO_2R^6$;

$R^1$ is a hydrogen atom, a hydroxyl group, a $C_{1-6}$alkoxy group, a $C_{1-6}$alkylcarbonyl group, or a carboxyl group;

$R^{2A}$, $R^{2B}$, $R^{2C}$, and $R^{2D}$ are identical or different, and each independently a hydrogen atom, a halogen atom, a $C_{1-6}$alkyl group, a $C_{3-10}$cycloalkyl group, a $C_{1-6}$alkoxy group, or a carboxyl group; and $R^8$ is a $C_{1-10}$alkyl group optionally substituted with one to three groups selected from the group consisting of a halogen atom, —$NR^6R^7$, a $C_{1-6}$alkoxy group, and a $C_{3-10}$cycloalkyl group.

In the compound represented by formula (1A), more preferable embodiments include the following (B).

(B)

A compound or a pharmaceutically acceptable salt thereof, wherein $A^1$ and $A^2$ are identical or different, and each independently —$CO_2B$, —$CONR^{3C}B$, or a hydrogen atom, wherein $A^1$ and $A^2$ are not both hydrogen atoms, wherein B is a 3- to 6-membered monocyclic heterocyclic group optionally substituted with one to two substituents selected from the group consisting of a fluorine atom, a carboxyl group, and —$CO_2R^6$, or a group represented by the formula (B), wherein X is (1) a single bond, (2) $C_{1-6}$alkylene (the alkylene is optionally substituted with one to three substituents selected from the group consisting of a halogen atom, a carboxyl group, —$NR^6R^7$, and —$CO_2R^6$), (3) $C_{3-10}$cycloalkylene (the cycloalkylene is optionally substituted with one to three substituents selected from the group consisting of a halogen atom, a carboxyl group, —$NR^6R^7$, and —$C_2R^6$), (4) a 3- to 12-membered monocyclic or polycyclic heterocycle (the heterocycle is optionally substituted with one to three substituents selected from the group consisting of a halogen atom, a carboxyl group, —$NR^6R^7$, and —$CO_2R^6$), or (5) a 3- to 12-membered cyclic aminyl linker group (the cyclic aminyl linker group is optionally substituted with one to three substituents selected from the group consisting of a halogen atom, a carboxyl group, —$NR^6R^7$, and —$CO_2R^6$), Y is a single bond, an oxygen atom, —$CONR^{4A}$—, —$NR^{4A}CO$—, or a sulfur atom;

$R^{4A}$ is a hydrogen atom or $C_{1-6}$alkyl,

Z is
(1) a single bond,
(2) $C_{1-6}$alkylene (the alkylene is optionally substituted with one to three substituents selected from the group consisting of a halogen atom, a carboxyl group, —NR$^6$R$^7$, and —CO$_2$R$^6$),
(3) $C_{3-10}$cycloalkylene (the cycloalkylene is optionally substituted with one to three substituents selected from the group consisting of a halogen atom, a carboxyl group, —NR$^6$R$^7$, and —C$_2$R$^6$),
(4) a 3- to 12-membered monocyclic or polycyclic heterocycle (the heterocycle is optionally substituted with one to three substituents selected from the group consisting of a halogen atom, a carboxyl group, —NR$^6$R$^7$, and —CO$_2$R$^6$), or
(5) a 3- to 12-membered cyclic aminyl linker group (the cyclic aminyl linker group is optionally substituted with one to three substituents selected from the group consisting of a halogen atom, a carboxyl group, —NR$^6$R$^7$, and —CO$_2$R$^6$),
n is 0 or 1,
V is
(1) —NHR$^5$,
(2) a 3- to 12-membered monocyclic or polycyclic heterocyclic group (the heterocyclic group is optionally substituted with one to three substituents selected from the group consisting of a halogen atom, a carboxyl group, —NR$^6$R$^7$, and —CO$_2$R$^6$), or
(3) a 3- to 12-membered cyclic amino group (the cyclic amino group is optionally substituted with one to three substituents selected from the group consisting of a halogen atom, a carboxyl group, —NR$^6$R$^7$, and —CO$_2$R$^6$),
wherein the 3- to 12-membered monocyclic or polycyclic heterocyclic group and the 3- to 12-membered cyclic amino group have at least one or more secondary nitrogen atoms in the ring,
R$^5$ is
(1) a hydrogen atom or
(2) a $C_{1-6}$alkyl group (the alkyl group is optionally substituted with one to three substituents selected from the group consisting of a halogen atom, a hydroxyl group, a carboxyl group, a sulfinate group, a sulfonate group, a phosphate group, a $C_{6-10}$aryl group, a $C_{1-6}$alkoxy group, a $C_{3-8}$cycloalkoxy group, —NR$^6$R$^7$, —CO$_2$R$^6$, —CONR$^6$R$^7$, —SO$_2$R$^6$, —SO$_2$NR$^6$R$^7$, —OCO$_2$R$^6$, —OCONR$^6$R$^7$, and —NR$^6$CO$_2$R$^7$), and
R$^6$ and R$^7$ are identical or different, and each independently a hydrogen atom, or a $C_{1-6}$alkyl group optionally substituted with one to two groups selected from the group consisting of a carboxyl group, wherein R$^6$ and R$^7$, when both are optionally substituted $C_{1-6}$alkyl groups, may be taken together with the nitrogen atom to which they are attached to form a 3- to 6-membered cyclic amino group, and
wherein
the 3- to 6-membered monocyclic heterocyclic group has at least one or more secondary nitrogen atoms in the ring, and
R$^{3C}$ is a hydrogen atom, or a $C_{1-6}$alkyl group optionally substituted with one to two substituents selected from the group consisting of a carboxyl group and —CO$_2$R$^6$;
R$^1$ is a hydrogen atom;
R$^{2A}$, R$^{2B}$, R$^{2C}$, and R$^{2D}$ are all hydrogen atoms;
R$^8$ is a $C_{1-6}$alkyl group optionally substituted with one to three halogen atoms.

In the compound represented by formula (1A), further preferable embodiments include the following (C).
(C)
A compound or a pharmaceutically acceptable salt thereof, wherein
A$^1$ and A$^2$ are identical or different, and each independently —CONR$^{3C}$B, or a hydrogen atom, wherein A$^1$ and A$^2$ are not both hydrogen atoms,
wherein
B is 3- to 6-membered monocyclic heterocyclic group, or a group represented by the formula (B),
wherein
X is a single bond, or $C_{1-6}$alkylene optionally substituted with one to two substituents selected from the group consisting of a fluorine atom, a carboxyl group, and —CO$_2$R$^6$,
Y is a single bond or an oxygen atom,
Z is a single bond, or $C_{1-6}$alkylene optionally substituted with one to two substituents selected from the group consisting of a fluorine atom, a carboxyl group, and —CO$_2$R$^6$,
n is 0 or 1,
V is —NHR$^5$, 3- to 6-membered monocyclic heterocyclic group, or a 3- to 6-membered cyclic amino group, wherein the 3- to 6-membered monocyclic heterocyclic group and the 3- to 6-membered cyclic amino group have at least one or more secondary nitrogen atoms in the ring,
R$^5$ is a hydrogen atom, or a $C_{1-6}$alkyl group optionally substituted with one to two substituents selected from the group consisting of a fluorine atom, a carboxyl group, a $C_{6-10}$aryl group, —NR$^6$R$^7$, —CO$_2$R$^6$, —CONR$^6$R$^7$, —SO$_2$R$^6$, —SO$_2$NR$^6$R$^7$, —OCO$_2$R$^6$, —OCONR$^6$R$^7$, and —NR$^6$CO$_2$R$^7$, and
R$^6$ is a $C_{1-6}$alkyl group optionally substituted with one to two carboxyl groups, and
wherein
the 3- to 6-membered monocyclic heterocyclic group has at least one or more secondary nitrogen atoms in the ring, and
R$^{3C}$ is a hydrogen atom;
R$^1$ is a hydrogen atom;
R$^{2A}$, R$^{2B}$, R$^{2C}$, and R$^{2D}$ are all hydrogen atoms; and
R$^8$ is a methyl group.

In the compound represented by formula (1A), most preferable embodiments include the following (D).
(D)
A compound or a pharmaceutically acceptable salt thereof, wherein
A$^1$ and A$^2$ are —CONR$^{3C}$B,
wherein
B is 3- to 6-membered monocyclic heterocyclic group, or a group represented by the formula (B),
wherein
X is a single bond, or $C_{1-6}$alkylene optionally substituted with one to two substituents selected from the group consisting of a carboxyl group and —CO$_2$R$^6$,
V is —NHR$^5$ or a 3- to 6-membered monocyclic heterocyclic group, wherein the 3- to 6-membered monocyclic heterocyclic group has at least one or more secondary nitrogen atoms in the ring,
R$^5$ is a hydrogen atom, or a $C_{1-6}$alkyl group optionally substituted with one to two carboxyl groups, and
R$^6$ is a $C_{1-6}$alkyl group, and wherein
the 3- to 6-membered monocyclic heterocyclic group has at least one or more secondary nitrogen atoms in the ring, and
$R^{3C}$ is a hydrogen atom;
$R^1$ is a hydrogen atom;
$R^{2A}$, $R^{2B}$, $R^{2C}$, and $R^{2D}$ are all hydrogen atoms; and
$R^8$ is a methyl group.

Preferable embodiments of the present invention include compounds represented by the following formulas (1-1a)-(3-4c).

A compound represented by the following formula (1-1a), (1-1b), (1-1c), (1-2a), (1-2b), (1-2c), (1-3a), (1-3b), (1-3c), (1-4a), (1-4b), (1-4c), (1-5a), (1-5b), (1-5c), (1-6a), (1-6b), or (1-6c), or a pharmaceutically acceptable salt thereof:

[Chem. 22]

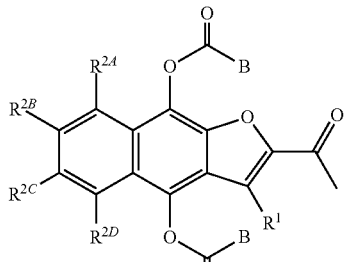
(1-1a)

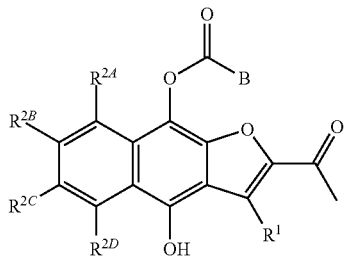
(1-1b)

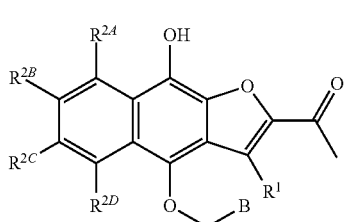
(1-1c)

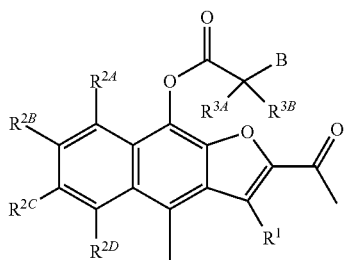
(1-2a)

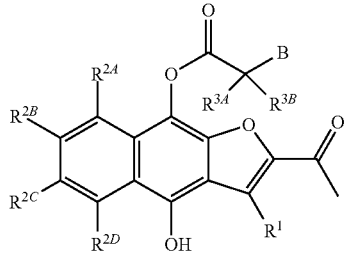
(1-2b)

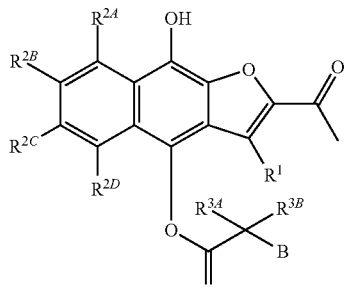
(1-2c)

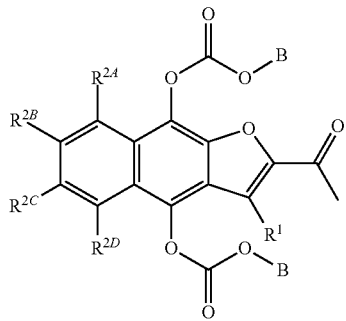
(1-3a)

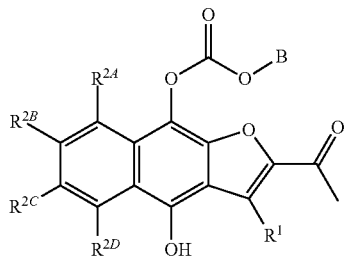
(1-3b)

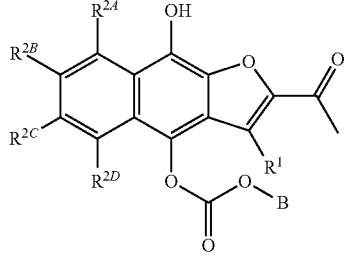
(1-3c)

(1-4a)
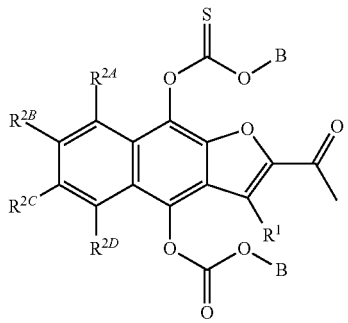

(1-4b)
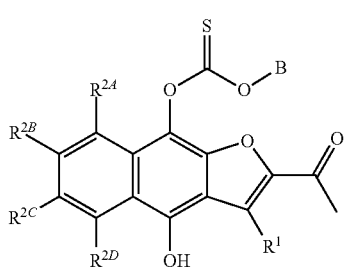

(1-4c)
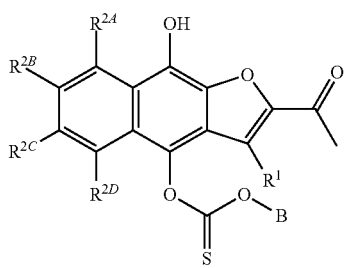

(1-5a)
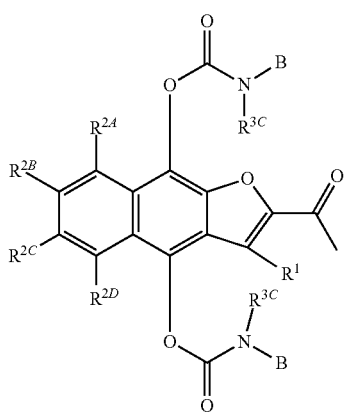

(1-5b)
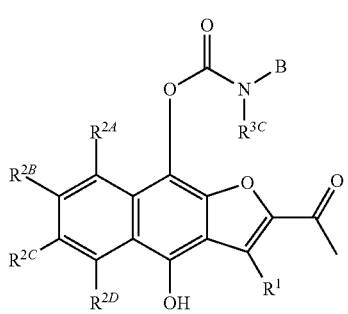

(1-5c)
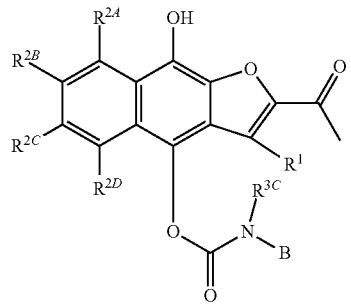

(1-6a)
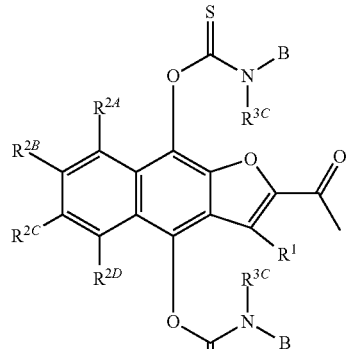

(1-6b)
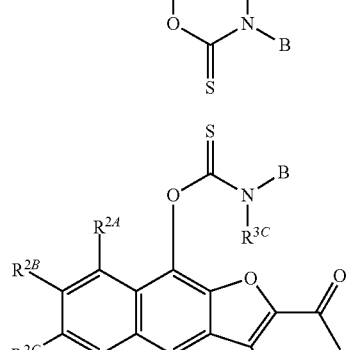

(1-6c)
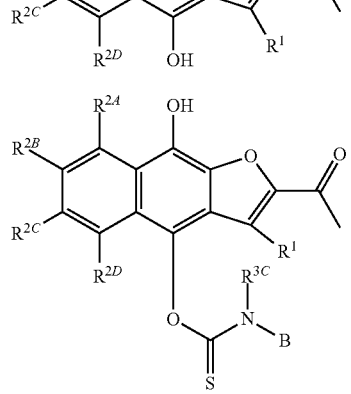

[each symbol in the formulas is defined the same as item 1 or 2].

Preferable embodiments of respective symbols in the compounds represented by the above-described formulas (1-1a), (1-1b), (1-1c), (1-2a), (1-2b), (1-2c), (1-3a), (1-3b), (1-3c), (1-4a), (1-4b), (1-4c), (1-5a), (1-5b), (1-5c), (1-6a), (1-6b), and (1-6c) are the same as the preferable embodiments in the compound represented by formula (1A) or (1).

A compound represented by the following formula (2-1a), (2-1b), (2-1c), (2-2a), (2-2b), (2-2c), (2-3a), (2-3b), (2-3c), (2-4a), (2-4b), or (2-4c), or a pharmaceutically acceptable salt thereof:

[Chem. 23]
(2-1a)
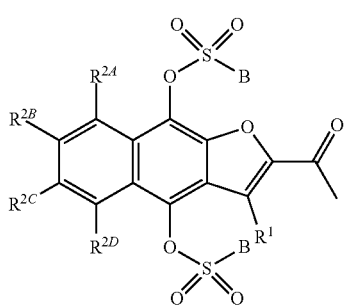
(2-1b)
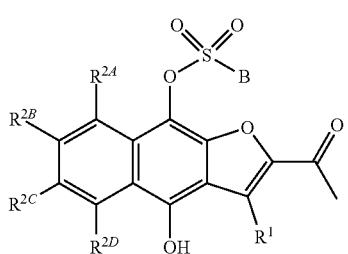
(2-1c)
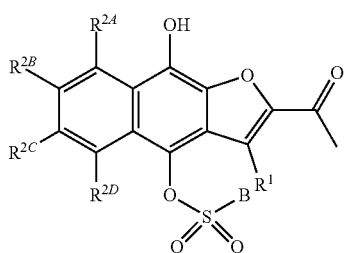
(2-2a)
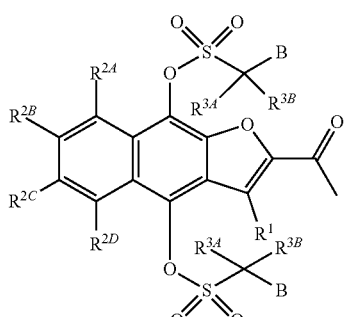
(2-2b)
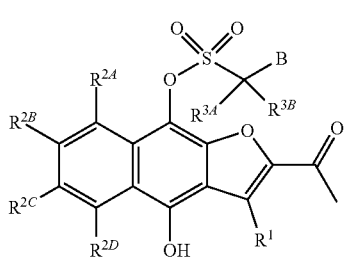
(2-2c)
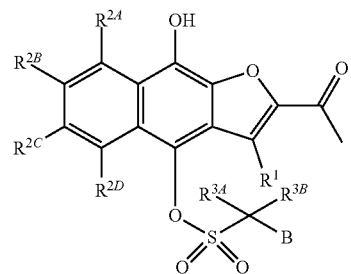
(2-3a)
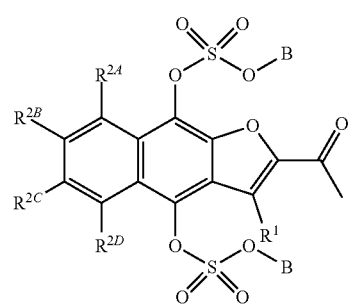
(2-3b)
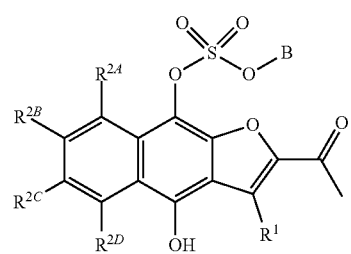
(2-3c)
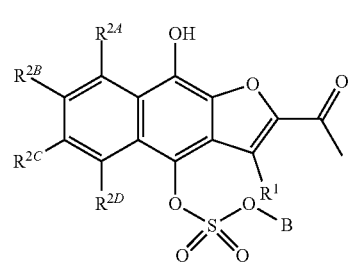
(2-4a)
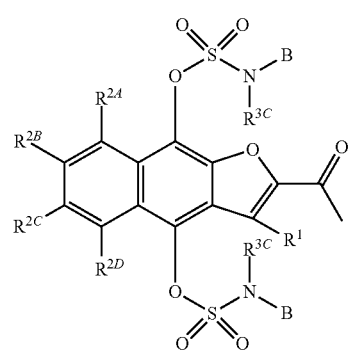

(2-4b)
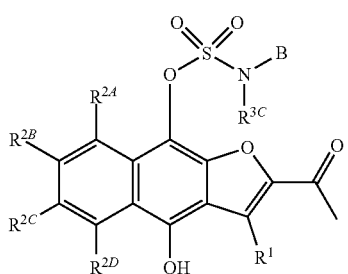

(2-4c)
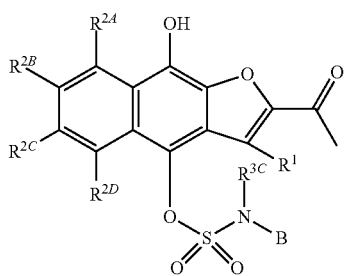

[each symbol in the formulas is defined the same as item 1 or 2].

Preferable embodiments of respective symbols in the compounds represented by the above-described formulas (2-1a), (2-1b), (2-1c), (2-2a), (2-2b), (2-2c), (2-3a), (2-3b), (2-3c), (2-4a), (2-4b), and (2-4c) are the same as the preferable embodiments in the compound represented by formula (1A) or (1).

A compound represented by the following formula (3-1a), (3-1b), (3-1c), (3-2a), (3-2b), (3-2c), (3-3a), (3-3b), (3-3c), (3-4a), (3-4b), or (3-4c), or a pharmaceutically acceptable salt thereof:

[Chem. 24]

(3-1a)
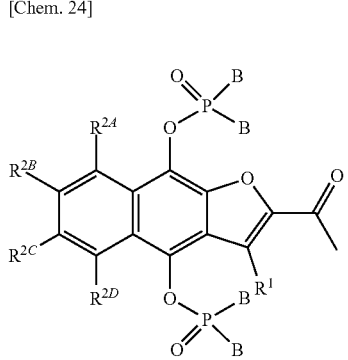

(3-1b)
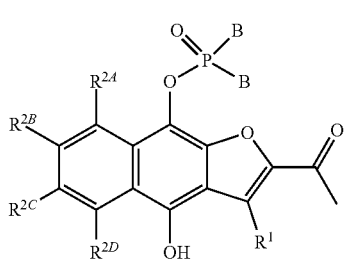

(3-1c)
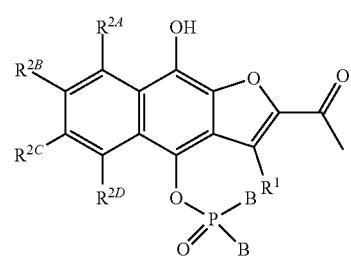

(3-2a)
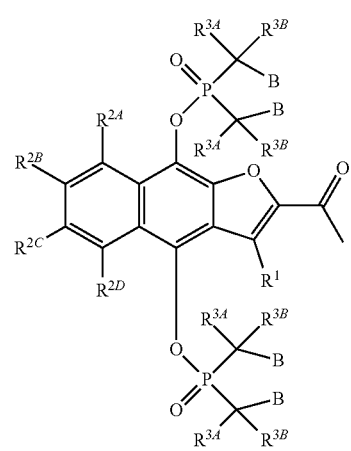

(3-2b)
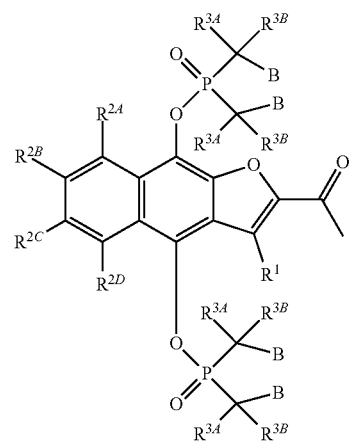

(3-2c)
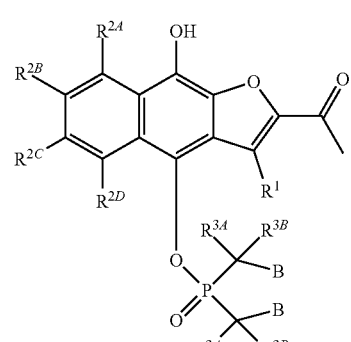

(3-3a)
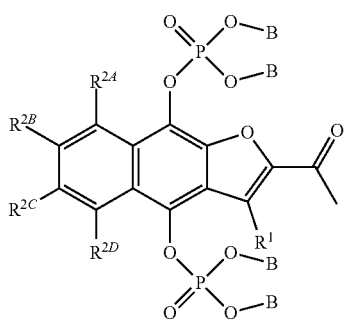

(3-3b)
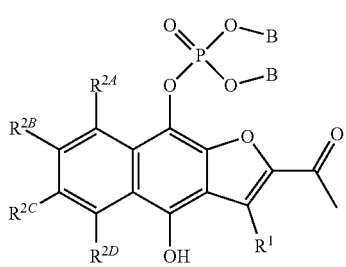

(3-3c)
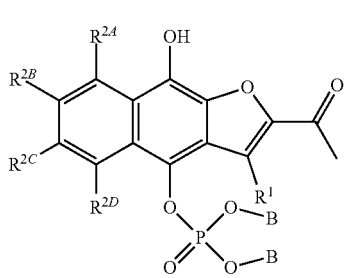

(3-4a)
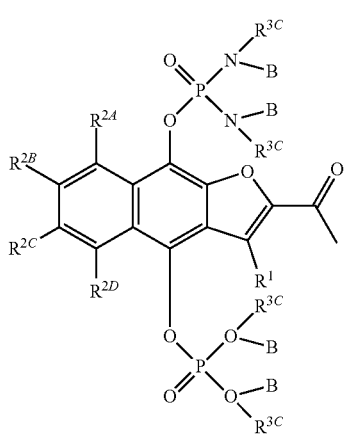

(3-4b)
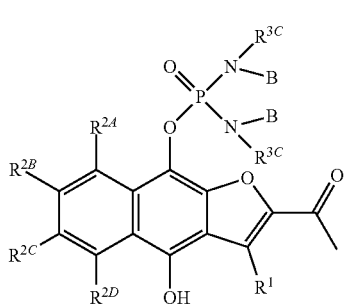

(3-4c)
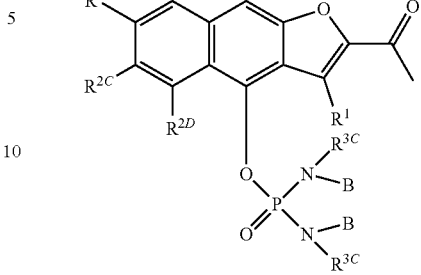

[each symbol in the formulas is defined the same as item 1 or 2].

Preferable embodiments of respective symbols in the compounds represented by the above-described formulas (3-1a), (3-1b), (3-1c), (3-2a), (3-2b), (3-2c), (3-3a), (3-3b), (3-3c), (3-4a), (3-4b), and (3-4c) are the same as the preferable embodiments in the compound represented by formula (1A) or (1).

A "pharmaceutically acceptable salt" includes acid addition salts and base addition salts. Examples of acid addition salts include: inorganic acid salts such as hydrochlorides, hydrobromides, sulfates, hydroiodides, nitrates, phosphates, and the like; and organic acid salts such as citrate, oxalate, phthalate, fumarate, maleate, succinate, malate, acetate, formate, propionate, benzoate, trifluoroacetate, methanesulfonate, benzenesulfonate, para-toluenesulfonate, camphorsulfonate, and the like; and examples of base addition salts include inorganic base salts such as sodium, potassium, calcium, magnesium, barium, and aluminum salts, and the like, organic base salts such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, and N,N-dibenzylethylamine, and the like, and further salts of an amino acid such as basic and acidic amino acids including arginine, lysine, ornithine, aspartic acid, glutamic acid, and the like.

Suitable salts and pharmaceutically acceptable salts of starting compounds and target compounds are conventional nontoxic salts. They include acid addition salts such as organic acid salts (e.g., acetate, trifluoroacetate, maleate, fumarate, citrate, tartrate, methanesulfonate, benzenesulfonate, formate, para-toluenesulfonate, or the like) and inorganic acid salts (e.g., hydrochloride, hydrobromide, hydroiodide, sulfate, nitrate, phosphate, or the like), salts with an amino acid (e.g., arginine, aspartic acid, glutamic acid, or the like), metal salts such as alkali metal salts (e.g., sodium salt, potassium salt, or the like), alkali earth metal salts (e.g., calcium salt, magnesium salt, or the like), and the like, ammonium salts, organic base salts (e.g., trimethylamine salts, triethylamine salts, pyridine salts, picoline salts, dicyclohexylamine salts, N,N'-dibenzylethylene diamine salts, or the like), or the like, and additionally those skilled in the art can appropriately select them.

When it is desired to obtain a salt of the present compound, if the present compound is obtained in a salt form, it may be purified as it is, or if it is obtained in free form, it may be dissolved or suspended in a suitable organic solvent, and an acid or a base is added thereto to form a salt in accordance with a general method.

In addition, although the present compounds and pharmaceutically acceptable salts thereof may be present in an adduct form with water or any kind of solvent, these adducts are also encompassed by the present invention.

In addition, the present invention encompasses compounds represented by formula (1A) or (1), or pharmaceutically acceptable salts thereof. It also encompasses hydrates or solvates (such as ethanol solvates and the like) thereof. Further, the present invention encompasses all tautomers and all present stereoisomers of the present compound (1A) or (1) as well as those in all modes of crystal forms.

Among the present compounds (1A) or (1), there are compounds that may be present as enantiomers based on an optically-active center, atropisomers based on axial or planar chirality caused by restriction of intramolecular rotation, other stereoisomers, tautomers, geometric isomer, and the like. However, all possible isomers and mixtures thereof, including these, are encompassed within the scope of the present invention.

In particular, an enantiomer and an atropisomer can be obtained as a racemic body, or an optically-active substance when an optically-active starting material or intermediate is used, respectively. If necessary, in an appropriate step of the above-described production method, a corresponding starting material, intermediate, or racemic body as a final product can be physically or chemically resolved into their optical enantiomers by a known separation method, such as a method using an optically active column, a fractional crystallization method, or the like. Specifically, for example, in a diastereomer method, two types of diastereomers are formed from a racemic body by reaction using an optical active resolving agent. Since these different diastereomers generally have different physical properties, they can be separated by a known method such as fractional crystallization and the like.

Production methods of compounds relating to the present invention are described below. The compounds relating to the present invention represented by formula (1A) or (1) or pharmaceutically acceptable salts thereof can be produced from known compounds, for example, the following production method A, B, C, D, E, F, G, H, I, and J, and methods in accordance therewith, or by appropriately combining synthesis methods well-known to those skilled in the art.

It should be noted that a compound in a reaction includes the case where it forms a salt, for example, salts similar to salts in compound (1A) or (1) and the like are used as such a salt.

In addition, a compound obtained in each step can be used in a next reaction as a reaction solution or as a composition. However, it can be isolated from a reaction mixture in accordance with a routine method, and readily purified by a separation means such as recrystallization, distillation, chromatography, and the like.

Each symbol of compounds in the following reactions is defined the same as above, unless specifically indicated.

Production Method A

Of the compound represented by formula (1), Compound A1 represented by formula [A1] wherein $A^1$ and $A^2$ are —CONHB can be produced, for example, by the following production method.

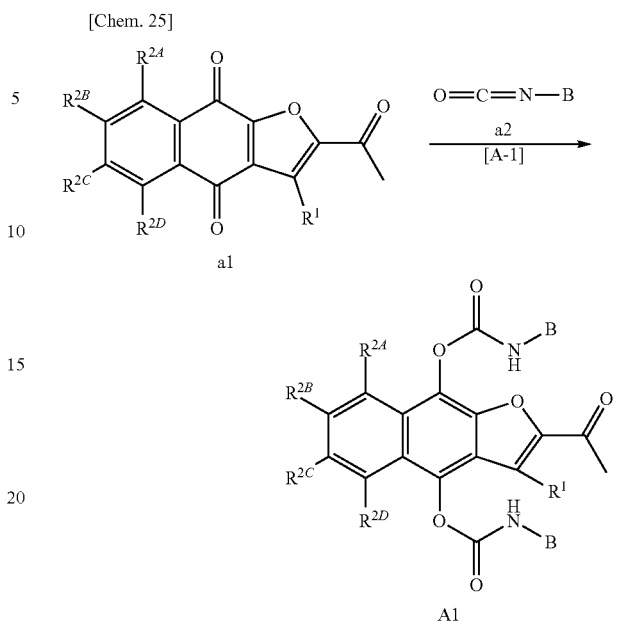

[Chem. 25]

In the formulas, $R^1$, $R^{2A}$, $R^{2B}$, $R^{2C}$, and $R^{2D}$ are as defined in item 1 or 2, and B is as defined in item 31.

Compound a1 can be produced by a method described in a Patent Literature (e.g., WO2009/036059 or the like).

[A-1 Step]

This step is a step of obtaining Compound A1 by reacting Compound a1 with Compound a2, which is obtained by the following production method, in the presence of an additive, a base, and a reductant in suitable solvent. The additive includes tetra-n-butylammonium chloride, tetra-n-butylammonium bromide, tetra-n-butylammonium iodide, and the like, and preferably, tetra-n-butylammonium bromide. The following can be used as the base: for example, basic salts such as sodium carbonate, potassium carbonate, cesium carbonate, sodium acetate, sodium hydride, calcium hydride, and the like; aromatic amines such as pyridine, lutidine, 4-dimethylaminopyridine, N,N-dimethylaniline, and the like; tertiary amines such as triethylamine, tripropylamine, tributylamine, cyclohexyldimethylamine, N,N-diisopropylethylamine, N-methylpiperidine, N-methylpyrrolidine, N-methylmorpholine, and the like; and the like. In particular, triethylamine or N,N-diisopropylethylamine is preferable. The reductant includes iron(II) ion, tin(II) ion, sodium, zinc, formic acid, oxalic acid, sodium dithionite, and the like, and preferably a mixed reductant of zinc and sodium dithionite. Solvent used in this step is selected from solvent and the like illustrated below. However, it includes aprotic solvent such as N,N-dimethylformamide, N-methyl-2-pyrrolidone, dimethyl sulfoxide, acetonitrile, propionitrile, and the like; ether-based solvent such as tetrahydrofuran, 1,4-dioxane, and the like; halogenated hydrocarbons such as dichloromethane, chloroform, 1,2-dichloroethane, chlorobenzene, and the like; hydrocarbons such as toluene, benzene, and the like; water; and mixed solvent thereof; and the like, and includes preferably N,N-dimethylformamide. The amount of a reductant used is generally 2 equivalents to 20 equivalents, preferably 4 equivalents to 8 equivalents, relative to one equivalent of Compound a1. The reaction time is generally about 0.5 hour to about 48 hours, and preferably about 0.5 hour to about 2 hours. The reaction temperature is generally about −20° C. to about 180° C., and preferably about 0° C. to about 50° C.

Production Method B

Of the compound represented by formula (1), Compound B1, B2, B3, or B4 represented by formulas [B1], [B2], [B3] and [B4] wherein $A^1$ and $A^2$ are —C(=O)B, —C(=O)CR$^{3A}$R$^{3B}$B, —CO$_2$B, or —CONR$^{3C}$B can be produced, for example, by the following production method.

[Chem. 26]

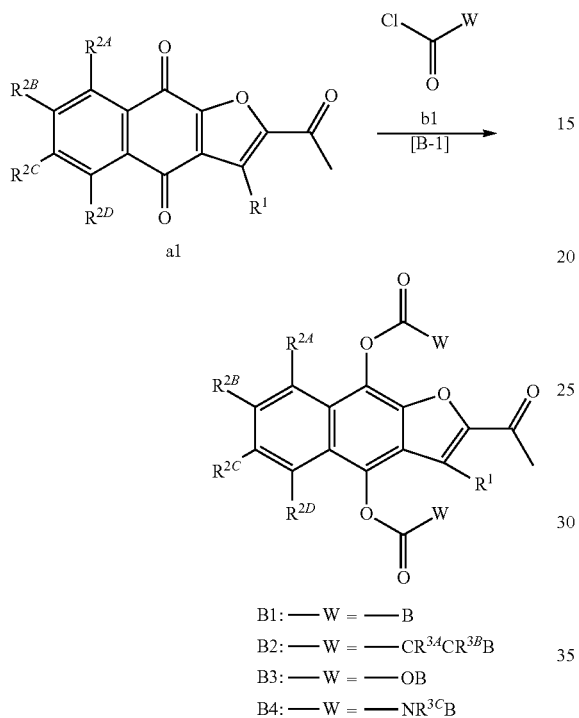

B1: —W = —B
B2: —W = —CR$^{3A}$CR$^{3B}$B
B3: —W = —OB
B4: —W = —NR$^{3C}$B

In the formulas, $R^1$, $R^{2A}$, $R^{2B}$, $R^{2C}$, $R^{2D}$, $R^{3A}$, $R^{3B}$, and $R^{3C}$ are as defined in item 1 or 2, B is as defined in item 31, and W means —B, —CR$^{3A}$R$^{3B}$B, —OB, or —NR$^{3C}$B.

[B-1 Step]

This is a step of obtaining Compound B1, B2, B3, or B4 by reacting Compound a1 with Compound b1, which is obtained by the following production method, under a condition in accordance with the above-described A-1 step.

Production Method C

Of the compound represented by formula (1), Compound C$_1$ represented by formula [C1] wherein $A^1$ is a hydrogen atom and $A^2$ is —CONHB can be produced, for example, by the following production method.

[Chem. 27]

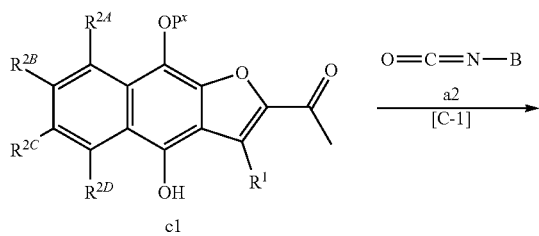

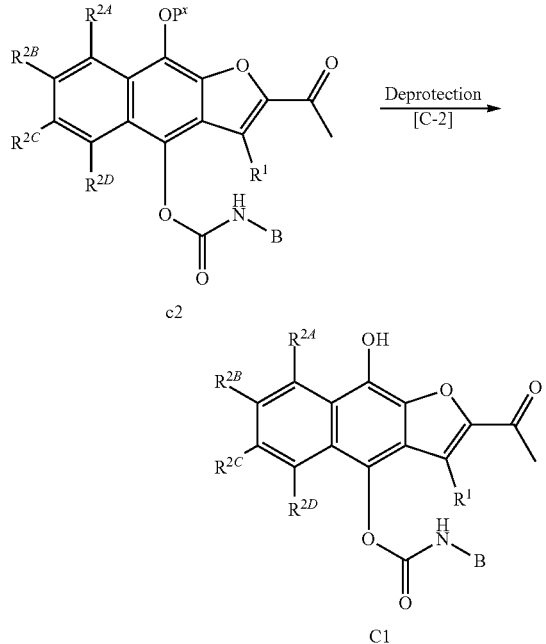

In the formulas, $R^1$, $R^{2A}$, $R^{2B}$, $R^{2C}$, and $R^{2D}$ are as defined in item 1 or 2, B is as defined in item 31, and $P^X$ means a protecting group for a phenolic hydroxyl group.

Protecting group $P^X$ is described as a protecting group for a phenolic hydroxyl group in Protective Groups in Organic Synthesis (written by Theodora W. Greene, Peter G. M. Wuts, published by John Wiley & Sons, Inc., 1999).

Compound c1 can be produced from Compound a1, for example, by is the same method as a method and the like described in a Patent Literature (e.g., WO2012/119265, WO2013/120229, WO2013/128037, or the like).

[C-1 step]

This step is a step of obtaining Compound c2 by reacting Compound c1 with Compound a2, which is obtained by the following production method, in the presence of a base in suitable appropriate solvent. Solvent used in the reaction may be any solvent as long as it is inactive in the reaction, and is not particularly limited. However, for example, tetrahydrofuran, 1,4-dioxane, dimethoxyethane, benzene, toluene, xylene, N,N-dimethylformamide, N-methyl-2-pyrrolidone, dimethyl sulfoxide, and the like can be used alone or as a mixture thereof, and in particular, tetrahydrofuran or N,N-dimethylformamide is preferable. The following can be used as the base: for example, basic salts such as sodium carbonate, potassium carbonate, cesium carbonate, sodium acetate, sodium hydride, calcium hydride, and the like; aromatic amines such as pyridine, lutidine, 4-dimethylaminopyridine, N,N-dimethylaniline, and the like; tertiary amines such as triethylamine, tripropylamine, tributylamine, cyclohexyldimethylamine, N,N-diisopropylethylamine, N-methylpiperidine, N-methylpyrrolidine, N-methylmorpholine, and the like; and the like. In particular, triethylamine or N,N-diisopropylethylamine is preferable.

The reaction temperature is generally a temperature between about 0° C. and the boiling point of a solvent used, and preferably, 0 to 80° C. The reaction time is generally 0.5 to 24 hours, and preferably about 0.5 hour to about 2 hours.

[C-2 Step]

This step is a step of obtaining Compound C1 by deprotecting a protecting group $P^X$ for the phenolic hydroxyl group of Compound c2, which is obtained in the above-described production method C-1. This step can be carried out in accordance with a method or the like described in Protective Groups in Organic Synthesis (written by Theodora W. Greene, Peter G. M. Wuts, published by John Wiley & Sons, Inc., 1999).

Production Method D

Of the compound represented by formula (1), Compound D1, D2, D3, or D4 represented by formula [D1], [D2], [D3], or [D4] wherein $A^1$ is a hydrogen atom and $A^2$ is —C(=O)B, —C(=O)CR$^{3A}$R$^{3B}$B, —CO$_2$B, or —CONR$^{3C}$B can be produced, for example, by the following production method.

[Chem. 28]

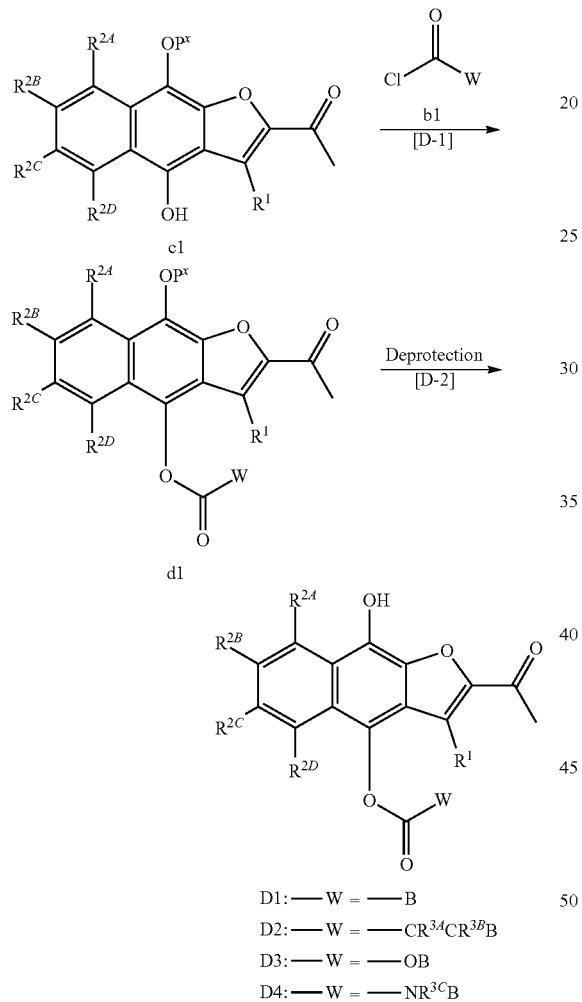

In the formulas, $R^1$, $R^{2A}$, $R^{2B}$, $R^{2C}$, $R^{2D}$, $R^{3A}$, $R^{3B}$, and $R^{3C}$ are as defined in item 1 or 2, B is as defined in item 1 or 2, W means —B, —CR$^{3A}$R$^{3B}$B, —OB, or —NR$^{3C}$B.

The protecting group $P^X$ is described as a protecting group for a phenolic hydroxyl group in Protective Groups in Organic Synthesis (written by Theodora W. Greene, Peter G. M. Wuts, published by John Wiley & Sons, Inc., 1999).

Compound c1 can be produced from Compound 1 by the same method as a method or the like described in a Patent Literature (e.g., WO2012/119265, WO2013/120229, WO2013/128037, or the like).

[D-1 Step]

This step is a step of obtaining Compound d1 by reacting Compound c1 with Compound b1, which is obtained by the following production method, under a condition in accordance with the above-described C-1 step.

[D-2 step]

This step is a step of obtaining Compound D1, D2, D3, or D4 by deprotecting a protecting group $P^X$ for the phenolic hydroxyl group of Compound d1, which is obtained by the above-described production method D-1, under a condition in accordance with the above-described C-2 step.

Production Method E

Of the compound represented by formula (1), Compound E1, E2, E3, or E4 represented by formula [E1], [E2], [E3], or [E4] wherein $A^1$ is —C(=O)B, —C(=O)CR$^{3A}$R$^{3B}$B, —CO$_2$B, or —CONR$^{3C}$B and $A^2$ is —CONHB can be produced, for example, by the following production method.

[Chem. 29]

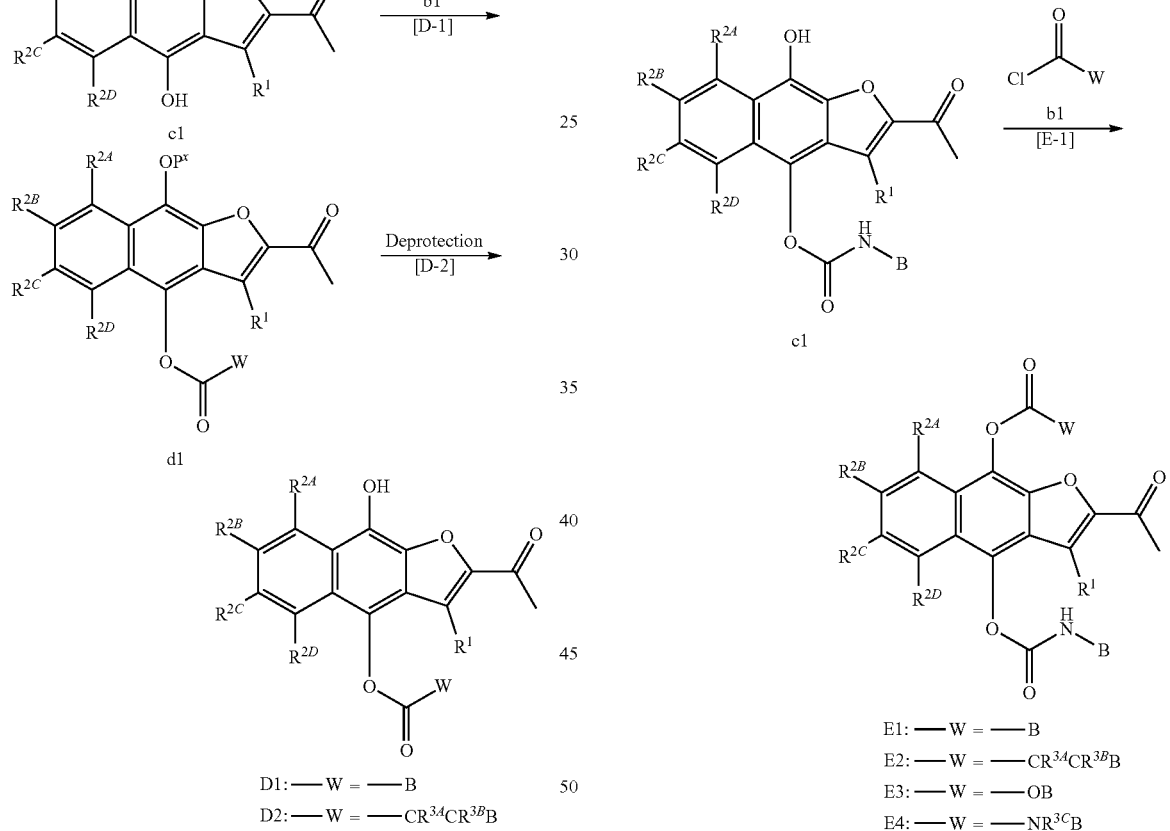

In the formulas, $R^1$, $R^{2A}$, $R^{2B}$, $R^{2C}$, $R^{2D}$, $R^{3A}$, $R^{3B}$, and $R^{3C}$ are as defined in item 1 or 2, B is as defined in item 1 or 2, and W means —B, —CR$^{3A}$R$^{3B}$B, —OB, or —NR$^{3C}$B.

[E-1 Step]

This step is a step of obtaining Compound E1, E2, E3, or E4 by reacting Compound $C_1$, which is obtained in the above-described C-2 step, with Compound b1, which is obtained by the following production method, under a condition in accordance with the above-described C-1 step.

Production Method F (Production Method of a Synthetic Intermediate)

A synthetic intermediate represented by the above-described a2 can be produced, for example, the following production method.

[Chem. 30]

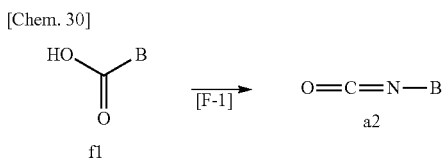

In the formulas, B is as defined in item 31.

[F-1 Step]

This step is a step of converting Compound f1 to Compound a2.

Compound a2 can be produced from Compound f1 by the same method as a method or the like described in a Non Patent Literature {e.g., J. Am. Chem. Soc., 6203, vol. 94 (1972), Tetrahedron, 2151, vol. 30 (1974), or the like}.

Production Method G (Production Method of a Synthetic Intermediate)

A synthetic intermediate represented by the above-described b1 can be produced, for example, by the following production method.

[Chem. 31]

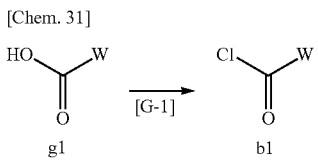

In the formulas, W means —B or —CR$^{3A}$R$^{3B}$B, wherein B is as defined in item 31.

[G-1 Step]

This step is a step of converting Compound g1 to Compound b1.

Compound b1 can be produced from Compound f1 by the same method as a method or the like described in a document {e.g., J. Am. Chem. Soc., 7442, vol. 135 (2013), J. Org. Chem., 4506, vol. 68 (2003), J. Med. Chem., 3582, vol. 44 (2001), or the like}.

Production Method H (Production Method of a Synthetic Intermediate)

A synthetic intermediate represented by the above-described b1 can be produced, for example, by the following production method.

[Chem. 32]

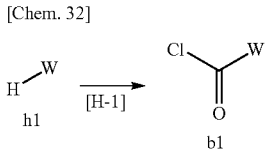

In the formulas, W means —OB or —NR$^{3C}$B, wherein B is as defined in item 31.

[H-1 Step]

This step is a step of converting Compound hi to Compound b1.

Compound b1 can be produced from Compound hi by the same method as a method or the like described in a document {e.g., J. Am. Chem. Soc., 5505, vol. 106 (1984), J. Org. Chem., 5342, vol. 72 (2007), Tetrahedron, 9153, vol. 63 (2007), J. Org. Chem., 5325, vol. 45 (1980), J. Org. Chem., 3787, vol. 69 (2004), or the like}.

Production Method I

Of the compound represented by formula (1A), Compound A1 represented by formula [A1] wherein A$^1$ and A$^2$ are —CONHB can be produced, for example, by the following production method.

[Chem. 33]

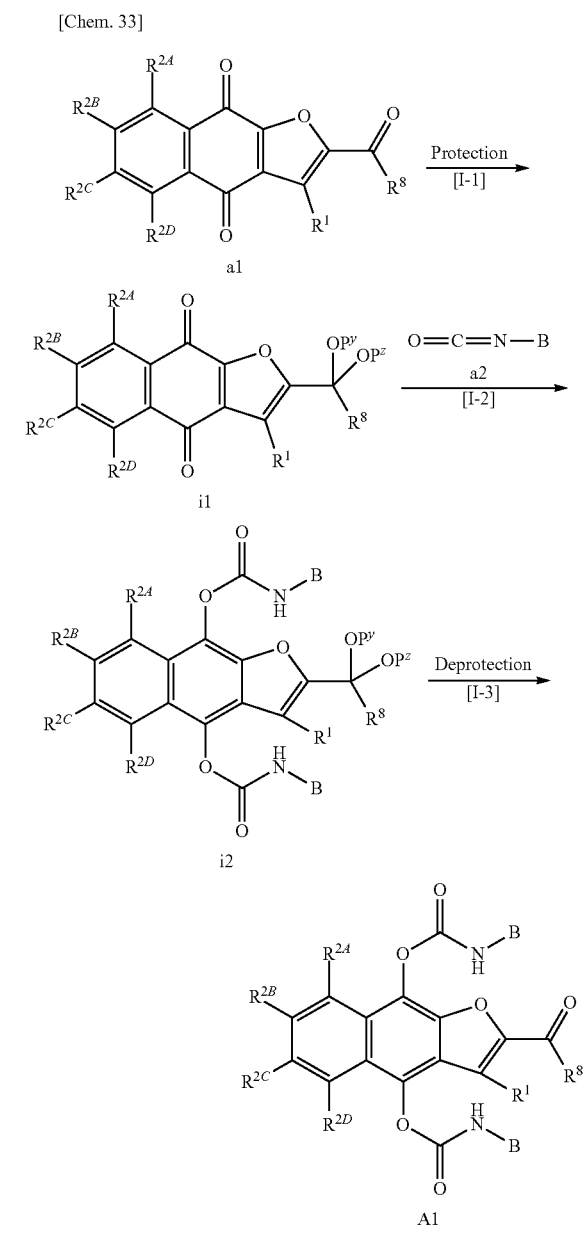

In the formulas, R$^1$, R$^{2A}$, R$^{2B}$, R$^{2C}$, R$^{2D}$, and R$^8$ are as defined in item 1 or 2 and B is as defined in item 31.

Protecting groups P$^y$ and P$^z$ are described as a protecting group for a ketone group in Protective Groups in Organic Synthesis (written by Theodora W. Greene, Peter G. M. Wuts, published by John Wiley & Sons, Inc., 1999).

Compound a1 can be produced, for example, by a method described in a Patent Literature (e.g., WO2009/036059, or the like).

[I-1 Step]

This step is a step of obtaining Compound i1 by protecting a ketone group of Compound a1 with an acetal. This step can be carried out in accordance with a method or the like described in Protective Groups in Organic Synthesis (written by Theodora W. Greene, Peter G. M. Wuts, published by John Wiley & Sons, Inc., 1999).

[I-2 step]

This step is a step of obtaining Compound i2 by reacting Compound a2, which is obtained by the above-described production method, with Compound i1, which is obtained in the above-described production method I-1, under a condition in accordance with the A-1 step.

[I-3 Step]

This step is a step of obtaining Compound A1 by deprotecting protecting groups $P^y$ and $P^z$ for the ketone group of Compound i2, which is obtained in the above-described production method I-2. This step can be carried out in accordance with a method or the like described in Protective Groups in Organic Synthesis (written by Theodora W. Greene, Peter G. M. Wuts, published by John Wiley & Sons, Inc., 1999).

Production Method J

Of the compound represented by formula (1A), Compound B1, B2, B3, or B4 represented by formula [B1], [B2], [B3], or [B4] wherein $A^1$ and $A^2$ are —C(=O)B, —C(=O)CR$^{3A}$R$^{3B}$B, —CO$_2$B, or —CONR$^{3C}$B can be produced, for example, by the following production method.

[Chem. 34]

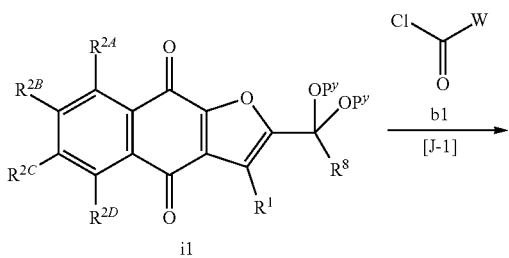

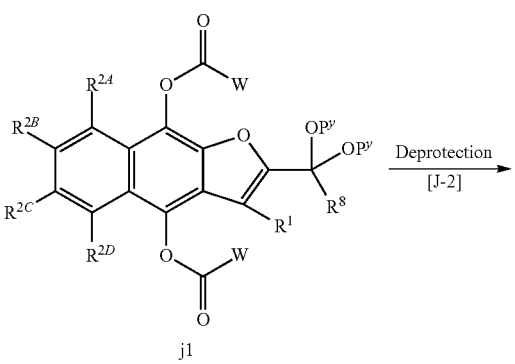

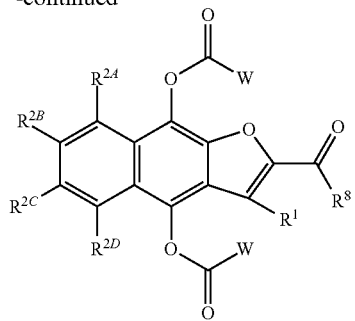

B1: —W = —B
B2: —W = —CR$^{3A}$CR$^{3B}$B
B3: —W = —OB
B4: —W = —NR$^{3C}$B

In the formulas, $R^1$, $R^{2A}$, $R^{2B}$, $R^{2C}$, $R^{2D}$, $R^{3A}$, $R^{3B}$, $R^{3C}$, and $R^8$ are as defined in item 1 or 2, B is as defined in item 31, and W means —B, —CR$^{3A}$R$^{3B}$B, —OB, or —NR$^{3C}$B.

Protecting groups $P^y$ and $P^z$ are described as a protecting group for a ketone group in Protective Groups in Organic Synthesis (written by Theodora W. Greene, Peter G. M. Wuts, published by John Wiley & Sons, Inc., 1999).

[J-1 Step]

This step is a step of obtaining Compound j1 by reacting Compound b1, which is obtained by the above-described production method, with Compound i1, which is obtained by the above-described production method, under a condition in accordance with the above-described A-1 step.

[J-2 Step]

This step is a step of obtaining Compound B1, B2, B3, or B4 by deprotecting protecting groups $P^y$ and $P^z$ for a ketone group of Compound j1, which is obtained in the above-described production method J-1. This step can be carried out in accordance with a method or the like described in Protective Groups in Organic Synthesis (written by Theodora W. Greene, Peter G. M. Wuts, published by John Wiley & Sons, Inc., 1999).

In respective reactions of the production methods described above, even in a case other than the case where the use of a protecting group is specifically and explicitly indicated, if any functional group other than a reaction point is modified under a described reaction condition or is unsuitable for performing the described method, a target compound can be obtained by protecting any point other than the reaction point as necessary, and unprotecting after the reaction is finished or a series of reactions are performed.

Conventional protecting groups can be used as the protecting group, such as those described in a document (e.g., Protective Groups in Organic Synthesis, 3$^{rd}$ ed., T. W. Greene, John Wiley & Sons Inc. (1999), or the like). Further specifically, examples of protecting groups for an amino group include benzyloxycarbonyl, tert-butoxycarbonyl, acetyl, benzyl, and the like, and examples of the protecting groups for a hydroxyl group include trialkylsilyl groups such as trimethylsilyl, tert-butyldimethylsilyl, or the like; acetyl, benzyl, and the like, respectively.

Introduction and elimination of a protecting group can be carried out by a method commonly used in synthetic organic chemistry (refer to, for example, the aforementioned Protective Groups in Organic Synthesis) or a method in accordance therewith.

Bases used in the respective steps described above should be appropriately selected depending on the types of reaction and a raw material compound, and the like. However examples thereof include alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium tert-butoxide; organic metal bases such as butyl lithium and lithium diisopropylamide; organic bases such as triethylamine, diisopropylethylamine, pyridine, 4-dimethylaminopyridine (DMAP), and 1,8-diazabicyclo[5.4.0]-7-undecene (DBU).

Solvents used in the respective steps described above should be appropriately selected depending on the types of reaction and a raw material compound, and the like. However, examples thereof include alcohols such as methanol, ethanol, and isopropanol; ketones such as acetone and ethyl methyl ketone; halogenated hydrocarbons such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethyl sulfoxide (DMSO); nitriles such as acetonitrile. These solvents can be used alone or as a mixture of two or more thereof. In addition, according to the type of reaction, organic bases may be used as solvent.

The present compound represented by formula (1A) or (1) or an intermediate therefor can be separated and purified by a known method to those skilled in the art. Examples thereof include extraction, distribution, reprecipitation, column chromatography (e.g., silica gel column chromatography, ion exchange column chromatography, or preparative liquid chromatography), recrystallization, and the like.

The following can be used as recrystallization solvent: for example, alcohol-based solvent such as methanol, ethanol, 2-propanol, or the like; ether-based solvent such as diethyl ether or the like; ester-based solvent such as ethyl acetate or the like; aromatic-hydrocarbon-based solvent such as benzene, toluene, or the like; ketone-based solvent such as acetone or the like; halogen-based solvent such as dichloromethane, chloroform, or the like; hydrocarbon-based solvent such as hexane or the like; aprotic solvent such as dimethylformamide, acetonitrile, or the like; water; or mixed solvent thereof; or the like. Other purification method can be used, such as methods described in *Jikken Kagaku Koza* (The Chemical Society of Japan ed., Maruzen), vol. 1, or the like. In addition, the determination of molecular structure of the present compound is easily performed with referencing structures derived from respective raw material compounds, and by spectrophotometric techniques such as the nuclear magnetic resonance method, the infrared absorption method, the circular dichroism spectrum analysis, and mass spectrometry.

In addition, intermediates or final products in the above-described production methods can be derived to other compounds encompassed by the present invention by appropriately converting a functional group thereof, and in particular, extend any kind of side chain using an amino group, a hydroxyl group, a carbonyl group, a halogen group, or the like as an aid, and at this time, as necessary, performing the above-described protection and deprotection. Conversion of a functional group and extension of a side chain can be performed by a routine, general method (refer to, e.g., Comprehensive Organic Transformations, R. C. Larock, John Wiley & Sons Inc. (1999), and the like).

In the present compounds represented by formula (1A) or (1) or pharmaceutically acceptable salts thereof, asymmetry may occur, or it may have a substituent having an asymmetric carbon. In such compounds, optical isomers are present. The present compound also encompasses mixtures of these respective isomers, and isolated isomers, and can be produced according to a general method. Examples of the production method include a method using a raw material having an asymmetric point, and a method in which an asymmetry is introduced in a half way. For example, in the case of an optical isomer, an optical isomer can be obtained by using an optically active raw material or performing optical resolution or the like in a suitable stage of a production step. Examples of optical resolution methods include a diastereomer method of forming a salt, when the compound represented by formula (1A) or (1) or intermediates therefor have a basic functional group, in inactive solvent (alcohol-based solvent such as methanol, ethanol, 2-propanol, or the like; ether-based solvent such as diethyl ether or the like; ester-based solvent such as ethyl acetate or the like; hydrocarbon-based solvent such as toluene or the like; aprotic solvent such as acetonitrile or the like; or mixed solvent thereof) using an optically active acid (e.g., monocarboxylic acid such as mandelic acid, N-benzyloxy-alanine, lactic acid, or the like, dicarboxylic acid such as tartaric acid, ortho-diisopropylidene tartaric acid, malic acid, or the like, sulfonic acid such as camphor sulfonic acid, bromocamphor sulfonic acid, or the like).

When an intermediate for the present compound represented by formula (1A) or (1) has an acidic functional group such as carboxyl and the like, optical resolution can be performed by forming a salt using an optically active amine (e.g., organic amines such as 1-phenylethylamine, quinine, quinidine, cinchonidine, cinchonine, strychnine, or the like).

A temperature to form a salt is selected from the range from room temperature to the boiling point of solvent. To improve the optical purity, it is desirable to increase a temperature to the vicinity of the boiling point of a solvent once. When a precipitated salt is collected by filtration, as necessary, it can be cooled to improve the yield. Regarding the amount of an optically active acid or amine used, the range from about 0.5 to about 2.0 equivalents, preferably the range of approximately 1 equivalent, relative to a substrate is suitable. As necessary, crystal can be recrystallized in inactive solvent (e.g., alcohol-based solvent such as methanol, ethanol, 2-propanol, or the like; ether-based solvent such as diethyl ether or the like; ester-based solvent such as ethyl acetate or the like; hydrocarbon-based solvent such as toluene or the like; aprotic solvent such as acetonitrile or the like; or mixed solvent thereof) to obtain an optically active salt in high purity. In addition, a salt that is optically resolved as necessary can be treated with an acid or a base by a general method to obtain its free form.

Among starting materials and intermediates in respective production methods described above, those of which production methods are not particularly and repeatedly described are commercially available compounds or can be synthesized from a commercially available compound by a known method to those skilled in the art or a method in accordance therewith.

Compounds represented by formulas (1A), (1), and (1-1a)-(3-4c) and pharmaceutically acceptable salts thereof exhibit high water-solubility suitable for oral administration and parenteral administration, and have at least one or more primary or secondary nitrogen atoms at a terminal. Due to this structural feature, formulas (1A), (1), and (1-1a)-(3-4c) act as prodrugs that are converted to an active form by chemical conversion. As used herein, the chemical conversion means the conversion to an activated form in vivo via a route other than the enzymatic conversion. For example, as represented by the following formulas:

[Chem.35]

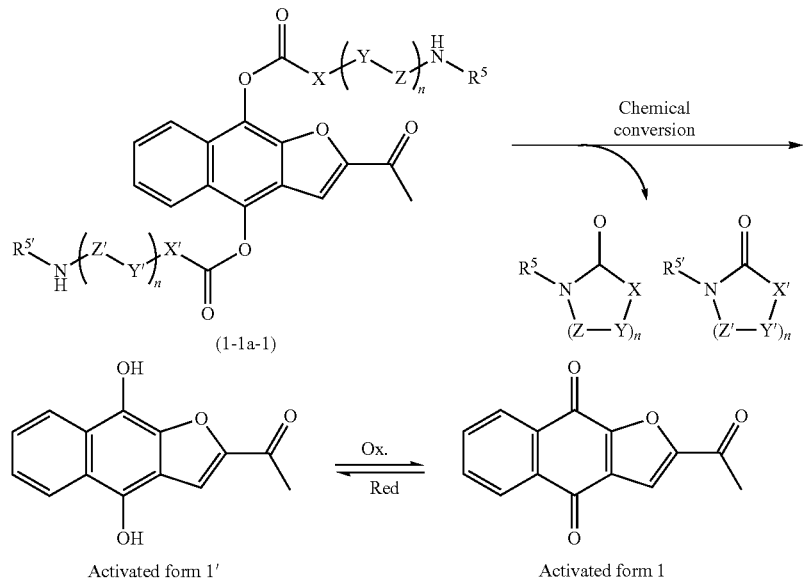

wherein each symbol is defined the same as item 1 or 2, a representative compound of formula (1A) or (1) represented by formula (1-1a-1), wherein $A^1$ and $A^2$ is —COB, $R^1$, $R^{2A}$, $R^{2B}$, $R^{2C}$, and $R^{2D}$ are hydrogen atoms, B is formula (B), and V is —NHR$^5$, is chemically converted to an active form represented by Activated form 1 as a result of that the nitrogen atoms respectively bound to terminal $R^5$ and $R^{5'}$ attack the corresponding carbonyl carbons in vivo.

It should be noted that Activated form 1 is an isomer that can be equilibrated with Activated form 1', where they have a relationship between an oxidant and a reductant, and can be considered to be synonymous therewith.

In a similar way to the above, as described below, a compound represented by formula (2-1a-1), wherein $A^1$ and $A^2$ are —S$_2$B, $R^1$, $R^{2A}$, $R^{2B}$, $R^{2C}$, and $R^{2D}$ are hydrogen atoms, B is formula (B), and V is —NHR$^5$, is chemically converted to an active form represented by Activated form 1 as a result of that the nitrogen atoms respectively bound to terminal $R^5$ and $R^{5'}$ attack the corresponding sulfur atoms in vivo. It should be noted that each symbol in the formulas is defined the same as item 1 or 2.

[Chem.36]

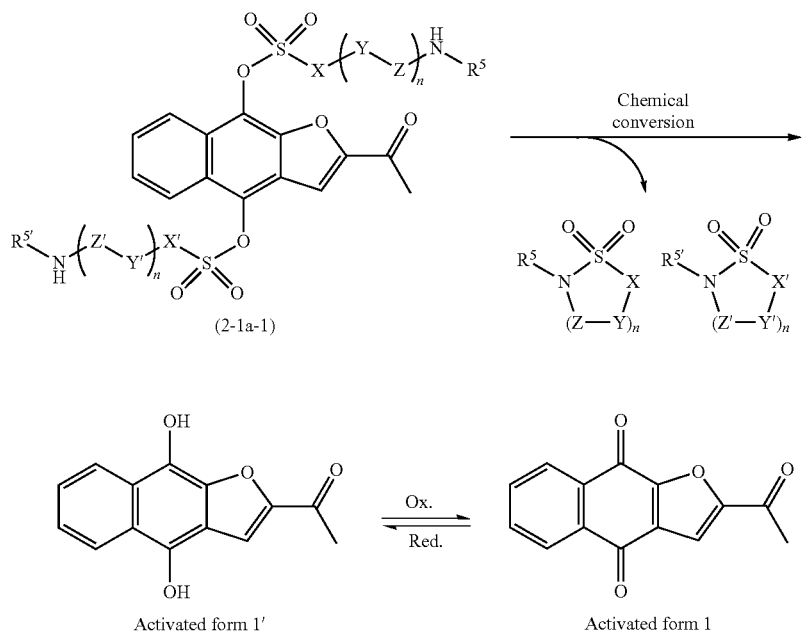

In a similar way to the above, as described above, a compound represented by formula (3-1a-1), wherein $A^1$ and $A^2$ are —P(=O)B2, $R^1$, $R^{2A}$, $R^{2B}$, $R^{2C}$, and $R^{2D}$ are hydrogen atoms, B is formula (B), and V is —$NHR^5$, is chemically converted to an active form represented by Activated form 1 as a result of that the nitrogen atoms respectively bound to terminal $R^5$ and $R^{5'}$ attack the corresponding phosphorus atoms in vivo. It should be noted that each symbol in the formulas is defined the same as item 1 or 2.

[Chem.37]

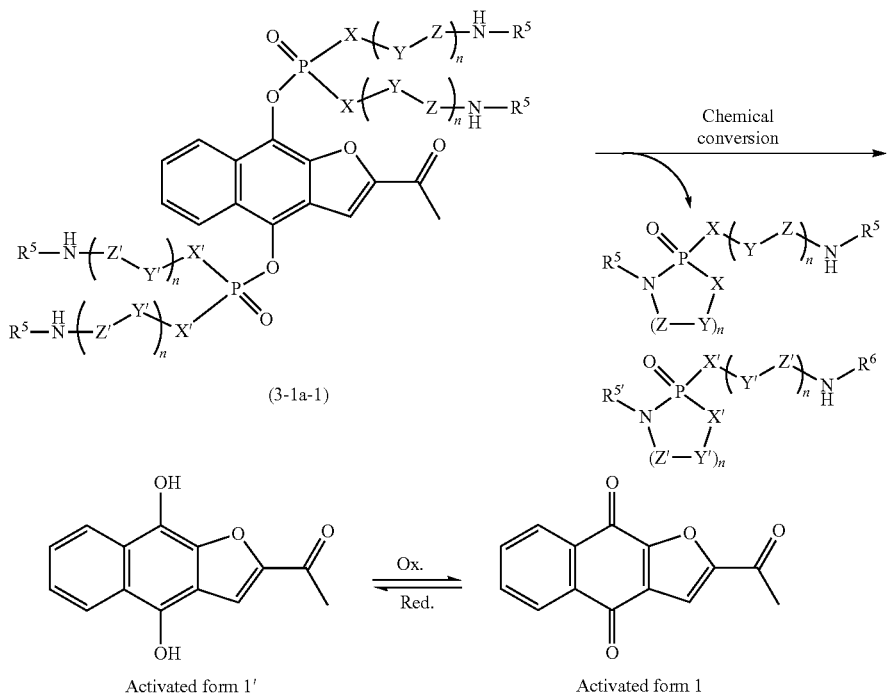

Likewise the above-described formulas (1-1a-1), (2-1a-1), and (3-1a-1), also regarding formulas (1A), (1), (1-1a), (1-1b), (1-1c), (1-2a), (1-2b), (1-2c), (1-3a), (1-3b), (1-3c), (1-4a), (1-4b), (1-4c), (1-5a), (1-5b), (1-5c), (1-6a), (1-6b), (1-6c), (2-a), (2-1b), (2-1c), (2-2a), (2-2b), (2-2c), (2-3a), (2-3b), (2-3c), (2-4a), (2-4b), (2-4c), (3-1a), (3-1b), (3-1c), (3-2a), (3-2b), (3-2c), (3-3a), (3-3b), (3-3c), (3-4a), (3-4b), and (3-4c), in a similar way to the above, the terminal primary or secondary nitrogen atoms attack the corresponding carbon, sulfur, or phosphorus atoms to produce Activated form 1 through chemical conversion.

The present compound is provided, for example, as an anticancer agent. Although the type of cancer to which it is applied is not limited, specific examples thereof include acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder.bile duct cancer, hepatoma, pancreatic cancer, colon cancer, rectal cancer, chorioepithelioma, chorioblastoma, choriocarcinoma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma. Hematological cancer in the present invention is an idea encompassing lymphoma and leukemia, and has an effect to reduce or annihilate carcinoma or to inhibit the growth of carcinoma for the purposes of preventing/or treating cancer. It should be noted that in the present invention, "prevention (preventing)" or "prophylaxis" is an action to administer an active ingredient of the present invention to a healthy human that does not develop a disease, and a purpose thereof is, for example, to prevent the onset of a disease. "Treatment (treating)" is an action to administer an active ingredient of the present invention to a person (patient) diagnosed as developing a disease by a medical doctor, and a purpose thereof is, for example, to alleviate the disease and symptoms, to inhibit the growth of carcinoma, or to return it to a state prior to the onset of the disease. In addition, even when the purpose of administration is to prevent a disease or symptoms from deteriorating or carcinoma from growing, if it is administered to a patient, it is an action for therapy.

When the present compound is administered, the amount of the compound used varies depending on symptoms, age, administration method, and the like. For example, in the case of intravenous injection, an effect is expected by administering to an adult 0.01 mg as the lower limit (preferably 0.1 mg) and 1000 mg as the upper limit (preferably 30 mg) once or in several batches daily depending on the symptoms. Examples of its administration schedule include single-dose administration, once a day administration for three days in a row, and the like. Further, each administration described above can be repeated at intervals of about 7 days to about 60 days.

In the case of oral administration, it is desirable to administer to an adult 0.01 mg as the lower limit (preferably 1 mg) and 5000 mg as the upper limit (preferably 500 mg) once or in several batches daily depending on the symptoms.

The compound of the present invention can be formulated using a suitable dosage form to administer by parenteral administration or oral administration. Examples of the dosage form include, but not limited to, a tablet, a capsule, powder, granules, a solution, a suspension, an injection, a patch, a poultice, and the like. A formulation is produced by a known method using a pharmaceutically acceptable additive.

The following can be used as an additive according to an object: excipient, disintegrator, binder, fluidizer, lubricant, coating agent, solvent, solubilizing agent, thickener, dispersing agent, stabilizing agent, sweetener, flavoring agent, and the like. Specific examples thereof include lactose, mannitol, crystalline cellulose, hydroxypropyl cellulose having low substitution degree, corn starch, partially pregelatinized starch, carmellose calcium, croscarmellose sodium, hydroxypropyl cellulose, hydroxypropylmethyl cellulose, polyvinyl alcohol, magnesium stearate, sodium stearyl fumarate, polyethylene glycol, propylene glycol, titanium oxide, talc, and the like.

A solution for injection includes solution, suspension, emulsion, and the like. Examples thereof include water-solution, water-propylene glycol solution, and the like. The solution can be produced in form of a solution of polyethylene glycol or/and propylene glycol that may contain water. A solution suitable for oral administration can be produced by adding the present compound to water, and as necessary adding a coloring agent, flavoring agent, stabilizing agent, sweetener, solvent, thickener, or the like. In addition, a solution suitable for oral administration can be produced by adding the present compound with a dispersing agent to water and thickening it. Examples of the thickener include pharmaceutically acceptable naturally-occurring or synthetic gum, resin, methylcellulose, sodium carboxymethylcellulose, known suspending agent, and the like.

It is possible to more effectively perform prophylactic treatment of cancer by combining one to three types selected from the group consisting of: (1) administering an effective amount of the present compound; and (2)(i) administering an effective amount of another anticancer agent, (ii) administering an effective amount of a hormonal therapeutic agent; and (iii) non-pharmacological therapy. Examples of non-pharmacological therapy include surgery, radiotherapy, gene therapy, thermotherapy, cryotherapy, laser cauterization therapy, and the like. Two or more types of these also can be combined.

In one embodiment, a first active substance and a second active substance used in the present invention are administered in therapeutically and/or prophylactically effective amounts. Meanwhile, in another embodiment, the amount of the first active substance administered and/or the amount of the second active substance administered are less than a therapeutically and/or prophylactically effective amount when administered alone, however, both may be administered in therapeutically and/or prophylactically effective amounts when they are combined. It is because the action mechanism of the first active substance of the present invention or the compound of the present invention or a pharmaceutically acceptable salt is different from that of anticancer agents and the like used as the second active substance and thus synergic action greater than that of the combination of general anticancer agents is expected.

The present compound can be used in combination with another drug for purpose of enhancing its effect. Specifically, the present compound can be used in combination with a drug selected from the group consisting of a hormonal therapeutic agent, a chemotherapeutic agent, an immuno-therapeutic agent, a biological agent, a cell growth factor inhibitor, a cell growth factor receptor inhibitor, a radio-therapeutic agent, an adjuvant agent, and an auxiliary agent. Hereinafter, a drug that may be used in combination with the present compound is abbreviated to a combination drug.

The present compound, even when used as a single agent, exhibits excellent anticancer effect, and further the combination use with one or several of the above-described combination drugs (polypharmacy) can further enhance its effect or improve the QOL of a patient.

Examples of "hormonal therapeutic agents" include an adrenal cortical hormone-based agent (e.g., a steroidal anti-inflammatory drug, an estrogen formulation, a progesterone formulation, an androgen formulation, and the like), an antiestrogen agent, an estrogen adjusting agent, an estrogen synthesis inhibitor, an anti-androgen agent, an androgen adjusting agent, an androgen synthesis agent, a LH-RH agonist formulation, a LH-RH antagonist formulation, an aromatase inhibitor, a steroid lactonase inhibitor, a pill formulation, retinoid and a pharmaceutical agent to delay the metabolism of retinoid, and the like.

Examples of "hormonal therapeutic agents" include Fosfestrol, Diethylstilbestrol, Fluoxymesterone, Chlorotri-anisene, Medroxyprogesterone acetate, Megestrol acetate, Chlormadinone acetate, Cyproterone acetate, Danazol, Dienogest, Asoprisnil, Allylestrenol, Gestrinone, Nomegestrol, Tadenan, Mepartricin, Raloxifene, Ormeloxifene, Levormeloxifene, Tamoxifen citrate, Toremifene citrate, Idoxifene, a pill formulation, Mepitiostane, Testololactone, Aminoglutethimide, Goserelin acetate, Buserelin, Leuprorelin, Leuprolide, Droloxifene, Epitiostanol, ethynyl estradiol sulfonate, Fadrozole hydrochloride, Anastrozole, Tetrazole, Ketoconazole, Letrozole, Exemestane, Vorozole, Formestane, Exemestane, Flutamide, Bicalutamide, Nilutamide, Enzalutamide, Mifepristone, Finasteride, Dexamethasone, Prednisolone, Betamethasone, Triamcinolone, Abiraterone, and Liarozole, Bexarotene, DN101, and the like.

As "chemotherapeutic agents", for example, alkylating agents, antimetabolites, topoisomerase inhibiting drugs, DNA intercalators, antimitotic agents, anticancer antibiotics, plant-derived anticancer agents, epigenome drugs, immuno-modulators, molecule-targeting therapeutic drugs, angiogenesis inhibitors, and other chemotherapeutic agents, and the like are used. Representative examples are described below.

Examples of "alkylating agents" include Nitrogen mustard, Nitrogen mustard N-oxide hydrochloride, Chlorambucil, Cyclophosphamide, Ifosfamide, Thiotepa, Carboquone, Improsulfan tosylate, Busulfan, Nimustine hydrochloride, Mitobronitol, Melphalan, Dacarbazine, Ranimustine, Estramustine phosphate sodium, Triethylenemelamine, Carmustine, Lomustine, Streptozocin, Pipobroman, Etoglucide, Carboplatin, Cisplatin, Miboplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, Adozelesin, Cystemustine, Bizelesin, Mechlorethamine, Uracil mustard, Streptozocin, Satraplatin, Trabectedin, Becatecarin, Chlormethine, Bendamustine, Uramustine, Semustine, Triplatin tetranitrate, Mannosulfan, Triaziquon, Procarbazine, Canfosfamide, Nitrosourea, and DDS formulations thereof, and the like.

Examples of "antimetabolites" include "a folic acid antagonist", "a pyrimidine metabolism-inhibiting drug", "a purine metabolism-inhibiting drug", "a ribonucleotide reductase inhibiting drug", and "a nucleotide analog".

Examples of "antimetabolites" include Mercaptopurine, 6-Mercaptopurine riboside, Thioinosine, Methotrexate, Pemetrexed, Enocitabine, Cytarabine, Cytarabin ocfosfate, Ancitabine hydrochloride, 5-FU type pharmaceutical agent (e.g., Fluorouracil, Tegafur, UFT, Doxifluridine, Carmofur, Galocitabine, Emitefur, Capecitabine, and the like), Aminopterin, Nelzarabine, Leucovorin calcium, tabloid, Butocin, calcium folinate, calcium levofolinate, Cladribine, Emitefur, Fludarabine, Gemcitabine, hydroxycarbamide, Pentostatin, Piritrexim, Idoxuridine, Mitoguazone, Tiazofurin, Ambamustine, Bendamustine, Floxuridine, Nelarabine, Leucovorin, Hydroxyurea, Thioguanine, Asparaginase, Bortezomib, Raltitrexed, Clofarabine, Enocitabine, Sapacitabine, Azacytidine, Sulfadiazine, Sulfamethoxazole, Trimethoprim, and DDS formulations thereof, and the like.

Examples of topoisomerase inhibiting drugs include Doxorubicin, Daunorubicin, Epirubicin, Idarubicin, Anthracenedione, Mitoxantrone, Mitomycin C, Bleomycin, Dactinomycin, Plicamycin, Irinotecan, Camptothecin, Rubitecan, Belotecan, Etoposide, Teniposide, Topotecan, Amsacrine, and DDS formulations thereof, and the like.

Examples of DNA intercalators include Proflavine, Doxorubicin (Adriamycin), Daunorubicin, Dactinomycin, Thalidomide, and DDS formulations thereof, and the like.

Examples of antimitotic agents include Paclitaxel, Paclitaxel derivatives (e.g., DHA Paclitaxel, Paclitaxel Polyglutamate, Nab-paclitaxel, Paclitaxel Micelle, 7α-Glucosyloxyacetylpaclitaxel, BMS-275183, and the like), Docetaxel, Vinorelbine, Vincristine, Vinblastine, Vindesine, Vinzolidine, Etoposide, Teniposide, Ixabepilone, Larotaxel, Ortataxel, Tesetaxel, Ispinesib, Colchicine, Vinflunine, and DDS formulations thereof, and the like.

Examples of "anticancer antibiotics" include Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Idarubicin hydrochloride, Mithramycin, and DDS formulations thereof, and the like.

Examples of "plant-derived anticancer agents" include Etoposide, Etoposide phosphate, Vinblastine sulfate, Vincristine sulfate, Vindesine sulfate, Teniposide, Paclitaxel, Docetaxel, DJ-927, Vinorelbine, Irinotecan, Topotecan, and DDS formulations thereof, and the like.

Examples of "epigenome drugs" include a histone deacetylase (HDAC) inhibitor, a DNA methyltransferase (DNMT) inhibitor, and the like.

Examples of "epigenome drugs" include Vorinostat, Belinostat, Entinostat, Romidepsin, Azacytidine, Decitabine, and DDS formulations thereof, and the like.

Examples of "immunomodulators" include Thalidomide, Lenalidomide, Pomalidomide, and DDS formulations thereof, and the like.

"A molecule-targeting therapeutic drug" may be a low molecular compound or an antibody. Examples of "molecule-targeting therapeutic drugs" include a kinase inhibitor, a proteasome inhibitor, a monoclonal antibody, a mTOR inhibitor, a TNF inhibiting drug, and a T-cell inhibiting drug, and the like.

Examples of "kinase inhibitors" include a tyrosine kinase inhibitor, a serine/threonine kinase inhibitor, a Raf kinase inhibitor, a CDK (cyclin-dependent kinase) inhibitor, a MEK (mitogen-activated protein kinase) inhibitor, and the like.

Examples of "kinase inhibitors" include Imatinib, Gefitinib, Erlotinib, Afatinib, Dasatinib, Bosutinib, Vandetanib, Sunitinib, Axitinib, Pazopanib, Lenvatinib, Lapatinib, Nintedanib, Nilotinib, Crizotinib, Ceritinib, Alectinib, Ruxolitinib, Tofacitinib, Ibrutinib, Sorafenib, Vemurafenib, Dabrafenib, Palbociclib, Trametinib, i5 Regorafenib, Cediranib, Lestaurtinib, Vandetinib, Vatalanib, Seliciclib, Tivantinib, Canertinib, Pelitinib, Tesevatinib, Cediranib, Motesanib, Midostaurin, Foretinib, Cabozantinib, Selumetinib, Neratinib, Volasertib, Saracatinib, Enzastaurin, Tandutinib, Semaxanib, Alvocidib, ICR-62, AEE788, PD0325901, PD153035, TK787, BBI503, and DDS formulations thereof, and the like.

Examples of "proteasome inhibitors" include Bortezomib, Carfilzomib, and DDS formulations thereof, and the like.

Examples of "monoclonal antibodies" include an anti-CD22 antibody, an anti-CD20 antibody, an anti-CD25 antibody, an anti-CD30 antibody, an anti-CD33 antibody, an anti-CD5 antibody, an anti-CD52 antibody, an anti-epidermal growth factor receptor antibody (an EGFR antibody), an anti-endothelial cell growth factor antibody (an VEGF antibody), an anti-TNF-α antibody, an anti-IL-1 receptor antibody, an anti-IL-2 receptor antibody, an anti-IL-5 receptor antibody, an anti-IL-6 receptor antibody, an anti-HER2 antibody, an anti-IgE antibody, an anti-IgG antibody, an anti-RS virus antibody, an anti-CCR4 antibody, an anti-CTLA-4 (cytotoxic T-lymphocyte-associated antigen 4, CD152) antibody, an anti-PD-1 antibody, an anti-RANKL (receptor activator of nuclear factor KB ligand) antibody, an anti-c-Met antibody, and the like.

Examples of "monoclonal antibodies" include Ibritumomab tiuxetan, Rituximab, Cetuximab, Infliximab, Basiliximab, Brentuximab vedotin, Tocilizumab, Trastuzumab, Bevacizumab, Omalizumab, Mepolizumab, Gemtuzumab, ozogamicin, Palivizumab, Ranibizumab, Certolizumab, Ocrelizumab, Mogamulizumab, Eculizumab, Pertuzumab, Alemtuzumab, Inotuzumab, Panitumumab, Ofatumumab, Golimumab, Adalimumab, Ramucirumab, Nivolumab, Infliximab, Anakinra, Denosumab, Ipilimumab, Pembrolizumab, matuzumab, and DDS formulations thereof, and the like.

Examples of "mTOR inhibitors" include Everolimus, Rapamycin (Sirolimus), Temsirolimus, and DDS formulations thereof, and the like.

Examples of "TNF inhibiting drugs" include Etanercept and the like.

Examples of "T-cell inhibiting drugs" include Abatacept and the like.

Examples of "angiogenesis inhibitors" include CM101, IFN-α, IL-12, platelet factor-4, Suramin, Semaxanib, Thrombospondin, a VEGFR antagonist, an angiogenesis inhibiting steroid plus heparin, cartilage-derived angiogenesis inhibitory factor, a matrix metalloproteinase inhibitor, Batimastat, Marimastat, Angiostatin, Endostatin, 2-methoxyestradiol, Tecogalan, Thrombospondin, an VB3 inhibitor, Linomide, ADH-1, and DDS formulations thereof, and the like.

Examples of "other chemotherapeutic agents" include Sobuzoxane, Obatoclax, Efaproxiral, Tipifarnib, Lonafarnib, and the like.

Examples of "immunotherapeutic agents (BRM)" include Picibanil, Krestin, Sizofiran, Lentinan, Ubenimex, interferon, interleukin, macrophage colony stimulating factor, granulocyte-colony stimulating factor, Erythropoietin, Lymphotoxin, BCG vaccine, *Corynebacterium parvum*, Levamisole, polysaccharide K, Procodazole, anti-CTLA4 antibody, PD-1 antibody, Toll-like Receptors agonist (e.g., TLR7 agonist, TLR8 agonist, TLR9 agonist, and the like).

Examples of "biological agents" include Interleukin-2 (Aldesleukin), Interferon-α, Interferon-β, Interferon-γ, Erythropoietin (EPO), granulocyte CSF (Filgrastim), granulocytes, macrophage CSF (Sargramostim), IL13-PE38QQR, *Bacillus* Calmette-Guerin, Levamisole, Octreotide, CPG7909, Provenge, GVAX, Myvax, Favld, Lenalidomide, Trastuzumab, Rituximab, Gemtuzumab ozogamicin, Alemtuzumab, Endostatin, Ibritumomab tiuxetan, Tositumomab, Cetuximab, Zanolimumab, Ofatumumab, HGS-ETR1, Pertuzumab, M200, SGN-30, matuzumab, Adecatumumab, Denosumab, Zalutumumab, MDX-060, Nimotuzumab, MORAb-003, Vitaxin, MDX-101, MDX-010, a DPC4 antibody, a NF-1 antibody, a NF-2 antibody, a Rb antibody, a p53 antibody, a WT1 antibody, a BRCA1 antibody, a BRCA2 antibody, Ganglioside (GM2), a prostate-specific antigen (PSA), α-Fetoprotein (AFP), a carcinoembryonic antigen (CEA), a melanoma-associated antigen (MART-1, gap 100, MAGE 1,3 tyrosine), and Papilloma virus E6 and E7 fragments, and DDS formulations thereof, and the like.

A cell growth factor may be any substance as long as it promotes cell growth. Generally, they include a factor that is a peptide having a molecular weight of 20,000 or less and exhibits an effect at a low concentration by binding with a receptor. Examples of "cell growth factors" include epidermal growth factor (EGF), insulin-like growth factor (IGF) (e.g., insulin, IGF-1, IGF-2, and the like), transforming growth factor (TGF) (e.g., TGFalpha, TGF-beta), nerve growth factor (NGF), brain-derived neurotrophic factor (BDNF), vesicular endothelial growth factor (VEGF), colony stimulating factor (CSF) (e.g., Granulocyte-colony stimulating factor (G-CSF)), granulocyte-macrophage-colony stimulating factor (GM-CSF), platelet-derived growth factor (PDGF), erythropoietin (EPO), fibroblast growth factor (FGF) (e.g., acidic FGF, basic FGF, KGK (keratinocyte growth factor), FGF-10, and the like), hepatocyte growth factor (HGF), heregulin, angiopoietin, and the like. It should be noted that cell growth factor is synonymous with growth factor.

Examples of "cell growth factor inhibitors" include an epidermal growth factor inhibitor (an EGF inhibitor), an insulin-like growth factor inhibitor (an IGF inhibitor), a nerve growth factor inhibitor (a NGF inhibitor), a brain-derived neurotrophic factor inhibitor (a NGF inhibitor), a vesicular endothelial growth factor inhibitor (a VEGF inhibitor), a colony stimulating factor inhibitor (a CSF inhibitor), a platelet-derived growth factor inhibitor (a PDGF inhibitor), an erythropoietin inhibitor (a EPO inhibitor), a fibroblast growth factor inhibitor (a FGF inhibitor), a hepatocyte growth factor inhibitor (a HGF inhibitor), a heregulin inhibitor, an angiopoietin inhibitor, and the like. It should be noted that cell growth factor inhibitor is synonymous with growth factor inhibitor.

Examples of "cell growth factor receptor inhibitors" include an epidermal growth factor receptor inhibitor (an EGFR inhibitor), an insulin-like growth factor receptor inhibitor (an IGFR inhibitor), a nerve growth factor receptor inhibitor (a NGFR inhibitor), a brain-derived neurotrophic factor receptor inhibitor (a NGFR inhibitor), a vesicular endothelial growth factor receptor inhibitor (a VEGFR inhibitor), a colony stimulating factor receptor inhibitor (a CSFR inhibitor), a platelet-derived growth factor receptor inhibitor (a PDGFR inhibitor), an erythropoietin receptor inhibitor (an EPOR inhibitor), a fibroblast growth factor receptor inhibitor (a FGFR inhibitor), a hepatocyte growth factor receptor inhibitor (a HGFR inhibitor), a heregulin receptor inhibitor, an angiopoietin receptor inhibitor, and the like. It should be noted that cell growth factor receptor inhibitor is synonymous with growth factor receptor inhibitor.

Examples of "radiotherapeutic agents" include a radioactive substance, a radioactive sensitizer, and the like.

Examples of "auxiliary agents" include Aprepitant, Ondansetron, Lorazepam, Dexamethason, Diphenhydramine, Ranitidine, Cimetidine, Ranitidine, Famotidine, Cimetidine, Procrit, Epoetin alfa, Filgrastim, Oprelvekin, Leucovorin, granulocyte.macrophage colony stimulating factor, and the like.

As another embodiment, the present compound can be used in combination with Decitabine, Canfosfamide, Efaproxiral, Tipifarnib, Lonafarnib, Tamoxifen, Toremifene, Raloxifene, Droloxifene, Idoxifene, Megestrol Acetate, Anastrozole, Letrozole, Vorozole, Exemestane, Flutamide, Nilutamide, Bicalutamide, Cyproterone Acetate, Goserelin Acetate, Leuprolide, Finasteride, a metalloprotease inhibitor, a urokinase plasminogen activator receptor function inhibitor, a growth factor inhibitor, a growth factor receptor inhibitor, Bevacizumab, Cetuximab, a serine/threonine kinase inhibitor, Methotrexate, Fluorouracil, a purine and adenosine analogue, Cytarabine, Doxorubicin, Daunorubicin, Epirubicin, Idarubicin, Mitomycin C, Dactinomycin, Mithramycin, Cisplatin, Carboplatin, Nitrogen mustard, Melphalan, Chlorambucil, Busulfan, Cyclophosphamide, Ifosfamide, Nitrosourea, Thiotepa, Vincristin, Vinorelbine, Vinblastine, Vinflunine, Paclitaxel, Docetaxel, an Epothilone analogue, a Discodermolide analogue, an Eleutherobin analogue, Etoposide, Teniposide, Amsacrine, Topotecan, Alvocidib, a proteasome inhibitor, an androgen receptor antagonist, a LH-RH derivative, a LH-RH antagonist, a Taxane analogue, an estrogen receptor antagonist, and DDS formulations thereof, and the like.

Examples of combination drugs with the present compound include, preferably, Cisplatin, Oxaliplatin, Temozolomide, Pemetrexed, Fluorouracil, Capecitabine, Gemcitabine, Leucovorin, Bortezomib, Irinotecan, Paclitaxel, Imatinib, Ibrutinib, Sorafenib, Regorafenib, Bortezomib, Cetuximab, Bevacizumab, Panitumumab, Nivolumab, Ipilimumab, Pembrolizumab, and Dexamethasone.

The period of administration of the present compound and a combination pharmaceutical agent is not limited, and these may be administered concurrently or at intervals to a subject to be administered. In addition, a mixture of the present compound and a combination pharmaceutical agent may be made. The dosage of a combination pharmaceutical agent can be appropriately selected using clinically used dose as criteria. In addition, the mixing ratio of the present compound and a combination pharmaceutical agent can be appropriately selected depending on a subject to be administered, an administration route, target disease, symptoms, combinations, and the like. For example, when a subject to be administered is a human, 0.01 to 100 parts by weight of a combination pharmaceutical agent may be used relative to one part by weight of the present compound. In addition, for purpose of inhibiting its side effect, they can be used in combination with a pharmaceutical agent (a combination pharmaceutical agent) such as an antiemetic agent, a sleep-inducing agent, an anticonvulsant, and the like.

Hereinafter, the present invention is further specifically described with reference examples, Examples, and test examples set forth. However, these do not limit to the present invention. It should be noted that the identification of a compound was performed with an elemental analysis value, a mass spectrum, a high performance liquid chromatography mass spectrometer; LC-MS, IR spectra, NMR spectra, high performance liquid chromatography (HPLC), and the like.

Hereinafter, the present invention is more specifically described with reference examples, Examples, and test examples. However, the scope of the present invention is certainly not limited to these examples. It should be noted that compound names shown in the following reference examples and Examples do not always follow the IUPAC nomenclature. It should be noted that although abbreviations are sometimes used to simplify a description, these abbreviations are defined the same as the above descriptions.

In the present specification, the following abbreviations are sometimes used.

In NMR and MS data of reference examples and Examples, the following abbreviations are used.
Me: a methyl group
Et: an ethyl group
Ns: a 2-nitrobenzenesulfonyl group
Ts: a para-toluenesulfonyl group
tert: tertiary
t-Bu: a tert-butyl group
Boc: a tert-butoxycarbonyl group
DMF: N,N-dimethylformamide
DMSO: dimethyl sulfoxide
HATU: O-(7-azabenzotriazol-1-yl)-N,N,N',N'-tetramethyluronium hexafluorophosphate
HOBt: 1-hydroxybenzotriazole
NMP: N-methylpyrrolidone
THF: tetrahydrofuran
WSC.HCl: 1-ethyl-3-(3-dimethylaminopropyl)carbodiimide hydrochloride
s: singlet
brs: broad singlet
d: doublet
dd: double doublet
t: triplet
q: quartet
m: multiplet
br: broad
J: coupling constant
Hz: Hertz
CDCl$_3$: deuterated chloroform
DMSO-d$_6$: deuterated dimethyl sulfoxide High performance chromatography mass spectrometry; The measurement condition of LC-MS is as described below, an observed mass analysis value [MS (m/z)] is shown as [M+H]$^+$, [M+2H]$^{2+}$, [M+Na]$^+$, or [M+2Na]$^{2+}$, and a retention time is shown as Rt (minute(s), min).
Measurement Condition
Detection instrument: ACQUITY (registered trademark) SQ detector (WATERS)
HPLC: ACQUITY UPLC (registered trademark) system
Column: WATERS ACQUITY UPLC (registered trademark) BEH C18 (1.7 um, 2.1 mm×30 mm)
Solvent: Solution A: 0.06% formic acid/H$_2$O, Solution B: 0.06% formic acid/MeCN
Gradient condition: 0.0-1.3 min linear gradient from B 2% to 96%
Flow rate: 0.8 mL/min
UV: 220 nm and 254 nm

EXAMPLES

Reference Example 1 tert-Butyl (3-isocyanatopropyl)carbamate

[Chem. 38]

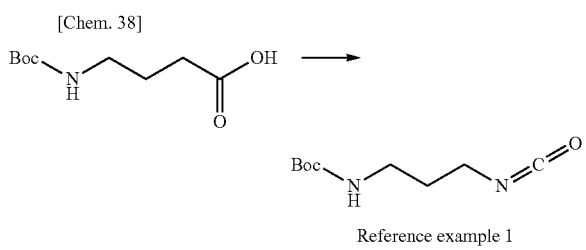

Reference example 1

Diisopropylethylamine (4.35 mL) and diphenylphosphoryl azide (4.71 mL) were added to a solution of 4-((tert-butoxycarbonyl)amino)butanoic acid (4.23 g) in toluene (41.6 mL). The reaction mixture was then stirred at room temperature for 15 minutes. After further stirring at 80° C. for 1 hour, the reaction solution was cooled to room temperature to yield a solution of Reference example 1 in toluene. The resulting solution was used in the next reaction as it was.

Example 1A

2-Acetylnaphtho[2,3-b]furan-4,9-diyl bis((3-((tert-butoxycarbonyl)amino)propyl)carbamate)

[Chem. 39]

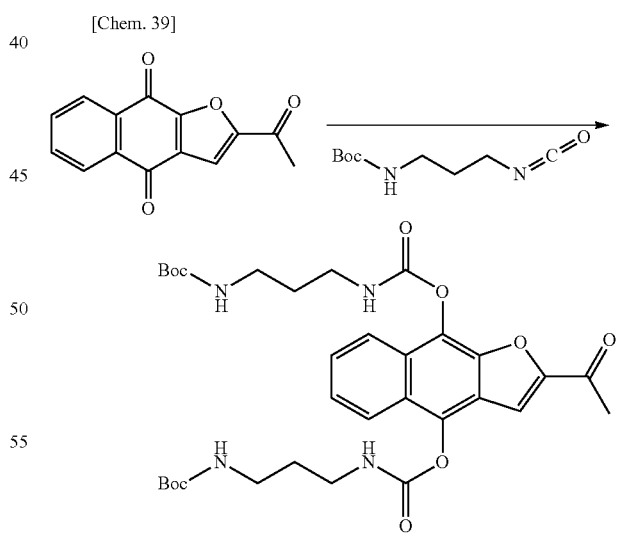

Example 1A

A suspension of 2-acetylnaphtho[2,3-b]furan-4,9-dione (1.00 g), zinc (1.09 g), sodium dithionite (3.62 g), diisopropylethylamine (7.25 mL), tetra-n-butylammonium bromide (134 mg) in N,N-dimethylformamide (59.5 mL) was stirred under nitrogen atmosphere at room temperature for 1 hour. Then, the suspension was cooled to 0° C., and the solution of tert-butyl (3-isocyanatopropyl)carbamate in toluene, which was prepared in Reference example 1, was added dropwise thereto over 15 minutes. After further stirring at room temperature for 1 hour, ethyl acetate and aqueous saturated ammonium chloride solution were added to the reaction solution. After the resulting mixture was filtered through Celite, the filtrate was distributed between an organic layer and an aqueous layer. The aqueous layer was then extracted with ethyl acetate twice. The resulting organic layer was washed with water once and dried over anhydrous sodium sulfate, and then it was filtered off and the solvent was evaporated under reduced pressure. The residue was purified by silica gel column chromatography (hexane/ethyl acetate=1:1-1:4) to yield Example 1A (560 mg).

(LC-MS: [M-t-Bu]$^+$/Rt (min))=587/1.05

Example 1

2-Acetylnaphtho[2,3-b]furan-4,9-diyl bis((3-aminopropyl)carbamate)dihydrochloride

[Chem. 40]

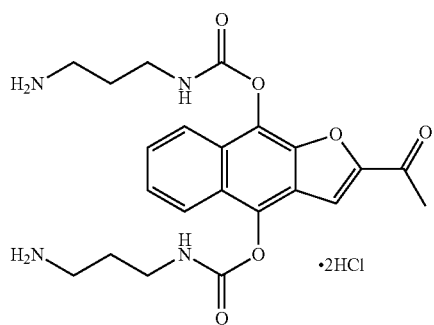

Example 1

A 4 mol/L hydrochloric acid/dioxane solution (20.0 mL) was added to Example 1A (733 mg). The reaction mixture was then stirred at 50° C. for 1 hour. The reaction solution was concentrated, and then the residue was washed with diethyl ether to yield Example 1 (568 mg).

$^1$H-NMR (400 MHz, DMSO-d$_6$) δ:1.80-1.91 (4H, m), 2.63 (3H, s), 2.86-2.95 (4H, m), 3.21-3.29 (4H, m), 7.60-7.70 (2H, m), 7.87-7.99 (6h, m), 7.99-8.07 (2H, m), 8.07 (1H, s), 8.44-8.50 (2H, m).

(LC-MS: [M+2H]$^{2+}$/Rt (min))=222/0.36

Reference Example 3

3-(Bis(tert-butoxycarbonyl)amino)propionic Acid

[Chem. 41]

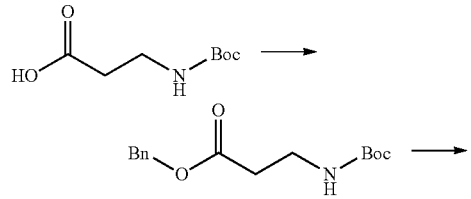

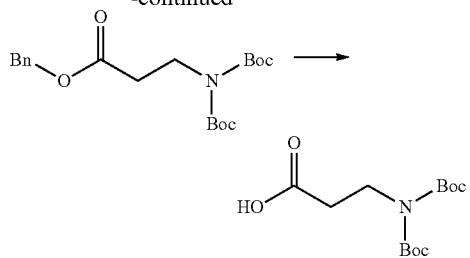

Reference example 3

Cesium carbonate (861 mg) was added to a solution of 3-((tert-butoxycarbonyl)amino)propionic acid (1.00 g) in methanol (24.0 mL) and water (2.40 mL). The reaction mixture was then stirred at room temperature for 5 minutes. The reaction solution was concentrated, and then the residue was dissolved in N,N-dimethylformamide (18.0 mL). Benzyl bromide (0.62 mL) was added dropwise thereto, and then the reaction mixture was stirred at room temperature for 16 hours. The reaction solution was concentrated, and then ethyl acetate and water were added to the residue to separate the organic layer. The aqueous layer was further extracted with ethyl acetate once. After the resulting organic layer was dried over anhydrous sodium sulfate, it was filtered off and the solvent was evaporated under reduced pressure to yield benzyl-3-((tert-butoxycarbonyl)amino)propionate (1.50 g). This was dissolved in acetonitrile (26.0 mL), di-tert-butyldicarbonate (2.31 g) and N,N-dimethylaminopyridine (65.0 mg) were added to the solution, and then it was stirred for 21 hours at room temperature. The reaction solution was diluted with water, and then extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=1:0 to 4:1) to yield benzyl-3-(bis(tert-butoxycarbonyl)amino)propionate (1.74 g). This was dissolved in methanol (23.0 mL), 10% palladium on carbon (500 mg) was added to the solution, and then it was stirred under hydrogen atmosphere at room temperature for 1.5 hours. The reaction solution was filtered through Celite, and then the Celite was washed with methanol. The filtrate was concentrated to yield Reference example 3 (1.25 g).

(LC-MS: [M-t-Bu]$^+$/Rt (min))=234/0.86

Example 2A tert-Butyl (2-((((2-acetyl-4-(((2-(bis(tert-butoxycarbonyl)amino)ethyl)carbamoyl)oxy)naphtho[2,3-b]furan-9-yl)oxy)carbonyl)amino)ethyl)(tert-butoxycarbonyl)carbamate

[Chem. 42]

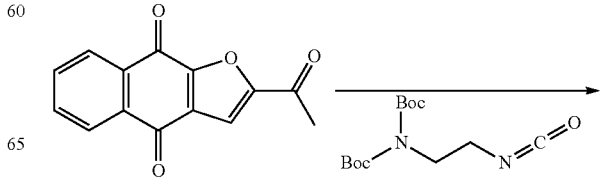

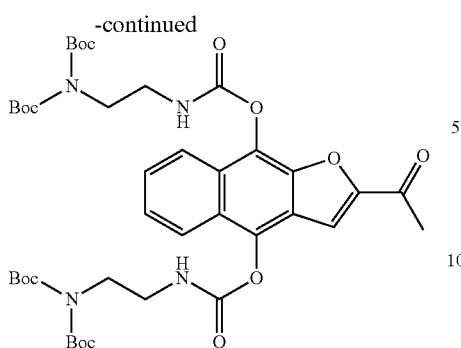

Example 2A

A suspension of 2-acetylnaphtho[2,3-b]furan-4,9-dione (100 mg), zinc (109 mg), sodium dithionite (362 mg), diisopropylethylamine (0.73 mL), and tetra-n-butylammonium bromide (13.0 mg) in N,N-dimethylformamide (5.90 mL) was stirred under nitrogen atmosphere at room temperature for 1 hour. The reaction mixture was then cooled to 0° C., and a solution of tert-butyl N-((tert-butoxy)carbonyl)-N-(2-isocyanatoethyl)carbamate in toluene, which had been prepared from Reference example 3 (482 mg) by the same method as Reference example 1, was added dropwise thereto over 7 minutes. After stirring at 0° C. for 30 minutes, the reaction solution was filtered through Celite, and the Celite was washed with ethyl acetate. Aqueous saturated ammonium chloride solution was added to the filtrate, the organic layer was separated, and then the aqueous layer was further extracted with ethyl acetate once. After the resulting organic layer was dried over anhydrous sodium sulfate, it was filtered off and the solvent was evaporated under reduced pressure. The residue was purified by silica gel column chromatography (hexane/ethyl acetate=4:1-3:2) to yield Example 2A (97.0 mg).

(LC-MS: $[M+Na]^+$/Rt (min))=837/1.32

Example 2

2-Acetylnaphtho[2,3-b]furan-4,9-diylbis((2-aminoethyl)carbamate) dihydrochloride

[Chem. 43]

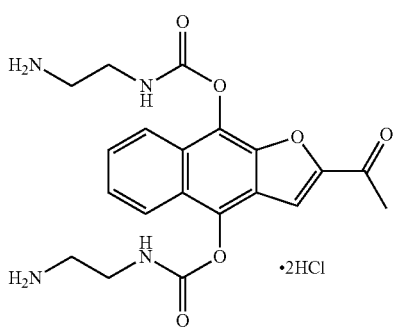

Example 2

To Example 2A (40.0 mg) was added 4 mol/L hydrochloric acid/dioxane solution (2.00 mL). The reaction mixture was then stirred at room temperature for 1.5 hours. The reaction solution was concentrated, and then the residue was washed with diethyl ether to yield Example 2 (20.0 mg).

$^1$H-NMR (400 MHz, DMSO-$d_6$) δ: 2.62 (3H, s), 2.98-3.07 (4H, m), 3.39-3.47 (4H, m), 7.59-7.71 (2H, m), 7.89-8.07 (6H, br), 8.07-8.20 (3H, m), 8.43-8.53 (2H, m).

(LC-MS: $[M+2H]^{2+}$/Rt (min))=208/0.33

Reference Example 5

(S)-5-(tert-Butoxy)-4-((tert-butoxycarbonyl)(methyl)amino)-5-oxopentanoic Acid

[Chem. 44]

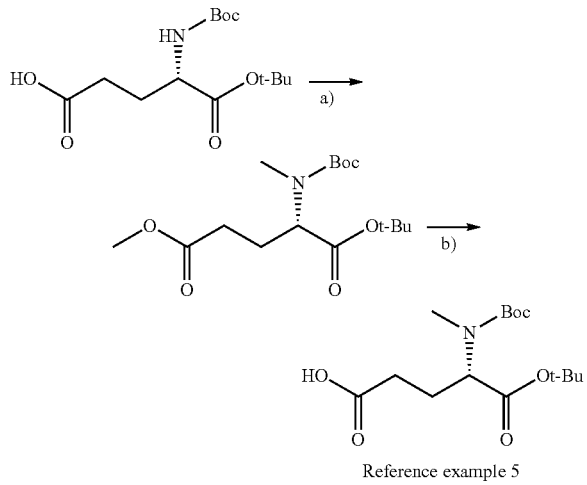

Reference example 5 a) A suspension of sodium hydride (330 mg) in N,N-dimethylformamide (8.00 mL) was cooled to 0° C., and a solution of ((S)-5-(tert-butoxy)-4-((tert-butoxycarbonyl)amino)-5-oxopentanoic acid (1.00 g) in N,N-dimethylformamide (8.00 mL) was added dropwise thereto. After stirring at 0° C. for 30 minutes, a solution of methyl iodide (0.51 mL) in N,N-dimethylformamide (2.00 mL) was added dropwise thereto. After stirring at 0° C. for 10 minutes, the reaction mixture was further stirred at room temperature for 3 hours. The reaction solution was diluted with aqueous saturated ammonium chloride solution, and then extracted with ethyl acetate twice. After the resulting organic layer was dried over anhydrous sodium sulfate, it was filtered off and the solvent was evaporated under reduced pressure to yield 1-(tert-butyl)$_5$-methyl N-(tert-butoxycarbonyl)-N-methyl-L-glutamate (1.05 g).

(LC-MS: $[M+H]^+$/Rt (min))=332/1.07 b) To a solution of 1-(tert-butyl) 5-methyl N-(tert-butoxycarbonyl)-N-methyl-L-glutamate (1.05 g) in tetrahydrofuran (14.0 mL) and water (2.40 mL) was added lithium hydroxide.monohydrate (138 mg). The reaction mixture was then stirred at 50° C. for 8 hours. The reaction solution was concentrated, and then suspended in methanol. The suspension was purified by a silica gel short column to yield Reference example 5 (1.20 g).

(LC-MS: $[M+H]^+$/Rt (min))=318/0.90

Example 3A tert-Butyl (S)-4-((((2-acetyl-4-((((R)-4-(tert-butoxy)-3-((tert-butoxycarbonyl)(methyl) amino)-4-oxobutyl)carbamoyl)oxy)naphtho[2,3-b]furan-9-yl)oxy)carbonyl)amino)-2-((tert-butoxycarbonyl)(methyl)amino)butanoate

[Chem. 45]

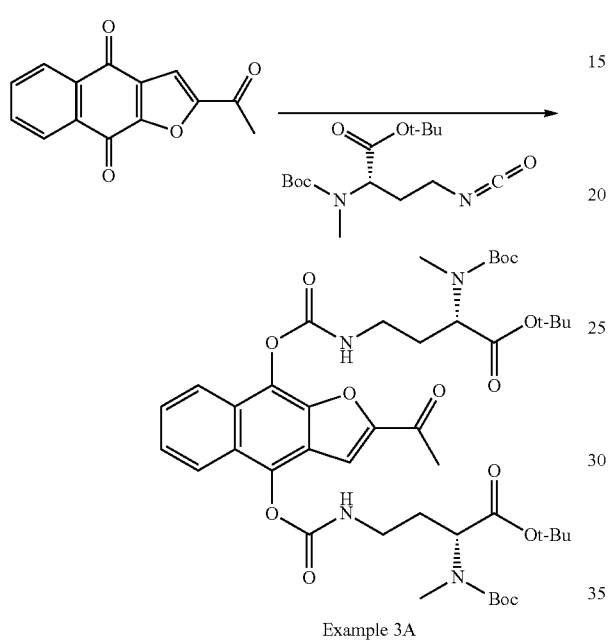

Example 3A

A suspension of 2-acetylnaphtho[2,3-b]furan-4,9-dione (100 mg), zinc (109 mg), sodium dithionite (362 mg), diisopropylethylamine (0.725 mL), tetra-n-butylammonium bromide (13.0 mg) in N,N-dimethylformamide (5.90 mL) was stirred under nitrogen atmosphere at room temperature for 1 hour. The reaction mixture was then cooled to 0° C., and a solution of tert-butyl (S)-2-((tert-butoxycarbonyl)(methyl)amino)-4-isocyanatobutanoate in toluene, which had been prepared from Reference example 5 (396 mg) by the same method as Reference example 1, was added dropwise thereto over 5 minutes. After stirring at 0° C. for 1 hour, the reaction solution was filtered through Celite, and then the Celite was washed with ethyl acetate. Aqueous saturated ammonium chloride solution was added to the filtrate, the organic layer was separated, and then the aqueous layer was further extracted with ethyl acetate once. After the resulting organic layer was dried over anhydrous sodium sulfate, it was filtered off and the solvent was evaporated under reduced pressure. The residue was purified by silica gel column chromatography (hexane/ethyl acetate=3:2-2:3) to yield Example 3A (141 mg).

(LC-MS: [M-Boc-t-Bu]$^+$/Rt (min))=715/1.34

Example 3

(S)-4-((((2-Acetyl-4-((((R)-3-carboxy-3-(methylamino)propyl)carbamoyl)oxy)naphtho[2,3-b]furan-9-yl)oxy)carbonyl)amino)-2-(methylamino)butanoic Acid dihydrochloride

[Chem. 46]

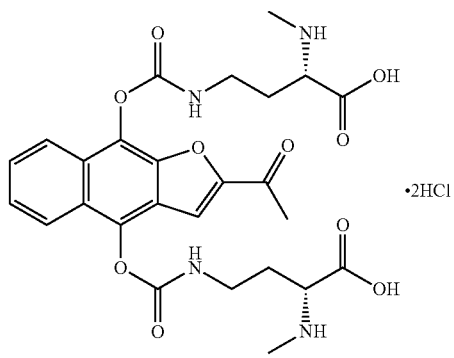

Example 3

A 4 mol/L hydrochloric acid/dioxane solution (10.0 mL) was added to Example 3A (140 mg). The reaction mixture was then stirred at 50° C. for 1.5 hours. The reaction solution was concentrated, and then the residue was washed with diethyl ether to yield Example 3 (102 mg).

$^1$H-NMR (400 MHz, D$_2$O) δ: 2.11-2.25 (4H, m), 2.52 (3H, s), 2.68 (6H, s), 3.31-3.50 (4H, m), 3.74-3.84 (2H, m), 7.50-7.64 (2H, m), 7.76 (1H, s), 7.95-8.03 (2H, m).

(LC-MS: [M+2H]$^{2+}$/Rt (min))=280/0.38

Reference Example 7

Methyl 3-((2-(tert-butoxy)-2-oxoethyl)(tert-butoxycarbonyl)amino)propionate

[Chem. 47]

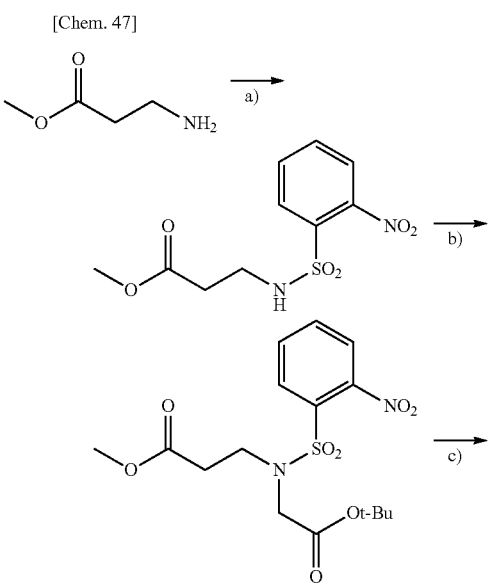

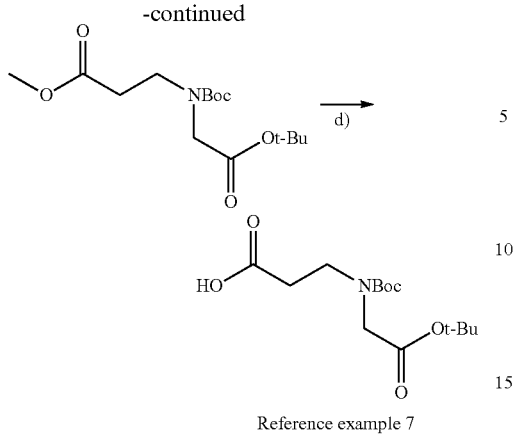

Reference example 7 a) Triethylamine (9.90 mL) and 2-nitrobenzenesulfonyl chloride (4.10 g) were added to a solution of methyl 3-aminopropionate (2.00 g) in methylene chloride (50.0 mL) at 0° C. The reaction mixture was then stirred at room temperature for 1 hour. The reaction solution was concentrated, ethyl acetate and saturated brine were added to the residue, and then the organic layer was separated. The aqueous layer was further extracted with ethyl acetate once. After the resulting organic layer was dried over anhydrous sodium sulfate, it was filtered off and the solvent was evaporated under reduced pressure to yield 4-((3-methoxy-3-oxopropyl)amino)-3-nitrobenzenesulfonic acid (4.30 g).

b) A suspension of 4-((3-methoxy-3-oxopropyl)amino)-3-nitrobenzenesulfonic acid (4.30 g), tert-butyl 2-bromoacetate (2.10 mL), and cesium carbonate (9.30 g) in acetonitrile (100 mL) was stirred at room temperature for 10 hours. The reaction solution was diluted with water, and then extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=1:0-1:2) to yield 4-((2-(tert-butoxy)-2-oxoethyl)(3-methoxy-3-oxopropyl)amino)-3-nitrobenzenesulfonic acid (5.00 g).

c) A suspension of 4-((2-(tert-butoxy)-2-oxoethyl)(3-methoxy-3-oxopropyl)amino)-3-nitrobenzenesulfonic acid (5.00 g), benzenethiol (2.10 mL), and cesium carbonate (11.0 g) in N,N-dimethylformamide (100 mL) was stirred under nitrogen atmosphere at room temperature 2 hours. Di-tert-butyl-dicarbonate (10.0 g) was added to the reaction mixture, and then it was further stirred at room temperature 2 hours. The reaction solution was filtered through Celite, and then the Celite was washed with ethyl acetate. The filtrate was concentrated, and then purified by silica gel column chromatography (hexane/ethyl acetate=1:0-1:2) to yield methyl 3-((2-(tert-butoxy)-2-oxoethyl)(tert-butoxycarbonyl)amino)propionate (2.40 g).

(LC-MS: [M+H]$^+$/Rt (min))=318/1.06 d) A suspension of methyl 3-((2-(tert-butoxy)-2-oxoethyl)(tert-butoxycarbonyl)amino)propionate (2.40 g), and potassium trimethylsilanolate (1.89 g) in tetrahydrofuran (50.0 mL) was stirred under nitrogen atmosphere at room temperature for 10 hours. The reaction solution was diluted with water, and then extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=1:0-0:1) to yield Reference example 7 (450 mg).

(LC-MS: [M+H]$^+$/Rt (min))=304/0.90

Example 4A

Di-tert-butyl 2,2'-((((((2-acetylnaphtho[2,3-b]furan-4,9-diyl)bis(oxy))bis(carbonyl))bis(azanediyl))bis(ethane-2,1-diyl))bis((tert-butoxycarbonyl)azanediyl))diacetate

[Chem. 48]

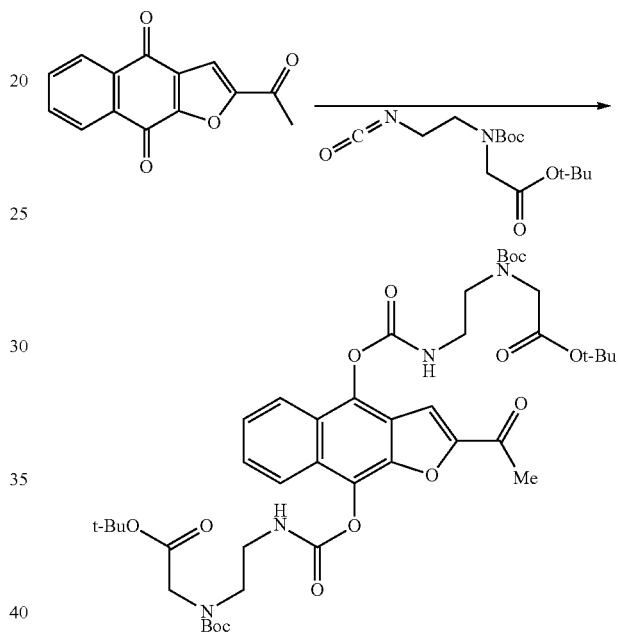

Example 4A

A suspension of 2-acetylnaphtho[2,3-b]furan-4,9-dione (50.0 mg), zinc (54.0 mg), sodium dithionite (181 mg), diisopropylethylamine (0.36 mL), and tetra-n-butylammonium bromide (7.00 mg) in N,N-dimethylformamide (3.00 mL) was stirred under nitrogen atmosphere at room temperature for 1 hour. The reaction mixture was then cooled to 0° C., and a solution of tert-butyl N-(tert-butoxycarbonyl)-N-(2-isocyanatoethyl)glycinate in toluene, which had been prepared from Reference example 7 (253 mg) by the same method as Reference example 1, was added dropwise thereto over 5 minutes. After stirring at 0° C. for 30 minutes, the reaction solution was filtered through Celite, and then the Celite was washed with ethyl acetate. Aqueous saturated ammonium chloride solution was added to the filtrate, the organic layer was separated, and then the aqueous layer was further extracted with ethyl acetate once. After the resulting organic layer was dried over anhydrous sodium sulfate, it was filtered off and the solvent was evaporated under reduced pressure. The residue was purified by silica gel column chromatography (hexane/ethyl acetate=1:1-3:7) to yield Example 4A (102 mg).

(LC-MS: [M-Boc+H]$^+$/Rt (min))=743/1.37

Example 4

2,2'-((((((2-Acetylnaphtho[2,3-b]furan-4,9-diyl)bis(oxy))bis(carbonyl))bis(azanediyl))bis(ethane-2,1-diyl))bis(azanediyl))diacetic Acid dihydrochloride

[Chem. 49]

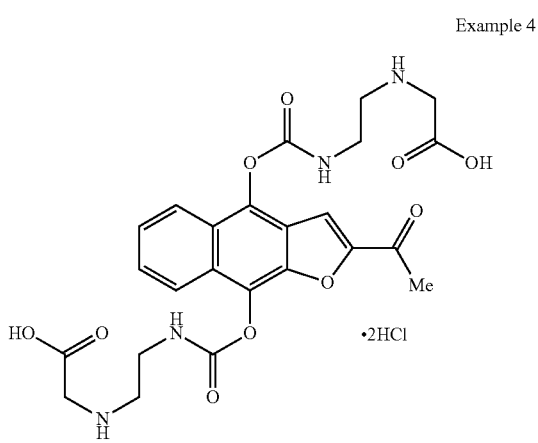

Example 4

A 4 mol/L hydrochloric acid/dioxane solution (10.0 mL) was added to Example 4A (101 mg). The reaction mixture was then stirred at 50° C. for 1 hour. The reaction solution was concentrated, and then the residue was washed with diethyl ether to yield Example 4 (59.0 mg).

$^1$H-NMR (400 MHz, DMSO-d$_6$) δ: 2.62 (3H, s), 3.13-3.22 (4H, m), 3.48-3.55 (4H, m), 3.96 (4H, s), 7.59-7.71 (2H, m), 8.04-8.18 (3H, m), 8.47-8.57 (2H, m), 9.15 (4H, br).

(LC-MS: [M+2H]$^{2+}$/Rt (min))=266/0.37

Reference Example 9

3-((3-(tert-Butoxy)-3-oxopropyl)(tert-butoxycarbonyl)amino)propionic Acid

[Chem. 50]

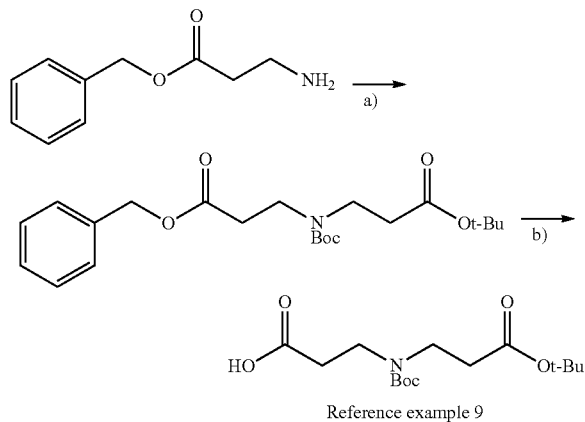

Reference example 9 a) Diisopropylethylamine (3.24 mL) and tert-butyl acrylate (1.35 mL) were added to a solution of benzyl 3-aminopropionate (2.00 g) in ethanol (20.0 mL). The reaction mixture was then stirred at room temperature for 10 hours. Di-tert-butyl-dicarbonate (5.00 g) was added to the reaction mixture, and it was further stirred at room temperature for 2 hours. The reaction solution was filtered through Celite, and then the Celite was washed with ethyl acetate. The filtrate was concentrated and then purified by silica gel column chromatography (hexane/ethyl acetate=1:0-1:1) to yield benzyl 3-((3-(tert-butoxy)-3-oxopropyl)(tert-butoxycarbonyl)amino)propionate (2.00 g).

(LC-MS: [M+H]$^+$/Rt (min))=408/1.10 b) A suspension of benzyl 3-((3-(tert-butoxy)-3-oxopropyl)(tert-butoxycarbonyl)amino)propionate (2.00 g), 10% palladium on carbon (500 mg), and ammonium formate (1.54 g) in methanol (20.0 mL) was stirred under nitrogen atmosphere at 50° C. for 1.5 hours. The reaction solution was filtered through Celite, and then the Celite was washed with methanol. The filtrate was concentrated, and then purified by silica gel column chromatography (hexane/ethyl acetate=1:0-0:1) to yield Reference example 9 (1.10 g).

(LC-MS: [M+H]$^+$/Rt (min))=318/0.94

Example 5A

Di-tert-butyl 3,3'-((((((2-acetylnaphtho[2,3-b]furan-4,9-diyl)bis(oxy))bis(carbonyl))bis(azanediyl))bis(ethane-2,1-diyl))bis((tert-butoxycarbonyl)azanediyl))dipropionate

[Chem. 51]

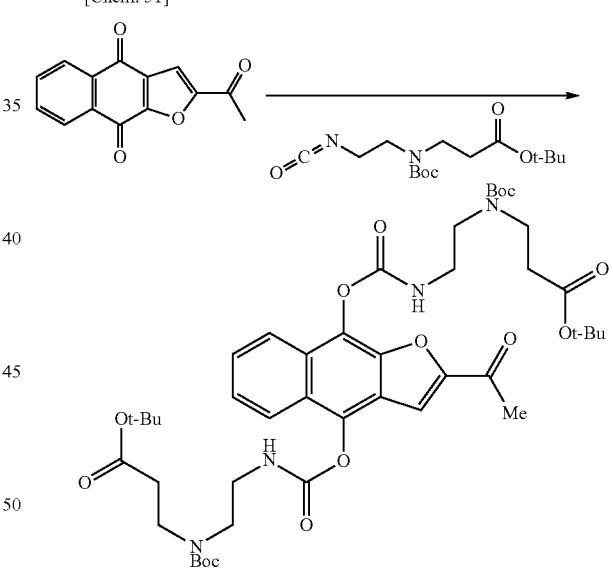

Example 5A

A suspension of 2-acetylnaphtho[2,3-b]furan-4,9-dione (59.0 mg), zinc (64.0 mg), sodium dithionite (214 mg), diisopropylethylamine (0.43 mL), and tetra-n-butylammonium bromide (8.00 mg) in N,N-dimethylformamide (3.50 mL) was stirred under nitrogen atmosphere at room temperature for 1 hour. The reaction mixture was then cooled to 0° C., and a solution of tert-butyl 3-((tert-butoxycarbonyl)(2-isocyanatoethyl)amino)propanoate in toluene, which had been prepared from Reference example 9 (312 mg) by the same method as Reference example 1, was added dropwise thereto over 5 minutes. After stirring at 0° C. for 30 minutes, the reaction solution was filtered through Celite, and then the Celite was washed with ethyl acetate. Aqueous saturated ammonium chloride solution was added to the filtrate, the organic layer was separated, and then the aqueous layer was further extracted with ethyl acetate once. After the resulting organic layer was dried over anhydrous sodium sulfate, it was filtered off and the solvent was evaporated under reduced pressure. The residue was purified by silica gel column chromatography (hexane/ethyl acetate=1:1-3:7) to yield Example 5A (105 mg).

(LC-MS: [M-t-Bu]$^+$/Rt (min))=815/1.36

Example 5

3,3'-((((((2-Acetylnaphtho[2,3-b]furan-4,9-diyl)bis(oxy))bis(carbonyl))bis-(azanediyl))bis(ethane-2,1-diyl))bis(azanediyl))dipropionic Acid dihydrochloride

[Chem. 52]

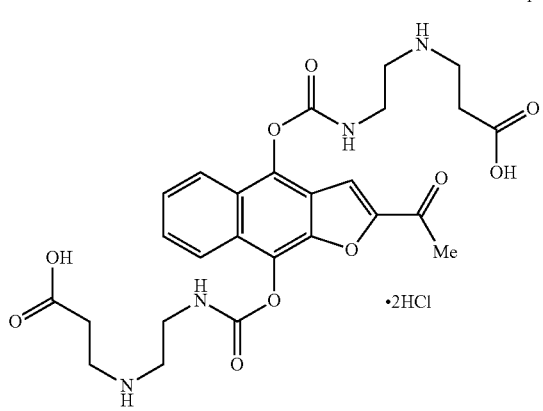

Example 5

A 4 mol/L hydrochloric acid/dioxane solution (10.0 mL) was added to Example 5A (103 mg). The reaction mixture was then stirred at 50° C. for 1 hour. The reaction solution was concentrated, and then the residue was washed with diethyl ether to yield Example 5 (65 mg).

$^1$H-NMR (400 MHz, DMSO-d$_6$) δ: 2.62 (3H, s), 2.68-2.81 (4H, m), 3.10-3.24 (8H, m), 3.43-3.54 (4H, m), 7.58-7.71 (2H, m), 8.05-8.15 (2H, m), 8.21-8.29 (1H, m), 8.46-8.58 (2H, m), 8.75-9.16 (4H, m), 12.71 (2H, br).

(LC-MS: [M+2H]$^{2+}$/Rt (min))=280/0.37

Examples 6-13 (Compounds analogous to Example 1)

Compounds shown in Table 1 were obtained by using corresponding raw material compounds and performing the reactions/treatments described in Reference example 1, Example 1A, and Example 1.

[Chem. 53]

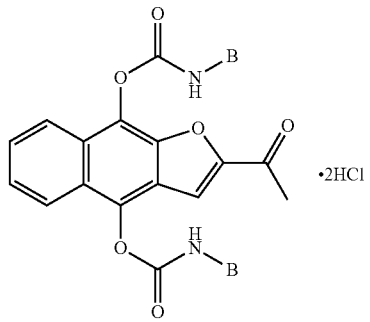

TABLE 1

| Example | B | (LC-MS: [M + 2H]$^{2+}$/ Rt (min)) |
|---|---|---|
| 6 | ![CH2-CH(NH2)-COOH] | 252/0.32 |
| 7 | ![cyclohexyl-NH2] | 262/0.41 |
| 8 | ![piperidine] | 248/0.36 |
| 9 | ![CH2CH2-O-CH2CH2-NH2] | 252/0.43 |
| 10 | ![azetidine-NH] | 220/0.36 |
| 11 | ![CH2CH2-CH(NH2)-COOMe] | 280/0.38 |
| 12 | ![CH2CH2-CH(NH2)-COOH] | 266/0.37 |
| 13 | ![pentyl-NH2] | 236/0.43 |

Reference Example 11

1-(2-Acetyl-4-(4-((tert-butoxy)carbonyl)piperazine-1-carbonyloxy)naphtho[2,3-b]furan-9-yl) 4-tert-butylpiperazine-1,4-dicarboxylate Example 14

2-Acetylnaphtho[2,3-b]furan-4,9-diyl bis(piperazine-1-carboxylate) dihydrochloride

[Chem. 54]

[Chem. 55]

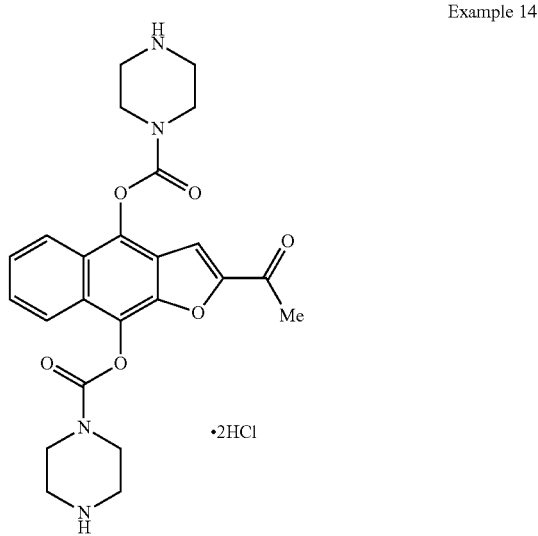

Example 14

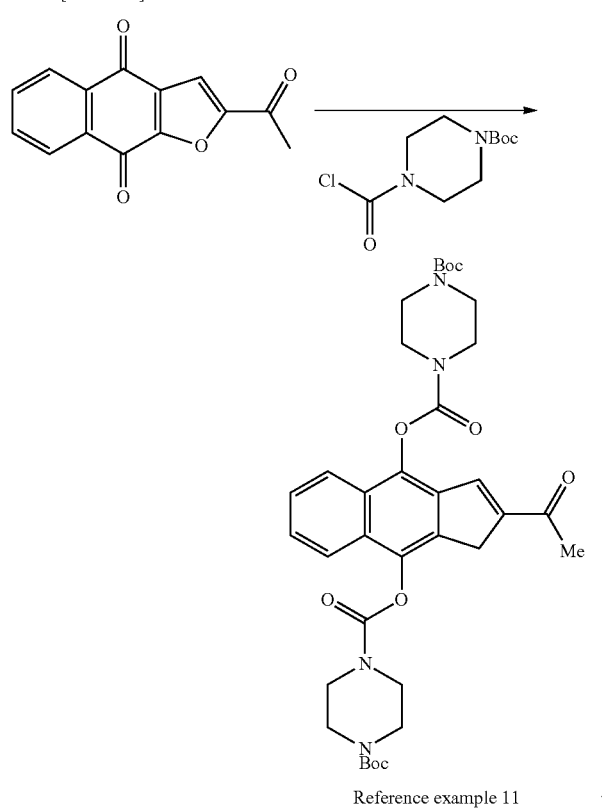

Reference example 11

A suspension of 2-acetylnaphtho[2,3-b]furan-4,9-dione (100 mg), zinc (109 mg), sodium dithionite (362 mg), diisopropylethylamine (0.36 mL), and tetra-n-butylammonium bromide (13.0 mg) in N,N-dimethylformamide (4.20 mL) was stirred under nitrogen atmosphere at room temperature for 10 minutes. Then, tert-butyl 4-(chlorocarbonyl)piperazine-1-carboxylate (259 mg) was added to the reaction mixture, and it was stirred at 70° C. for 4.5 hours. The reaction solution was filtered through Celite, and then the Celite was washed with ethyl acetate. Aqueous saturated ammonium chloride solution was added to the filtrate, the organic layer was separated, and then the aqueous layer was further extracted with ethyl acetate once. After the resulting organic layer was dried over anhydrous sodium sulfate, it was filtered off and the solvent was evaporated under reduced pressure. The residue was purified by silica gel column chromatography (hexane/ethyl acetate=3:2-2:3) to yield Reference example 11 (55 mg).

(LC-MS: [M-t-Bu]$^+$/Rt (min))=611/1.24

A 4 mol/L hydrochloric acid/dioxane solution (5.00 mL) was added to Reference example 11 (55.0 mg). The reaction mixture was then stirred at 60° C. for 30 minutes. The reaction solution was concentrated, and then the residue was washed with diethyl ether to yield Example 14 (41.0 mg).

$^1$H-NMR (400 MHz, DMSO-$d_6$) δ: 2.63 (3H, s), 3.24-3.30 (4H, br), 3.34-3.41 (4H, br), 3.70-3.78 (4H, br), 4.04-4.13 (4H, br), 7.60-7.71 (2H, m), 8.12 (2H, t, J=8.9 Hz), 8.19 (1H, s), 9.18 (4H, br).

(LC-MS: [M+2H]$^{2+}$/Rt (min))=234/0.35

Reference Example 12

2-Acetylnaphtho[2,3-b]furan-4,9-diyl di-tert-butyl bis(carbonate)

[Chem. 56]

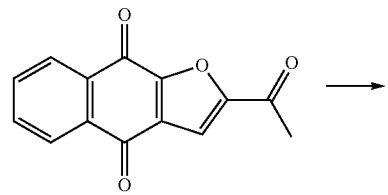

125

-continued

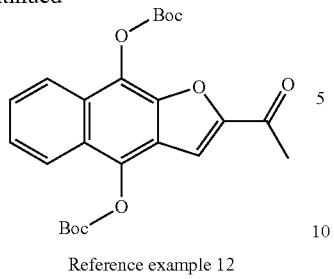

Reference example 12

A suspension of 2-acetylnaphtho[2,3-b]furan-4,9-dione (300 mg), zinc (327 mg), sodium dithionite (1.09 g), diisopropylethylamine (2.18 mL), and tetra-n-butylammonium bromide (40.0 mg) in N,N-dimethylformamide (12.5 mL) was stirred under nitrogen atmosphere at room temperature for 1 hour. The reaction mixture was then cooled to 0° C., and then a solution of di-tert-butyl-dicarbonate (3.69 g) in N,N-dimethylformamide (8.30 mL) was added dropwise thereto over 5 minutes. After stirring at room temperature for 3.5 hours, the reaction solution was filtered through Celite, and then the Celite was washed with ethyl acetate. The resulting filtrate was distributed between an organic layer and an aqueous layer, and then the aqueous layer was extracted with ethyl acetate twice. After the resulting organic layer was dried over anhydrous sodium sulfate, it was filtered off and the solvent was evaporated under reduced pressure. The residue was purified by silica gel column chromatography (chloroform) to yield Reference example 12 (370 mg).

(LC-MS: [M-t-Bu]$^+$/Rt (min))=387/1.28

Reference Example 13

2-Acetyl-4-hydroxynaphtho[2,3-b]furan-9-yl tert-butyl carbonate

Reference Example 14

2-Acetyl-9-hydroxynaphtho[2,3-b]furan-4-yl tert-butyl carbonate

[Chem. 57]

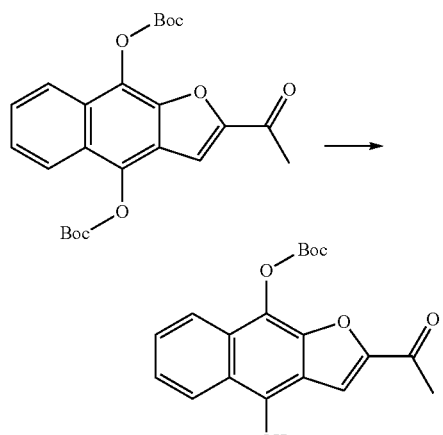

Reference example 13

126

-continued

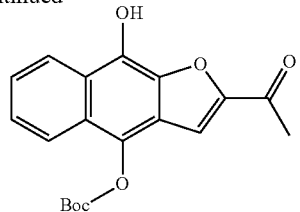

Reference example 14

A suspension of Reference example 12 (360 mg) and potassium carbonate (562 mg) in methanol (35.0 mL) and tetrahydrofuran (18.0 mL) was stirred at room temperature for 85 minutes. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=5:1-3:2) to yield Reference example 13 (157 mg) and Reference example 14 (68.0 mg).

Reference example 13: (LC-MS: [M+H]$^+$/Rt (min))=343/1.04

Reference example 14: (LC-MS: [M-t-Bu]$^+$/Rt (min))=287/1.03

Reference Example 15

2-Acetyl-9-((tert-butoxycarbonyl)oxy)naphtho[2,3-b]furan-4-yl tert-butyl propane-1,3-diyldicarbamate

[Chem. 58]

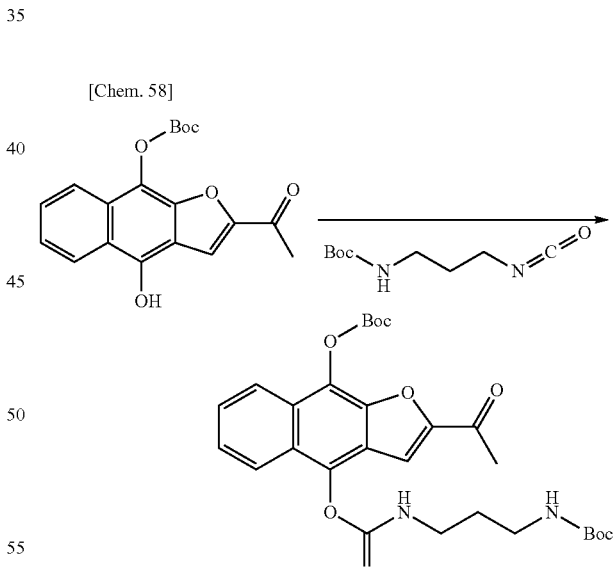

Reference example 15

A solution of Reference example 13 (50.0 mg), diisopropylethylamine (0.13 mL) in N,N-dimethylformamide (2.90 mL) was added dropwise under nitrogen atmosphere at 0° C. to a solution of tert-butyl (3-isocyanatopropyl)carbamate in toluene (2.90 mL), which had been prepared from 4-((tert-butoxycarbonyl)amino))butanoic acid (119 mg) by the same method as Reference example 1. The reaction mixture was then stirred for 2 hours. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=2:1-1:1) to yield Reference example 15 (64.0 mg).

(LC-MS: [M-Boc+H]⁺/Rt (min))=443/1.15

Example 15

2-Acetyl-9-hydroxynaphtho[2,3-b]furan-4-yl (3-aminopropyl)carbamate hydrochloride

[Chem. 59]

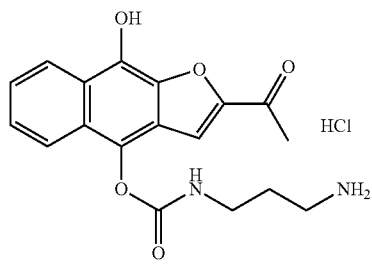

Example 15

A 4 mol/L hydrochloric acid/dioxane solution (3.00 mL) was added to Reference example 15 (62.0 mg). The reaction mixture was stirred at 50° C. for 1 hour. The reaction solution was concentrated, and then the residue was washed with diethyl ether to yield Example 15 (37.0 mg).

¹H-NMR (400 MHz, DMSO-d₆) δ:1.79-1.87 (2H, m), 2.63 (3H, s), 2.85-2.92 (2H, m), 3.19-3.25 (2H, m), 7.48-7.53 (2H, m), 7.73-7.82 (2H, br), 7.87-7.91 (2H, m), 8.24-8.29 (1H, m), 8.29-8.34 (1H, m), 10.78 (1H, s).

(LC-MS: [M+H]⁺/Rt (min))=343/0.53

Example 16

(S)-3-((((2-Acetyl-9-hydroxynaphtho[2,3-b]furan-4-yl)oxy)carbonyl)-amino)-2-aminopropionic Acid hydrochloride

[Chem. 60]

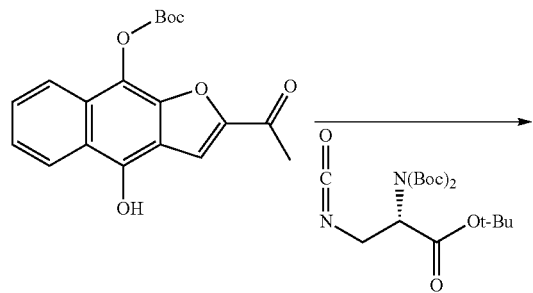

-continued

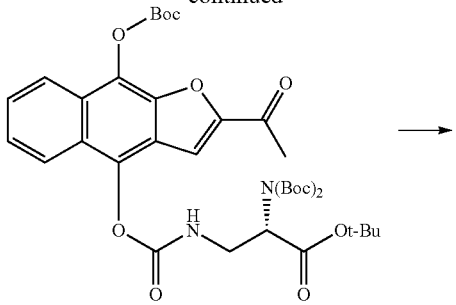

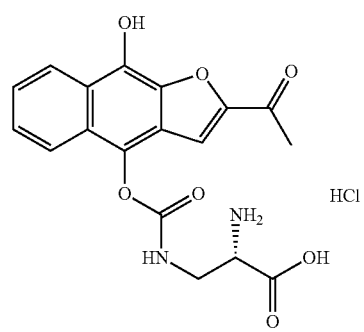

Example 16

A solution of Reference example 13 (50.0 mg) and diisopropylethylamine (0.13 mL) in N,N-dimethylformamide (2.90 mL) was added dropwise under nitrogen atmosphere at 0° C. to a solution of tert-butyl (2S)-2-(bis((tert-butoxy)carbonyl)amino)-3-isocyanatopropionate in toluene, which had been prepared from (3S)-3-(bis((tert-butoxy)carbonyl)amino)-4-(tert-butoxy)-4-oxobutanoic acid (228 mg) by the same method as Reference example 1. The reaction mixture was stirred for 2 hours. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=9:1-7:3) to yield tert-butyl (S)-3-((((2-acetyl-9-((tert-butoxycarbonyl)oxy)naphtho[2,3-b]furan-4-yl)oxy)carbonyl)amino)-2-(bis(tert-butoxycarbonyl)amino)propionate (100 mg). Subsequently, 4 mol/L hydrochloric acid/dioxane solution (1.5 mL) was added to the above-described compound. The reaction mixture was then stirred at 50° C. for 1 hour. The reaction solution was concentrated, and then the residue was washed with diethyl ether to yield Example 16 (37.0 mg).

¹H-NMR (400 MHz, DMSO-d₆) δ: 2.63 (3H, s), 3.60-3.72 (2H, m), 4.05-4.11 (1H, m), 7.46-7.54 (2H, m), 7.95-8.02 (2H, m), 8.28-8.34 (1H, m), 8.40-8.45 (1H, m), 8.54 (3H, br), 10.78 (1H, br).

(LC-MS: [M+H]⁺/Rt (min))=373/0.48

Example 17

3-((2-((((2-Acetyl-9-hydroxynaphtho[2,3-b]furan-4-yl)oxy)carbonyl)amino)ethyl)amino)propionic Acid hydrochloride

[Chem. 61]

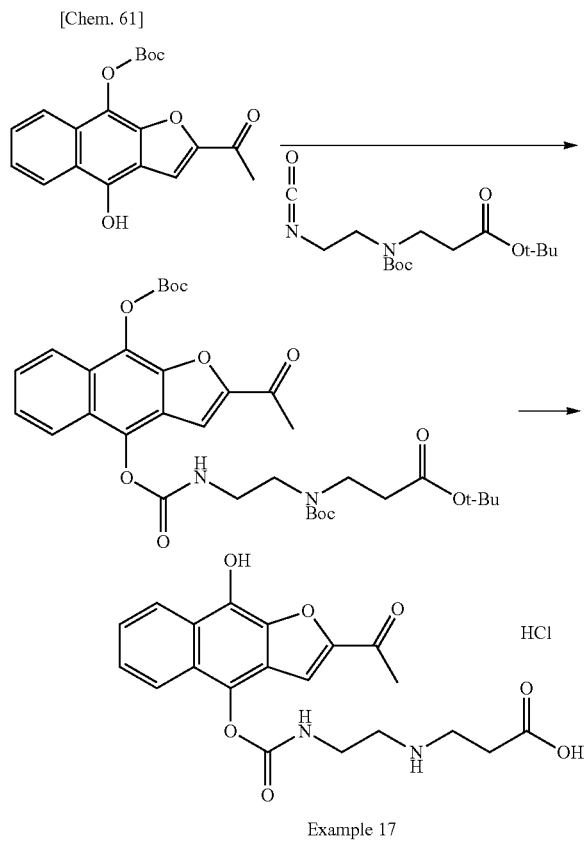

Example 17

A solution of Reference example 13 (50.0 mg) and diisopropylethylamine (0.13 mL) in N,N-dimethylformamide (3.70 mL) was added dropwise under nitrogen atmosphere at 0° C. to a solution of tert-butyl 3-((tert-butoxycarbonyl)(2-isocyanatoethyl)amino)propionate in toluene, which had been prepared from 3-((3-(tert-butoxy)-3-oxopropyl)(tert-butoxycarbonyl)amino)propionic acid (185 mg) by the same method as Reference example 1. The reaction mixture was then stirred for 3 hours. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=7:3-1:1) to yield tert-butyl 3-((2-((((2-acetyl-9-((tert-butoxycarbonyl)oxy)naphtho[2,3-b]furan-4-yl)oxy)carbonyl)amino)ethyl)(tert-butoxycarbonyl)amino)propionate (42.0 mg). Subsequently, 4 mol/L hydrochloric acid/dioxane solution (5.00 mL) was added to the above-described compound. The reaction mixture was then stirred at 50° C. for 30 minutes. The reaction solution was concentrated, and then the residue was washed with diethyl ether to yield Example 17 (28.0 mg).

$^1$H-NMR (400 MHz, DMSO-$d_6$) δ: 2.60-2.65 (3H, m), 2.67-2.76 (2H, m), 3.11-3.24 (4H, m), 3.42-3.51 (2H, m), 7.47-7.55 (2H, m), 7.91-8.04 (2H, m), 8.26-8.35 (2H, m), 8.79 (1H, br), 10.79 (1H, br).

(LC-MS: [M+H]$^+$/Rt (min))=401/0.50

Examples 18-19 (Compounds analogous to Example 15)

Compounds shown in Table 2 were obtained by using corresponding raw material compounds and performing the reactions/treatments described in Reference example 15 and Example 15.

[Chem. 62]

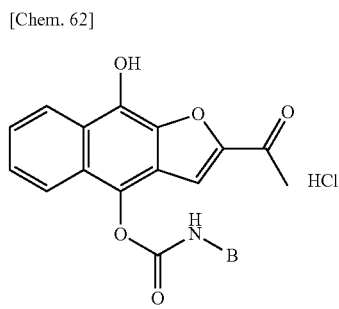

TABLE 2

| Example | B | (LC-MS: [M + H]$^+$/ Rt (min)) |
|---|---|---|
| 18 | ⇃⌃⌄NH$_2$ | 329/0.48 |
| 19 | ⇃⌃⌄⇃(CO$_2$H)NH$_2$ | 387/0.51 |

Reference Example 16

2-Acetyl-4-((tert-butoxycarbonyl)oxy)naphtho[2,3-b]furan-9-yl tert-butyl propane-1,3-diyldicarbamate

[Chem. 63]

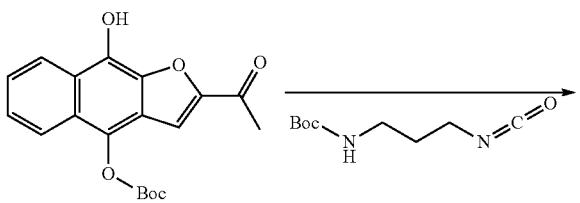

131
-continued

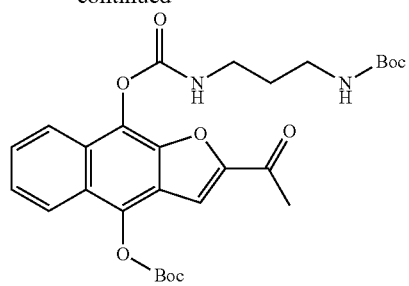

Reference example 16

A solution of Reference example 14 (44.0 mg) and diisopropylethylamine (0.11 mL) in N,N-dimethylformamide (2.50 mL) was added dropwise under nitrogen atmosphere at 0° C. to a solution of tert-butyl (3-isocyanatopropyl)carbamate in toluene (2.50 mL), which had been prepared from 4-((tert-butoxycarbonyl)amino))butyric acid (104 mg) by the same method as Reference example 1. The reaction mixture was then stirred at 0° C. for 3.5 hours. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=2:1-1:1) to yield Reference example 16 (49.0 mg).

(LC-MS: $[M+H]^+$/Rt (min))=543/1.15

Example 20

2-Acetyl-4-hydroxynaphtho[2,3-b]furan-9-yl (3-aminopropyl)carbamate hydrochloride

[Chem. 64]

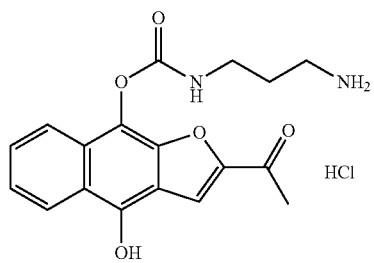

Example 20

A 4 mol/L hydrochloric acid/dioxane solution (3.00 mL) was added to Reference example 16 (48.0 mg). The reaction mixture was then stirred at 50° C. for 1 hour. The reaction solution was concentrated, and then the residue was washed with diethyl ether to yield Example 20 (20.0 mg).

$^1$H-NMR (400 MHz, DMSO-$d_6$) δ:1.79-1.88 (2H, m), 2.56 (3H, s), 2.85-2.94 (2H, m), 3.18-3.26 (2H, m), 7.41-7.47 (1H, m), 7.56-7.62 (1H, m), 7.81-7.92 (4H, m), 8.25 (1H, s), 8.27-8.34 (2H, m), 11.31 (1H, s).

(LC-MS: $[M+H]^+$/Rt (min))=343/0.54

132
Reference Example 17

4-((tert-Butoxycarbonyl)amino)butyl carbonochloridate

[Chem. 65]

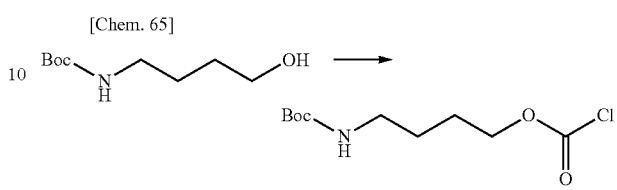

Reference example 17

Diisopropylethylamine (7.26 mL) and triphosgene (432 mg) were added to a solution of tert-butyl (4-hydroxybutyl) carbamate (788 mg) in tetrahydrofuran (10.0 mL) at 0° C. The reaction mixture was stirred at room temperature for 1 hour, and thereby a solution of Reference example 17 in tetrahydrofuran was produced. The resulting solution was used in the next reaction as it was.

Reference Example 18

Di-tert-butyl (((((2-acetylnaphtho[2,3-b]furan-4,9-diyl)bis(oxy)bis(carbonyl)bis(oxy))bis(butane-4,1-diyl))dicarbamate

[Chem. 66]

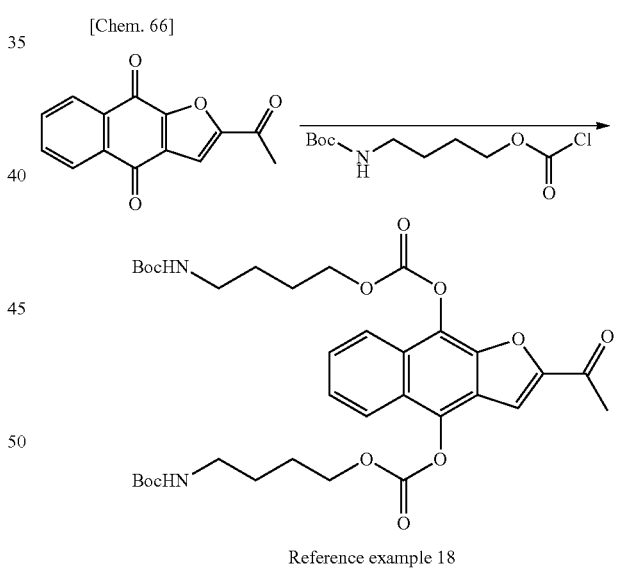

Reference example 18

A suspension of 2-acetylnaphtho[2,3-b]furan-4,9-dione (100 mg), zinc (108 mg), sodium dithionite (362 mg), diisopropylethylamine (7.25 mL), and tetra-n-butylammonium bromide (13.5 mg) in N,N-dimethylformamide (10 mL) was stirred under nitrogen atmosphere at room temperature for 1 hour. The reaction mixture was then cooled to 0° C., and a solution of 4-((tert-butoxycarbonyl)amino)butyl carbonochloridate in tetrahydrofuran, which had been prepared in Reference example 17, was added dropwise over 15 minutes. After further stirring at 0° C. for 1 hour, ethyl acetate and aqueous saturated ammonium chloride solution were added to the reaction solution. After the resulting mixture was filtered through Celite, the filtrate was distributed between an organic layer and an aqueous layer, and then the aqueous layer was extracted with ethyl acetate twice. The resulting organic layer was washed with water once and dried over anhydrous sodium sulfate, and then it was filtered off and the solvent was evaporated under reduced pressure. The residue was purified by silica gel column chromatography (hexane/ethyl acetate=1:1-1:4) to yield Reference example 18 (103 mg).

(LC-MS: [M+H]$^+$/Rt (min))=673/1.39

Example 21

2-Acetylnaphtho[2,3-b]furan-4,9-diylbis(4-aminobutyl)bis(carbonate) dihydrochloride

[Chem. 67]

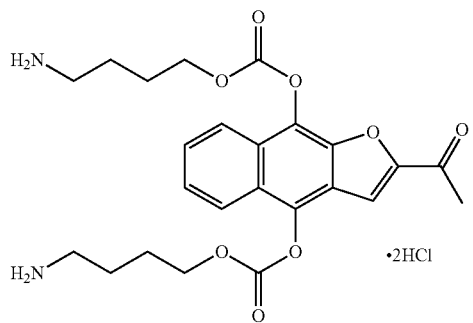

Example 21

A 4 mol/L hydrochloric acid/dioxane (10 mL) solution was added to Reference example 18 (103 mg). The reaction mixture was then stirred at 50° C. for 1 hour. The reaction solution was concentrated, and then the residue was washed with diethyl ether to yield Example 21 (39.0 mg).

(LC-MS: [M+H]$^+$/Rt (min))=473/0.44

Reference Example 19 tert-Butyl (S)-2-((tert-butoxycarbonyl)amino)-5-hydroxypentanoate

[Chem. 68]

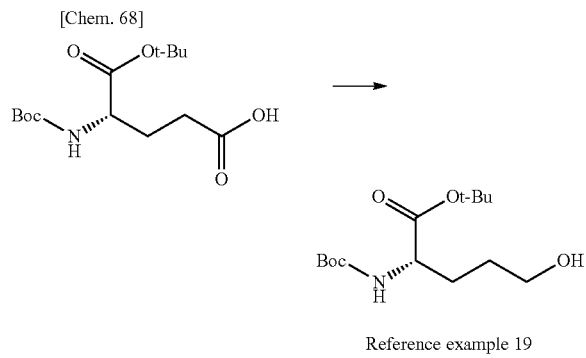

Reference example 19

A 2.0 mol/L solution of dimethyl sulfide borane in tetrahydrofuran (5.40 mL) was added to a solution of (S)-5-(tert-butoxy)-4-((tert-butoxycarbonyl)amino)-5-oxopentanoic acid (3.00 g) in tetrahydrofuran (100 mL) at 0° C. The reaction mixture was stirred at room temperature for 10 hours. Ethyl acetate and saturated brine were added to the reaction solution. After the resulting mixture was filtered through Celite, the filtrate was distributed between an organic layer and an aqueous layer, and then the aqueous layer was extracted with ethyl acetate twice. The resulting organic layer was washed with water once and dried over anhydrous sodium sulfate, and then it was filtered off and the solvent was evaporated under reduced pressure. The residue was purified by silica gel column chromatography (hexane/ethyl acetate=1:0-1:1) to yield Reference example 19 (450 mg).

(LC-MS: [M+H]$^+$/Rt (min))=290/0.86

Reference Example 20

Di-tert-butyl 5,5'-(((((2-acetylnaphtho[2,3-b]furan-4,9-diyl)bis(oxy))bis(carbonyl))bis(oxy))(2S,2S')-bis(2-((tert-butoxycarbonyl)amino)pentanoate

[Chem. 69]

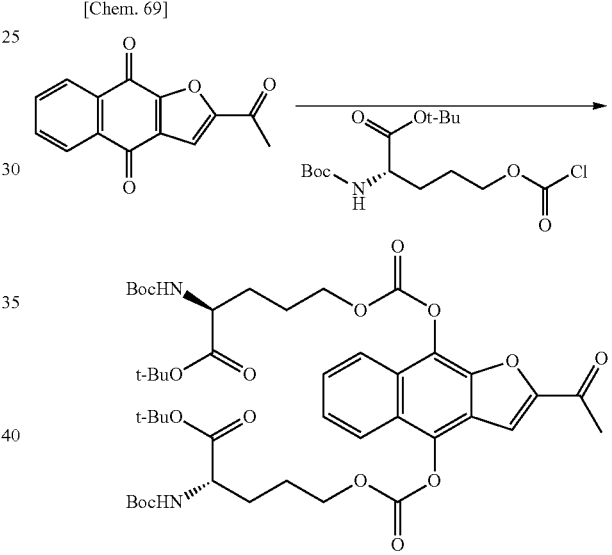

Reference example 20

A suspension of 2-acetylnaphtho[2,3-b]furan-4,9-dione (62.0 mg), zinc (68.0 mg), sodium dithionite (221 mg), diisopropylethylamine (451 uL), and tetra-n-butylammonium bromide (8.30 mg) in N,N-dimethylformamide (10.0 mL) was stirred under nitrogen atmosphere at room temperature for 1 hour. The reaction mixture was then cooled to 0° C., and a solution of tert-butyl (S)-2-((tert-butoxycarbonyl)amino)-5-((chlorocarbonyl)oxy)pentanoate in tetrahydrofuran, which had been prepared from tert-butyl (S)-2-((tert-butoxycarbonyl)amino)-5-hydroxypentanoate (450 mg) by the same method as Reference example 17, was added dropwise thereto over 15 minutes. After further stirring at 0° C. for 1 hour, ethyl acetate and aqueous saturated ammonium chloride solution were added to the reaction solution. After the resulting mixture was filtered through Celite, the filtrate was distributed between an organic layer and an aqueous layer, and then the aqueous layer was extracted with ethyl acetate twice. The resulting organic layer was washed with water once and dried over anhydrous sodium sulfate, and then it was filtered off and the solvent was evaporated under reduced pressure. The residue was purified by silica gel column chromatography (hexane/ethyl acetate=1:0-1:2) to yield Reference example 20 (71.0 mg).

(LC-MS: [M+Na]⁺/Rt (min))=895/1.43

Example 22

(2S,2S')-5,5'-(((((2-Acetylnaphtho[2,3-b]furan-4,9-diyl)bis(oxy))bis(carbonyl)bis(oxy))bis(2-aminopentanoic acid)dihydrochloride

[Chem. 70]

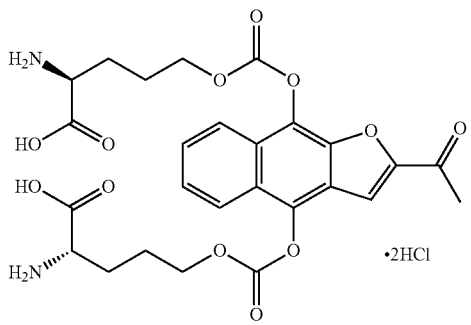

Example 22

A 4 mol/L hydrochloric acid/dioxane (10.0 mL) solution was added to Reference example 20 (71.0 mg). The reaction mixture was stirred at 60° C. for 1 hour. The reaction solution was concentrated, and then the residue was washed with diethyl ether to yield Example 22 (29.0 mg).

(LC-MS: [M+H]⁺/Rt (min))=561/0.49

Reference Example 21 tert-Butyl N-(tert-butoxycarbonyl)-N-(4-hydroxybutyl)glycinate

[Chem. 71]

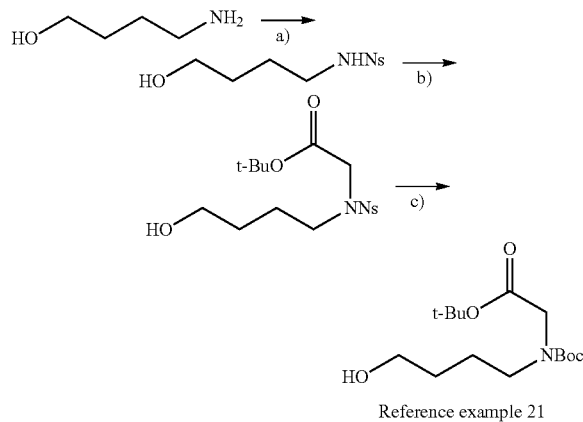

Reference example 21 a) Triethylamine (10.3 mL) and 2-nitrobenzenesulfonyl chloride (6.04 g) were added to a solution of 4-aminobutan-1-ol (2.21 g) in acetonitrile (50.0 mL) were added at 0° C. The reaction mixture was stirred at room temperature for 1 hour. The reaction solution was concentrated, ethyl acetate and saturated brine were added to the residue, and then the organic layer was separated. The aqueous layer was further extracted with ethyl acetate once. The resulting organic layer was dried over anhydrous sodium sulfate, and then it was filtered off and the solvent was evaporated under reduced pressure to yield 4-((4-hydroxybutyl)amino)-3-nitrobenzenesulfonic acid (2.70 g). The resulting compound was used in the next reaction as it was.

b) A solution of 4-((4-hydroxybutyl)amino)-3-nitrobenzenesulfonic acid (7.00 g), tert-butyl 2-bromoacetate (4.10 mL), and potassium carbonate (10.0 g) in acetonitrile (100 mL) was stirred at room temperature for 10 hours. The reaction solution was diluted with water, and then extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=1:0-0:1) to yield 4-((2-(tert-butoxy)-2-oxoethyl)(4-hydroxybutyl)amino)-3-nitrobenzenesulfonic acid (6.00 g).

(LC-MS: [M+H]⁺/Rt (min))=389/0.90 c) A suspension of 4-((2-(tert-butoxy)-2-oxoethyl)(4-hydroxybutyl)amino)-3-nitrobenzenesulfonic acid (6.00 g), benzenethiol (1.90 mL), and cesium carbonate (10.0 g) in acetonitrile (100 mL) was stirred under nitrogen atmosphere at room temperature for 2 hours. Di-tert-butyl-dicarbonate (6.80 g) was added to the reaction mixture, and it was further stirred at room temperature for 2 hours. The reaction solution was filtered through Celite, and then the Celite was washed with ethyl acetate. The filtrate was concentrated, and then purified by silica gel column chromatography (hexane/ethyl acetate=1:0-0:1) to yield Reference example 21 (3.10 g).

(LC-MS: [M+H]⁺/Rt (min))=304/0.93

Reference Example 22

Di-tert-butyl 2,2'-((((((2-acetylnaphtho[2,3-b]furan-4,9-diyl)bis(oxy)bis(carbonyl))bis(oxy))bis(butane-4,1-diyl))bis((tert-butoxycarbonyl)azanediyl))diacetic Acid

[Chem. 72]

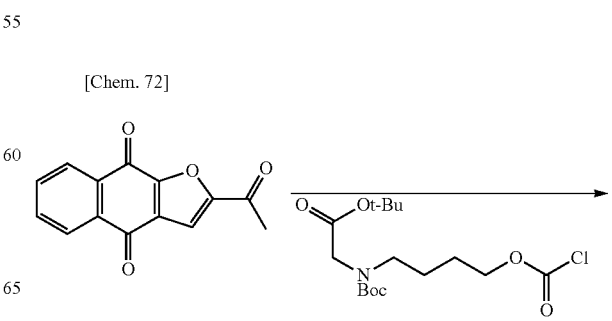

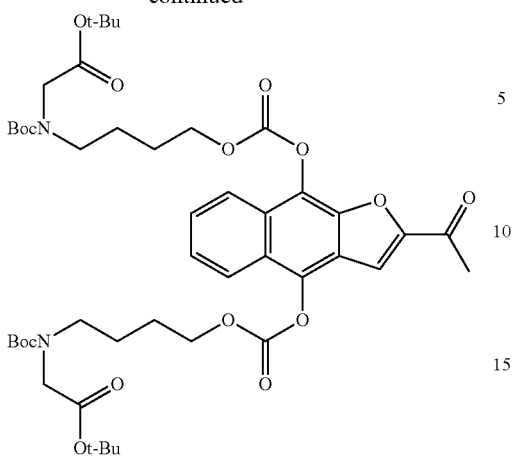

Reference example 22

A suspension of 2-acetylnaphtho[2,3-b]furan-4,9-dione (118 mg), zinc (125 mg), sodium dithionite (432 mg), diisopropylethylamine (860 uL), and tetra-n-butylammonium bromide (16.0 mg) in N,N-dimethylformamide (20.0 mL) was stirred under nitrogen atmosphere at room temperature for 1 hour. The reaction mixture was then cooled to 0° C., and a solution of tert-butyl N-(tert-butoxycarbonyl)-N-((chlorocarbonyl)oxy)butyl)glycinate in tetrahydrofuran, which had been prepared from tert-butyl N-(tert-butoxycarbonyl)-N-(4-hydroxybutyl)glycinate (900 mg) in the same way as Reference example 17, was added dropwise thereto over 15 minutes. After further stirring at 0° C. for 1 hour, ethyl acetate and aqueous saturated ammonium chloride solution were added to the reaction solution. After the resulting mixture was filtered through Celite, the filtrate was distributed between an organic layer and an aqueous layer, and then the aqueous layer was extracted with ethyl acetate twice. The resulting organic layer was washed with water once and dried over anhydrous sodium sulfate, and then it was filtered off and the solvent was evaporated under reduced pressure. The residue was purified by silica gel column chromatography (hexane/ethyl acetate=1:0-1:1) to yield Reference example 22 (111 mg).

(LC-MS: [M+Na]$^+$/Rt (min))=923/1.47

Example 23

2,2'-((((((2-Acetylnaphtho[2,3-b]furan-4,9-diyl)bis(oxy)bis(carbonyl))bis(oxy))bis(butane-4,1-diyl))bis(azanediyl))diacetic Acid dihydrochloride

[Chem. 73]

Example 23

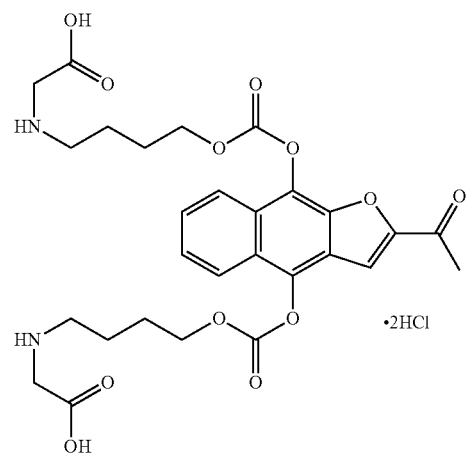

A 4 mol/L hydrochloric acid/dioxane (10.0 mL) solution was added to Reference example 22 (111 mg). The reaction mixture was stirred at 70° C. for 1 hour. The reaction solution was concentrated, and then the residue was washed with diethyl ether to yield Example 23 (56.8 mg).

(LC-MS: [M+2H]$^{2+}$/Rt (min))=295/0.55

Examples 24-28 (Compounds analogous to Example 21)

Compounds shown in Table 3 were obtained by using corresponding raw material compounds and performing the reactions and treatments described in Reference example 17, Reference example 18, and Example 21.

[Chem. 74]

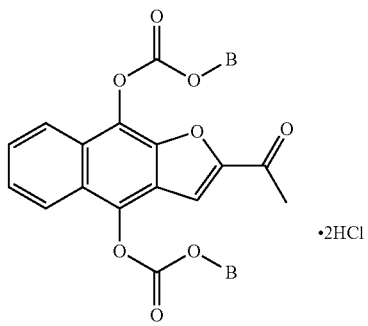

TABLE 3

| Example | B | (LC-MS: [M + 2H]$^{2+}$/Rt (min)) |
|---|---|---|
| 24 | ⟋⟍⟋⟍NH$_2$ | 209/0.32 |

TABLE 3-continued

| Example | B | (LC-MS: [M + 2H]$^{2+}$/ Rt (min)) |
|---|---|---|
| 25 | ![structure with NH2] | 223/0.32 |
| 26 | ![structure with COOH, NH2] | 267/0.32 |
| 27 | ![pyrrolidine structure] | 263/0.53 |
| 28 | ![structure with NHMe] | 265/0.32 |

Reference Example 23 tert-Butyl (S)-5-((((2-acetyl-9-((tert-butoxycarbonyl)oxy)naphtho[2,3-b]furan-4-yl)oxy)carbonyl)oxy)-2-((tert-butoxycarbonyl)amino)pentanoate

[Chem. 75]

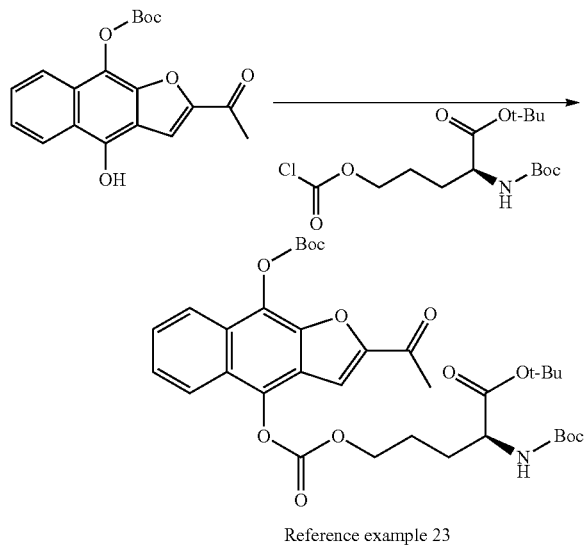

Reference example 23

A solution of Reference example 13 (70.0 mg) and diisopropylethylamine (0.50 mL) in N,N-dimethylformamide (10.0 mL) was added dropwise under nitrogen atmosphere at 0° C. to a solution of tert-butyl (S)-2-((tert-butoxycarbonyl)amino)-5-((chlorocarbonyl)oxy)pentanoate in tetrahydrofuran (10.0 mL), which had been prepared from tert-butyl (S)-2-((tert-butoxycarbonyl)amino)-5-hydroxypentanoate (500 mg) by the same method as Reference example 17. The reaction mixture was then stirred for 2 hours. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=2:1-1:1) to yield Reference example 23 (101 mg).

(LC-MS: [M+Na]$^+$/Rt (min))=680/1.37

Example 29

(S)-5-((((2-Acetyl-9-hydroxynaphtho[2,3-b]furan-4-yl)oxy)carbonyl)oxy)-2-aminopentanoic Acid hydrochloride

[Chem. 76]

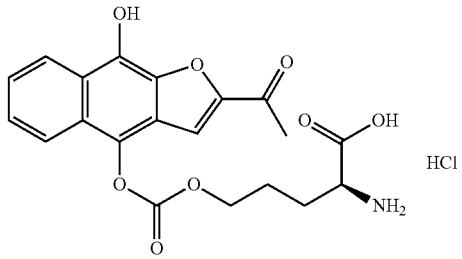

Example 29

A 4 mol/L hydrochloric acid/dioxane (10.0 mL) solution was added to Reference example 23 (101 mg). The reaction mixture was then stirred at 50° C. for 1 hour. The reaction solution was concentrated, and then the residue was washed with diethyl ether to yield Example 29 (41.0 mg).

(LC-MS: [M+H]$^+$/Rt (min))=402/0.60

Reference Example 24 tert-Butyl N-(4-((((2-acetyl-9-((tert-butoxycarbonyl)oxy)naphtho-[2,3-b]furan-4-yl)oxy)carbonyl)oxy)butyl)-N-(tert-butoxycarbonyl)-glycinate

[Chem. 77]

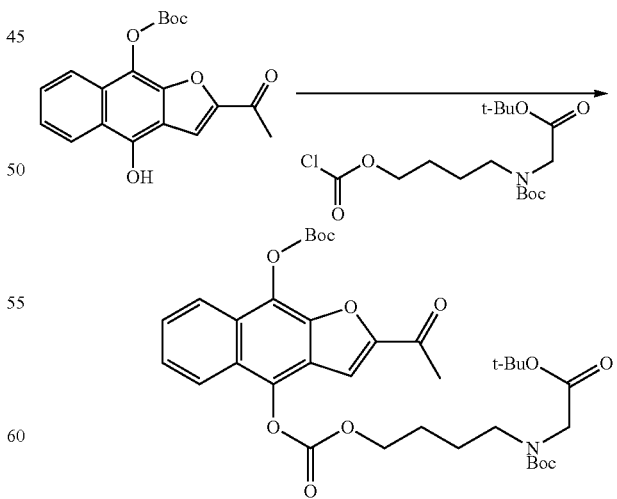

Reference example 24

A solution of Reference example 13 (81.0 mg) and diisopropylethylamine (0.50 mL) in N,N-dimethylformamide (10.0 mL) was added dropwise under nitrogen atmosphere at 0° C. to a solution of tert-butyl N-(tert-butoxycarbonyl)-N-((chlorocarbonyl)oxy)butyl)glycinate in tetrahydrofuran (10.0 mL), which had been prepared from tert-butyl N-(tert-butoxycarbonyl)-N-(4-hydroxybutyl) glycinate (600 mg) by the same method as Reference example 17. The reaction mixture was then stirred for 2 hours. Aqueous saturated ammonium chloride solution was added to the reaction solution, and then it was extracted with ethyl acetate twice. After the resulting organic layer was dried over anhydrous sodium sulfate, it was filtered off and the solvent was evaporated under reduced pressure. The residue was purified by silica gel column chromatography (hexane/ethyl acetate=2:1-1:1) to yield Reference example 24 (98.0 mg).

(LC-MS: [M+Na]$^+$/Rt (min))=694/1.42

Example 30

(4-((((2-Acetyl-9-hydroxynaphtho[2,3-b]furan-4-yl)oxy)carbonyl)oxy)-butyl)glycine hydrochloride

[Chem. 78]

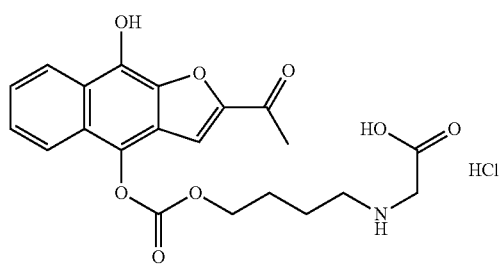

Example 30

A 4 mol/L hydrochloric acid/dioxane (10.0 mL) solution was added to Reference example 24 (98.0 mg). The reaction mixture was stirred at 50° C. for 1 hour. The reaction solution was concentrated, and then the residue was washed with diethyl ether to yield Example 30 (51.0 mg).

(LC-MS: [M+H]$^+$/Rt (min))=416/0.64

Example 31

2-Acetylnaphtho[2,3-b]furan-4,9-diyl (2S,2'S)-bis(2-aminopropanoate) dihydrochloride

[Chem. 79]

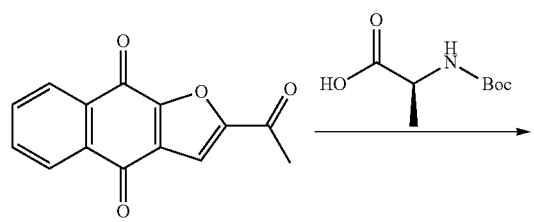

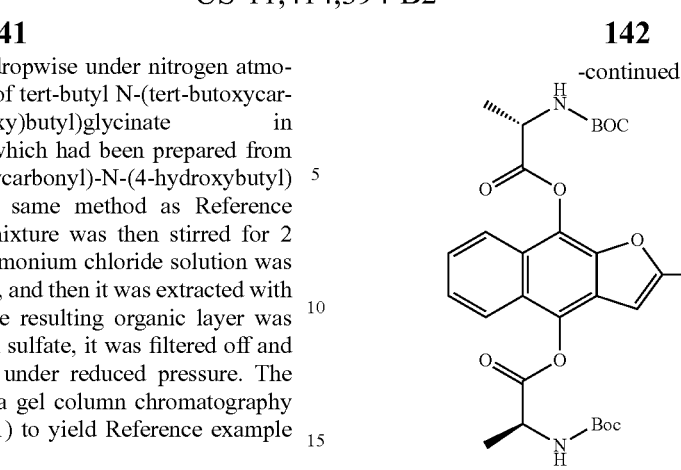

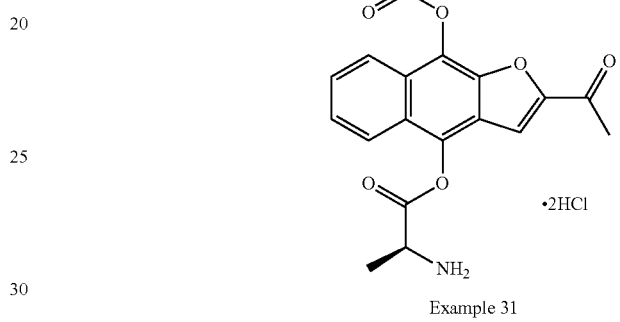

Example 31

A suspension of 2-acetylnaphtho[2,3-b]furan-4,9-dione (50.0 mg), sodium dithionite (109 mg), and tetra-n-butylammonium bromide (7.00 mg) in THF (1.30 mL) and water (0.70 mL) was stirred under nitrogen atmosphere at room temperature for 40 minutes. The reaction solution was diluted with ethyl acetate, and then washed with water twice. The resulting organic layer was concentrated, and then the resulting solid was dissolved in tetrahydrofuran (2.00 mL). Diisopropylethylamine (0.18 mL), dimethylaminopyridine (4.00 mg), 1-ethyl-3-(3-dimethyl-aminopropyl)carbodiimide hydrochloride (160 mg), and tert-butoxycarbonyl-L-alanine (158 mg) were added to the solution, and then it was stirred at room temperature for 16 hours. The reaction solution was diluted with water, and then extracted with ethyl acetate three times. The resulting organic layer was washed with aqueous saturated sodium hydrogen carbonate solution twice and dried over anhydrous sodium sulfate, and then it was filtered off and the solvent was evaporated under reduced pressure. The residue was purified by silica gel column chromatography (hexane/ethyl acetate=4:1-1:1) to yield 2-acetylnaphtho[2,3-b]furan-4,9-diyl (2S,2'S)-bis(2-((tert-butoxy-carbonyl)amino)propanoate) (7.00 mg). Subsequently, 4 mol/L hydrochloric acid/dioxane (5.00 mL) solution was added to the above-described compound. The reaction mixture was stirred at room temperature for 4 hours. The reaction solution was concentrated, and then the residue was washed with diethyl ether to yield Example 31 (3.00 mg).

$^1$H-NMR (400 MHz, DMSO-d$_6$) δ: 1.99 (6H, d, J=6.7 Hz), 2.66 (3H, s), 3.56-3.75 (2H, m), 7.66-7.76 (2H, m), 7.89 (1H, s), 8.15 (2H, t, J=8.9 Hz).

Reference Example 25

2-(2-methyl-1,3-dioxoran-2-yl)naphtho[2,3-b]furan-4,9-dione

[Chem. 80]

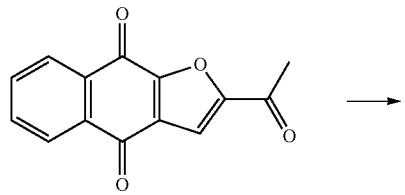 

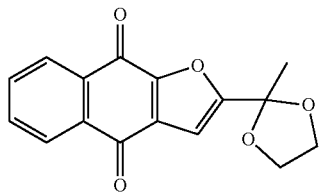

Reference example 25

A solution of 2-acetylnaphtho[2,3-b]furan-4,9-dione (6.0 g), tosylic acid hydrate (0.48 g), and ethylene glycol (70 mL) in toluene (0.25 L) was heated to reflux for 3.5 hours. Then, water and ethyl acetate were added thereto and the organic layer was separated. After the resulting organic layer was dried over anhydrous sodium sulfate, it was filtered off and the solvent was evaporated under reduced pressure. The residue was purified by recrystallization operation (hexane-ethyl acetate) to yield Reference example 25 (5.4 g).

(LC-MS: [M+H]⁺/Rt (min))=285/0.92

Reference Example 26

Di-tert-butyl 2,2'-((((((2-(2-methyl-1,3-dioxoran-2-yl)naphtho[2,3-b]furan-4,9-diyl)bis(oxy))bis(carbonyl))bis(azanediyl))bis(ethane-2,1-diyl))bis((tert-butoxycarbonyl)azanediyl))diacetate

[Chem. 81]

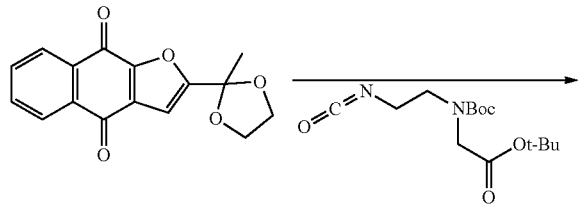

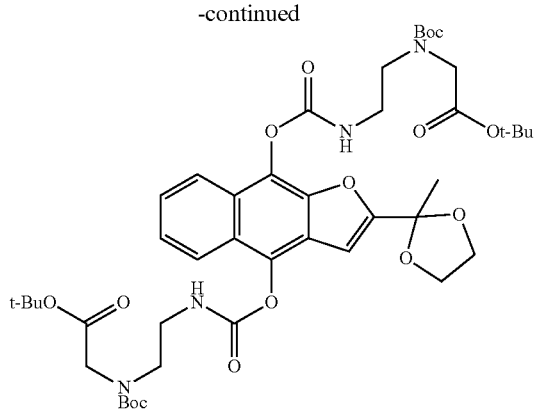

Reference example 26

A suspension of Reference example 25 (2.13 g), zinc (0.460 g), sodium dithionite (1.23 g), diisopropylethylamine (1.23 mL), and tetra-n-butylammonium bromide (57.0 mg) in N,N-dimethylformamide (17.6 mL) was stirred under nitrogen atmosphere at room temperature for 2 hours. Then, the suspension was cooled to 0° C., and the solution of tert-butyl N-(tert-butoxycarbonyl)-N-(2-isocyanatoethyl)glycinate in toluene, which was prepared from N-(tert-butoxycarbonyl)-N-(2-tert-butoxy-2-oxoethyl)-b-alanine (0.500 g) according to the same method as in Reference example 1, was added dropwise thereto over 6 minutes. After stirring at 0° C. for 1 hour, the reaction solution was filtered through Celite, and the Celite was washed with ethyl acetate. Then, 0.1 mol/L hydrochloric acid was added to the filtrate and the organic layer was separated. The aqueous layer was then further extracted with ethyl acetate once. After the resulting organic layer was dried over anhydrous sodium sulfate, it was filtered off and the solvent was evaporated under reduced pressure. The residue was purified by silica gel column chromatography (hexane/ethyl acetate=1:1-2:3) to yield Reference example 26 (1.22 g).

(LC-MS: [M-Boc+H]⁺/Rt (min))=787/1.38

Example 4

2,2'-((((((2-acetylnaphtho[2,3-b]furan-4,9-diyl)bis(oxy))bis(carbonyl))bis-(azanediyl))bis(ethane-2,1-diyl))bis(azanediyl))diacetic Acid dihydrochloride

[Chem. 82]

Example 4

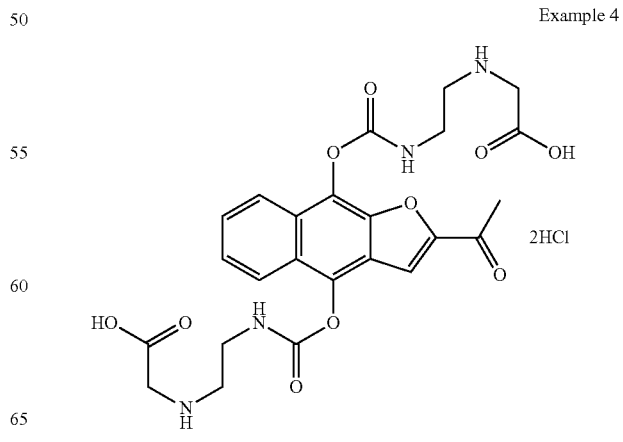

A 4 mol/L hydrochloric acid/dioxane solution (7.0 mL), water (20 uL), and acetonitrile (7.0 mL) were added to Reference example 26 (0.50 g). The reaction mixture was stirred at 70° C. for 1.5 hours. The precipitated solid was washed with acetonitrile and diethyl ether to yield Example 4 (0.33 g).

Reference Example 27

2-(1,1-dimethoxyethyl)naphtho[2,3-b]furan-4,9-dione

[Chem. 83]

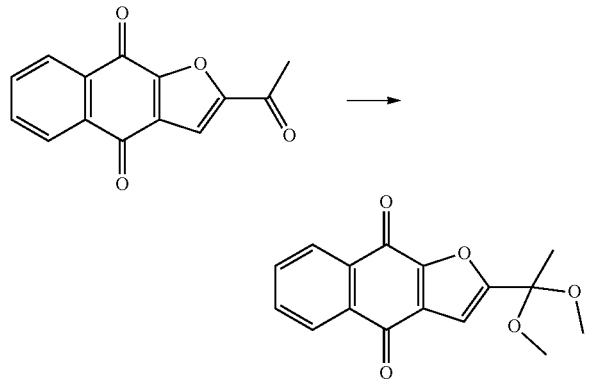

Reference example 27

A solution of 2-acetylnaphtho[2,3-b]furan-4,9-dione (0.50 g), tosylic acid hydrate (0.40 g), and trimethyl orthoformate (0.64 mL) in methanol (30 mL) was heated to reflux for 3.5 hours. Then, ethyl acetate was added thereto and the solution was washed with saturated saline and water. After the resulting organic layer was dried over anhydrous sodium sulfate, it was filtered off and the solvent was evaporated under reduced pressure. The residue was purified by silica gel column chromatography (hexane-ethyl acetate) to yield Reference example 27 (0.53 g).

(LC-MS: [M-OMe+H]$^+$/Rt (min))=255/1.00

Reference Example 28

Di-tert-butyl 2,2'-((((((2-(1,1-dimethoxyethyl)naphtho[2,3-b]furan-4,9-diyl)bis(oxy))-bis(carbonyl))bis(azanediyl))bis(ethane-2,1-diyl))bis((tert-butoxycarbonyl)azanediyl))diacetate

[Chem. 84]

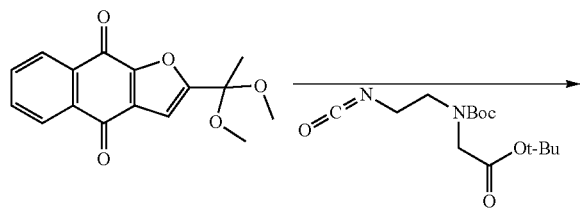

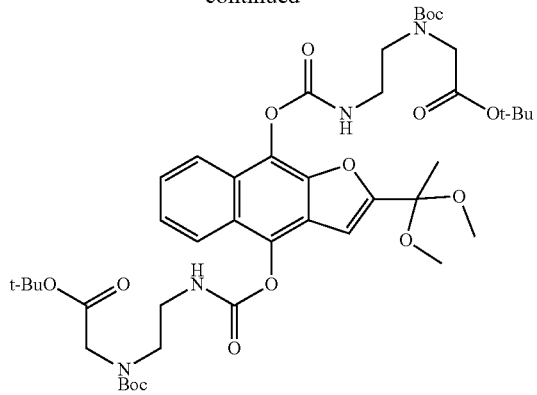

Reference example 28

A suspension of Reference example 27 (0.10 g), zinc (0.18 g), sodium dithionite (0.30 g), Diisopropylethylamine (0.24 mL), and tetra-n-butylammonium bromide (0.011 g) in N,N-dimethylformamide (6.0 mL) was stirred under nitrogen atmosphere at room temperature for 2 hours. Then, the suspension was cooled to 0° C. and the solution of tert-butyl N-(tert-butoxycarbonyl)-N-(2-isocyanatoethyl)glycinate in toluene, which was prepared from N-(tert-butoxycarbonyl)-N-(2-tert-butoxy-2-oxoethyl)-b-alanine (0.37 g) according to the same method as in Reference example 1, was added dropwise over 10 minutes. After stirring at 0° C. for 1 hour, the reaction solution was filtered through Celite and the Celite was washed with ethyl acetate. Water was added to the filtrate and the organic layer was separated. Then, the aqueous layer was further extracted with ethyl acetate once. After the resulting layer was dried over anhydrous sodium sulfate, it was filtered off and the solvent was evaporated under reduced pressure. The residue was purified by silica gel column chromatography (hexane/ethyl acetate=4:1-1:2) to yield Reference example 28 (0.23 g).

(LC-MS: [M-OMe+H]$^+$/Rt (min))=857/1.42

Example 4

2,2'-((((((2-acetylnaphtho[2,3-b]furan-4,9-diyl)bis(oxy))bis(carbonyl))-bis(azanediyl))bis(ethane-2,1-diyl))bis(azanediyl))diacetic Acid dihydrochloride

[Chem. 85]

Example 4

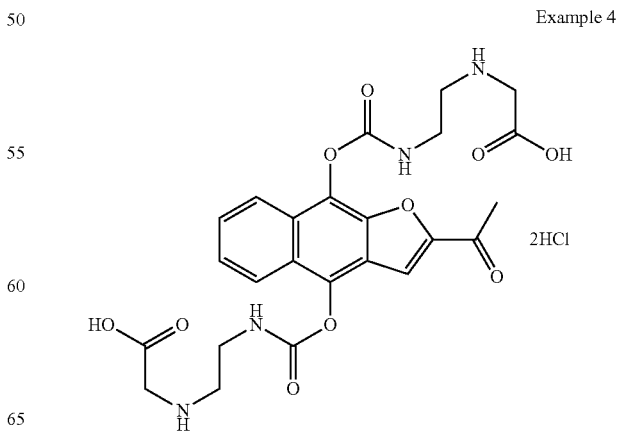

2HCl

A 4 mol/L hydrochloric acid/dioxane solution (7.0 mL), water (20 uL), and acetonitrile (7.0 mL) were added to Reference example 28 (0.50 g), and the reaction mixture was stirred at 70° C. for 1.5 hours. The precipitated solid was washed with acetonitrile and diethyl ether to yield Example 4 (0.33 g).

Examples 32 to 70 (Compounds analogous to Example 1) Compounds shown in Table 4 were obtained by using corresponding raw material compounds prepared by reactions/treatments described in Reference example 7 and Reference example 9, and by performing reactions/treatments described in Reference example 1, Reference example 2, and Example 1.

[Chem. 86]

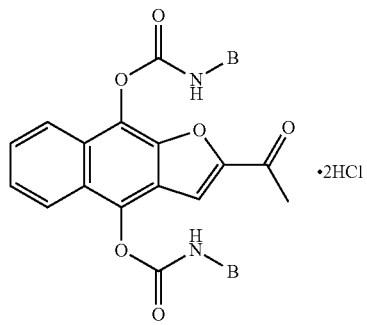

TABLE 4-1

| Example | B | (LC-MS: [M + 2H]²⁺/ Rt (min)) |
|---|---|---|
| 32 | (structure with NH₂, ester) | 266/0.44 |
| 33 | (structure with NH₂) | 450/0.44 |
| 34 | (structure with NH, ester) | 321/0.50 |
| 35 | (structure with NH, COOH) | 308/0.50 |
| 36 | (structure with NH, ester) | 280/0.54 |
| 37 | (structure with NH₂) | 264/0.50 |
| 38 | (structure with NH₂) | 278/0.55 |
| 39 | (structure with NH₂) | 292/0.90 |
| 40 | (structure with NH, COOH) | 280/0.40 |

TABLE 4-1-continued

| Example | B | (LC-MS: [M + 2H]²⁺/ Rt (min)) |
|---|---|---|
| 41 | (structure with NH, amide, COOH) | 323/0.40 |
| 42 | (structure with NH, COOH) | 294/0.35 |

TABLE 4-2

| Example | B | (LC-MS: [M + 2H]²⁺/ Rt (min)) |
|---|---|---|
| 43 | (structure with NH, F) | 254/0.32 |
| 44 | (structure with NH, F, F) | 272/0.34 |
| 45 | (structure with NH, CF₃) | 290/0.69 |
| 46 | (structure with NH, NH₂) | 251/0.19 |
| 47 | (structure with NH, ester) | 294/0.37 |
| 48 | (pyrrolidine NH) | 234/0.34 |
| 49 | (piperidine NH) | 248/0.37 |
| 50 | (structure with NH, COOH, chiral) | 280/0.37 |
| 51 | (structure with NH, COOH, chiral ethyl) | 294/0.39 |
| 52 | (structure with NH, NH₂) | 265/0.22 |
| 53 | (structure with NH, CF₃) | 304/0.51 |

TABLE 4-2-continued

| 54 | (structure) | 324/0.37 |

TABLE 4-3

| 55 | (structure) | 298/0.50 |
| 56 | (structure) | 383/0.67 |
| 57 | (structure) | 343/0.52 |
| 58 | (structure) | 342/0.60 |
| 59 | (structure) | 357/0.52 |
| 60 | (structure) | 328/0.39 |
| 61 | (structure) | 314/0.39 |
| 62 | (structure) | 305/0.38 |
| 63 | (structure) | 319/0.40 |
| 64 | (structure) | 337/0.38 |

TABLE 4-3-continued

| 65 | (structure) | 295/0.33 |
| 66 | (structure) | 309/0.37 |

TABLE 4-4

| 67 | (structure) | 309/0.37 |
| 68 | (structure) | 323/0.39 |
| 69 | (structure) | 296/0.33 |
| 70 | (structure) | 324/0.42 |

Examples 71 to 77 (Compounds Analogous to Example 15)

Compounds shown in Table 5 were obtained by using corresponding raw material compounds prepared by reactions/treatments described in Reference example 7 and Reference example 9, and by performing reactions/treatments described in Reference example 15 and Example 15.

[Chem. 87]

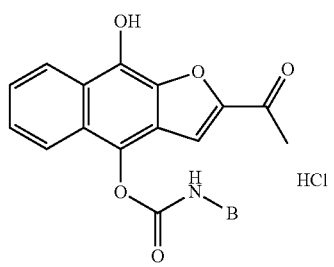

TABLE 5

| Example | B | (LC-MS: [M + H]+/ Rt (min)) |
|---|---|---|
| 71 | (structure) | 387/0.51 |
| 72 | (structure) | 371/0.54 |

TABLE 5-continued

| Example | B | (LC-MS: [M + H]+/ Rt (min)) |
|---|---|---|
| 73 | ~~~~~NH₂ | 399/0.61 |
| 74 | ~~~~NH₂ | 357/0.52 |
| 75 | ~~~~~~NH₂ | 413/0.70 |
| 76 | ~~~~~NH-CH₂-COOH | 429/0.57 |
| 77 | ~~~NH-CH₂-COOH | 401/0.52 |

Examples 78 to 92 (Compounds Analogous to Example 20)

Compounds shown in Table 6 were obtained by using corresponding raw material compounds prepared by reactions/treatments described in Reference example 7 and Reference example 9, and by performing reactions/treatments described in Reference example 16 and Example 20.

[Chem. 88]

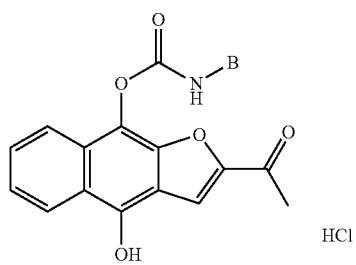

HCl

TABLE 6-1

| Example | B | (LC-MS: [M + H]+/ Rt (min)) |
|---|---|---|
| 78 | ~~~NH-CH₂-COOH | 387/0.51 |
| 79 | ~~~NH-CH₂CH₂-SO₂-N(CH₃)₂ | 464/0.55 |
| 80 | ~~~~NH-CH₂CH₂-SO₂-N(CH₃)₂ | 478/0.56 |
| 81 | ~~~NH-CH₂CH₂-SO₂-CH₃ | 435/0.50 |
| 82 | ~~~NH-CH₂CH₂-SO₂-CH₃ | 449/0.53 |
| 83 | ~~~NH-CH₂-CO-NH-CH₂-COOH | 444/0.55 |
| 84 | ~~~~NH-CH₂-CO-NH-CH₂-COOH | 458/0.51 |
| 85 | ~~~NH-CH₂-CO-azetidine | 426/0.51 |
| 86 | ~~~~NH-CH₂-CO-azetidine | 440/0.50 |
| 87 | ~~~NH-CH₂CH₂-O-CO-NH₂ | 416/0.48 |
| 88 | ~~~~NH-CH₂CH₂-O-CO-NH₂ | 430/0.50 |
| 89 | ~~~NH-CH₂CH₂-NH-CO-O-CH₃ | 430/0.52 |

TABLE 6-2

| Example | B | (LC-MS: [M + H]+/ Rt (min)) |
|---|---|---|
| 90 | ~~~~NH-CH₂CH₂-NH-CO-O-CH₃ | 440/0.54 |
| 91 | ~~~NH-CH₂CH₂-O-CO-O-CH₃ | 431/0.58 |
| 92 | ~~~~NH-CH₂CH₂-O-CO-O-CH₃ | 445/0.56 |

Example 93

2,2'-((((((2-acetylnaphtho[2,3-b]furan-4,9-diyl)bis(oxy))bis(carbonyl))bis(azanediyl))bis(ethane-2,1-diyl))bis(azanediyl))diacetic Acid monohydrochloride dihydrate

[Chem. 89]

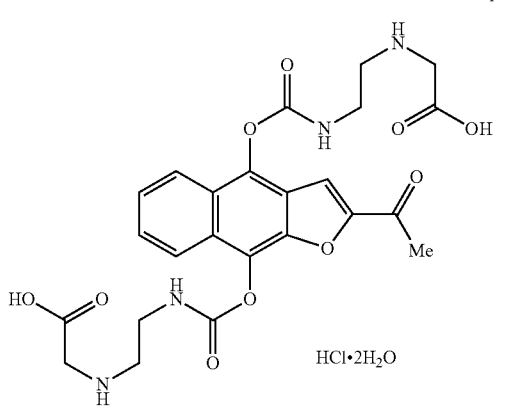

Example 93

Example 4 (1.00 g) was recrystallized from 0.1% aqueous hydrochloric acid solution (5.00 mL) to yield Example 93 (689 mg).

$^1$H-NMR (400 MHz, 0.1M DCl) δ 2.45 (3H, s), 3.35 (4H, t, J=5.8 Hz), 3.64 (4H, t, J=5.8 Hz), 3.99 (4H, s), 7.52-7.55 (1H, m), 7.58-7.62 (1H, m), 7.64 (1H, s), 7.97 (2H, d, J=9.2 Hz).

Example 94

2,2'-((((((2-acetylnaphtho[2,3-b]furan-4,9-diyl)bis(oxy))bis(carbonyl))bis-(azanediyl))bis(ethane-2,1-diyl))bis(azanediyl))diacetic Acid dimethanesulfonate Salt monohydrate

[Chem. 90]

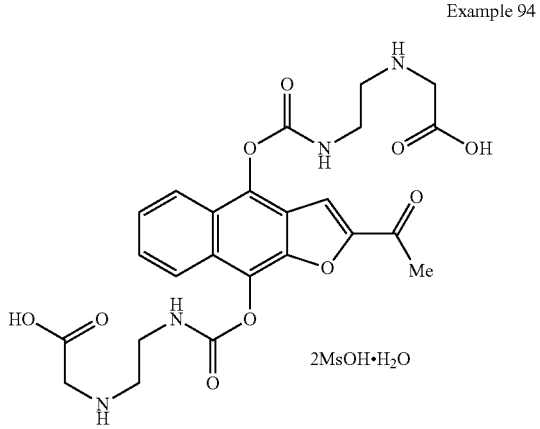

Example 94

A solution of Example 4A (0.30 g) and methanesulfonic acid (0.23 mL) in THF (3.0 mL)-water (0.20 mL) was stirred at 70° C. for 1.5 hours and then stirred at room temperature overnight. The precipitated solid was washed with THF to yield Example 94 (0.25 g).

$^1$H-NMR (400 MHz, DMSO-d$_6$) δ 2.29 (6H, s), 2.63 (3H, s), 3.20 (4H, m), 3.53 (4H, m), 4.02 (4H, m), 7.11 (4H, d), 7.48 (4H, d), 7.67 (2H, m), 8.11 (2H, m), 8.12 (1H, s), 8.51 (2H, m), 9.05 (4H, m), 13.87 (2H, br).

(LC-MS: [M+2H]$^{2+}$/Rt (min))=266/0.39

Example 95

2,2'-((((((2-acetylnaphtho[2,3-b]furan-4,9-diyl)bis(oxy))bis(carbonyl))bis(azanediyl))bis(ethane-2,1-diyl))bis(azanediyl))diacetic Acid ditoluenesulfonate Salt monohydrate

[Chem. 91]

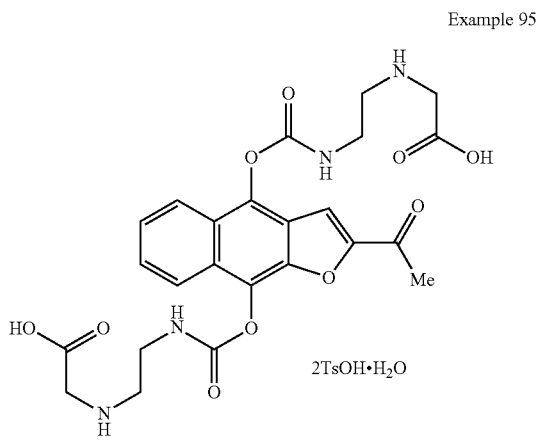

Example 95

A solution of Example 4A (0.10 g) and toluenesulfonic acid (0.11 g) in acetonitrile (1.0 mL)-water (0.064 mL) was stirred at 70° C. for 4 hours. Then, the solution was diluted with ethyl acetate and stirred at room temperature for 15 minutes. After ethyl acetate was removed, the residue was further washed with ethyl acetate twice to yield Example 95 (0.099 g).

$^1$H-NMR (400 MHz, DMSO-d$_6$) δ 2.29 (6H, s), 2.63 (3H, s), 3.20 (4H, m), 3.53 (4H, m), 4.02 (4H, m), 7.11 (4H, d), 7.48 (4H, d), 7.67 (2H, m), 8.11 (2H, m), 8.12 (1H, s), 8.51 (2H, m), 9.05 (4H, m), 13.87 (2H, br).

(LC-MS: [M+2H]$^{2+}$/Rt (min))=266/0.36

Example 96

2,2'-((((((2-acetylnaphtho[2,3-b]furan-4,9-diyl)bis(oxy))bis(carbonyl))bis(azanediyl))bis(ethane-2,1-diyl))bis(azanediyl))diacetic Acid dibenzenesulfonate Salt

[Chem. 92]

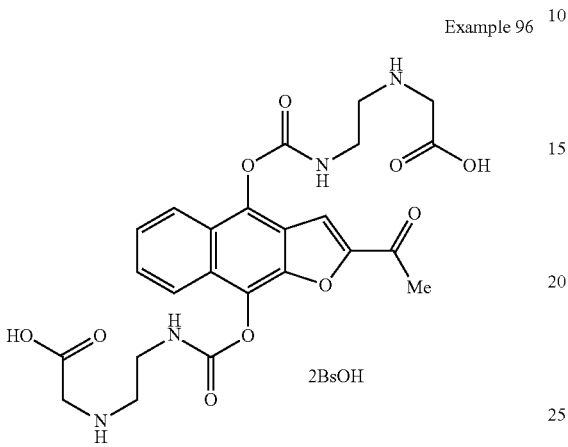

Example 96

A solution of Example 4A (0.10 g) and benzenesulfonic acid (0.38 g) in THF (3.0 mL)-water (0.10 mL) was stirred at 70° C. for 2.5 hours. Then, the solution was diluted with ethyl acetate and stirred at room temperature for 20 minutes. After ethyl acetate was removed, the residue was further washed with ethyl acetate twice to yield Example 96 (0.080 g).
$^1$H-NMR (400 MHz, DMSO-$d_6$) δ 2.63 (3H, s), 3.20 (4H, m), 3.53 (4H, m), 4.02 (4H, m), 7.31 (4H, m), 7.60 (4H, m), 7.67 (2H, m), 8.11 (2H, m), 8.12 (1H, s), 8.52 (2H, m), 9.05 (4H, m), 13.87 (2H, br).
(LC-MS: [M+2H]$^{2+}$/Rt (min))=266/0.36

Example 97

2,2'-((((((2-acetylnaphtho[2,3-b]furan-4,9-diyl)bis(oxy))bis(carbonyl))bis-(azanediyl))bis(ethane-2,1-diyl))bis(azanediyl))diacetic Acid monosulfate Salt monohydrate

[Chem. 93]

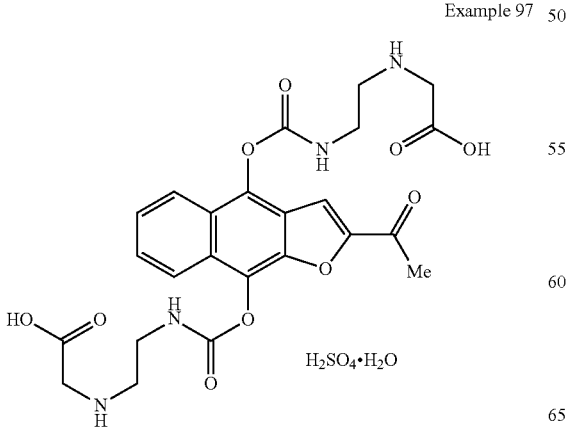

Example 97

To a solution of Example 4A (0.21 g) in acetonitrile (3.0 mL) heated to 70° C., 1 mol/L sulfuric acid (1.0 mL) was added, and the solution was stirred at 90° C. for 3 hours. The reaction solution was diluted with THF (20 mL) and then stirred at room temperature for 30 minutes. The precipitated solid was washed with THF to yield Example 97 (0.15 g).
1H-NMR (400 MHz, D$_2$O) δ: 2.62 (3H, s), 3.39 (4H, m), 3.71 (4H, m), 3.85 (4H, m), 7.67 (2H, m), 7.92 (1H, s), 8.12 (2H, m).
(LC-MS: [M+2H]$^{2+}$/Rt (min))=266/0.38

Example 98

2,2'-((((((2-acetylnaphtho[2,3-b]furan-4,9-diyl)bis(oxy))bis(carbonyl))bis(azanediyl))bis(ethane-2,1-diyl))bis(azanediyl))diacetic Acid 1/3 trifluoroacetate Salt monohydrate

[Chem. 94]

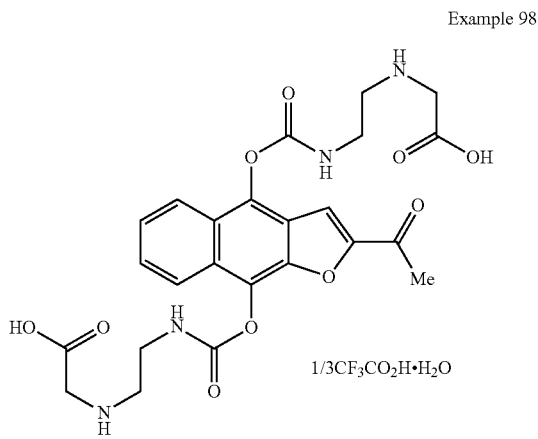

Example 98

A solution of Example 4A (0.20 g) in trifluoroacetic acid (0.50 mL)-water (0.10 mL) heated to 70° C. was stirred at 70° C. for 2 hours. Trifluoroacetic acid (0.25 mL) and water (0.05 mL) were added to the reaction solution and it was further stirred at 70° C. for 1.5 hours. The reaction solution was diluted with THF (20 mL) and then stirred at 0° C. for 30 minutes. The precipitated solid was washed with THF to yield Exampled 98 (0.10 g).
$^1$H-NMR (400 MHz, D$_2$O) δ: 2.57 (3H, s), 3.38 (4H, m), 3.68 (4H, m), 4.02 (4H, m), 7.62 (2H, m), 7.87 (1H, s), 8.07 (2H, m).
(LC-MS: [M+2H]$^{2+}$/Rt (min))=266/0.36

Example 99

3,3'-((((((2-acetylnaphtho[2,3-b]furan-4,9-diyl)bis(oxy))bis(carbonyl))bis(azanediyl))bis(ethane-2,1-diyl))bis(azanediyl))dipropionic Acid dimethanesulfonate Salt monohydrate

[Chem. 95]

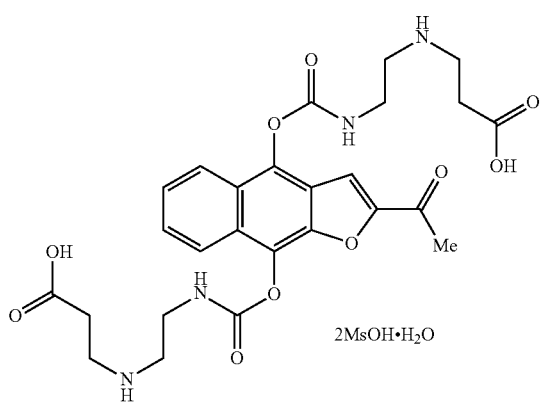

Example 99

2MsOH·H₂O

A solution of Example 5A (0.17 g) and methanesulfonic acid (0.13 mL) in acetonitrile (3.0 mL)-water (0.1 mL) was stirred at 70° C. for 2 hours. Then, the solution was diluted with ethyl acetate and stirred at room temperature for 1 hour. The precipitated solid was washed with ethyl acetate to yield Example 99 (0.13 g).

¹H-NMR (400 MHz, DMSO-d₆) δ: 2.34 (6H, s), 2.63 (3H, s), 2.71 (4H, m), 3.15-3.28 (8H, m), 3.51 (4H, m), 7.62-7.72 (2H, m), 8.11 (2H, m), 8.13 (1H, s), 8.50 (2H, m), 8.61 (4H, br), 12.74 (2H, br).

(LC-MS: $[M+2H]^{2+}$/Rt (min))=280/0.39

Example 100

3,3'-((((((2-acetylnaphtho[2,3-b]furan-4,9-diyl)bis(oxy))bis(carbonyl))bis(azanediyl))bis(ethane-2,1-diyl))bis(azanediyl))dipropionic Acid ditoluenesulfonate Salt monohydrate

[Chem. 96]

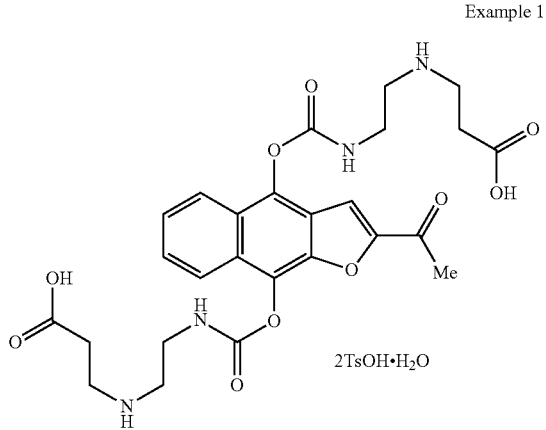

Example 100

2TsOH·H₂O

A solution of Example 5A (0.095 g) and toluenesulfonic acid (0.21 g) in THF (3.0 mL)-water (0.059 mL) was stirred at 80° C. for 1 hour. The precipitated solid was washed with THF and chloroform to yield Example 100 (0.075 g).

¹H-NMR (400 MHz, DMSO-d₆) δ: 2.28 (6H, s), 2.62 (3H, s), 2.70 (4H, m), 3.14-3.29 (8H, m), 3.47-3.53 (4H, m), 7.11 (4H, d), 7.47 (4H, d), 7.62-7.72 (2H, m), 8.10 (2H, m), 8.11 (1H, s), 8.50 (2H, m), 8.58 (4H, br), 12.76 (2H, br).

(LC-MS: $[M+2H]^{2+}$/Rt (min))=280/0.45

Example 101

3,3'-((((((2-acetylnaphtho[2,3-b]furan-4,9-diyl)bis(oxy))bis(carbonyl))bis(azanediyl))bis(ethane-2,1-diyl))bis(azanediyl))dipropionic Acid dibenzenesulfonate Salt

[Chem. 97]

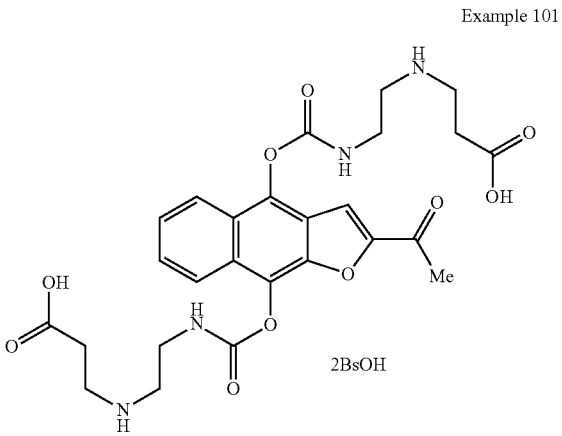

Example 101

2BsOH

A solution of Example 5A (0.10 g) and benzenesulfonic acid (0.18 g) in THF (3.0 mL)-water (0.062 mL) was stirred at 80° C. for 1 hour and then concentrated. The residue was washed with chloroform, and then suspended in THF and stirred at room temperature for 1 minute. The precipitated solid was washed with THF to yield Example 101 (0.043 g).

¹H-NMR (400 MHz, DMSO-d₆) δ: 2.63 (3H, s), 2.67-2.81 (4H, m), 3.14-3.31 (8H, m), 3.47-3.53 (4H, m), 7.28-7.34 (6H, m), 7.58-7.61 (4H, m), 7.67 (2H, m), 8.10 (2H, m), 8.11 (1H, s), 8.50 (2H, m), 8.60 (4H, br).

(LC-MS: $[M+2H]^{2+}$/Rt (min))=280/0.35

Example 102

3,3'-((((((2-acetylnaphtho[2,3-b]furan-4,9-diyl)bis(oxy))bis(carbonyl))bis-(azanediyl))bis(ethane-2,1-diyl))bis(azanediyl))dipropionic Acid monosulfate Salt monohydrate

[Chem. 98]

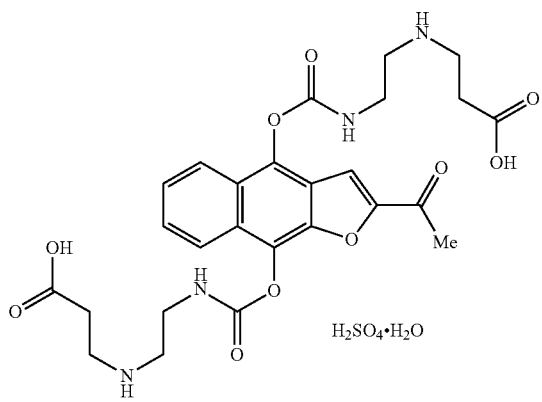

Example 102

To a solution of Example 5A (0.15 g) in acetonitrile (3.0 mL) heated to 70° C., 1 mol/L sulfuric acid (0.70 mL) was added and the solution was stirred at 90° C. for 2 hours. The reaction solution was diluted with ethyl acetate and then stirred at room temperature for 1 hour. The precipitated solid was washed with ethyl acetate to yield Example 102 (0.11 g).

$^1$H-NMR (400 MHz, D$_2$O): δ2.50 (3H, s), 2.75 (4H, t), 3.25-3.32 (8H, m), 3.58 (4H, t), 7.49-7.60 (2H, m), 7.79 (1H, s), 8.00 (2H, d).

(LC-MS: [M+2H]$^{2+}$/Rt (min))=280/0.48

Example 103

3,3'-((((((2-acetylnaphtho[2,3-b]furan-4,9-diyl)bis(oxy))bis(carbonyl))bis(azanediyl))bis(ethane-2,1-diyl))bis(azanediyl))dipropionic Acid 1/3 trifluoroacetate Salt monohydrate

[Chem. 99]

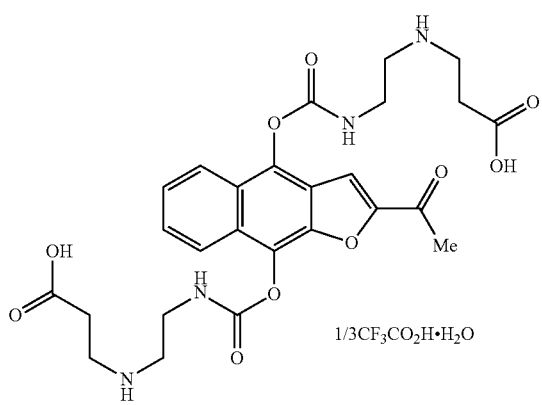

Example 103

A solution of Example 5A (0.15 g) in trifluoroacetic acid (0.40 mL)-water (0.080 mL) was stirred at 70° C. for 50 minutes. The reaction solution was diluted with THF (XX mL) and then stirred at room temperature for 30 minutes. The precipitated solid was washed with THF to yield Example 103 (0.11 g).

$^1$H-NMR (400 MHz, D$_2$O): δ2.54 (3H, s), 2.70 (4H, m), 3.25-3.31 (8H, m), 3.59 (4H, t), 7.51-7.61 (2H, m), 7.85 (1H, s), 8.02 (2H, d).

(LC-MS: [M+2H]$^{2+}$/Rt (min))=280/0.39

Example 104A

Dimethyl 4,4'-(((((2-acetylnaphtho[2,3-b]furan-4,9-diyl)bis(oxy))bis(carbonyl))bis(azanediyl))(2S,2'S)-bis(2-((tert-butoxycarbonyl)amino)butanoate

[Chem. 100]

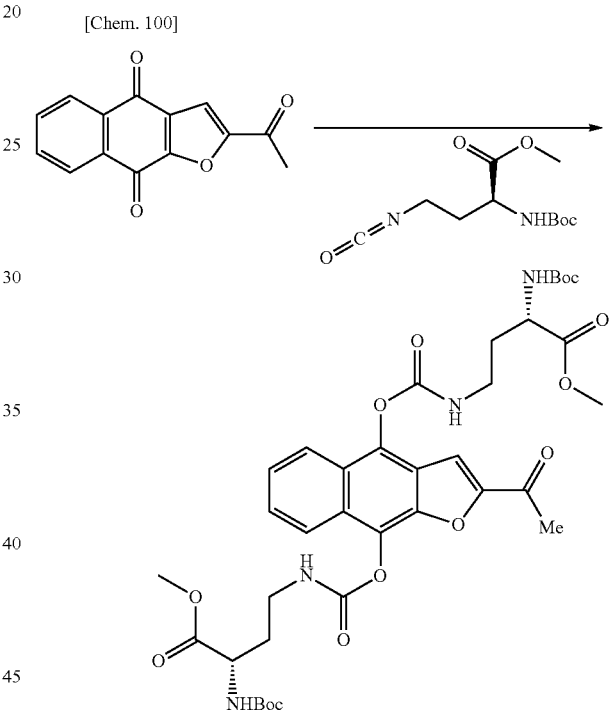

Example 104A

A suspension of 2-acetylnaphtho[2,3-b]furan-4,9-dione (200 mg), zinc (218 mg), sodium dithionite (725 mg), diisopropylethylamine (1.45 mL), and tetra-n-butylammonium bromide (27 mg) in N,N-dimethylformamide (11.9 mL) was stirred under nitrogen atmosphere at room temperature for 1 hour. Then, the suspension was cooled to 0° C., and the solution of methyl (S)-2-((tert-butoxycarbonyl)amino)-4-isocyanatobutanoate in toluene, which was prepared from (S)-4-((tert-butoxycarbonyl)amino)-5-methoxy-5-oxopentanoic acid (653 mg) according to the same method as in Reference example 1, was added dropwise over 15 minutes. After stirring at 0° C. for 40 minutes, the reaction solution was filtered through Celite and the Celite was washed with ethyl acetate. Aqueous saturated ammonium chloride solution was added to the filtrate and the organic layer was separated. Then, the aqueous layer was further extracted with ethyl acetate twice. After the resulting organic layer was dried over anhydrous sodium sulfate, it was

Example 104

Dimethyl 4,4'-((((2-acetylnaphtho[2,3-b]furan-4,9-diyl)bis(oxy))bis(carbonyl))bis-(azanediyl))(2S,2'S)-bis(2-aminobutanoate) dimethanesulfonate Salt

[Chem. 101]

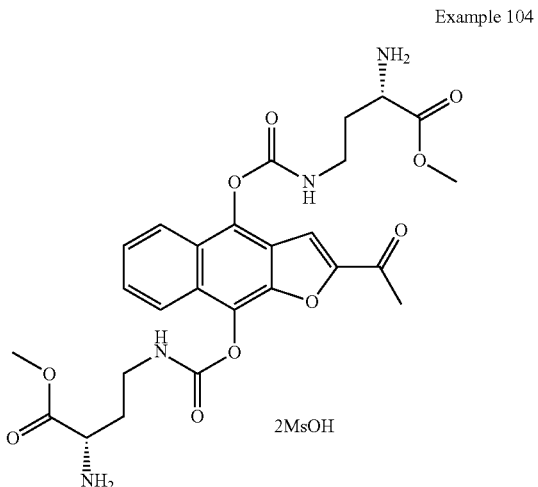

Example 104

2MsOH

A solution of Example 104A (0.052 g) and methanesulfonic acid (0.018 mL) in acetonitrile (0.50 mL) was stirred at 90° C. for 1 hour. The reaction solution was diluted with ethyl acetate and stirred at room temperature for 10 minutes. The precipitated solid was washed with ethyl acetate to yield Example 104 (0.046 g).

$^1$H-NMR (400 MHz, DMSO-$d_6$) δ: 2.02-2.19 (4H, m), 2.31 (6H, s), 2.63 (3H, s), 3.25-3.42 (4H, m), 3.80 (3H, s), 3.81 (3H, s), 4.21 (2H, m), 7.61-7.71 (2H, m), 8.04 (2H, m), 8.07 (1H, s), 8.36-8.52 (6H, m).

(LC-MS: [M+2H]$^{2+}$/Rt (min))=280/0.46

Example 105

Dimethyl 4,4'-((((2-acetylnaphtho[2,3-b]furan-4,9-diyl)bis(oxy))bis(carbonyl))bis(azanediyl))(2S,2'S)-bis(2-aminobutanoate) ditoluenesulfonate Salt monohydrate

[Chem. 102]

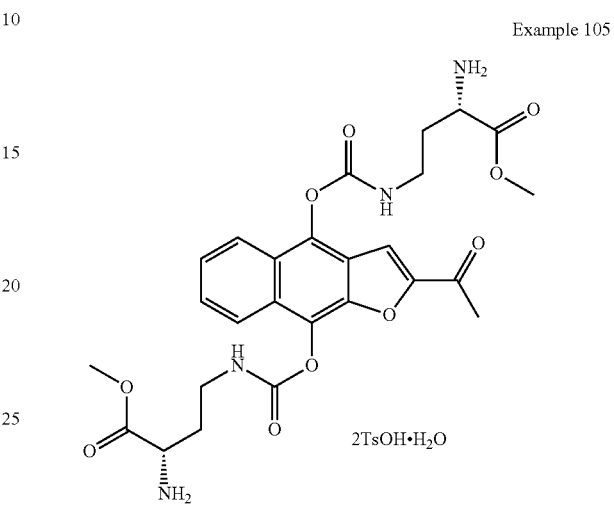

Example 105

2TsOH·H$_2$O

A solution of Example 104A (0.10 g) and toluenesulfonic acid (0.26 g) in THF (3.0 mL)-water (0.073 mL) was stirred at 80° C. for 1.5 hours and then stirred at room temperature overnight. The precipitated solid was washed with THF and chloroform to yield Example 105 (0.10 g).

$^1$H-NMR (400 MHz, DMSO-$d_6$) δ: 2.00-2.21 (4H, m), 2.28 (6H, s), 2.62 (3H, s), 3.27-3.41 (4H, m), 3.80 (3H, s), 3.81 (3H, s), 4.22 (2H, m), 7.11 (4H, d), 7.47 (4H, d), 7.66 (2H, m), 8.04 (2H, m), 8.06 (1H, s), 8.38-8.52 (6H, m).

(LC-MS: [M+2H]$^{2+}$/Rt (min))=280/0.42

Example 106

Dimethyl 4,4'-((((2-acetylnaphtho[2,3-b]furan-4,9-diyl)bis(oxy))bis(carbonyl))bis(azanediyl))(2S,2'S)-bis(2-aminobutanoate)dibenzenesulfonate Salt

[Chem. 103]

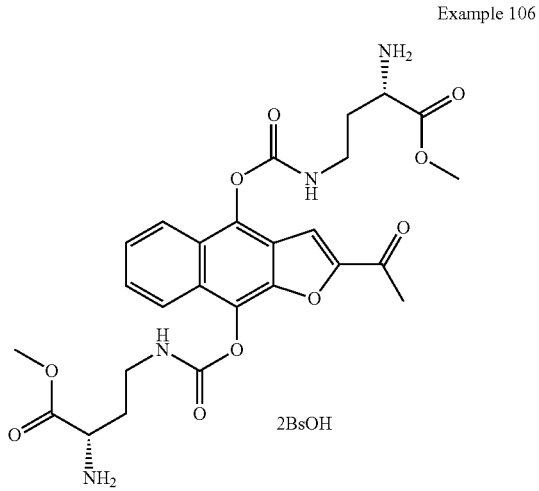

Example 106

2BsOH

A solution of Example 104A (0.078 g) and benzenesulfonic acid (0.16 g) in THF (2.5 mL)-water (0.055 mL) was stirred at 80° C. for 1 hour. The precipitated solid was washed with THF and chloroform to yield Example 106 (0.10 g).

$^1$H-NMR (400 MHz, DMSO-$d_6$) δ: 2.01-2.20 (4H, m), 2.63 (3H, s), 3.26-3.41 (4H, m), 3.80 (3H, s), 3.81 (3H, s), 4.22 (2H, m), 7.27-7.34 (6H, m), 7.58-7.71 (6H, m), 8.04 (2H, m), 8.07 (1H, s), 8.38-8.51 (6H, m).

(LC-MS: [M+2H]$^{2+}$/Rt (min))=280/0.48

Example 107

Dimethyl 4,4'-((((2-acetylnaphtho[2,3-b]furan-4,9-diyl)bis(oxy))bis(carbonyl))bis(azanediyl))(2S,2'S)-bis(2-aminobutanoate)monosulfate Salt monohydrate

[Chem. 104]

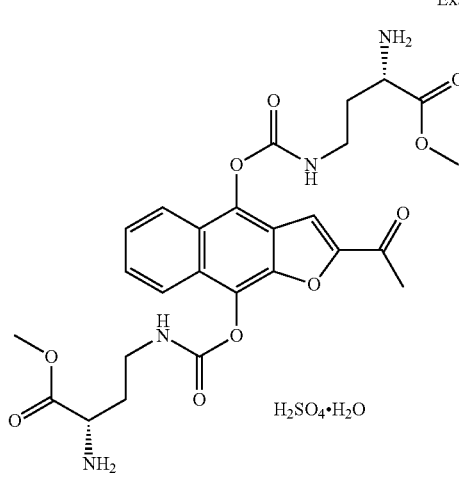

Example 107

To a solution of Example 104A (0.070 g) in acetonitrile (3.0 mL) heated to 50° C., concentrated sulfuric acid (one drop) was added and the solution was stirred at 50° C. for 30 minutes. The precipitated solid was washed with ethyl acetate to yield Example 107 (0.066 g).

$^1$H-NMR (400 MHz, D$_2$O): δ2.08-2.27 (4H, m), 2.50 (3H, s), 3.37-3.43 (4H, m), 3.76 (3H, s), 3.78 (3H, s), 4.15-4.21 (2H, m), 7.48-7.59 (2H, m), 7.72-7.75 (1H, br), 7.93-7.98 (2H, m).

(LC-MS: [M+2H]$^{2+}$/Rt (min))=280/0.48

Example 108

Dimethyl 4,4'-((((2-acetylnaphtho[2,3-b]furan-4,9-diyl)bis(oxy))bis(carbonyl))bis(azanediyl))(2S,2'S)-bis(2-aminobutanoate)ditrifluoroacetate Salt

[Chem. 105]

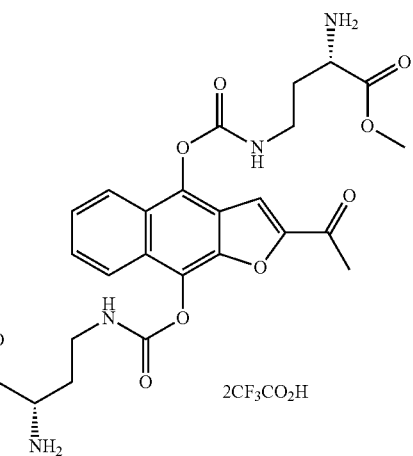

Example 108

A solution of Example 104A (0.11 g) in trifluoroacetic acid (1.0 mL) was stirred at room temperature for 30 minutes and then concentrated. The residue was suspended in ethyl acetate and then stirred at room temperature for 30 minutes. The precipitated solid was washed with ethyl acetate to Example 108 (0.076 g).

$^1$H-NMR (400 MHz, D$_2$O) δ:2.11-2.28 (4H, m), 2.53 (3H, s), 3.37-3.44 (4H, m), 3.77 (3H, s), 3.78 (3H, s), 4.18 (2H, m), 7.50-7.60 (2H, m), 7.79 (1H, s), 7.96-8.00 (2H, m).

(LC-MS: [M+2H]$^{2+}$/Rt (min))=280/0.49

Test Examples

Hereinafter, test results of representative compounds of the present invention are shown, and the chemical characteristics and pharmacokinetics of the compounds are described. However, the present invention is not limited to these test examples.

Test Example 1. Evaluation of a Conversion Rate to 2-acetylnaphtho[2,3-b]furan-4,9-dione For test compounds, the decrease rate of the test compounds and the conversion rate thereof to 2-acetylnaphtho[2,3-b]furan-4,9-dione in human plasma, CD1 mouse plasma, and pH 7.4 phosphate buffer solution were measured.

Test compounds were incubated at the concentration of 1 umol/L in human plasma (cat. no. 12250210, COSMO BIO), CD1 mouse plasma (cat. no. AP3054, KAC), and phosphate buffer solution at 37° C., and removed at predetermined times (0, 5, 10, 30, 60, and 120 minutes). After protein-removing treatment was performed, they are analyzed with LC-MS. It should be noted that the protein-removing treatment used acetonitrile containing: 10% volume of 1 mol/L hydrochloric acid; 1% volume of 46% citric acid; and phenytoin as an internal standard.

The measurement condition of LC-MS is as described below. LC-MS condition column: Kinetex 2.6u PFP 100A 50×2.1 mm Column temperature: 40° C.
Mobile phase: A: 0.1% formic acid-containing water
B: 0.1% formic acid-containing acetonitrile
A/B(min): 95/5(0)→5/95(3)→5/95(4)→95/5(4.1)→95/5(6)
Flow rate: 0.4 mL/min
Detection: ESI (positive mode)
Injection volume: 10 uL The result was shown in Table 7. The decomposition of the present compound typified by Example 6 rapidly proceeds in all conditions of the human plasma, the CD1 mouse plasma, and the pH 7.4 phosphate buffer solution. It was confirmed that there is no interspecies difference.

Regarding the conversion rate, it was confirmed that the activated form, 2-acetylnaphtho[2,3-b]furan-4,9-dione (Activated form 1) was quickly produced even in the pH 7.4 phosphate buffer solution not containing an enzyme, which is in the same level as the human plasma and the CD1 mouse plasma. This result indicates that the test compounds are prodrugs that are converted to the activated form via a route other than an enzymatic conversion and exhibit a slight interspecies difference.

TABLE 7

(% Measurement value)

| Incubation time (min) | | 0 | 5 | 20 | 30 | 60 | 120 |
|---|---|---|---|---|---|---|---|
| Human plasma | Sxample 6 | 100 | 0 | 0 | 0 | 0 | 0 |
| | Activated form | 0 | 24 | 31 | 48 | 64 | 71 |
| CD1 mouse plasma | Example 6 | 100 | 0 | 0 | 0 | 0 | 0 |
| | Activated form | 0 | 23 | 31 | 63 | 67 | 76 |
| Phosphate buffer solution (pH 7.4) | Example 6 | 100 | 0 | 0 | 0 | 0 | 0 |
| | Activated form | 0 | 20 | 29 | 55 | 61 | 78 |

Measurement values are calculated from the peak area ratio in LC-MS between an internal standard material, phenytoin and an active form, 2-acetylnaphtho[2,3-b]furan-4,9-dione, and are expressed in %.

In the same way as Example 6, the incubation time was set as 120 minutes later, and the conversion rate of each of various test compounds to 2-acetylnaphtho[2,3-b]furan-4,9-dione in human plasma, CD1 mouse plasma, and pH 7.4 phosphate buffer solution was measured. The results are shown in Table 8. A series of the present compounds were confirmed to be converted to 2-acetylnaphtho[2,3-b]furan-4,9-dione in pH 7.4 phosphate buffer solution in addition to human plasma and CD1 mouse plasma. Therefore, a series of the test compounds of the present invention were confirmed to be converted to the activated form via a route other than an enzymatic conversion.

TABLE 8

(% Measurement value)

| Incubation time (120 min) | Human plasma | CD1 mouse plasma | Phosphate buffer solution (pH 7.4) |
|---|---|---|---|
| Example 1 | 74 | 100 | 79 |
| Example 2 | 87 | 76 | 59 |
| Example 3 | 82 | 72 | 40 |
| Example 4 | 93 | 79 | 53 |
| Example 5 | 96 | 80 | 70 |
| Example 7 | 69 | 51 | 41 |
| Example 8 | 79 | 79 | 49 |
| Example 9 | 65 | 81 | 50 |

TABLE 8-continued (% Measurement value)

| Incubation time (120 min) | Human plasma | CD1 mouse plasma | Phosphate buffer solution (pH 7.4) |
|---|---|---|---|
| Example 10 | 89 | 59 | 58 |
| Example 11 | 100 | 100 | 58 |
| Example 12 | 63 | 78 | 63 |
| Example 13 | 95 | 50 | 13 |
| Example 15 | 89 | 93 | 100 |
| Example 17 | 80 | 81 | 80 |
| Example 18 | 81 | 73 | 80 |
| Example 20 | 65 | 73 | 57 |
| Example 21 | 40 | 44 | 24 |
| Example 22 | 37 | 56 | 22 |
| Example 28 | 73 | 85 | 34 |
| Example 32 | 81 | 74 | 46 |
| Example 33 | 100 | 100 | 47 |
| Example 34 | 41 | 52 | 24 |
| Example 35 | 78 | 70 | 38 |
| Example 36 | 73 | 66 | 46 |
| Example 37 | 35 | 33 | 17 |
| Example 38 | 85 | 72 | 39 |
| Example 39 | 80 | 62 | 31 |
| Example 40 | 89 | 86 | 50 |
| Example 41 | 86 | 81 | 52 |
| Example 42 | 69 | N.T. | 54 |
| Example 43 | 81 | N.T. | 63 |
| Example 44 | 88 | N.T. | 48 |
| Example 45 | 84 | N.T. | 48 |
| Example 46 | 59 | N.T. | 54 |
| Example 47 | 92 | N.T. | 65 |
| Example 48 | 71 | N.T. | 59 |
| Example 49 | 77 | N.T. | 58 |
| Example 50 | 96 | N.T. | 61 |
| Example 51 | 70 | N.T. | 55 |
| Example 52 | 78 | N.T. | 55 |
| Example 53 | 100 | N.T. | 41 |
| Example 55 | 86 | N.T. | 63 |
| Example 56 | 63 | N.T. | 30 |
| Example 57 | 68 | N.T. | 34 |
| Example 58 | 81 | N.T. | 40 |
| Example 59 | 81 | N.T. | 66 |
| Example 60 | 68 | N.T. | 39 |
| Example 61 | 87 | N.T. | 55 |
| Example 62 | 65 | N.T. | 37 |
| Example 63 | 59 | N.T. | 51 |
| Example 64 | 57 | N.T. | 40 |
| Example 65 | 81 | N.T. | 73 |
| Example 66 | 59 | N.T. | 44 |
| Example 67 | 78 | N.T. | 60 |
| Example 68 | 73 | N.T. | 59 |
| Example 69 | 90 | N.T. | 71 |
| Example 70 | 66 | N.T. | 48 |
| Example 71 | 61 | 68 | 70 |
| Example 72 | 53 | 42 | 38 |
| Example 73 | 88 | 63 | 66 |
| Example 74 | 70 | 62 | 82 |
| Example 75 | 79 | 60 | 45 |
| Example 76 | 68 | 71 | 57 |
| Example 77 | 68 | 70 | 66 |
| Example 78 | 54 | 66 | 43 |
| Example 79 | 71 | N.T. | 39 |
| Example 80 | 54 | N.T. | 32 |
| Example 81 | 74 | N.T. | 27 |
| Example 82 | 74 | N.T. | 25 |
| Example 83 | 67 | 67 | 31 |
| Example 84 | 42 | N.T. | 31 |
| Example 85 | 38 | N.T. | 37 |
| Example 86 | 55 | N.T. | 38 |
| Example 87 | 38 | N.T. | 36 |
| Example 88 | 27 | N.T. | 26 |
| Example 89 | 63 | N.T. | 58 |
| Example 90 | 34 | N.T. | 26 |
| Example 91 | 61 | N.T. | 45 |
| Example 92 | 34 | N.T. | 26 |
| Example 93 | 95 | N.T. | 72 |
| Example 94 | 75 | N.T. | 53 |

TABLE 8-continued (% Measurement value)

| Incubation time (120 min) | Human plasma | CD1 mouse plasma | Phosphate buffer solution (pH 7.4) |
|---|---|---|---|
| Example 95 | 70 | N.T. | 54 |
| Example 97 | 81 | N.T. | 61 |
| Example 98 | 90 | N.T. | 66 |
| Example 99 | 83 | N.T. | 60 |
| Example 100 | 100 | N.T. | 76 |
| Example 101 | 71 | N.T. | 56 |
| Example 102 | 79 | N.T. | 59 |
| Example 103 | 77 | N.T. | 53 |
| Example 104 | 82 | N.T. | 57 |
| Example 105 | 99 | N.T. | 65 |
| Example 106 | 86 | N.T. | 55 |
| Example 107 | 81 | N.T. | 50 |
| Example 108 | 77 | N.T. | 44 |

Measurement values are calculated from the peak area ratio in LC-MS between an internal standard material, phenytoin and an active form, 2-acetylnaphtho[2,3-b]furan-4,9-dione, and are expressed in %. N.T. means that the test was not carried out.

Test Example 2. Solution Stability Test

For Example 6, Example 11, and Example 22, the stability in each pH was measured. Test compounds at a concentration of 25 umol/L in respective buffer solutions prepared at pH 2.0, 3.0, 5.0, 7.4, and 9.0 were allowed to stand at 25° C. After 0, 3, 6, 9, 12, and 24 hours, they were measured with HPLC.

The buffer solutions used at respective pHs are as described below.
pH 2.0: 50 mmol/L glycine buffer solution
pH 3.0: 50 mmol/L citrate buffer solution
pH 5.0: 50 mmol/L citrate buffer solution
pH 7.4: 50 mmol/L phosphate buffer solution
pH 9.0: 50 mmol/L glycine buffer solution The measurement condition of HPLC is as described below.
HPLC condition column: Acquity UPLC BEH C18, 1.7 um, 50×2.1 mm
Column temperature: 40° C.
Mobile phase: A: 0.1% trifluoroacetic acid-containing water
B: acetonitrile
A/B(min): 95/5(0)→0/100(3.5)→0/100(4)→95/5(4.01)→95/5(5)
Flow rate: 0.8 mL/min
Detection: Ultraviolet-visible detector, Measurement wave length 254 nm
Injection volume: 5 uL The test results are shown in Tables 9, 10, and 11.

Example 6 and Example 11 were confirmed to be very stable at pH 2.0, and to have sufficient stability at pH 3. In the case of pH 5.0, the residual ratio in 12 hours later was confirmed as 0%, and the residual ratios at pH 7.4 and pH 9.0 were confirmed as already 0% in 3 hours later.

Example 22 was confirmed to have sufficient stability although a slight decomposition was observed at pH 2.0 and pH 3.0. In the case of pH 5.0, the residual ratio in 24 hours later was confirmed as 24.5%, and the residual ratios at pH 7.4 and pH 9.0 were confirmed as already 0% in 3 hours later.

From the above-described results, it was confirmed that the decomposition of a series of the present compounds typified by Example 6, Example 11, and Example 22 proceeds pH-dependently and chemically. From the present test result, it was shown that a series of the present compounds can become a prodrug for intravenous administration having sufficient stability by preparing an administration solution at pH 2.0 or pH 3.0 therefrom.

TABLE 9

(% residual ratio of example 6)

| Time (hr) | 0 | 3 | 6 | 9 | 12 | 24 |
|---|---|---|---|---|---|---|
| pH 2.0 | 100 | 100 | 100 | 100 | 100 | 99.8 |
| pH 3.0 | 100 | 99.0 | 98.2 | 97.5 | 96.6 | 93.6 |
| pH 5.0 | 100 | 27.3 | 10.8 | 3.6 | 0 | 0 |
| pH 7.4 | 100 | 0 | 0 | 0 | 0 | 0 |
| pH 9.0 | 100 | 0 | 0 | 0 | 0 | 0 |

TABLE 10

(% residual ratio of example 11)

| Time (hr) | 0 | 3 | 6 | 9 | 12 | 24 |
|---|---|---|---|---|---|---|
| pH 2.0 | 100 | 100 | 102 | 102 | 104 | 102 |
| pH 3.0 | 100 | 98.6 | 97.3 | 98.8 | 94.5 | 90.7 |
| pH 5.0 | 100 | 36.0 | 14.0 | 5.2 | 0 | 0 |
| pH 7.4 | 100 | 0 | 0 | 0 | 0 | 0 |
| pH 9.0 | 100 | 0 | 0 | 0 | 0 | 0 |

TABLE 11

(% Residual ratio of example 22)

| Time (hr) | 0 | 3 | 6 | 9 | 12 | 24 |
|---|---|---|---|---|---|---|
| pH 2.0 | 100 | 97.0 | 96.3 | 97.8 | 97.1 | 91.8 |
| pH 3.0 | 100 | 98.6 | 97.8 | 96.9 | 96.0 | 92.6 |
| pH 5.0 | 100 | 81.2 | 69.4 | 58.8 | 49.7 | 24.5 |
| pH 7.4 | 100 | 0 | 0 | 0 | 0 | 0 |
| pH 9.0 | 100 | 0 | 0 | 0 | 0 | 0 |

Test Example 3. Solubility Test

The solubility of water-soluble prodrugs described in the EXAMPLES was measured. A water-soluble prodrug was added into 50 mmol/L glycine buffer solution (pH 2.0). After shaking at room temperature for 24 hours, the mixture was filtered through a membrane filter, and then the filtrate was measured with HPLC.

The measurement condition of HPLC is as described below.
HPLC condition column: Acquity UPLC BEH C18, 1.7 um, 50×2.1 mm
Column temperature: 40° C.
Mobile phase: A: 0.1% trifluoroacetic acid-containing water
B: acetonitrile
A/B(min): 95/5(0)→0/100(3.5)→0/100(4)→95/5(4.01)→95/5(9)
Flow rate: 0.4 mL/min
Detection: Ultraviolet-visible detector, Measurement wave length 254 nm
Injection volume: 5 uL The test result is shown in Table 12. It was clarified that a series of water-soluble prodrugs relating to the present invention exhibit high water-solubility, which enables intravenous administration. It should be noted that each of 2-acetylnaphtho[2,3-b]furan-4,9-diyl bis(2,2-dimethylpropanoate), which is a prodrug for oral administration described in WO2012/119265, and 2-acetylnaphtho[2,3-b]furan-4,9-diyl dioctanoate, which is a prodrug for parenteral administration described in WO2013/120229, is completely different from a series of the present compounds, and exhibits very low solubility.

TABLE 12

| Example number or Compound name | Solubility in pH 2.0 buffer solution |
|---|---|
| 4 | >5.0 mg/mL |
| 5 | >5.0 mg/mL |
| 6 | 2.8 mg/mL |
| 10 | >5.0 mg/mL |
| 11 | >5.0 mg/mL |
| 22 | >5.0 mg/mL |
| 23 | >5.0 mg/mL |
| 32 | >5.0 mg/mL |
| 33 | >5.0 mg/mL |
| 34 | >5.0 mg/mL |
| 35 | >5.0 mg/mL |
| 36 | >5.0 mg/mL |
| 37 | >5.0 mg/mL |
| 38 | >5.0 mg/mL |
| 39 | >5.0 mg/mL |
| 40 | >5.0 mg/mL |
| 41 | >5.0 mg/mL |
| 42 | >5.0 mg/mL |
| 43 | >5.0 mg/mL |
| 44 | >5.0 mg/mL |
| 45 | >5.0 mg/mL |
| 46 | >5.0 mg/mL |
| 47 | >5.0 mg/mL |
| 48 | >5.0 mg/mL |
| 49 | >5.0 mg/mL |
| 50 | 0.1 mg/mL |
| 51 | 0.1 mg/mL |
| 52 | >5.0 mg/mL |
| 53 | >5.0 mg/mL |
| 55 | >5.0 mg/mL |
| 56 | 3.3 mg/mL |
| 57 | >5.0 mg/mL |
| 58 | 1.5 mg/mL |
| 59 | >5.0 mg/mL |
| 60 | >5.0 mg/mL |
| 61 | 2.5 mg/mL |
| 62 | >5.0 mg/mL |
| 63 | >5.0 mg/mL |
| 64 | >5.0 mg/mL |
| 65 | >5.0 mg/mL |
| 66 | >5.0 mg/mL |
| 67 | >5.0 mg/mL |
| 68 | >5.0 mg/mL |
| 69 | >5.0 mg/mL |
| 70 | >5.0 mg/mL |
| 71 | 0.1 mg/mL |
| 72 | 2.4 mg/mL |
| 73 | 0.1 mg/mL |
| 74 | 4.9 mg/mL |
| 75 | 0.1 mg/mL |
| 76 | 0.4 mg/mL |
| 77 | 0.5 mg/mL |
| 78 | 0.1 mg/mL |
| 79 | 0.3 mg/mL |
| 80 | 1.0 mg/mL |
| 81 | 0.9 mg/mL |
| 82 | 0.1 mg/mL |
| 83 | >5.0 mg/mL |
| 84 | >5.0 mg/mL |
| 85 | 4.1 mg/mL |
| 86 | >5.0 mg/mL |
| 87 | 4.0 mg/mL |
| 88 | 3.2 mg/mL |
| 89 | >5.0 mg/mL |
| 90 | >5.0 mg/mL |
| 91 | 3.6 mg/mL |
| 92 | >5.0 mg/mL |
| 93 | 3.5 mg/mL |
| 94 | >5.0 mg/mL |
| 95 | >5.0 mg/mL |
| 97 | 2.9 mg/mL |
| 98 | >5.0 mg/mL |
| 99 | >5.0 mg/mL |
| 100 | >5.0 mg/mL |
| 101 | >5.0 mg/mL |
| 102 | >5.0 mg/mL |
| 103 | >5.0 mg/mL |
| 104 | >5.0 mg/mL |
| 105 | >5.0 mg/mL |
| 106 | >5.0 mg/mL |
| 107 | >5.0 mg/mL |
| 108 | >5.0 mg/mL |
| 2-acetylnaphtho[2,3-b]furan-4,9-diyl bis(2,2-dimethylpropanpate) | <0.0001 mg/mL |
| 2-acetylnaphtho[2,3-b]furan-4,9-diyl dioctanoate | <0.0001 mg/mL |

Test Example 4. Pharmacokinetics Tests

For water-soluble prodrugs described in the EXAMPLES, the concentration of 2-acetylnaphtho[2,3-b]furan-4,9-dione (Activated form 1) in plasma was measured. Animal species, an administration method, a method of making standard solutions, and a method of measuring the concentration in plasma are as described below.

Animal: Seven-week-aged male CD1 (ICR) mice were used as an experimental animal.

Administration method: A test substance was weighed, and then dissolved in 50 mmol/L glycine buffered saline (pH 2.0) to produce an administration solution. The body weight of a mouse was measured, and the prepared administration solution was intravenously administered.

Blood collecting method: Heparin was added to a blood-collecting vessel, and blood was collected from a mouse. To the obtained blood, 46% of Citric acid was added in 1% volume. It was then centrifuged to obtain plasma. To the collected plasma, 1 mol/L HCl was added in 10% volume to produce a plasma sample. A sample obtained by adding 10% volume of 1 mol/L HCl to blank plasma was used as a blank sample.

Making of a standard solution: One mg of a test sample was weighed, and dissolved in 10 mL of acetonitrile using a measuring flask to make a standard solution of 100 ug/mL.

Measurement of the concentration in plasma: One hundred ug/mL of the standard solution was diluted in 50% acetonitrile solution to make calibration curve samples of target concentrations. Twenty uL of a blank sample was added to 18 uL of the calibration curve sample to make a plasma calibration curve sample. Eighteen uL of 50% acetonitrile solution was added to 20 uL of the administered plasma sample to make a sample for plasma analysis. One hundred uL of acetonitrile (containing 1% volume of 10 mol/L HCl) containing an internal standard was added to the plasma calibration curve sample and the sample for plasma analysis, respectively. It should be noted that phenytoin was used as the internal standard and its concentration was prepared in 100 nmol/L. 10 uL of each sample was analyzed with LC-MS. A calibration curve was made from a value (peak ratio) of the peak area of a test substance in MS divided by the peak area of the internal standard, and the concentrations of plasma calibration curve samples. The concentration in a sample was calculated from the peak ratio of each sample and the calibration curve.

The test results are shown in Tables 13, 14, 15, 16, and 17. It was confirmed that by intravenously administering each of Examples 4, 5, 6, 11, and 23, 2-acetylnaphtho[2,3-b]furan-4,9-dione (Activated form 1) was rapidly produced from each of the Examples.

In view of the result of test example 1 in addition to the result of test example 4, for a series of the present compounds, the production of 2-acetylnaphtho[2,3-b]furan-4,9-dione can also be expected in human as in the case of mouse. Therefore, expansion of the use of 2-acetylnaphtho[2,3-b]furan-4,9-dione, of which the use in parenteral administration is limited, can be expected, and the present compounds are extremely useful.

TABLE 13

| Plasma 10.0 mg/kg | Example 4 Compound Concentration (umol/L) | | | | |
|---|---|---|---|---|---|
| (i.v.) | 1 | 2 | 3 | mean | S.D. |
| 0.083 hr | 5.87 | 4.62 | 6.37 | 5.62 | 0.90 |
| 0.5 hr | 1.04 | 2.05 | 1.14 | 1.41 | 0.56 |
| 1.0 hr | 0.53 | 0.75 | 1.37 | 0.88 | 0.44 |
| 2.0 hr | 0.17 | 0.14 | 0.14 | 0.15 | 0.02 |

TABLE 14

| Plasma 10.5 mg/kg | Example 5 Compound Concentration (umol/L) | | | | |
|---|---|---|---|---|---|
| (i.v.) | 1 | 2 | 3 | mean | S.D. |
| 0.083 hr | 6.16 | 7.37 | 4.20 | 5.91 | 1.60 |
| 0.5 hr | 1.82 | 2.59 | 2.04 | 2.15 | 0.39 |
| 1.0 hr | 0.83 | 0.55 | 0.39 | 0.59 | 0.22 |
| 2.0 hr | 0.20 | 0.67 | 0.12 | 0.33 | 0.30 |

TABLE 15

| Plasma 9.6 mg/kg | Example 6 Compound Concentration (umol/L) | | | | |
|---|---|---|---|---|---|
| (i.v.) | 1 | 2 | 3 | mean | S.D. |
| 0.083 hr | 4.95 | 5.87 | 5.79 | 5.54 | 0.51 |
| 0.5 hr | 1.17 | 1.07 | 1.66 | 1.30 | 0.32 |
| 1.0 hr | 0.53 | 0.28 | 0.38 | 0.40 | 0.12 |
| 2.0 hr | 0.25 | 0.50 | 0.41 | 0.39 | 0.13 |

TABLE 16

| Plasma 10.5 mg/kg | Example 11 Compound Concentration (umol/L) | | | | |
|---|---|---|---|---|---|
| (i.v.) | 1 | 2 | 3 | mean | S.D. |
| 0.083 hr | 3.74 | 4.41 | 5.29 | 4.48 | 0.78 |
| 0.5 hr | 0.69 | 1.17 | 1.39 | 1.08 | 0.36 |
| 1.0 hr | 0.42 | 0.62 | 0.63 | 0.56 | 0.12 |
| 2.0 hr | 0.36 | 0.28 | 0.08 | 0.24 | 0.15 |

TABLE 17

| Plasma 11.0 mg/kg | Example 23 Compound Concentration (umol/L) | | | | |
|---|---|---|---|---|---|
| (i.v.) | 1 | 2 | 3 | mean | S.D. |
| 0.083 hr | 6.87 | 8.20 | 8.49 | 7.85 | 0.87 |
| 0.5 hr | 1.12 | 0.85 | 1.67 | 1.22 | 0.42 |
| 1.0 hr | 0.47 | 0.29 | 0.36 | 0.37 | 0.09 |
| 2.0 hr | 0.08 | 0.06 | 0.12 | 0.09 | 0.03 |

Animal: Seven-week-aged male CD1 (ICR) mice were used as an experimental animal.

Administration method: A test substance was weighed, and then dissolved in 50 mmol/L glycine buffered solution (pH 2.0) containing 0.5% methylcellulose, to produce an administration solution. The body weight of a mouse was measured, and the prepared administration solution was orally administered.

Blood collecting method: Heparin was added to a blood-collecting vessel, and blood was collected from a mouse. To the obtained blood, 46% of Citric acid was added in 1% volume. It was then centrifuged to obtain plasma. To the collected plasma, 1 mol/L HCl was added in 10% volume to produce a plasma sample. A sample obtained by adding 10% volume of 1 mol/L HCl to blank plasma was used as a blank sample.

Making of a standard solution: One mg of a test sample was weighed, and dissolved in 10 mL of acetonitrile using a measuring flask to make a standard solution of 100 ug/mL.

Measurement of the concentration in plasma: One hundred ug/mL of the standard solution was diluted in 50% acetonitrile solution to make calibration curve samples of target concentrations. Twenty uL of a blank sample was added to 18 uL of the calibration curve sample to make a plasma calibration curve sample. Eighteen uL of 50% acetonitrile solution was added to 20 uL of the administered plasma sample to make a sample for plasma analysis. One hundred uL of acetonitrile (containing 1% volume of 10 mol/L HCl) containing an internal standard was added to the plasma calibration curve sample and the sample for plasma analysis, respectively. It should be noted that phenytoin was used as the internal standard and its concentration was prepared in 100 nmol/L. 10 uL of each sample was analyzed with LC-MS. A calibration curve was made from a value (peak ratio) of the peak area of a test substance in MS divided by the peak area of the internal standard, and the concentrations of plasma calibration curve samples. The concentration in a sample was calculated from the peak ratio of each sample and the calibration curve.

The test results are shown in Tables 18, 19, and 20. It was confirmed that by orally administering each of Examples 4, 5, and 11, a high concentration of 2-acetylnaphtho[2,3-b]furan-4,9-dione (Activated form 1) was observed from each of the Example compounds.

In view of the result of test example 3 in addition to the result of test example 4, a series of the present compounds are extremely useful since the improvement in oral absorbability by increasing the water-solubility of 2-acetylnaphtho[2,3-b]furan-4,9-dione, of which the absorption in oral administration is an object due to its high crystallizability, can be expected.

TABLE 18

| Plasma 251.2 mg/kg | Example 4 Compound Concentration (umol/L) | | | | |
|---|---|---|---|---|---|
| (p.o.) | 1 | 2 | 3 | mean | S.D. |
| 0.25 hr | 2.74 | 2.17 | 2.88 | 2.60 | 0.37 |
| 0.5 hr | 5.70 | 2.58 | 2.99 | 3.76 | 1.70 |
| 1.0 hr | 10.91 | 3.01 | 3.82 | 5.91 | 4.35 |
| 2.0 hr | 8.95 | 3.02 | 1.14 | 4.37 | 4.08 |
| 4.0 hr | 6.00 | 9.28 | 4.70 | 6.66 | 2.36 |
| 6.0 hr | 5.33 | 5.83 | 3.80 | 4.98 | 1.06 |
| 24.0 hr | 0.06 | 0.24 | 0.08 | 0.13 | 0.10 |

TABLE 19

| Plasma 262.9 mg/kg | Example 5 Compound Concentration (umol/L) | | | | |
|---|---|---|---|---|---|
| (p.o.) | 1 | 2 | 3 | mean | S.D. |
| 0.25 hr | 4.62 | 4.25 | 3.98 | 4.28 | 0.32 |
| 0.5 hr | 4.66 | 3.20 | 2.23 | 3.36 | 1.23 |
| 1.0 hr | 14.74 | 7.58 | 10.28 | 10.87 | 3.62 |
| 2.0 hr | 10.37 | 7.99 | 8.70 | 9.02 | 1.22 |
| 4.0 hr | 8.37 | 8.20 | 7.99 | 8.19 | 0.19 |
| 6.0 hr | 1.24 | 1.28 | 0.50 | 1.01 | 0.44 |
| 24.0 hr | ND | ND | 0.03 | 0.01 | 0.02 |

TABLE 20

| Plasma 232.5 mg/kg | Example 11 Compound Concentration (umol/L) | | | | |
|---|---|---|---|---|---|
| (p.o.) | 1 | 2 | 3 | mean | S.D. |
| 0.25 hr | 18.86 | 19.65 | 25.31 | 21.27 | 3.52 |
| 0.5 hr | 17.48 | 11.45 | 17.11 | 15.35 | 3.38 |
| 1.0 hr | 10.87 | 18.98 | 15.93 | 15.26 | 4.10 |
| 2.0 hr | 13.53 | 6.62 | 13.57 | 11.24 | 4.00 |
| 4.0 hr | 6.12 | 3.73 | 11.49 | 7.11 | 3.98 |
| 6.0 hr | 2.37 | 0.60 | 0.75 | 1.24 | 0.98 |
| 24.0 hr | ND | ND | 0.04 | 0.01 | 0.02 |

INDUSTRIAL APPLICABILITY

Pharmaceutical compositions comprising a novel water-soluble prodrug of 2-acetylnaphtho[2,3-b]furan-4,9-dione relating to the present invention, a pharmaceutically acceptable salt, or a hydrate or solvate thereof; or solution-type formulation comprising them in an water solution exhibit excellent solubility due to having a carbamate chain or carbonate chain of a certain structure containing an amine having nucleophilicity. Further, since 2-acetylnaphtho[2,3-b]furan-4,9-dione, which is an activated form, is rapidly produced through pH-dependent and chemical conversion, interspecies difference and individual difference, which are clinical problems, are made small. Therefore, the present compounds are extremely useful since it is possible to expand the use of 2-acetylnaphtho[2,3-b]furan-4,9-dione, of which the absorption in oral administration is an object and of which the use in parenteral administration is also limited due to its high crystallizability.

The invention claimed is:

1. A compound:

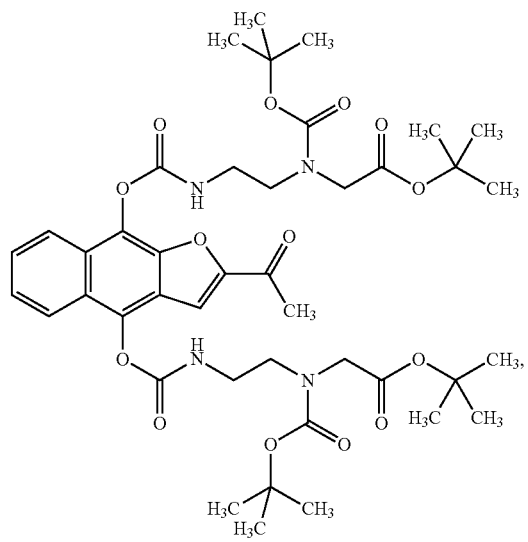 [SMILES: CC(=O)c1cc2c(OC(=O)NCCN(CC(=O)OC(C)(C)C)C(=O)OC(C)(C)C)c3ccccc3c(OC(=O)NCCN(CC(=O)OC(C)(C)C)C(=O)OC(C)(C)C)c2o1]

or a pharmaceutically acceptable salt thereof.

2. A process for producing a hydrate of a hydrochloride salt of 2,2'-((((((2-acetylnaphtho[2,3-b]furan-4,9-diyl)bis(oxy))bis(carbonyl))bis(azanediyl))bis(ethane-2,1-diyl))bis(azanediyl))diacetic acid, wherein 2,2'-((((((2-acetylnaphtho[2,3-b]furan-4,9-diyl)bis(oxy))bis(carbonyl))bis(azanediyl))bis(ethane-2,1-diyl))bis(azanediyl)diacetic acid is of the formula:

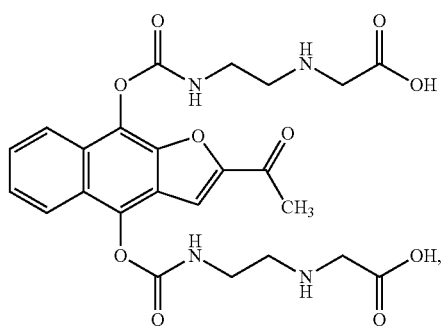 [SMILES: CC(=O)c1cc2c(OC(=O)NCCNCC(=O)O)c3ccccc3c(OC(=O)NCCNCC(=O)O)c2o1]

wherein the process comprises the following step:
recrystallizing a hydrochloride salt of 2,2'-((((((2-acetylnaphtho[2,3-b]furan-4,9-diyl)bis(oxy))bis(carbonyl))bis(azanediyl))bis(ethane-2,1-diyl))bis(azanediyl)diacetic acid, wherein 2,2'-((((((2-acetylnaphtho[2,3-b]furan-4,9-diyl)bis(oxy))bis(carbonyl))bis(azanediyl))bis(ethane-2,1-diyl))bis(azanediyl))diacetic acid is of the formula:

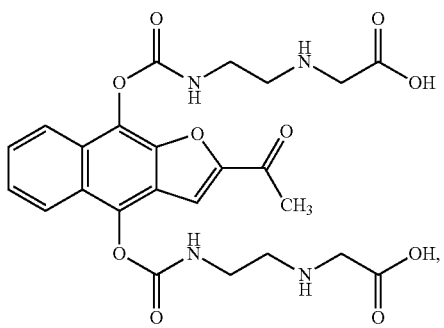 [SMILES: CC(=O)c1cc2c(OC(=O)NCCNCC(=O)O)c3ccccc3c(OC(=O)NCCNCC(=O)O)c2o1]

in the presence of hydrochloric acid and a recrystallization solvent;

wherein the recrystallization solvent is water; or wherein the recrystallization solvent is a mixture of water and one or more additional solvents selected from the group consisting of acetone, acetonitrile, benzene, chloroform, dichloromethane, diethyl ether, N,N-dimethylformamide, ethanol, ethyl acetate, hexane, isopropanol, methanol, and toluene.

3. The process of claim 2, wherein the hydrate of the hydrochloride salt of 2,2'-((((((2-acetylnaphtho[2,3-b]furan-4,9-diyl)bis(oxy))bis(carbonyl))bis(azanediyl))bis(ethane-2,1-diyl))bis(azanediyl))diacetic acid is 2,2'-((((((2-acetylnaphtho[2,3-b]furan-4,9-diyl)bis(oxy))bis(carbonyl) bis(azanediyl))bis(ethane-2,1-diyl))bis(azanediyl)diacetic acid is a hydrate of 2,2'-((((((2-acetylnaphtho[2,3-b]furan-4,9-diyl)bis(oxy))bis(carbonyl))bis(azanediyl))bis(ethane-2,1-diyl))bis(azanediyl)diacetic acid monohydrochloride.

4. The process of claim 2, wherein the process further comprises the following step:

deprotecting di-tert-butyl 2,2'-((((((2-acetylnaphtho[2,3-b]furan-4,9-diyl)bis(oxy))bis(carbonyl)bis(azanediyl)) bis(ethane-2,1-diyl))bis((tert-butoxycarbonyl) azanediyl))diacetate of the formula:

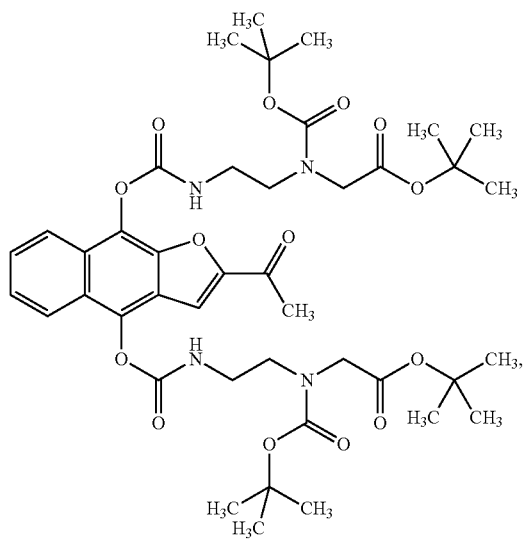 [SMILES: CC(=O)c1cc2c(OC(=O)NCCN(CC(=O)OC(C)(C)C)C(=O)OC(C)(C)C)c3ccccc3c(OC(=O)NCCN(CC(=O)OC(C)(C)C)C(=O)OC(C)(C)C)c2o1]

with hydrochloric acid, to produce a hydrochloride salt of 2,2'-((((((2-acetylnaphtho[2,3-b]furan-4,9-diyl)bis (oxy))bis(carbonyl)bis(azanediyl))bis(ethane-2,1-diyl))bis(azanediyl))diacetic acid, wherein 2,2'-((((((2-acetylnaphtho[2,3-b]furan-4,9-diyl)bis(oxy))bis (carbonyl))bis(azanediyl))bis(ethane-2,1-diyl))bis (azanediyl))diacetic acid is of the formula:

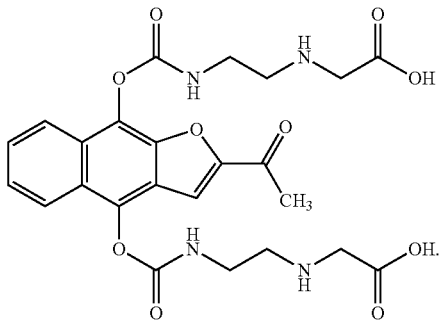 [SMILES: CC(=O)c1cc2c(OC(=O)NCCNCC(=O)O)c3ccccc3c(OC(=O)NCCNCC(=O)O)c2o1]

5. The process of claim 4, wherein the process further comprises the following step:

reacting 2-acetylnaphtho[2,3-b]furan-4,9-dione of the formula:

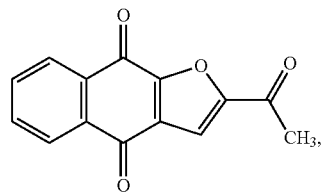 [SMILES: CC(=O)c1cc2c(o1)C(=O)c1ccccc1C2=O]

with tert-butyl N-(tert-butoxycarbonyl)-N-(2-isocyanatoethyl)glycinate of the formula:

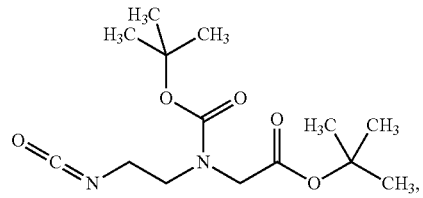 [SMILES: CC(C)(C)OC(=O)CN(CCN=C=O)C(=O)OC(C)(C)C]

in the presence of a base, and a reductant in a solvent, to produce di-tert-butyl 2,2'-((((((2-acetylnaphtho[2,3-b] furan-4,9-diyl)bis(oxy))bis(carbonyl))bis(azanediyl)) bis(ethane-2,1-diyl))bis((tert-butoxycarbonyl) azanediyl))diacetate of the formula:

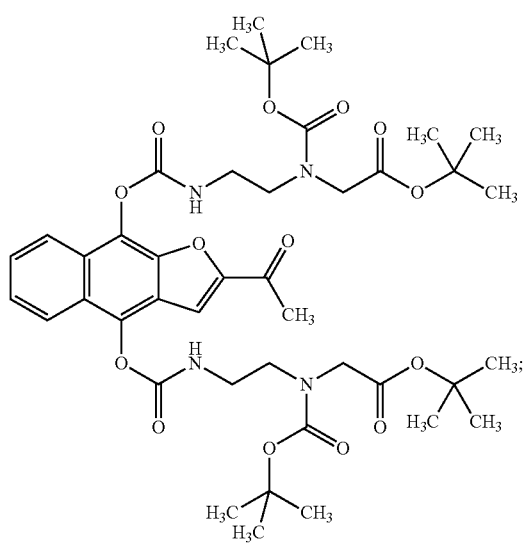 [SMILES: CC(=O)c1cc2c(OC(=O)NCCN(CC(=O)OC(C)(C)C)C(=O)OC(C)(C)C)c3ccccc3c(OC(=O)NCCN(CC(=O)OC(C)(C)C)C(=O)OC(C)(C)C)c2o1]

wherein the base is selected from the group consisting of calcium hydride, cesium carbonate, cyclohexyldimethylamine, N,N-diisopropylethylamine, 4-(N,N-dimethylamino)pyridine, N,N-dimethylaniline, lutidine, N-methylmorpholine, N-methylpiperidine, N-methylpyrrolidine, potassium carbonate, pyridine, sodium acetate, sodium carbonate, sodium hydride, triethylamine, tripropylamine, and tributylamine, or a mixture thereof;

wherein the reductant is selected from the group consisting of formic acid, iron(II) ion, oxalic acid, sodium, sodium dithionite, tin(II) ion, and zinc, or a mixture thereof; and wherein the solvent is selected from the group consisting of acetonitrile, benzene, chlorobenzene, chloroform, 1,2-dichloroethane, dichloromethane, dimethylsulfoxide, N,N-dimethylformamide, 1,4-dioxane, N-methyl-2-pyrrolidone, propionitrile, tetrahydrofuran, toluene, and water, or a mixture thereof.

6. The process of claim 5, wherein the base is N,N-diisopropylethylamine or triethylamine.

7. The process of claim 5, wherein the reductant is sodium dithionite.

8. The process of claim 2, wherein the recrystallization solvent is water.

* * * * *